United States Patent [19]

Crowley

[11] Patent Number: 5,561,053
[45] Date of Patent: Oct. 1, 1996

[54] METHOD FOR SELECTING HIGH-EXPRESSING HOST CELLS

[75] Inventor: Craig W. Crowley, Portola Valley, Calif.

[73] Assignee: Genentech, Inc., South San Francisco, Calif.

[21] Appl. No.: 286,740

[22] Filed: Aug. 5, 1994

[51] Int. Cl.$^6$ .............................. C12P 21/00; C12N 5/10; C12N 15/11; C07H 21/04
[52] U.S. Cl. ................. 435/69.1; 435/172.3; 435/240.2; 435/320.1; 536/23.2
[58] Field of Search ........................ 536/23.2; 435/69.1, 435/172.3, 240.2, 320.1; 935/34

[56] References Cited

U.S. PATENT DOCUMENTS

| | | |
|---|---|---|
| 4,399,216 | 8/1983 | Axel et al. . |
| 4,634,665 | 1/1987 | Axel et al. . |
| 4,965,199 | 10/1990 | Capon et al. . |
| 5,043,270 | 8/1991 | Abrams et al. . |

FOREIGN PATENT DOCUMENTS

| | | |
|---|---|---|
| 160457 | 11/1985 | European Pat. Off. . |
| 215548 | 3/1987 | European Pat. Off. . |
| 260148 | 3/1988 | European Pat. Off. . |
| WO90/12025 | 10/1990 | WIPO . |
| WO92/17566 | 10/1992 | WIPO . |
| WO94/05784 | 3/1994 | WIPO . |

OTHER PUBLICATIONS

Kaufman, "Selection and Coamplification of Heterologous Genes in Mammalian Cells", Methods in Enzymology, vol. 185, pp. 537–566.

Cepko et al., "Construction and Applications of a Highly Transmissable Murine Retrovirus Shuttle Vector", Cell, vol. 37, pp. 1053–1062.

Brown et al., "Retroviral Vectors", in DNA Cloning, vol. III, D. M. Glover, Editor, IRL Press, Oxford, pp. 189–212.

Brown and Scott, "Retroviral vectors" *DNA Cloning, vol. III*, D. M. Glover, Oxford:IRL Press pp. 189–212 (1987).

Miller et al., "Generation of a Helper–Free Amphotropic Retroviruses that Transduce a Dominant–Acting, Methotrexate–Resistant Dihydrofolate Reductase Gene" *Molecular & Cellular Biology* 5(3):431–437 (1985).

Vidaud et al., "A 5' splice–region G–C mutation in exon 1 of the human β–globin gene inhibits pre–mRNA splicing: A mechanism for β+–thalassemia" *Proc. Natl. Acad. Sci.* USA 86:1041–1045 (1989).

Andreason, Grai L., "Electroporation as a technique for the transfer of macromolecules into mammalian cell lines" *J. Tiss. Cult. Meth.* 15:56–62 (1993).

Ashkenazi et al., "Protection against endotoxic shock by a tumor necrosis factor receptor immunoadhesion" *Proc. Natl. Acad. Sci.* 88:10535–10539 (1991).

(List continued on next page.)

Primary Examiner—George C. Elliott
Attorney, Agent, or Firm—Wendy M. Lee

[57] ABSTRACT

A method for selecting recombinant host cells expressing high levels of a desired protein is described. This method utilizes eukaryotic host cells harboring a DNA construct comprising a selectable gene (preferably an amplifiable gene) and a product gene provided 3' to the selectable gene. The selectable gene is positioned within an intron defined by a splice donor site and a splice acceptor site and the selectable gene and product gene are under the transcriptional control of a single transcriptional regulatory region. The splice donor site is generally an efficient splice donor site and thereby regulates expression of the product gene using the transcriptional regulatory region. The transfected cells are cultured so as to express the gene encoding the product in a selective medium comprising an amplifying agent for sufficient time to allow amplification to occur, whereupon either the desired product is recovered or cells having multiple copies of the product gene are identified.

20 Claims, 81 Drawing Sheets

OTHER PUBLICATIONS

Boggs et al., "Efficient transformation and frequent single-site, single-copy insertion of DNA can be obtained in mouse erythroleukemia cells transformed by electroporation" *Exp. Hematol.* 14:988–994 (1986).

Bovenberg et al., "In vitro splicing analysis of mini-gene constructs of the alternatively processed human calcitonin/CGRP-I pre-mRNA" *Biochimica et Biophysica Acta* 1008:223–233 (1989).

Cohen & Levinson, "A point mutation in the last intron responsible for increased expression and transforming activity of the c-Ha-ras oncogene" *Nature* 334:119–124 (1988).

Cohen et al., "Expression of the H-ras Proto-Oncogene Is Controlled by Alternative Splicing" *Cell* 58:461–472 (1989).

Eperon et al., "The role of nucleotide sequences in splice site selection in eukaryotic pre-messenger RNA" *Nature* 324:280–282 (1986).

Hendershot et al., "Assembly and secretion of heavy chains that do not associate posttranslationally with immunoglobulin heavy chain-binding protein" *Journal of Cell Biology* 104:761–767 (1987).

Liu, Chung-Cheng et al., "Initiation of translation at internal AUG codons in mammalian cells" *Nature* 309:82–85 (1984).

Ohshima & Gotoh, "Signals for the Selection of a Splice Site In Pre-mRNA:Computer Analysis of Splice Junction Sequences and Like Sequences" *J. Mol. Biol.* 195:247–259 (1987).

Vancanneyt et al., "Construction of an intron-containing marker gene: Splicing of the intron in transgenic plants and its use in monitoring early events in Agrobacterium mediated plant transformation" *Biological Abstracts* 89(9):AB-432, abs. 92,287 (May 1990).

Abrams et al., "Intronic Positioning Maximizes Co-expression and Co-amplification of Nonselectable Heterologous Genes" *Journal of Biological Chemistry* 264(24):14016–14021 (1989).

Assaraf et al., "Identification of methotrexate transport deficiency in mammalian cells using fluoresceinated methotrexate and flow cytometry" *Proc. Natl. Acad. Sci. USA* 84:7154–7158 (1987).

Beggs, "Gene cloning in yeast" *Genetic Engineering* 2:175–203 (1981).

Bendig, "The production of foreign proteins in mammalian cells" *Genetic Engineering* 7:91–127 (1988).

Cepko et al., "Construction and Applications of a Highly Transmissible Murine Retrovirus Shuttle Vector" *Cell* 37:1053–1062 (1984).

Federspiel et al., "Novel DNA Rearrangements Are Associated with Dihydrofolate Reductase Gene Amplification" *Journal of Biological Chemistry* 259(14):9127–9140 (1984).

Haber et al., "Chromosome-Mediated Transfer and Amplification of an Altered Mouse Dihydrofolate Reductase Gene" *Somatic Cell Genetics* 8(4):499–508 (1982).

Haber et al., "Properties of an Altered Dihydrofolate Reductase Encoded by Amplified Genes in Cultured Mouse Fibroblasts" *Journal of Biological Chemistry* 256(18):9501–9510 (1981).

Haber et al., "Unstable Amplification of an Altered Dihydrofolate Reductase Gene Associated with Double-Minute Chromosomes" *Cell* 26:355–362 (1981).

Hung et al., "Molecular cloning of the neu gene: Absence of gross structural alteration in oncogenic alleles" *Proc. Natl. Acad. Sci. USA* 83:261–264 (1986).

Jang et al., "Initiation of Protein Synthesis by Internal Entry of Ribosomes into the 5' Nontranslated Region of Encephalomyocarditis Virus RNA In Vivo" *Journal of Virology* 63(4):1651–1660 (1989).

Kaetzel et al., "Methotrexate-induced Amplification of the Bovine Lutropin Genes in Chinese Hampster Ovary Cells" *Journal of Biological Chemistry* 263(13):6344–6351 (1988).

Kaufman, "High Level Production of Proteins in Mammalian Cells" *Genetic Engineering*, New York and London:Plenum Press vol. 9:155–198 (1987).

Kaufman, "Selection and Coamplification of Heterologous Genes in Mammalian Cells" *Methods in Enzymology* 185:537–566 (1990).

Kaufman, "Vectors Used for Expression in Mammalian Cells" *Methods in Enzymology* 185:487–511 (1990).

Kaufman et al., "Amplification and Expression of Sequences Cotransfected with a Modular Dihydrofolate Reductase Complementary DNA Gene" *J. Mol. Biol.* 159:601–621 (1982).

Kaufman et al., "Amplification and Loss of Dihydrofolate Reductase Genes in a Chinese Hamster Ovary Cell Line" *Molecular & Cellular Biology* 1(12):1069–1076 (1981).

Kaufman et al., "Coamplification and Coexpression of Human Tissue-Type Plasminogen Activator and Murine Dihydrofolate Reductase Sequences in Chinese Hamster Ovary Cells" *Molecular & Cellular Biology* 5(7):1750–1759 (1985).

Kaufman, et al., "Translational efficiency of polycistronic mRNAs and their utilization to express heterologous genes in mammalian cells" *EMBO Journal* 6(1):187–193 (1987).

Kim et al., "Stable Reduction of Thymidine Kinase Activity in Cells Expressing High Levels to Anti-Sense RNA" *Cell* 42:129–138 (1985).

Kriegler, "Assembly of Enhancers, Promoters, and Splice Signals to Control Expression of Transferred Genes" *Methods in Enzymology* 185:512–527 (1990).

Levinson, "Expression of Heterologous Genes in Mammalian Cells" *Methods in Enzymology* 185:485–487 (1990).

Maniatis et al., "Regulation of Inducible and Tissue-Specific Gene Expression" *Science* 236:1237–1245 (1987).

Page et al., "High Level Expression of the Humanized Monoclonal Antibody Campath-1H in Chinese Hamster Ovary Cells" *Bio/Technology* 9:64–68 (1991).

Pelletier et al., "Internal initiation of translation of eukaryotic mRNA directed by a sequence derived from poliovirus RNA" *Nature* 334:320–325 (1988).

Schimke, "Gene Amplification in Cultured Animal Cells" *Cell* 37:705–713 (1984).

Schimke, "Gene Amplification in Cultured Cells" *Journal of Biological Chemistry* 263(13):5989–5992 (1988).

Simonsen et al., "Isolation and expression of an altered mouse dihydrofolate reductase cDNA" *Proc. Natl. Acad. Sci. USA* 80:2495–2499 (1983).

Stephens et al., "The bovine papillomavirus genome and its uses as a eukaryotic vector" *Biochemistry* 248:1–11 (1987).

Urlaub et al., "Deletion of the Diploid Dihydrofolate Reductase Locus from Cultured Mammalian Cells" *Cell* 33:405–412 (1983).

Urlaub et al., "Isolation of Chinese hamster cell mutants deficient in dihydrofolate reductase activity" *Proc. Natl. Acad. Sci. USA* 77(7):4216–4220 (1980).

Wigler et al., "Transformation of mammalian cells with an amplifiable dominant–acting gene" *Proc. Natl. Acad. Sci. USA* 6:3567–3570 (1980).

Wigler et al., "Transformation of Mammalian Cells with Genes from Procaryotes and Eucaryotes" *Cell* 16:777–785 (1979).

Wold et al., "Introduction and expression of a rabbit Beta–globin gene in mouse fibroblasts" *Proc. Natl. Acad. Sci. USA* 76(11):5684–5688 (1979).

Yates et al., "Stable replication of plasmids derived from Epstein–Barr virus in various mammalian cells" *Nature* 313:812–815 (1985).

a) WT ras (efficient SD)
b) MUTANT ras (less efficient SD)
c) ▲GT (inefficient SD)

a) WT ras
b) MUTANT ras
c) ▲GT

FIG. 3A

```
    aluI
    sstI
    sacI
    hgiJII
    hgiAI/aspHI
    ecl136II
    bsp1286
    bsiHKAI
    bmyI                     rmaI      tru9I
    banII                    maeI      mseI                                                                              thaI
    taqI            speI     aseI/asnI/vspI                                       bslI                                   fnuDII/mvnI
                                                                                                                         bstUI
                                                                                                                         bsh1236I
                                                                                                                         aciI maeIII
  1 TTCGAGCTCG CCCGACATTG ATTATTGACT AGTAATCAAT TACGGGGTCA TTAGTTCATA GCCCATATAT GGAGTTCCGC GTTACATAAC
    AAGCTCGAGC GGGCTGTAAC TAATAACTGA TCATTAGTTA ATGCCCCAGT AATCAAGTAT CGGGTATATA CCTCAAGGCG CAATGTATTG scrFI
                 mvaI
                 ecoRII
                 dsaV
                 aciI
                 bglI bstNI                         maeII
                 sau96I                             hinlI/acyI                                           maeII
                 haeIII/palI               aciI     ahaII/bsaHI                                          hinlI/acyI
                 asuI apyI[dcm+]                    aatII       maeII            maeIII                  ahaII/bsaHI
101 TTACGTAAA TGGGCCGCCT GGCTGACCGC CCAACGACCC ACGTCAATAA TGACGTATGT TCCCATAGTA ACGCCAATAG GGACTTTCCA
    AATGCCATTT ACCGGGGCGA CCGACTGGCG GGTTGCTGGG TGCAGTTATT ACTGCATACA AGGGTATCAT TGCGGTTATC CCTGAAAGGT maeII                                                                                                    maeII
    hinlI/acyI                                             rsaI                                               hinlI/acyI
    ahaII/bsaHI                                            csp6I      ndeI           rsaI                     ahaII/bsaHI
    aatII                                     bglI                                   csp6I                    aatII
201 TTGACGTCAA TGGGTGGAGT ATTTACGGTA AACTGCCCAC TTGGCAGTAC ATCAAGTGTA TCATATGCCA AGTACGCCCC CTATTGACGT CAATGACGGT
    AACTGCAGTT ACCCACCTCA TAAATGCCAT TTGACGGGTG AACCGTCATG TAGTTCACAT AGTATACGGT TCATGCGGGG GATAACTGCA GTTACTGCCA scrFI
                mvaI
                ecoRII                                                                              nlaIII
                aciI                                                                    styI
                bglI dsaV                                                  maeII                    ncoI
                sau96I bstNI                rsaI                           snaBI                    dsaI hphI aciI
                haeIII/palI                 csp6I                    rsaI  bsaAI                    bsaJI     sfaNI
                asuI apyI[dcm+] bsrI nlaIII       csp6I
301 AAATGGCCCG CCTGGCATTA TGCCCAGTAC ATGACCTTAT GGGACTTTCC TACTTGGCAG TACATCTACG TATTAGTCAT CGCTATTACC ATGGTGATGC
    TTTACCGGGC GGACCGTAAT ACGGGTCATG TACTGGAATA CCCTGAAAGG ATGAACCGTC ATGTAGATGC ATAATCAGTA GCGATAATGG TACCACTACG
```

FIG. 3B

```
                                                              maeII
                                                              hinII/acyI
                                                              ahaII/bsaHI          nlaIV
                          pleI                                aatII                hgiCI
     rsaI      aciI       hinfI               bsmAI                                banI
     csp6I
401  GGTTTTGGCA GTACATCAAT GGGCGTGGAT AGCGGTTTGA CTCACGGGGA TTTCCAAGTC TCCACCCCAT TGACGTCAAT GGGAGTTTGT TTTGGCACCA
     CCAAAACCGT CATGTAGTTA CCCGCACCTA TCGCCAAACT GAGTGCCCCT AAAGGTTCAG AGGTGGGGTA ACTGCAGTTA CCCTCAAACA AAACCGTGGT
                                                                                                        aluI
                                                                                                        sstI
                                                                                                        sacI
                                                                                                        hgiJII
                                                                                                        hgiAI/aspHI
                                                                                                        ecl136II
                                                                                                        bsp1286
                                                                                                        bsiHKAI
                                                                                                        bmyI
                                                            rsaI                                         banII
                                                            csp6I    mnlI
                    maeIII    aciI    hgaI     aciI
501  AAATCAACGG GACTTTCCAA AATGTCGTAA CAACTCCGCC CCATTGACGC AAATGGGCGG TAGGCGTGTA CGGTGGGAGG TCTATATAAG CAGAGCTCGT
     TTTAGTTGCC CTGAAAGGTT TTACAGCATT GTTGAGGCGG GGTAACTGCG TTTACCCGCC ATCCGCACAT GCCACCCTCC AGATATATTC GTCTCGAGCA
             esp3I
         scrFI
         mvaI bsmAI                                                                   haeIII/palI
         ecoRII                                                                       mcrI
         dsaV                                                                         eagI/xmaIII/eclXI
         bstNI hinlI/acyI                                                             eaeI
         apyI[dcm+]                                                                   cfrI
         sau3AI gsuI/bpmI                                                             fnu4HI
         mboI/ndeII[dam-]                                                             aciI
         dpnI[dam+] hgaI ahaII/bsaHI                                                  thaI
         dpnII[dam-]                                                                  fnuDII/mvnI
                                                      sau96I           sacII/sstII
                                              scrFI                    nspBII
                                              nciI           asuI      kspI  scrFI
                                              mspI           avaII     dsaI  nciI
                                              hpaII          nlaIV           bglI bslI mspI
                                      mboII   dsaV                           sau3AI mnlI bstUI
                                      bpuAI   cauII                          mboI/ndeII[dam-] hpaII
                                      bbsI                 mnlI              dpnI[dam+] bsaJI dsaV
                                                                             dpnII[dam-] bsh1236I
                                                                             alwI[dam-] aciI cauII
601  TTAGTGAACC GTCAGATCGC CTGAGACGAC CATCCACGCT GTTTTGACCT CCATAGAAGA CACCGGGACC GATCCAGCCT CCGCGGCCGG GAACGGTGCA
     AATCACTTGG CAGTCTAGCG GACTCTGCGC GTAAACTGGA GGTATCTTCT GTGGCCCTGG CTAGGTCGGA GGCGCCGGCC CTTGCCACGT
```

FIG. 3C

```
        tfiI
        acil
        thaI hinfI
        fnuDII/mvnI                                                                    fnu4HI
        bstUI                                                            aciI          bbvI
        bsh1236I                                         rsaI                          nspBI        taqI
                                                         csp6I  scfI             mnlI aciI  nlaIII
701 TTGGAACGCG GATTCCCGT GCCAAGAGTG CTGTAAGTAC CGCCTATAGA GCGATAAGAG GATTTTATCC CCGCTGCCAT CATGGTTCGA CCATTGAACT
    AACCTTGCGC CTAAGGGCA CGGTTCTCAC GACATTCATG GCGGATATCT CGCTATTCTC CTAAAATAGG GGCGACGGTA GTACCAAGCT GGTAACTTGA thaI
                                                                                    fnuDII/mvnI
                                                                                    bstUI
                                                                                    bsh1236I
                                                                         bsrBI      mluI
                pflMI                                    bsmAI           aciI  afliII  rsaI
    sfaNI       bslI                                     bsaI       mnlI  ddeI  xmnI  csp6I
801 GCATCGTCGC CGTGTCCCAA AATATGGGGA TTGGCAAGAA CGGAGACCTA CCCTGCCCTC CGCTCAGGAA CGCGTTCAAG TACTTCCAAA GAATGACCAC
    CGTAGCAGCG GCACAGGGTT TTATACCCCT AACCGTTCTT GCCTCTGGAT GGGACGGGAG GCGAGTCCTT GCGCAAGTTC ATGAAGGTTT CTTACTGGTG scrFI
                                                       mvaI
                                                       ecoRII
                                                       dsaV
            eco57I                                     bstNI
            mboII                    tfiI              apyI[dcm+]                            tfiI     tru9I
            earI/ksp632I             hinfI                         sexAI             ddeI    mboII    taqI     mseI
            mnlI                     alwNI    hphI                                                    hinfI    ahaIII/draI  aseI/asnI/vspI
901 AACCTCTTCA GTGAAGGTA AACAGAATCT GGTGATTATG GGTAGGAAAA CCTGGTTCTC CATTCCTGAG AAGAATCGAC CTTTAAAGGA CAGAATTAAT
    TTGGAGAAGT CACCTTCCAT TTGTCTTAGA CCACTAATAC CCATCCTTTT GGACCAAGAG GTAAGGACTC TTCTTAGCTG GAAATTTCCT GTCTTAATTA aluI
                                              sstI
                                              sacI
                                              hgiJII
                                              hgiAI/aspHI
                                              ecl136II
                                              bsp1286
                                              bsiHKAI
                                              bmyI                                                    tru9I
                                              banII                                         sfaNI    mseI           mspI
                                                                                                     aflIII/bfrI    hpaII
            ddeI                     bslI  mnlI                                       bstXI  fokI   aflIII/bfrI     bsaWI
1001 ATAGTTCTCA GTAGAGAACT CAAAGAACCA CCACGAGGAG CTCATTTTCT TGCCAAAAGT TTGGATGATG CCTTAAGACT TATTGAACAA CCGGAATTGG
     TATCAAGAGT CATCTCTTGA GTTTCTTGGT GGTGCTCCTC GAGTAAAAGA ACGGTTTTCA AACCTACTAC GGAATTCTGA ATAACTTGTT GGCCTTAACC
```

```
                                                                    scrFI
                                                                    mvaI
                                                                    ecoRII
                                                                    dsaV
                                                                    bstNI
                                                              apyI[dcm+]          mnlI                               bspMI
                                                              gsuI/bpmI           bsaJI                              scfI
       scfI                                                   hincII/hindIII      ddeI              aluI      bsgI          pstI
       fokI                                     maeIII                                              hindIII   fnu4HI        bbvI                     tru9I
                                                                                                                                                     mseI
1501 CACTATAGAA TAACATCCAC TTTGCCTTTC TCTCCACAGG TGTCACTCCA GGTCAACTGC ACCTCGGTTC TAAGCTTGGG CTGCAGGTCG CCGTGAATTT
     GTGATATCTT ATTGTAGGTG AAACGGAAAG AGAGGTGTCC ACAGTGAGGT CCAGTTGACG TGGAGCCAAG ATTCGAACCC GACGTCCAGC GGCACTTAAA
                                                                                                                    scrFI
                                                                                                                    mvaI
                                             hgiJII                                                                 ecoRII
                                             bsp1286                                                                dsaV
                                             bmyI                                                                   bstNI
                       sfaNI             mnlI                        fnu4HI                                         apyI[dcm+] nlaIII
              hgaI     fokI              mboII  banII                bbvI                           mboII
                       nlaIII            earI/ksp632I                fnu4HI                         bpuAI
1601 AAGGACGCT GTGAAGCAAT CATGGATGCA GGCTCTGCTG ATGAAGAGAG TGTGCTGCTG CAGTCTTCGT TTCGCCCAGC CAGGAAATCC
     TTCCCTGCGA CACTTCGTTA GTACCTACGT CCGAGACGAC TACTTCTCTC ACACGACGAC GTCAGAAGCA AGCGGGTCG GTCCTTTAGG
                                             scfI
                                             pstI
                             sau3AI          bsgI
                             mboI/ndeII[dam-]
                   nlaIV     dpnI[dam+]      sau3AI
                   mnlI      bstYI/xhoI      mboI/ndeII[dam-]
            tfiI   mboII     bglII           dpnI[dam+]                                                                              hgiAI/aspHI
            hinfI  earI/ksp632I dpnII[dam-]  dpnII[dam-]                                                         hinPI      bsp1286
                                                                                                                 fnu4HI     bsiHKAI
                                                                                                                 bbvI       bmyI
1701 ATGCCCGATT CAGAAGAGA GCCAGATCTT ACCAAGTGAT CTGCAGAGAT GAAAAAAAGC AGATGATATA CCAGCAACAT CAGTCATGGC TGCGCCCTGT
     TACGGGCTAA GTCTTCTCCT CGGTCTAGAA TGGTTCACTA GACGTCTCTA CTTTTTTTCG TCTACTATAT GGTCGTTGTA GTCAGTACCG ACGCGGGACA
                                                                                                                 nlaIII  hhaI/cfoI
       scrFI
       nciI
       mspI                                                       alwNI
       hpaII                                         bsp1286      ddeI
       dsaV                                          bmyI         draIII                                         fnu4HI      styI
       ddeI    cauII   sspI                                                                                      bbvI        bsaJI
1801 GCTCAGAAGC AACCGGGTGG AATATTGCTG GTGCAACAGT GGCAGGGCAC AGTGCCACTC AGTGCCTGTC AAAAGTTGCA GCGAGCCAAG GTGTTTCAAC
     CGAGTCTTCG TTGGCCCACC TTATAACGAC CACGTTGTCA CCGTCCCGTG TCACGGTGAG TCACGGACAG TTTTCAACGT CGCTCGGTTC CACAAAGTTG
```

```
                                 fnu4HI
                                 bbvI
                        alwI     scfI
                        rsaI     pstI
              aciI      csp6I ddeI bsgI                                        mnlI     maeIII
                                                                               ddeI     alwNI
2201 AAGGCGGGGA AGTACAGCTC AGAGTTCTGC CCTGCTCTGA GGGAAACAGT GACTGCTACT TTGGGAATGG GTCAGCCTAC CGTGGCACGC
     TTCCGCCCCT TCATGTCGAG TCTCAAGACG GGACGAGACT CCCTTTGTCA CTGACGATGA AACCCTTACC CAGTCGGATG GCACCGTGCG dsaI
                                                                                                  bsaJI
                                                  sau3AI                                          scrFI
                                                  mboI/ndeII[dam-]                                pflMI
                                                  dpnI[dam+]                                      mvaI
                         pleI nlaIV               dpnII[dam-]             ecoRI                   ecoRII
              hphI       hinfI hgiCI              alwI[dam-]      dsaI  apoI                      dsaV
     mnlI     bcgI       banI mnlI     mnlI bsaJI nlaIII                                          bstNI
                                                                                                  bslI
                                                                                                  apyI[dcm+] haeIII/palI
                                                                                   bsp1286        sau96I
                                                                                   bmyI alwNI     asuI
                                                                           bsrI bsaJI             bsrI
2301 ACAGCCTCAC CGAGTCGGGT GCCTCCTGCC TCCCGTGGAA TTCCATGATC CTGATAGGCA AGGTTTACAC AGCACAGAAC CCCAGTGCCC AGGCACTGGG
     TGTCGGAGTG GCTCAGCCCA CGGAGGACGG AGGGCACCTT AAGGTACTAG GACTATCCGT TCCAAATGTG TCGTGTCTTG GGGTCACGGG TCCGTGACCC
                                                                                       nlaIV
                                                                                       hgiCI
                                                                                       banI     maeII
     scrFI
     mvaI                                                                        scrFI
     ecoRII                                                                      pmlI
     dsaV                                                               mvaI     ecoRII
     bstNI                                                              bstNI
     bsaJI                                   tfiI                       pflMI                                              rsaI
     apyI[dcm+]              mspI            hinfI                      sfaNI    apyI[dcm+]              mboII
              bsmAI          hpaII           sfaNI     fokI bslI bsaJI           bbrPI     eco57I aciI   maeII  csp6I     bsp1286
2401 CCTGGGCAAA CATAATTACT GCCGGAATCC TGATGGGGAT GCCAAGCCCT GGTGCCACGT GCTGAAGAAC CGCAGGCTGA CGTGGGAGTA CTGTGATGTG
     GGACCCGTTT GTATTAATGA CGGCCTTAGG ACTACCCCTA CGGTTCGGGA CCACGGTGCA CGACTTCTTG GCGTCCGACT GCACCCTCAT GACACTACAC
                                                                                                                          scaI  bmyI mboII                          scrFI
                                                                                           earI/ksp632I                   mvaI
                                                                                           hgiJII                         ecoRII
                              fnu4HI                                                       bsp1286                        dsaV
                              aciI  ddeI                                                   bmyI                           bstNI
              fnu4HI bsmAI                  rsaI                         ddeI              banI                           apyI[dcm+]       fnu4HI
     mnlI     bspMI haeIII/palI csp6I                           mnlI     sfaNI    mnlI sapI                     mnlI bslI bsaJI bslI bbvI
2501 CCCTCCCTGCT CCACCTGCGG CCTGAGACAG TACAGCCAGC CTCAGTTTCG CATCAAAGGA GGGCTCCTTG CCGACATCGC CTCCCACCCC TGGCAGGCTG
     GGGAGGGACGA GGTGGACGCC GGACTCTGTC ATGTCGGTCG GAGTCAAAGC GTAGTTTCCT CCCGAGAAGC GGCTGTAGCG GAGGGTGGGG ACCGTCCGAC
```

```
                                                     aluI
                                                     sstI
                                                     sacI
                                                     hgiJII
                                                     hgiAI/aspHI
                                                     ecl136II                  haeIII/palI
                            pvulI                    bsp1286                   stuI
                            scfI                     bsiHKAI                   haeI
             mspI           pstI    fnu4HI           bmyI        mspI          mnlI
             hpaII   bspMI          bbvI             banII       hpaII         nlaIII     bsmAI
      scrFI          sau96I nspBII                                                                                      
      nciI           avaII fnu4HI           bsrI
      dsaV    asuI   bbvI    mspI
      cauII   bsaJI  aciI    bsgI   alu1    hpaII
      draIII  bslI bsaJI aciI GCGGACCTGC AGTGCCGGA CTGGACGGAG TGTGAGCTCT CCGGCTACGG CAAGCATGAG GCCTTGTCTC CTTTCTATTC
2901 GCACTGTGTG CCTTCCCCG GCGGACCTGC AGTGCCGGA CTGGACGGAG TGTGAGCTCT CCGGCTACGG CAAGCATGAG GCCTTGTCTC CTTTCTATTC
     CGTGACACAC GGAAGGGGC CGCCTGGACG TCGACGGCCT GACCTGCCTC ACACTCGAGA GGCCGATGCC GTTCGTACTC CGAACAGAGA GAAAGATAAG fnu4HI
                                           nspBII                                                           nlaIII
       fnu4HI                              aciI                                        tru9I       hphI     nspI
       aciI                                fnu4HI                                      mseI        maeIII   nspHI       gsuI/bpmI
       bsrBI eco57I mnlI nlaIII    rsaI foKI csp6I alwNI bbvI
3001 GGAGCGGCTG AAGGAGCTC ATGTCAGACT GTACCCATCC AGCCGCTGCA CATCACAACA TTTACTTAAC AGAACAGTCA CCGACAACAT GCTGTGTGCT
     CCTCGCCGAC TTCCTCCGAG TACAGTCTGA CATGGGTAGG TCGGCGACGT GTAGTGTTGT AAATGAATTG TCTTGTCAGT GGCTGTTGTA CGACACACGA sau96I
               nlaIV                                                        scrFI
               haeIII/palI                                                  mvaI
               asuI                                              scrFI      ecoRII
               sau96I                                            mvaI       dsaV
               nlaIV scrFI                                       ecoRII
               hgiJII                                            dsaV
               eco0109I/draII                          sau96I
               bsp1286                                 nlaIV
               bsp120I                       bstNI     haeIII/palI
               bmyI mvaI                     bsaJI                                        aciI
               banII ecoRII         hinII/acyI        tfiI      asuI apyI[dcm+]           fnu4HI
               aciI dsaV            hgaI apyI[dcm+]   hinfI     eco0109I/draII             haeIII/palI  eaeI
       fnu4HI         bstNI         ahaII/bsaHI                 mnlI bsaJI                              cfrI    nlaIII
       aciI asuI apyI[dcm+]
       bsmAI  bsrBI apaI bsaJI
3101 GGAGCGGCGG GCCCAGGCA AACTTGCACG ACGCCTGCCA GGGCGATTCG GAGGCCCCC TGGTGTGTCT GAAGCGATGGC CGCATGACTT
     CCTCGCCGCC CGGGTCCGT TTGAACGTGC TGCGGACGGT CCCGCTAAGC CCTCCGGGG ACCACACAGA CTTGCTACCG GCGTACTGAA
```

FIG. 3J

```
                                 scrFI
                                 ncII
                          mspI        hpaII
                                 dsaV
                                 cauII
                          xmaI/pspAI
                          smaI
                          scrFI
                          ncII
                          dsaV
                          cauII    rsaI  styI maeIII            tfiI      nspI
                          bsaJI         csp6I bsaJI       rmaI hinfI     nspHI
                          foKI  avaI   bspl407I bstEII    maeI bsrI      maeIII nlaIII
          sfaNI  CATCAGCTGG  GCCTGGGCT  GTGGACAGAA  GGATGTCCCG  GGTGTGTACA  CCAAGGTTAC  CAACTACCTA  GACTGGATTC  GTGACAACAT
3201 TGGTGGGCAT CATCAGCTGG GCCTGGGCT GTGGACAGAA GGATGTCCCG GGTGTGTACA CCAAGGTTAC CAACTACCTA GACTGGATTC GTGACAACAT
     ACCACCCGTA GTAGTCGACC CCGGACCCGA CACCTGTCTT CCTACAGGGC CCACACATGT GGTTCCAATG GTTGATGGAT CTGACCTAAG CACTGTGTA
                                                          mboII
                                                 aciI earI/ksp632I
                                                 sau3AI mnII
                                                 mboI/ndeII[dam-]
                                                 dpnII[dam-]                   mboII
         scrFI                                   dpnI[dam+]                    eco57I
         mvaI                                    alwI[dam-]                 mboII  bpuAI
         ecoRII                        mnII      bstYI/xhoII     mboII      mboII  bbsI        hinPI            scfI
         dsaV                pleI                                                              hhaI/cfoI
         bstNI               hinfI
    bslI apyI[dcm+]
    mcrI maeIII
3301 GCGACCGTGA CCAGGAACAC CCGACTCCTC AAAAGCAAAT GAGATCCCGC CTCTTCTCT TCAGAAGACA CTGCAAAGGC GCAGTGCTTC TCTACAGACT
     CGCTGGCACT GGTCCTTGTG GGCTGAGGAG TTTTCGTTTA CTCTAGGGCG GAGAGAAGA AGTCTTCTGT GACGTTTCCG CGTCACGAAG AGATGTCTGA bsmAI
          gsuI/bpmI    aciI   bsaI scfI             mnII earI/ksp632I                                         tth111I/aspI
     bpuAI            acsI   bsaI scfI   ACAGGAGAGG GAAGAGTGCA TTTTCCCAGA TACTTCCCAT TTTGAAGTT TTCAGACTT
3401 TCTCCAGACC CACCACACCG CAGAAGCGGG ACGAGACCCT ACAGGAGAGG GAAGAGTGCA TTTTCCCAGA TACTTCCCAT TTTGAAGTT TTCAGACTT
     AGAGGTCTGG GTGGTGTGGC GTCTTCGCCC TGCTCTGGGA TGTCCTCTCC CTTCTCACGT AAAAGGGTCT ATGAAGGGTA AAACCTTCAA AAGTCCTGAA scrFI
                                                              mvaI      ecoRII
                                                              ecoRII
                                                              dsaV
                                                              bstNI
                                 bsmI                         gsuI/bpmI mnII     bsaJI
                           bpuAI                              mnII apyI[dcm+]   bsaJI
                           bbsI nlaIII                                                           ecoRI  taqI
               bsmI      rmaI                                                                    apoI   claI/bsp106
3501 GGTCTGATTT CAGGATACTC TGTCAGATGA GAAGACATGA ATGCACACTA GCCTCCAG GAATGCCTCC TCCCTGGGCA GAAGTGGGGG GAATTCAATC
     CCAGACTAAA GTCCTATGAG ACAGTCTACT CTTCTGTACT TACGTGTGAT CGGAGGTC CTTACGGAGG AGGGACCCGT CTTCACCCCC CTTAAGTTAG
```

FIG. 3K

```
            styI
            aciI
       fnu4HI   sau96I
       bglI    nlaIII
       sfiI ncoI haeIII/palI
       haeIII/palI        aluI
       eaeI dsaI asuI    fnu4HI
       cfrI bsaJI        bbvI       maeIII                                 sfaNI   apoI                              bsmI
3601 GATGGCCGCC ATGGCCCAAC TTGTTTATTG CAGCTTATAA TGGTTACAAA TAAAGCAATA GCATCACAAA TTTCACAAAT AAAGCATTTT TTTCACTGCA
     CTACCGGCGG TACCGGGTTG AACAAATAAC GTCGAATATT ACCAATGTTT ATTTCGTTAT CGTAGTGTTT AAAGTGTTTA TTTCGTAAAA AAAGTGACGT
                                                            sau3AI
                                                            mboI/ndeII[dam-]
                                                            dpnI[dam+]
                                                            dpnII[dam-]
                                                            pvuI/bspCI
                                                            mcrI
                                                            taqI[dam-] tru9I
                                                            claI/bsp106[dam-]      styI
                                                            sau3AI         mseI       fnu4HI    haeI
                                                            mboI/ndeII[dam-]              bbvI     ncoI
                                                            dpnI[dam+]  xmnI          hinPI      dsaI haeIII/palI
                                                            dpnII[dam-]  alwI[dam-] aseI/asnI/vspI  bsaJI
                                         rmaI                  nlaIII alwI[dam-] asp700  hhaI/cfoI nlaIII     mnlI
                                         maeI
3701 TTCTAGTTGT GGTTTGTCCA AACTCATCAA TGTATCTTAT CATGTCTGGA TCGATCGGGA ATTAATTGGG CGCAGCACCA TGGCCTGAAA TAACCTCTGA
     AAGATCAACA CCAAACAGGT TTGAGTAGTT ACATAGAATA GTACAGACCT AGCTAGCCCT TAATTAACCC GCGTCGTGGT ACCGGACTTT ATTGGAGACT
                                                                                                            nlaIV
                                                                                                            scrFI
                                                                                                            mvaI
                                                                                                            ecoRII
                                                                                                            dsaV
                              aluI                                                                          bstNI
                              pvuII                                                                         apyI[dcm+]
         rsaI                 nspBII                                                                        bsaJI
         csp6I
         nlaIV
         kpnI
         hgiCI
         banI
         asp718
mnlI    acc65I   ddeI aciI
3801 AAGAGGAACT TGGTTAGGTA CCTTCTGAGG CGGAAAGAAC CAGCTGTGGA ATGTGTGTCA GTTAGGGTGT GGAAAGTCCC CAGGCTCCCC AGCAGGCAGA
     TTCTCCTTGA ACCAATCCAT GGAAGACTCC GCCTTTCTTG GTCGACACCT TACACACAGT CAATCCCACA CCTTTCAGGG GTCCGAGGGG TCGTCCGTCT
```

FIG. 3L

```
                       sfaNI
       sfaNI           ppu10I                scrFI                              nlaIV
       ppu10I          nsiI/avaIII           mvaI        scrFI                  sfaNI
       nsiI/avaIII     nlaIII                ecoRII      mvaI                   nsiI/avaIII
       nlaIII                                dsaV        ecoRII                 nlaIII
       sphI                                  bstNI       dsaV          bstNI            sphI
       nspI                                  apyI[dcm+]              apyI[dcm+]         nspI
       nspHI                                 sexAI                     bsaJI            nspHI
3901 AGTATGCAAA GCATGCATCT CAATTAGTCA GCAACCAGGT GTGGAAAGTC CCCAGGCTCC CCAGCAGGCA GAAGTATGCA AAGCATGCAT CTCAATTAGT
     TCATACGTTT CGTACGTAGA GTTAATCAGT CGTTGGTCCA CACCTTTCAG GGGTCCGAGG GGTCGTCCGT CTTCATACGT TTCGTACGTA GAGTTAATCA nlaIII
                                                                                  styI
                                                                                  ncoI
                                             aciI                         bslI    dsaI
            aciI          aciI   fokI        aciI bsrI aciI               aciI    bsaJI
4001 CAGCAACCAT AGTCCCGCCC CTAACTCCGC CCATCCCGCC CCTAACTCCG CCCAGTTCCG CCCATTCTCC GCCCCATGGC TGACTAATTT TTTTTATTTA
     GTCGTTGGTA TCAGGGCGGG GATTGAGGCG GGTAGGGCGG GGATTGAGGC GGGTCAAGGC GGGTAAGAGG CGGGGTACCG ACTGATTAAA AAAAATAAAT rmaI
                                                                  styI
                                                                  bsaJI
            aciI                                                  blnI
            fnu4HI                                                avrII                       tru9I
            sfiI                                                  haeIII/palI                 hpaI
            haeIII/palI                                           stuI                        hincII/hindII
     bsaJI bglI         ddeI                                      haeI                aluI msel aluI
     haeIII/palI mnlI bsaJI mnlI haeIII/palI             mnlI     mnlI maeI
     mnlI mnlI bsaJI mnlI alul
4101 TGCAGAGGCC GAGGCCCGCT CGGCCTCTGA GCTATTCCAG AAGTAGTGAG GAGGCTTTTT TGGAGGCCTA GGCTTTTGCA AAAAGCTGTT AACAGCTTGG
     ACGTCTCCGG CTCCGGGCGA GCCGGAGACT CGATAAGGTC TTCATCACTC CTCCGAAAAA ACCTCCGGAT CCGAAAACGT TTTTCGACAA TTGTCGAACC scrFI
                                        mvaI
                                        ecoRII
                                        dsaV
                                        bstNI                                                      aluI
     haeIII/palI                 bsrI   apyI[dcm+]        tru9I                                    pvuII
     eaeI                        maeII  bsaJI maeIII      msel           fnu4HI                    nspBII
     cfrI          bsrI maeII maeIII
     bsrI
4201 CACTGGCCGT CGTTTTACAA CGTCGTGACT GGGAAAACCC TGGCGTTACC CAACTTAAAT GCCTTGCAGC ACATCCCCCC TTCGCCAGCT GGCGTAATAG
     GTGACCGGCA GCAAAATGTT GCAGCACTGA CCCTTTTGGG ACCGCAATGG GTTGAATTTA CGGAACGTCG TGTAGGGGGG AAGCGGTCGA CCGCATTATC
```

FIG. 3M

```
                                                          hinPI
                                                          hhaI/cfoI
                                                          nlaIV
                                                          narI
                 sau3AI                                   kasI
         haeIII/palI  mboI/ndeII[dam-]                    hinlI/acyI
         asuI        dpnI[dam+]                           hgiCI
         mnlI        dpnII[dam-]                          haeII     aciI
     mboII  aciI  pvuI/bspCI                              banI      sfaNI                                    sfaNI       aciI
     earI/ksp632I mcrI             bglI                   ahaII/bsaHI
4301 CGAAGAGGCC CGCACCGATC GCCCTTCCCA ACAGTTGCGT AGCCTGAATG GCGAATGGCG CCTGATGCGG TATTTTCTCC TTACGCATCT GTGCGGTATT
     GCTTCTCCGG GCGTGGCTAG CGGGAAGGGT TGTCAACGCA TCGGACTTAC CGCTTACCGC GGACTACGCC ATAAAAGAGG AATGCGTAGA CACGCCATAA aciI
                                                              fnu4HI                fnu4HI
                                                              thaI                  hinPI
                                    hinPI                     fnuDII/mvnI           hhaI/cfoI
                                    thaI                      bstUI                 thaI
                                    fnuDII/mvnI               hinPI                 fnuDII/mvnI
                                    bstUI scfI     hinPI      hhaI/cfoI             bstUI
                                    bsh1236I       hhaI/cfoI fnu4HI tru9I aciI       bsh1236I      aciI
               aciI                 rsaI hhaI/cfoI fnu4HI    aciI                   maeII bbvI maeIII
     aciI     maeII                 csp6I bslI   aciI        mseI bsh1236I
4401 TCACACCGCA TACGTCAAAG CAACCATAGT ACGCGCCCTG TAGCGGCGCA TTAAGCGCGA CGGGTGTGGT GGTTACGCGC AGCGTGACCG CTACACTTGC
     AGTGTGGCGT ATGCAGTTTC GTTGGTATCA TGCGCGGGAC ATCGCCGCGT AATTCGCGCT GCCCACACCA CCAATGCGCG TCGCACTGGC GATGTGAACG nlaIV
           hinPI                                                                                            hgiJII
           hhaI/cfoI                                      mspI                                              bsp1286
         rmaI  haeII                                      hpaII                                             bmyI
         hinPI  haeII                                     naeI                         aluI                 banII       nlaIV
         hhaI/cfoI  bsrBI                      mboII      cfr10I                                                        
         haeII maeI  aciI
4501 CAGGCCCCTA GCGCCCGCTC CTTTCGCTTT CTTCCCCTCC TTTCTCGCCA CGTTCCGCGG CTTTCCCCGT CAAGCTCTAA ATCGGGGCT CCCTTTAGGG
     GTCCGGGGAT CGCGGGCGAG GAAAGCGAAA GAAGGGGAGG AAAGAGCGGT GCAAGCGGCC GAAAGGGGCA GTTCGAGATT TAGCCCCCGA GGGAAATCCC nlaIV                                      maeII    haeIII/palI
                  hgiCI  taqI                                draIII   sau96I
                  banI   mnlI                                bsaAI    asuI              bslI
                                                        hphI                             bslI  avaI
4601 TTCCGATTTA GTGCTTTACG GCACCTCGAC CCCAAAAAAC TTGATTTGGG TGATGGTTCA CGTAGTGGGC CATCGCCCTG ATAGACGGTT TTTCGCCCTT
     AAGGCTAAAT CACGAAATGC CGTGGAGCTG GGGTTTTTTG AACTAAACCC ACTACCAAGT GCATCACCCG GTAGCGGGAC TATCTGCCAA AAAGCGGGAA maeII pleI      tru9I
     drdI hinfI maeII msel             pleI
                          bsrI         hinfI
4701 TGACGTTGGA GTCCACGTTC TTTAATAGTG GACTCTTGTT CCAAACTGGA ACAACACTCA ACCCTATCTC GGGCTATTCT TTTGATTTAT AAGGGATTTT
     ACTGCAACCT CAGGTGCAAG AAATTATCAC CTGAGAACAA GGTTTGACCT TGTTGTGAGT TGGGATAGAG CCCGATAAGA AACTAAATA TTCCCTAAAA
```

FIG. 3N

```
                                                                                  hgiAI/aspHI
                                                                                  bsp1286
                                                               thaI               bsiHKAI
                                                               fnuDII/mvnI        bmyI  ddeI
                                          tru9I                tru9I  apoI tru9I  apaLI/snoI
                                    tru9I msel bstUI  msel     psp1406I           alw44I/snoI
               haeIII/palI   aluI   msel  apoI       bshl236I  tru9I msel         GTGCACTCTC
4801 GCCGATTTCG GCCTATTGGT TAAAAATGA GCTGATTTAA CAAAAATTTA ACGCGAATTT TAACAAAATA TTAACGTTTA CAATTTTATG GTGCACTCTC
     CGGCTAAAGC CGGATAACCA ATTTTTTACT CGACTAAATT GTTTTTAAAT TGCGCTTAAA ATTGTTTTAT AACTGCAAAT GTTAAAATAC CACGTGAGAG hinPI
                                                                                                          hhaI/cfoI
              aciI                                                             hinPI                      thaI
              fnu4HI   tru9I                maeIII                             fnu4HI                     fnuDII/mvnI
      rsaI    sfaNI    msel       aciI      maeII bsrI    nlaIII hhaI/cfoI                                bstUI
      csp6I                                 bsaAI tth111I/aspI bbvI                            aciI       nspBII bsh1236I
4901 AGTACAATCT GCTCTGATGC CGCATAGTTA AGCCAACTCC GCTATCGGG CGTGACTGCTA TCATGGCTGC GCCCCGACAC CGGCCAACAC CCGCTGACGC
     TCATGTTAGA CGAGACTACG GCGTATCAAT TCGGTTGAGG CGATAGCGAT GCACTGACCC AGTACCGACG CGGGGCTGTG GGCCGTTGTG GGCGACTGCG scrFI
                        nciI
              sfaNI     mspI
              mspI      hpaII
              hpaII     dsaV      nspI
              scrFI               nspHI
              nciI       esp3I    fnu4HI
              dsaV fokI  maeIII bsmAI  bbvI
       drdI   cauII   aciI    aluI   bslI cauII aluI nlaIII   mnlI    hphI     hphI
5001 GCCCTGACGG GCTTGTCTGC TCCCGGCATC CGCTTACAGA CAAGCTGTGA CCGTCTCCGG GAGCTGCATG TGTCAGAGGT TTTCACCGTC ATACCGAAA
     CGGGACTGCC CGAACAGACG AGGGCCGTAG GCGAATGTCT GTTCGACACT GGCAGAGGCC CTCGACGTAC ACAGTCTCCA AAGTGGCAG TAGTGGCTTT thaI
     fnuDII/mvnI
     bstUI
     bsh1236I
     hinPI              mnlI
     hhaI/cfoI          haeIII/palI                                                              hinII/acyI
     thaI  mnlI         sau96I                                                                   ahaII/bsaHI
     fnuDII/mvnI  mboII asuI                                      nlaIII                         aatII
     bstUI        bpuAI                                  tru9I    rcaI                           ddeI maeII
     bsh1236I     bbsI  ecoO109I/draII                   msel    bspHI
5101 CGGCGAGGC AGTATTCTTG AAGACGAAAG GGCCTCGTGA TACGCCTATT TTTATAGGTT AATGTCATGA TAATAATGGT TTCTTAGACG TCAGGTGGCA
     GCCGCTCCG TCATAAGAAC TTCTGCTTTC CCGGAGCACT ATGCGGATAA AAATATCCAA TTACAGTACT ATTATTACCA AAGAATCTGC AGTCCACCGT
```

FIG. 30

```
                      nlaIV
                      aciI
                      thaI
                      fnuDII/mvnI
                      bstUI
                      bsh1236I
                      hinPI
                      hhaI/cfoI                                                                      rcaI
                                                                                                     bspHI
                                                                                               bsrBI  bsmAI
                                                                                               aciI  nlaIII
5201 CTTTTCGGGG AAATGTGCGC GGAACCCCTA TTTGTTATT CATTCAAATA TGTATCCGCT CATGAGACAA TAACCCTGAT AAATGCTTCA
     GAAAAGCCCC TTTACACGCG CCTTGGGGAT AAACAAATAA AAAGATTTAT GTAAGTTTAT ACATAGGCGA GTACTCTGTT ATTGGGACTA TTTACGAAGT sspI                                                               fnu4HI                      hphI
           earI/ksp632I                                                       aciI
5301 ATAATATTGA AAAGGAAGA GTATGAGTAT TCAACATTTC CGTGTCGCCC TTATTCCCTT TTTGCGGCA TTTGCCTTC CTGTTTTTGC TCACCCAGAA
     TATTATAACT TTTTCCTTCT CATACTCATA AGTTGTAAAG GCACAGCGGG AATAAGGGAA AAAACGCCGT AAAACGGAAG GACAAAAACG AGTGGGTCTT hgiAI/aspHI
                                    bsp1286
                                    bsiHKAI
                            sau3AI  bmyI                                               sau3AI  nspBII
                            mboI/ndeII[dam-]                                           mboI/ndeII[dam-]
                            dpnI[dam+]                                                 dpnI[dam+]
                            dpnII[dam-]                                                dpnII[dam-]
           eco57I           apaLI/snoI                                       bsrI  dpnII[dam-]       alwI[dam-]
     hphI  sfaNI  mboII[dam-]  alw44I/snoI  maeIII taqI                      bstYI/xhoII  aciI  bstYI/xhoII
5401 ACGCTGGTGA AAGTAAAAGA TGCTGAAGAT CAGTTGGGTG CACGAGTGGG TTACATCGAA CTGGATCTCA ACAGCGGTAA GATCCTTGAG AGTTTTCGCC
     TGCGACCACT TTCATTTTCT ACGACTTCTA GTCAACCCAC GTGCTCACCC AATGTAGCTT GACCTAGAGT TGTCGCCATT CTAGGAACTC TCAAAGCGG scrFI
                                                                           nciI
                                                                           mspI
                                                       aciI                hpaII
                                                       thaI                dsaV
                            hgiAI/aspHI                fnuDII/mvnI
            maeII           bsp1286    tru9I           bstUI               hinII/acyI         bcgI  mcrI  fnu4HI
            psp1406I        bsiHKAI    mseI            bsh1236I            hgaI  cauII              aciI
            xmnI            bmyI  ahaIII/draI          hinPI               ahaII/bsaHI
            asp700                                     hhaI/cfoI
            mboII
5501 CCGAAGAACG TTTTCCAATG ATGAGCACTT TTAAAGTTCT GCTATGTGGC CCGGTATTAT CCCGTGATGA CGCCGGGCAA GAGCAACTCG GTCGCCGCAT
     GGCTTCTTGC AAAAGGTTAC TACTCGTGAA AATTTCAAGA CGATACACCG GGCCATAATA GGGCACTACT GCGGCCCGTT CTCGTTGAGC CAGCGGCGTA rsaI                                                                                      fnu4HI
           csp6I  bsrI                                                                               bbvI       nlaIII
           scaI   hphI  maeIII            sfaNI  fokI  nlaIII
5601 ACACTATTCT CAGAATGACT TGGTTGAGTA CTCACCAGTG ACAGAAAAGC ATCTTACGGA TGGCATGACA GTAAGAGAAT TATGCAGTGC TGCCATAACC
     TGTGATAAGA GTCTTACTGA ACCAACTCAT GAGTGGTCAG TGTCTTTTCG TAGAATGCCT ACCGTACTGT CATTCTCTTA ATACGTCACG ACGGTATTGG
```

FIG. 3P

```
                                              sau96I
                                              avaII
                                    sau3AI    asuI                                                      nlaIII
                           haeIII/palI         mboI/ndeII[dam-]                                         sau3AI maeIII
                           eaeI                 dpnI[dam+]                                              mboI/ndeII[dam-]
                           cfrI                  dpnII[dam-]                                             dpnI[dam+]
                           fnu4HI                 pvuI/bspCI                                              dpnII[dam-]
                           aciI                    mcrI    mnlI         aluI       aciI          nlaIII alwI[dam-]
5701 ATGAGTGATA ACACTGCGGC CAACTTACTT CTGACAACGA TCGGAGACC GAAGAGCTA ACCGCTTTT TGCACAAACAT GGGGATCAT GTAACTCGCC
     TACTCACTAT TGTGACGCCG GTTGAATGAA GACTGTTGCT AGCCTCCTGG CTTCCTCGAT TGGCGAAAAA ACGTGTTGTA CCCCTAGTA CATTGAGCGG hinPI
                                                                                            hhaI/cfoI
             mspI                                                                           mstI
     sau3AI  nlaIV                                                                            aviII/fspI       bsrI
     mboI/ndeII[dam-] aluI                                                                     maeII          tru9I
      dpnI[dam+] hpaII                                                       fnu4HI            psp1406I       mseI
       dpnII[dam-] bsaWI                               maeIII       sfaNI    bbvI
5801 TTGATCGTTG GGAACCGGAG CTGAATGAAG CCATACCAAA CGACGAGCGT GACACCACGA TGCCAGCAGC AATGGCAACA ACGTTGCGCA AACTATTAAC
     AACTAGCAAC CCTTGGCCTC GACTTACTTC GGTATGGTTT GCTGCTCGCA CTGTGGTGCT ACGGTCGTCG TTACCGTTGT TGCAACGCGT TTGATAATTG mspI
                  hpaII
                  scrFI                                                                           bglI
         aluI     nciI     tru9I       fokI                                                       sau96I
         rmaI     dsaV     mseI        bsrI    aciI                                     sau96I    haeIII/palI
         maeI     cauII    aseI/asnI/vspI  mnlI                                         avaII     hinPI asuI    mspI
                                                                                         asuI      hhaI/cfoI    hpaII
5901 TGGCGAACTA CTTACTCTAG CTTCCCGGCA ACAATTAATA GACTGGATGG AGGCGGATAA AGTTGCAGGA CCACTTCTGC GCTCGGCCCT TCCGGCTGGC
     ACCGCTTGAT GAATGAGATC GAAGGGCCGT TGTTAATTAT CTGACCTACC TCCGCCTATT TCAACGTCCT GGTGAAGACG CGAGCCGGGA AGGCCGACCG thaI
                    mspI                  fnuDII/mvnI           haeIII/palI
                    hpaII                 bstUI                  sau96I
                    cfr10I                bsmAI aciI              nlaIV
                    nlaIV hphI             bbvI bsrI asuI
          gsuI/bpmI       bsaI bshl236I                                           mnlI
6001 TGGTTTATTG CTGATAAATC TGGAGCCGGT GAGCGTGGGT CTCGCGGTAT CATTGCAGCA CTGGGGCCAG ATGGTAAGCC CTCCCGTATC GTAGTTATCT
     ACCAAATAAC GACTATTTAG ACCTCGGCCA CTCGCACCCA GAGCGCCATA GTAACGTCGT GACCCCGGTC TACCATTCGG GAGGGCATAG CATCAATAGA ddeI
                                              sau3AI        nlaIV
                                              mboI/ndeII[dam-]
                  pleI                         dpnI[dam+]   hgiCI            tru9I
                  hinfI                         dpnII[dam-] banI mnlI        mseI       maeIII
     eaml105I     fokI
6101 ACACGACGGG GAGTCAGGCA ACTATGGATG AACGAAATAG ACAGATCGCT GAGATAGGTG CCTCACTGAT TAAGCATTGG TAACTGTCAG ACCAAGTTTA
     TGTGCTGCCC CTCAGTCCGT TGATACCTAC TTGCTTTATC TGTCTAGCGA CTCTATCCAC GGAGTGACTA ATTCGTAACC ATTGACAGTC TGGTTCAAAT
```

FIG. 3Q

```
                                                              rmaI     sau3AI
                                                              sau3AI hphI  mboI/ndeII[dam-]
                                                              mboI/ndeII[dam-]
                                                                dpnI[dam+]     dpnI[dam+]
                                                                dpnII[dam-]    dpnII[dam-]                                    maeII
                                              tru9I     tru9I mseI bstYI/xhoII   alwI[dam-]                        nlaIII      tru9I
                              tru9I            mseI      tru9I mseI  alwI[dam-]  bstYI/xhoII                        rcaI       mseI
                              mseI            ahaIII/draI mseI ahaIII/draI maeI mboII[dam-]                          bspHI
6201 CTCATATATA CTTTAGATTG ATTTAAAACT TCATTTTAA TTTAAAAGGA TCTAGGTGAA GATCCTTTTT GATAATCTCA TGACCAAAAT CCCTTAACGT
     GAGTATATAT GAAATCTAAC TAAATTTTGA AGTAAAATT AAATTTTCCT AGATCCACTT CTAGGAAAAA CTATTAGAGT ACTGGTTTTA GGGAATTGCA sau3AI
                                                mboI/ndeII[dam-]
                                                  dpnI[dam+]    sau3AI
                                                  dpnII[dam-]   mboI/ndeII[dam-] thaI
                                                    bstYI/xhoII   dpnI[dam+]     fnuDII/mvnI
                                                      alwI[dam-]  dpnII[dam-]   bstUI
                                           sau3AI                  alwI[dam-]   bsh1236I
                                           mboI/ndeII[dam-]                     hinPI       fnu4HI
                             hgaI            dpnI[dam+]   mboI[dam-]            hhaI/cfoI   bbvI
                             ddeI            dpnII[dam-]                bstYI/xhoII
6301 GAGTTTTCGT TCCACTGAGC GTCAGACCCC GTAGAAAAGA TCAAAGGATC TTCTTGAGAT CCTTTTTTC TGCGCGTAAT CTGCTGCTTG CAAACAAAAA
     CTCAAAAGCA AGGTGACTCG CAGTCTGGGG CATCTTTTCT AGTTTCCTAG AAGAACTCTA GGAAAAAAAG ACGCGCATTA GACGACGAAC GTTTGTTTTT sau3AI
                                  mboI/ndeII[dam-]
                                    dpnI[dam+]
                                    dpnII[dam-]                                                         hinPI
                                      alwI[dam-]                                  bsrI                  hhaI/cfoI
                aciI         mspI                                                 maeIII      eco57I
                nspBII       hpaII   aluI                                                                               fnu4HI
                                                                                                             alwNI      bbvI
         aciI                                                                                                bsrI  fnu4HI
6401 AACCACCGCT ACCAGCGGTG GTTTGTTTGC CGGATCAAGA GCTACCAACT CTTTTTCCGA AGTAACTGG CTTCAGCAGA GCGCAGATAC CAAATACTGT
     TTGGTGGCGA TGGTCGCCAC CAAACAAACG GCCTAGTTCT CGATGGTTGA GAAAAAGCT TCCATTGACC GAAGTCGTCT CGCGTCTATG GTTTATGACA bsrI
                       haeIII/palI                                                                      bsrI  fnu4HI
           rmaI        haeI          scfI    aciI              mnlI                      maeIII  bbvI   bsrI
           maeI  bslI                                                                                          bsrI
6501 CCTTCTAGTG TAGCCGTAGT TAGCCACCA CTTCAAGAAC TCTGTAGCAC CGCCTACATA CCTCGCTCTG CTAATCCTGT TACCAGTGGC TGCTGCCAGT
     GGAAGATCAC ATCGGCATCA ATCGGTGGT GAAGTTCTTG AGACATCGTG GCGGATGTAT GGAGCGAGAC GATTAGGACA ATGGTCACCG ACGACGGTCA
```

FIG. 3R

```
                scrFI
                ncil
                mspI                                                    aciI                          hgiAI/aspHI
                hpaII                                                   nspBII                        bsp1286
                dsaV                                           mspI     fnu4HI                        bsiHKAI
                cauII                                          hpaII    bbvI                          bmyI
                                                               bsaWI    hinPI  mcrI                   apaLI/snoI
                       pleI                                    bsaIII   hhaI/cfoI                     alw44I/snoI   aluI
6601 GGGCGATAAGT CGTGTCTTAC CGGGTTGGAC TCAAGACGAT AGTTACCGGA TAAGGGCGAG CGGTCGGGCT GAACGGGGGG TTCGTGCACA CAGCCCAGCT
     CCGCTATTCA GCACAGAATG GCCCAACCTG AGTTCTGCTA TCAATGGCCT ATTCCCGCTC GCCAGCCCGA CTTGCCCCCC AAGCACGTGT GTCGGGTCGA
                                                                                                              mspI
                                                                                                              hpaII      fnu4HI
                                                               hinPI                                          bsII       aciI
                           ddeI           scfI                 hhaI/cfoI                             aciI     bsaWI
6701 TGGAGGCGAAC GACCTACACC GAACTGAGAT ACCTACAGCG TGAGCATTGA GAAAGCGCCA CGCTTCCCGA AGGGAGAAAG GCGGACAGGT ATCCGGTAAG
     ACCTCGCTTG CTGGATGTGG CTTGACTCTA TGGATGTCGC ACTCGTAACT CTTTCGCGGT GCGAAGGGCT TCCCTCTTTC CGCCTGTCCA TAGGCCATTC scrFI
                                         mvaI   scrFI
                                         ecoRII mvaI
                                         dsaV   ecoRII
                                         bstNI  dsaV
                                         bsaJI  bstNI                                                                 taqI
                       hinPI mnlI               apyI[dcm+]                                                  mnlI drdI hgaI
                       hhaI/cfoI         aluI apyI[dcm+]  CCTGGTATCT TTATAGTCCT GTCGGGTTTC GCCACCTCTG ACTTGAGCGT
6801 CGGCAGGGTC GGAACAGGAG AGCGCACGAG GGAGCTTCCA GGGGAAACG CCCTGGTATCT TTATAGTCCT GTCGGGTTTC GCCACCTCTG ACTTGAGCGT
     GCCGTCCCAG CCTTGTCCTC TCGCGTGCTC CCTCGAAGGT CCCCCTTTGC GGACCATAGA AATATCAGGA CAGCCCAAAG CGGTGAGAC TGAACTCGCA haeIII/paII
                                                              haeIII/paII  scrFI
                                                              fnu4HI       mvaI bsII
                                                              aciI         ecoRII                         nlaIII
                                                              thaI bsII    dsaV
                                                              fnuDII/mvnI  bstNI                                   nspI
                                     nlaIV                    bstUI        apyI[dcm+]    haeIII/paII nspHI
               sfaNI                 aciI                     bsh1236I     nlaIV  haeI   haeI        afIIII
6901 CGATTTTTGT GATGCTCGTC AGGGGGGCGG AGCCTATGGA AAAACGCCAG CAACGCGGCC TTTTTACGGT TCCTGGCCTT TTGCTGGCCT TTTGCTCACA
     GCTAAAAACA CTACGAGCAG TCCCCCCGCC TCGGATACCT TTTTGCGGTC GTTGCGCCGG AAAAATGCCA AGGACCGGAA AACGACCGGA AAACGAGTGT fnu4HI
                                                                                                      bbvI
                                                                                       fnu4HI         hinPI pleI
               tfiI                                                         bsrBI      bbvI           hhaI/cfoI
               hinfI                                               aluI     aciI       aciI  fnu4HI   mcrI
7001 TGTTCTTTCC TGCGTTATCC CCTGATTCTG TGGATAACCG TATTACCGCC TTTGAGTGAG CTGATACCGC TCGCCGCAGC CGAACGACCG AGCCAGCGGA
     ACAAGAAAGG ACGCAATAGG GGACTAAGAC ACCTATTGGC ATAATGGCGG AAACTCACTC GACTATGGCG AGCGGCGTCG GCTTGCTGGC TCGGTCGCCT
```

FIG. 3S

```
                                                                    thaI
                                                                    fnuDII/mvnI
                                                                    bstUI
                                                                    bsh1236I
                                                                    hinPI
                                                                    hhaI/cfoI
                                                                    thaI
                                                                    fnuDII/mvnI
                                              sapI hinPI            bstUI   haeIII/palI     aluI
                                              mboII hhaI/cfoI       bsh1236I       tru9I   pvuII
                                              earI/ksp632I                    bslI  eaeI  tfiI aseI/asnI/vspI
                         mnlI  aciI   haeII                   mnlI       aciI  cfrI  hinfI  mseI   nspBII        bsrI
        7101 GTCAGTGAGC GAGGAAGCGG AATACGCCCC TTCTCGGGGG  aciI  CCGGGCGGTTG GCCGATTCAT TAATCCAGCT GGCACGACAG GTTTCCCGAC
             CAGTCACTCG CTCCTTCGCC TTATGCGGGG AAGAGCCCCC       GGGCCGCCAAC CGGCTAAGTA ATTAGGTCGA CCGTGCTGTC CAAAGGGCTG
                                                                              scrFI
                                                                              mvaI
                                                                              ecoRII
                                                                              dsaV
                                                          tru9I           nlaIV bstNI
                                     hinPI     mseI       maeIII          hgiCI apyI[dcm+]           mspI
             aciI      hhaI/cfoI  aseI/asnI/vspI  mnlI                    banI bsaJI                  hpaII
        7201 TGGAAAGCGG GCAGTGAGCG CAACGCAATT AATGTGAGTT ACCTCACTCA TTAGGCACCC CAGGCTTTAC ACTTTATGCT TCCGGCTCGT ATGTTGTGTG
             ACCTTTCGCC CGTCACTCGC GTTGCGTTAA TTACACTCAA TGGAGTGAGT AATCCGTGGG GTCCGAAATG TGAAATACGA AGGCCGAGCA TACACACAC tru9I
                                                           mseI
                                                      aseI/asnI/vspI
                          aciI                   aluI      xmnI            nlaIII
                          bsrBI                                            asp700
        7301 GAATTGTGAG CGGATAACAA TTTCACACAG GAAACAGCTA TGACCATGAT TACGAATTAA
             CTTAACACTC GCCTATTGTT AAAGTGTGTC CTTTGTCGAT ACTGGTACTA ATGCTTAATT >length: 7360
```

```
                                                                                            maeII
                                                                                            hinlI/acyI                nlaIV
                          pleI                                                              ahaII/bsaHI               hgiCI
           rsaI   aciI    hinfI                              bsmAI                          aatII                     banI
           csp6I
401 GGTTTTGGCA GTACATCAAT GGGCGTGGAT CTCACGGGGA TTTCCAAGTC TCCACCCCAT TGACGTCAAT GGGAGTTTGT TTTGGCACCA
    CCAAAACCGT CATGTAGTTA CCCGCACCTA GAGTGCCCCT AAAGGTTCAG AGGTGGGGTA ACTGCAGTTA CCCTCAAACA AAACCGTGGT
                                                                                                                      aluI
                                                                                                                      sstI
                                                                                                                      sacI
                                                                                                                      hgiJII
                                                                                                                      hgiAI/aspHI
                                                                                                                      ecl136II
                                                                                                                      bsp1286
                                                                                                                      bsiHKAI
                                                                                     rsaI                             bmyI
                           maeIII   ·aciI       hgaI     aciI         csp6I   mnlI                                    banII
501 AAATCAACGG GACTTTCCAA AATGTCGTAA CAACTCCGCC CCAATGACGC AAATGGGCGG TAGGCGTGTA CGGTGGGAGG TCTATATAAG CAGAGCTCGT
    TTTAGTTGCC CTGAAAGGTT TTACAGCATT GTTGAGGCGG GGTAACTGCG TTTACCCGCC ATCCGCACAT GCCACCCTCC AGATATATTC GTCTCGAGCA haeIII/palI
                                                                                        mcrI
                                                                                        eagI/xmaIII/eclXI
                                                                                        eael
                                                                                        cfrI
                                                                                        fnu4HI
                                                                                        aciI
                                                                                        thaI
                                                                                        fnuDII/mvnI
                                                                    sacII/sstII
                                                         sau96I     nspBII
                                                                    kspI     scrFI
                                                         asuI       dsaI     nciI
                                                         avaII
                                                         nlaIV              bglI bslI mspI
               esp3I                                                scrFI    sau3AI mnlI bstUI
          scrFI                                                     nciI     mboI/ndeII[dam-] hpaII
          mvaI bsmAI                                                mspI     dpnI[dam+] bsaJI dsaV
          ecoRII                                                    hpaII    dpnII[dam-] bsh1236I
          dsaV                                      mboII           dsaV     alwI[dam-] aciI caulI
          bstNI hinlI/acyI                          bpuAI           cauII
          apyI[dcm+]                                bbsI
    sau3AI gsuI/bpmI
    mboI/ndeII[dam-]
    dpnI[dam+]    hgaI  fokI                                     mnlI
    dpnII[dam-]  ahaII/bsaHI
601 TTAGTGAACC GTCAGATCGC CTGGAGACGC CATCCACGCT GTTTTGACCT CCATAGAAGA CACCGGACC GATCCAGCCT CCGCGGCCGG GAACGTGCA
    AATCACTTGG CAGTCTAGCG GACCTCTGCG GTAGGTGCGA CAAAACTGGA GGTATCTTCT GTGGCCCTGG CTAGGTCGGA GGCGCCGGCC CTTGCCACGT
```

FIG. 6C

```
      tfiI
      aciI
      thaI hinfI
      fnuDII/mvnI                                                      fnu4HI
      bstUI                                             nspBII          bbvI
      bsh1236I                       aciI               aciI            taqI
                                     rsaI               ↓               ↓
                                     csp6I   scfI     mnlI            nlaIII
  701 TTGGAACGCG GATTCCCCGT GCCAAGAGTG CTGTAAGTAC CGCCTATAGA GCGATAAGAG GATTTTATCC CCGGCTGCCAT CATGGTTCGA CCATTGAACT
      AACCTTGCGC CTAAGGGGCA CGGTTCTCAC GACATTCATG GCGGATATCT CGCTATTCTC CTAAAATAGG GGCCGACGGTA GTACCAAGCT GGTAACTTGA thaI
                                                                        fnuDII/mvnI
                                                                        bstUI
                                                                        bsh1236I
                             pflMI                                      mluI
                             bslI                            bsrBI      aflIII   rsaI
      sfaNI                  bsaI              mnlI   aciI   mnlI ddeI xmnI    csp6I
                                                                        asp700    scaI
  801 GCATCGTCGC CGTGTCCCGC CGTGTCCCAA AATATGGGGA TTGGCAAGAA CGGAGACCTA CCCTGCCCTC CGCTCAGGAA CGCGTTCAAG TACTTCCAAA GAATGACCAC
      CGTAGCAGCG GCACAGGGCG GCACAGGGTT TTATACCCCT AACCGTTCTT GCCTCTGGAT GGGACGGGAG GCGAGTCCTT GCGCAAGTTC ATGAAGGTTT CTTACTGGTG scrFI
                                                        mvaI
                                                        ecoRII
                                                        dsaV
      eco57I                                            bstNI                                                  tfiI        tru9I
      mboII                              tfiI           apyI[dcm+]                                             mboII taqI  mseI       tru9I
      earI/ksp632I                       hinfI          sexAI                              ddeI  hinfI         ahaIII/draI aseI/asnI/vspI
      mnlI                               alwNI  hphI                                                                       CAGAATTAAT
  901 AACCTCTTCA GTGGAAGGTA AACAGAATCT GGTGATTATG GGTAGGAAAA CCTGGTTCTC CATTCCTGAG AAGAATCGAC CTTTAAAGGA CAGAATTAAT
      TTGGAGAAGT CACCTTCCAT TTGTCTTAGA CCACTAATAC CCATCCTTTT GGACCAAGAG GTAAGGACTC TTCTTAGCTG GAAATTTCCT GTCTTAATTA aluI
                                         sstI
                                         sacI
                                         hgiJII
                                         hgiAI/aspHI
                                         ecl136II
                                         bsp1286
                                         bsiHKAI
                                         bmyI                                         tru9I                       mspI
                                         banII                           sfaNI        mseI                        hpaII
                      ddeI       bslI   mnlI          bstXI      fokI   aflIII/bfrI                               bsaWI
 1001 ATAGTTCTCA GTAGAGAACT CAAAGAACCA CCACGAGGAG CTCATTTTCT TGCCAAAAGT TTGGATGATG CCTTAAGACT TATTGAACAA CCGGAATTGG
      TATCAAGAGT CATCTCTTGA GTTTCTTGGT GGTGCTCCTC GAGTAAAAGA ACGGTTTTCA AACCTACTAC GGAATTCTGA ATAACTTGTT GGCCTTAACC
```

FIG. 6D

```
                                                                                                       haeIII/palI
                                                                                                       haeI
                                                       scrFI               scrFI
                                                       mvaI                mvaI
                                                       ecoRII              ecoRII                                                     nlaIII
                                                       dsaV      tfiI      dsaV       pleI                              mboI/ndeII[dam-]    sau3AI
                                                       bstNI     nlaIII    bstNI                                        dpnI[dam+]
                              accI  nlaIII             apyI[dcm+] hinfI    apyI[dcm+] hinfI   ddeI                      hinfI  maeIII  alwI[dam-]  dpnII[dam-]
                                           mnlI
1101 CAAGTAAAGT AGACATGGTT TGGATAGTCG GAGGCAGTTC TGTTTACCAG GAAGCCATGA ATCAACCAGG CCACCTTAGA CTCTTTGTGA CAAGGATCAT
     GTTCATTTCA TCTGTACCAA ACCTATCAGC CTCCGTCAAG ACAAATGGTC CTTCGGTACT TAGTTGGTCC GGTGGAATCT GAGAAACACT GTTCCTAGTA mnlI
                                                                                      hinlI/acyI                        scrFI
                                                                                      ahaII/bsaHI                       mvaI
                                                                              scrFI            ecoRII                   dsaV
                                                                              mvaI    ecoNI    sau96I
                                                                              ecoRII           avaII
                                                                              dsaV
                                                                              bstNI   bslI              asuI   mnlI
                                                                              apyI[dcm+]                mnlI   bstNI
                                                                   mnlI       bsaJI  hgaI               ddeI   apyI[dcm+]
1201 GCAGGAATTT GAAAGTGACA CGTTTTTCCC AGAAAATTGAT TTGGGGAAAT ATAAACCTCT CCCAGAATAC CCAGGCGTCC TCTCTGAGGT CCAGGAGGAA
     CGTCCTTAAA CTTTCACTGT GCAAAAAGGG TCTTTAACTA AACCCCTTTA TATTTGGAGA GGGTCTTATG GGTCCGCAGG AGAGACTCCA GGTCCTCCTT ppu10I
                                                                     sfaNI                                              nsiI/avaIII
                                                             mboII                                            mnlI
                                                             accI                                             aluI
1301 AAAGGCATCA AGTATAAGTT TGAAGTCTAC GAGAAGAAAG ACTAACAGGA AGATGCTTTC AAGTTCTCTG CTCCCCTCCT AAAGCTATGC ATTTTTATAA
     TTTCCGTAGT TCATATTCAA ACTTCAGATG CTCTTCTTTC TGATTGTCCT TCTACGAAAG GAGGGGAGGA TTTCGATACG TAAAAATATT fnu4HI
                      aciI
              nlaIII  thaI
              styI    fnuDII/mvnI tru9I
              ncoI    bstUI    mseI                                                                            maeIII
              dsaI    bshl236I  aseI/asnI/vspI                                                                 hphI
1401 GACCATGGGA CTTTTGCTGG CTTTAGACCC GTTAGAACGC GGCTACAATT AATACATAAC CTTATGTTATC ATACACATAG ATTTAGGTGA
     CTGGTACCCT GAAAACGACC GAAATCTGGG GAATTCTTGCG CCGATGTTAA TTATGTATTG GAATACATAG TATGTGTATC TAAATCCACT
                     styI
                     bsaJI
```

FIG. 6E

```
                                                                            haeIII/palI
                                                                            eaeI
                                                              cfrI
                                                              mspI
                                                    hpaII
                                                    scrFI
                                          ncil
                                          ecoRI dsaV
                            scrFI         apoI cauII
                            mvaI          taqI bsp106 bsaJI
                            ecoRII        clal/bsp106                              aluI
                            dsaV          
                            bstNI         
                            apyI[dcm+]    mnlI
                            gsuI/bpmI     bsaJI
                maeIII      hincII/hindII
scfI  fokI
1501 CACTATAGAA TAACATCCAC TTTGCCTTTC TCTCCACAGG TGTCACTCCA GGTCAACTGC ACCTCGGTTC TATCGATTGA ATTCCCGGGC CATAGCTGTC
     GTGATATCTT ATTGTAGGTG AAACGGAAAG AGAGGTGTCC ACAGTGAGGT CCAGTTGACG TGGAGCCAAG ATAGCTAACT TAAGGGCCCG GTATCGACAG gsuI/bpmI
                            scrFI
                            mvaI
                            ecoRII
                            dsaV                                                          mnlI
                  nspBII    bstNI                                                         ecoNI
                  fnu4HI    hgiAI/aspHI                                                   sau96I
                  fnu4HI acil  bsp1286                                     ddeI           nlaIV
       mnlI       bbvI  fnu4HI  bsiHKAI  aluI                              mnlI           avaII
       haeIII/palI     bspMI  bbvI  bmyI apyI[dcm+]                        eco81I   asuI  hphI
       sau96I                                                              bsu36I/mstII/sauI  bsrI bslI
       asuI                                                                bslI
       nlaIII
1601 TGGCATGGGC CTCTCCACCG TGCCTGACCT GCTGCTGCCG CTGGTGCTCC TGGAGCTGTT GGTGGGAATA TACCCCTCAG GGGTTATTGG ACTGGTCCCT
     ACCGTACCCG GAGAGGTGGC ACGGACTGGA CGACGACGGC GACCACGAGG ACCTCGACAA CCACCCTTAT ATGGGGAGTC CCCAATAACC TGACCAGGGA rmaI
     maeI
     styI
     bsaJI           styI
     blnI    mboII   bsaJI                                                rsaI
     avrII   earI/ksp632I                                  mnlI   taqI    csp6I                       nlaIV
1701 CACCTAGGGG ACAGGGAGAA GAGAGATAGT GTGTGTCCCC AAGGAAAATA TATCCACCCT CAAAATAATT CGATTTGCTG TACCAAGTGC CACAAAGGAA
     GTGGATCCCC TGTCCCTCTT CTCTCTATCA CACACAGGGG TTCCTTTTAT ATAGGTGGGA GTTTTATTAA GCTAAACGAC ATGGTTCACG GTGTTTCCTT
```

```
                                                                     hgiAI/aspHI
                                                                     bsp1286
                                                                     bsiHKAI          hgiAI/aspHI
                                              hgiAI/aspHI             bmyI            bsp1286
                                              bsp1286                 apaLI/snoI      bsiHKAI
                                              bsiHKAI    scrFI        alw44I/snoI     bmyI
                              sau96I          bmyI       mvaI                         apaLI/snoI
                              avaII bmyI mnlI apaLI/snoI ecoRII                       alw44I/snoI
              mnlI            asuI  alw44I/snoI dsaV                                  draIII
              alwNI           nlaIV           apyI[dcm+] bstNI
              fnu4HI
       bsrI   munI bbvI  mnlI
2001 CGGCATTATT GGAGTGAAAA CCTTTTCCAG TGCTTCAATT GCAGCCCTCTG CCTCAATGGG ACCGTGCACC TCTCCTGCCA GGAGAAACAG AACACCGTGT
     GCCGTAATAA CCTCACTTTT GGAAAAGTC ACGAAGTTAA CGTCGGGAGAC GGAGTTACCC TGGCACGTGG AGAGGACGGT CCTCTTTGTC TTGTGGCACA hgiAI/aspHI
                                                                                      bsp1286
                                                                                      bsiHKAI
                                                                                      bmyI
                                                                          gsuI/bpmI
                                                                          scrFI
                                                                          mvaI        apaLI/snoI
                                                                          ecoRII
                                                                          dsaV
                      bspMI                  scfI                         bstNI       alw44I/snoI
       bspMI nlaIII   bsmAI       maeIII                                  apyI[dcm+]
2101 GCACCTGCCA TGCAGGTTTC TTTCTAAGAG TGTCTCCTGT AGTAACTGTA AAAACGAGTG GGAGTGCACG AAGTTGTGCC TACCCAGAT
     CGTGGACGGT ACGTCCAAAG AAAGATTCTC ACAGAGGACA TCATTGACAT TTTTGCTCAC CCTCACGTGC TTCAACACGG ATGGGGTCTA aluI
                                  sstI
                                  sacI
                                  hgiJII
                                  hgiAI/aspHI
                                  ecl136II
                                  bsp1286
                                  bsiHKAI                                                            bsp1286
                nlaIV             bmyI                                                               nlaIV
      bsp1286   hgiCI             banII                                      nlaIII       nlaIII     hgiCI
      tru9I  mnlI ddeI                                                                    nspI dsaI banI
      mseI bmyI ddeI hinfI banI                                     maeIII    hphI        nspHI bsaJI bmyI
2201 TGAGAATGTT AAGGCACTG AGGACTCAGG AGCTCCAAAG CACCACAGAC AAGAGAGTTG AGCTCAAAAC CCCACTTGGT GACACAACTC ACACATGCCC ACGGTGCCA
     ACTCTTACAA TTCCCGTGAC TCCTGAGTCC GTCGGAGTTT TG TTCTCTCAAC TCGAGTTTTG GGGTGAACCA CTGTGTTGAG TGTGTACGG TGCCACGGGT bsp1286
              bsp1286                                                             nlaIV
              nlaIV                                                               hgiCI
              hgiCI  pleI hgiCI                                                              hgiJII
              hgiI bmyI                                                            dsaI hgiCI bsp1286
              bsp1286 banI                                                         bsaJI bmyI bmyI
              bmyI bsaJI                                                                      banII banI
2301 GAGCCCAAAT CTGTGACAC ACCTCCCCCG TGCCCAGGGT GCCCAGAGCC CAAATCTGTT GCCCATGGCC CCCATGGCCA GGGTCAGCCC ACGGTGCCA TGCCACGGGT CTCGGGTTA
     CTCGGGTTTA GAACACTGTG TGGAGGGGGC ACGGGTCCCA CGGGTCTCGG GTTTAGAACA CGGTACCGG GGGTACCGGT CCCAGTCGGG TGCCACGGGT ACGGTGCCCA GAGCCCAAAT
```

FIG. 6H

```
                                                              eam1105I
                                                              sau96I
                                                scrFI
                                                mvaI   avaII
                                                ecoRII
                                                dsaV
                                                bstNI  asuI         mboII mboII
                                  bsp1286       bsaJI mnlI          bpuAI earI/ksp632I    styI
                                  nlaIV         apyI[dcm+]          bbsI mnlI             bsaJI
                                  hgiCI
                         dsaI bmyI
             maeIII               bsaJI
             mnlI    nlaIII  banI alwNI
       maeIII                                                                                                      ATACCCTTAT
2401 CTTGTGACAC ACCTCCCCCA TGCCCACGGT GCCCAGCACC TGAACTCCTG GGAGGACCGT CAGTCTTCCT CTTCCCCCCA AAACCCAAGG TATGGAATA
     GAACACTGTG TGGAGGGGGT ACGGGTGCCA CGGGTCGTGG ACTTGAGGAC CCTCCTGGCA GTCAGAAGGA GAAGGGGGGT TTTGGGTTCC sau96I
     nlaIV
     avaII
     asuI                                                sau96I
     mspI              maeII                             avaII                         maeII
     hpaII             pmlI                                                            bsaAI
     scrFI    mnlI     eco72I                    mboII   mnlI                          rsaI
     nciI     ddeI     bsaAI                     bpuAI   bsaJI  bsrI                   csp6I
     dsaV     eco81I   bbrPI                     bbsI    avaI   asuI                         mnlI
     cauII    bsu36I/mstII/sauI    maeII         drdI
2501 GATTTCCCGG ACCCTGAGG TCACGTGCT GGTGGTGGAC GTGAGCCACG AAGACCCCGA GGTCCAGTTC AAGTGGTACG TGGACGGCGT GGAGGTGCAT
     CTAAAGGGCC TGGGACTCC AGTGCACGA CCACCACCTG CACTCGGTGC TTCTGGGGCT CCAGGTCAAG TTCACCATGC ACCTGCCGCA CCTCCACGTA
              aciI
              thaI
              fnuDII/mvnI
              bstUI
              bsh1236I
              sacII/sstII
              nspBII
              kspI
              dsaI                                                               scrFI
              bsaJI                                                              mvaI bsrI
              aciI                                                               ecoRII
                                                                                 dsaV
                              maeII                        mnlI  hphI            bstNI              rsaI
              fnu4HI  mnlI                         hgaI    bslI  apyI[dcm+]                         csp6I
2601 AATGCCAAGA CAAAGCCGCG GGAGGAGCAG TTCAACAGCA CGTTCCGTGT GGTTCAGTCG CTCACCGTCC TGCACCAGGA CTGGCTGAAC GGCAAGGAGT
     TTACGGTTCT GTTTCGGCGC CCTCCCTCGTC AAGTTGTCGT GCAAGGCACA CCAGTCGCAG GAGTGGCAGG ACGTGGTCCT GACCGACTTG CCGTTCCTCA
```

FIG. 6I

```
              bsmAI                                                                                    rsaI
              bsaI             mnlI               taqI                                                 csp6I
                                                                                    avaI               bsp1407I             bslI
2701 ACAAGTGCAA GGTCTTCCAAC AAAGCCCTCC CAGCCCCCAT CGAGAAAACC ATCTCCAAAA CCAAAGGACA GCCCGAGAA CCACAGGTGT ACACCCTGCC
     TGTTCACGTT CCAGAGGTTG TTTCGGGAGG GTCGGGGGTA GCTCTTTTGG TAGAGGTTTT GGTTTCCTGT CGGGGCTCTT GGTGTCCACA TGTGGGACGG
     scrFI
     nciI
     mspI
     hpaII
     dsaV
     cauII
     xmaI/pspAI
     smaI
     scrFI             scrFI              scrFI
     nciI              mvaI               mvaI
     dsaV              ecoRII             ecoRII
     cauII             dsaV               dsaV
     bsaJI             bstNI              bstNI
     fokI              apyI[dcm+]         apyI[dcm+]                                        dsaI                    nspBII
     bslI avaI mnlI    sexAI              bspMI                                             bslI             fnu4HI fnu4HI
                                                                                            bsaJI            bbvI   bbvI
2801 CCCATCCCGG GAGGAGATGA CCAAGAACCA GGTCAGCCTG ACCTGCCTGG TCAAAGGCTT CTACCCCAGC GACATCGCCG TGGAGTGGGA GAGCAGCGGG
     GGGTAGGGCC CTCCTCTACT GGTTCTTGGT CCAGTCGGAC TGGACGGACC AGTTTCCGAA GATGGGGTCG CTGTAGCGGC ACCTCACCCT CTCGTCGCCC
                                                                                            dsaI
     mspI                              mnlI              pleI                               hphI             fnu4HI
     hpaII                     mnlI nlaIII hinfI   nlaIV mboII     mnlI    scfI      aluI bsaJI    bspMI     bbvI
2901 CAGCCGGAGA ACAACTACAA CACCACGCCT CCCATGCTGG ACTCCGACGG CTCCTTCTTC CTCTACAGCA AGCTCACCGT GGACAAGAGC AGTGGCAGC
     GTCGGCCTCT TGTTGATGTT GTGGTGCGGA GGGTACGACC TGAGGCTGCC GAGGAAGAAG GAGATGTCGT TCGAGTGGCA CCTGTTCTCG TCCACCGTCG
                                                                                                                     scrFI
                                                                                                                     nciI
                                                                                                                     mspI
                                                                                                                     hpaII
                                                                                                                     dsaV
                                                                                                    scrFI            cauII
                                                                                                    nciI             bsaJI
                                                                                                    mspI             haeIII/palI
                                                                               sapI                 hpaII            mcrI
                  nlaIII                                                       mboII   mnlI         dsaV             eagI/xmaIII/ec1XI
            xmnI  ppu10I                                                       earI/ksp632I  bslI   bsmAI            eaeI
            asp700 nlaIII nsiI/avaIII        aciI                                    cauII                           cfrI
3001 AGGGAACAT CTTCTCATGC TCCGTGATGC ATGAGGCTCT GCACAACCGC TTCACGCGCA AGAGCCTCTC CCTGTCTCCG GGTAAATGAG TGCGACGGCC
     TCCCCTTGTA GAAGAGTACG AGGCACTACG TACTCCGAGA CGTGTTGGCG AAGTGCGCGT TCTCGGAGAG GGACAGAGGC CCATTTACTC ACGCTGCCGG
```

```
                nlaIV
     scrFI
     mvaI                                                   nlaIV
     ecoRII                                scrFI  scrFI
     dsaV                ppul0I            mvaI
     bstNI          nsiI/avaIII            ecoRII ecoRII
     apyI[dcm+]       nlaIII               dsaV   dsaV            bstNI
     bsaJI             sphI                bstNI                  apyI[dcm+]
                       nspI sfaNI          apyI[dcm+]             bsaJI
                       nspHI               sexAI
3401 GAAAGTCCCC AGGCTCCCCA GCAGGCAGAA GTATGCAAAG CATGCATCTC AATTAGTCAG CAACCAGTG TGGAAAGTCC CCAGGCTCCC CAGCAGGCAG
     CTTTCAGGGG TCCGAGGGGT CGTCCGTCTT CATACGTTTC GTACGTAGAG TTAATCAGTC GTTGGTCCAC ACCTTTCAGG GGTCCGAGGG GTCGTCCGTC sfaNI
                ppul0I
                nsiI/avaIII
                nlaIII
                sphI
                nspI                                                                                     bslI
                nspHI                   aciI       aciI  fokI       aciI          aciI bsrI aciI        aciI
3501 AAGTATGCAA AGCATGCATC TCAATTAGTC AGCAACCATA GTCCCGCCCC TAACTCCGCC CATCCCGCC CTAACTCCGC CCAGTTCCCGC CCATTCTCCG
     TTCATACGTT TCGTACGTAG AGTTAATCAG TCGTTGGTAT CAGGGCGGGG ATTGAGGCGG GTAGGGCGG GATTGAGGCG GGTCAAGGCG GGTAAGAGGC rmaI
                                                                                                        styI
                                                                                                        bsaJI
                              fnu4HI                                                                    blnI
                              sfiI mnlI                                                                 avrII
            nlaIII            haeIII/pall  ddeI                                                         haeIII/pall
            styI              bsaJI bglI   haeIII/pall bsaJI mnlI aluI               mnlI               stuI
            ncoI              haeIII/pall mnlI aciI    haeIII/pall                                      haeI
            dsaI              mnlI mnlI aciI                                                            mnlI maeI
3601 CCCCATGGCT GACTAATTTT TTTTATTTAT GCAGAGGCCG AGGCCGCCTC GGCCTCTGAG CTATTCCAGA AGTAGTGAGG AGGCTTTTTT GGAGGCCTAG
     GGGGTACCGA CTGATTAAAA AAAATAAATA CGTCTCCGGC TCCGGCGGAG CCGGAGACTC GATAAGGTCT TCATCACTCC TCCGAAAAAA CCTCCGGATC scrFI
                                                                                       mvaI
                                                                                       ecoRII
                                                                                       dsaV
                                                                                       bstNI
                       tru9I       haeIII/pall                                         apyI[dcm+]
                       hpaI        eaeI              bsrI                              bsaJI maeIII      tru9I     fnu4HI
                       hincII/hindII cfrI            bsrIII                  maeII     maeIII           mseI      bbvI
          aluI mseI aluI                    bsrI maeI
3701 GCTTTTTGCAA AAAGCTGTTA ACAGCTTGGC ACTGGCCGTC GTTTTACAAC GTCGTGACTG GGAAAACCCT GGCGTTACCC AACTTAATCG CCTTGCAGCA
     CGAAAACGTT TTTCGACAAT TGTCGAACCG TGACCGGCAG CAAAATGTTG CAGCACTGAC CCTTTTGGGA CCGCAATGGG TTGAATTAGC GGAACGTCGT
```

FIG. 6L

```
                                                                                                 hinPI
                                                                                                 hhaI/cfoI
                                                                                                 nlaIV
                                                                                                 narI
                                                             sau3AI                              kasI
                                                             mboI/ndeII[dam-]                    hinlI/acyI
                                               sau96I                                            hgiCI
                                               haeIII/palI                                       haeII     aciI
                                               asuI          dpnI[dam+]                          banI      sfaNI
                             aluI              mnlI          dpnII[dam-]                         ahaII/bsaHI
                             pvuII     mboII   aciI          pvuI/bspCI
                             nspBII    earI/ksp632I                               bglI
      fokI
3801  CATCCCCCCT  TCGCCAGCTG  GCGTAATAGC  GCACCGATCG  CCCTTCCCAA  CAGTTGCGTA  GCCTGAATGG  CCTGATGCGGT
      GTAGGGGGGA  AGCGGTCGAC  CGCATTATCG  CGTGGCTAGC  GGGAAGGGTT  GTCAACGCAT  CGGACTTACC  GGACTACGCCA aciI
                                                                                                 fnu4HI
                                                                   hinPI                         aciI
                                                                   thaI                          thaI
                                                                   fnuDII/mvnI                   fnuDII/mvnI
                                                                   bstUI  scfI                   bstUI
                                                                   bsh1236I                      hinPI  hhaI/cfoI
                                                        rsaI hhaI/cfoI       fnu4HI  tru9I bsh1236I
                                              sfaNI     aciI maeII     csp6I bslI     aciI msel hhaI/cfoI
3901  ATTTTCTCCT  TACGGATCTG  TGCGGTATTT  CACACCGCAT  ACGTCAAAGC  AACCATAGTA  CGCGCCCTGT  AGCGGCGCAT  TAAGCGCGGC  GGGTGTGGTG
      TAAAAGAGGA  ATGCCTAGAC  ACGCCATAAA  GTGTGGCGTA  TGCAGTTTCG  TTGGTATCAT  GCGCGGGACA  TCGCCGCGTA  ATTCGCGCCG  CCCACCACAC fnu4HI
      hinPI
      hhaI/cfoI
      thaI                                         hinPI                                                              mspI
      fnuDII/mvnI                                  hhaI/cfoI                                                           hpaII
      bstUI                       rmaI                                                                                naeI
      bsh1236I      aciI          hinPI haeII                                                              maeII      cfr10I
      maeIII bbvI   maeIII        hhaI/cfoI  maeI  haeIII  aciI            bsrBI
4001  GTTACGCGCA  GGTGACGGC  TACACCTTGCC  AGCGCCCTAG  CGCCCGCTCC  TTTCGCTTTC  TTCCCTTCCT  TTCTCGCCAC  GTTCGCCGGC  TTTCCCCGTC
      CAATGCGCGT  CCACTGGCG  ATGTGAACGG  TCGCGGGATC  GCGGGCGAGG  AAAGCGAAAG  AAGGGAAGGA  AAGAGCGGTG  CAAGCGGCCG  AAAGGGGCAG nlaIV
                              hgiJII
                              bsp1286                                                                      maeII      haeIII/palI
                              bmyI                                           nlaIV                         draIII     sau96I
                    aluI      banII     nlaIV                                hgiCI  taqI                   bsaAI      asuI
                                                                             banI   mnlI            hphI
4101  AAGCTCTAAA  TCGGGGCTC  CCTTTAGGGT  TGCTTTACGG  CACCTCGACC  CCAAAAAACT  TGATTTGGGT  GATGGTTCAC  GTAGTGGCC  CATCACCCGG
      TTCGAGATTT  AGCCCCCGAG  GGAAATCCCA  ACGAAATGCC  GTGGAGCTGG  GGTTTTTTGA  ACTAAACCCA  CTACCAAGTG  CATCACCGG
```

FIG. 6M

```
                              maeII pleI                tru9I      pleI
                              drdI hinfI maeII          mseI       hinfI                    bsrI                      thaI                              bslI
4201 ATCGCCCTGA TAGACGGTTT TTCGCCCTTT GACGTTGGAG TCCACGTTCT TTAATAGTGG ACTCTTGTTC CAAACTGGAA CAACACTCAA CCCTATCTCG
     TAGCGGGACT ATCTGCCAAA AAGCGGGAAA CTGCAACCTC AGTTGCAAGA AATTATCACC TGAGAACAAG GTTTGACCTT GTTGTGAGTT GGGATAGAGC
                                                                                                        fnuDII/mvnI
                                                                 tru9I                         tru9I apoI tru9I       tru9I
                                                                 mseI              aluI  tru9I mseI bstUI mseI        mseI
                                                 haeIII/palI                             mseI      apoI bsh1236I       sspI
4301 GGCTATTCTT TTGATTTATA AGGGATTTTG CCGATTTCGG CCTATTGGTT AAAAAATGAG CTGATTTAAC AAAAATTTAA CGCGAATTTT AACAAATAT
     CCGATAAGAA AACTAAATAT TCCCTAAAAC GGCTAAAGCC GGATAACCAA TTTTTTACTC GACTAAATTG TTTTTAAATT GCGCTTAAAA TTGTTTTATA
          hgiAI/aspHI
          bsp1286
          bsiHKAI                                       aciI                                                                                   hinPI
          bmyI   ddeI                                   fnu4HI      tru9I                                        maeIII                        fnu4HI
     maeII  apaLI/snoI    rsaI                          sfaNI       mseI            aciI            maeII bsrI   nlaIII hhaI/cfoI
     psp1406I alw44I/snoI csp6I                                                                     bsaAI tth111I/aspI bbvI
4401 TAACGTTTAC AATTTTATGG TGCACTCTCA GTACAATCTG CTCTGATGCC GCATAGTTAA GCCAACTCCG CTATGCTCTAC GTGACTGGGT CATGGCTGCG
     ATTGCAAATG TTAAAATACC ACGTGAGAGT CATGTTAGAC GAGACTACGG CGTATCAATT CGGTTGAGGC GATAGCGATG CACTGACCCA GTACCGACGC
                                                                          scrFI
                                                                          nciI
                    hinPI                                   sfaNI         mspI
                    hhaI/cfoI                               mspI          hpaII                                                        nspI
                    thaI                                    hpaII         scrFI                                                        nspHI
                    fnuDII/mvnI                             scrFI         nciI                             esp3I                       fnu4HI
                    bstUI                                   nciI          dsaV fokI                        maeIII bsmAI                 bbvI
          nspBII bsh1236I                     drdI         dsaV           cauII  aciI         aluI  bslI  cauII   cauII nlaIII
     aciI aciI hgaI                                                                                                 alnI tnlaIII
4501 CCCGACACCC CGCCAACACC CGCTGACGCG CCCTGACGGG CTTGTCCTGCT CCCGGCATCC GCTTACAGAC AAGCTGTGAC CGTCCCGGG AGCTGCATGT
     GGGGCTGTGG GCGGTTGTGG GCGACTGCGC GGGACTGCCC GAACAGACGA GGGCCGTAGG CGAATGTCTG TTCGACACTG GCAGAGGCCC TCGACGTACA
                                                             mnII
                                                             haeIII/palI
                                                             sau96I
                                thaI                         asuI
                                fnuDII/mvnI    mboII         ecoO109I/draII
                                bstUI          bpuAI
                                bsh1236I       bbsI
                                hinPI
                                hhaI/cfoI                                                                                                 nlaIII
                                thaI                                                                                              tru9I  rcaI
                                fnuDII/mvnI                                                                                       mseI   bspHI
                                bstUI mnlI
               hphI              bsh1236I
     mnlI     hphI  hphI
4601 GTCAGAGGTT TTCACCGTCA TCACCGAAAC GCGGAGGCA GTATTCTTGA AGACGAAAGG GCCTCGTGAT ACGCCTATTT TTATAGGTTA ATGTCATGAT
     CAGTCTCCAA AAGTGGCAGT AGTGGCTTTG CGCGCTCCGT CATAAGAACT TCTGCTTTCC CGGAGCACTA TGCGGATAAA AATATCCAAT TACAGTACTA
```

FIG. 6N

```
                                                       nlaIV
                                                       aciI
                                                       thaI
                                                       fnuDII/mvnI                                    rcaI
                         hinlI/acyI                    bstUI                                          bspHI
                         ahaII/bsaHI                   bsh1236I                                       bsrBI
                         aatII                         hinPI                                          aciI nlaIII
                         ddeI maeII                    hhaI/cfoI                                      fnu4HI
             bsmAI                    mboII                                                           aciI
4701 AATAAATGGTT TCTTAGACGT CAGGTGGCAC TTTTCGGGA AATGTGCGCG GAACCCCTAT TTGTTTATTT TTCTAAATAC ATTCAAATAT GTATCCGCTC
     TTATTTACCAA AGAATCTGCA GTCCACCGTG AAAAGCCCCT TTACACGCGC CTTGGGGATA AACAAATAAA AAGATTTATG TAAGTTTATA CATAGGCGAG sspI               earI/ksp632I
4801 ATGAGACAAT AACCCTGATA AATGCTTCAA TAATATTGAA AAAGGAAGAG TATGAGTATT CAACATTTCC GTGTCGCCCT TATTCCCTTT TTTGCGGCAT
     TACTCTGTTA TTGGGACTAT TTACGAAGTT ATTATAACTT TTTCCTTCTC ATACTCATAA GTTGTAAAGG CACAGCGGGA ATAAGGGAAA AAACGCCGTA hgiAI/aspHI
                                                                       bsp1286
                                                                       bsiHKAI
                                                           sau3AI                         apaLI/snoI
                                                           mboI/ndeII[dam-]               alw44I/snoI maeIII taqI
                                                           dpnI[dam+] bmyI                                               sau3AI
                                                           dpnII[dam-]                                                   mboI/ndeII[dam-]
                                            hphI                           eco57I                                        dpnI[dam+]
                          sau3AI                        sfaNI mboII[dam-]                      bsrI dpnII[dam-]          bstYI/xhoII
                          mboI/ndeII[dam-]                                                                               alwI[dam-]
                          dpnI[dam+]                                                                                     
                          dpnII[dam-]                                                                                    
             hphI        CACCCAGAAA CGCTGGTGAA AGTAAAAGAT GCTGAAGATC AGTTGGGTGC ACGAGTGGGT TACATCGAAC TGGATCTCAA
4901 TTTGCCTTCC TGTTTTTGCT CACCCAGAAA CGCTGGTGAA AGTAAAAGAT GCTGAAGATC AGTTGGGTGC ACGAGTGGGT TACATCGAAC TGGATCTCAA
     AAACGGAAGG ACAAAAACGA GTGGGTCTTT GCGACCACTT TCATTTTCTA CGACTTCTAG TCAACCCACG TGCTCACCCA ATGTAGCTTG ACCTAGAGTT aciI
                                                                                                      thaI
                                 maeII                                                                fnuDII/mvnI
                                 psp1406I                                                             bstUI
                                 xmnI          hgiAI/aspHI                                            bsh1236I          hinlI/acyI
                                 asp700         bsp1286 tru9I                                         hinPI             hgaI
                                  mboII         bsiHKAI mseI                                          hhaI/cfoI         ahaII/bsaHI
                                                 bmyI ahaIII/draI
     aciI  bstYI/xhoII
     nspBI bstYI/xhoII
5001 CAGCGGTAAG ATCCTTGAGA GTTTTCGCCC CGAAGAACGT TTTCCAATGA TGAGCACTTT TAAAGTTCTG CTATGTGGCG CGGTATTATC CCGTGATGAC
     GTCGCCATTC TAGGAACTCT CAAAAGCGGG GCTTCTTGCA AAAGGTTACT ACTCGTGAAA ATTTCAAGAC GATACACCGC GCCATAATAG GGCACTACTG scrFI
     ncil
     mspI                                                      rsaI
     hpaII                                                     csp6I           bsrI
     dsaV                                   aciI               scaI hphI maeIII       sfaNI   fokI       nlaIII
     cauII    bcgI mcrI fnu4HI    ddeI
5101 GCCGGGCAAG AGCAACTCGG TCGCCGCATA CACTATTCTC AGAATGACTT GGTTGAGTAC TCACCAGTCA CAGAAAAGCA TCTTACGGAT GGCATGACAG
     CGGCCCGTTC TCGTTGAGCC AGCGGCGTAT GTGATAAGAG TCTTACTGAA CCAACTCATG AGTGGTCAGT GTCTTTTCGT AGAATGCCTA CCGTACTGTC
```

FIG. 60

```
                                                                                           sau96I
                                                                                           avaII
                                                                          sau3AI    asuI
                                                                          mboI/ndeII[dam-]
                                                                          dpnI[dam+]
                                              haeIII/palI                 dpnII[dam-]
                                              eaeI                        pvuI/bspCI
                                              cfrI
                                              fnu4HI                      mcrI    mnlI         aluI      aciI
              fnu4HI                          aciI
              bbvI      nlaIII
5201 TAAGAGAATT ATGCAGTGCT GCCATAACCA TGAGTGATAA CACTGCGGCC AACTTACTTC TGACAACGAT CGGAGGACCG AAGGAGCTAA CCGCTTTTTT
     ATTCTCTTAA TACGTCACGA CGGTATTGGT ACTCACTATT GTGACGCCGG TTGAATGAAG ACTGTTGCTA GCCTCCTGGC TTCCTCGATT GGCGAAAAAA maeIII                                                                                      fnu4HI
              nlaIII                                                                          maeIII     sfaNI    bbvI
              sau3AI                           mspI
              mboI/ndeII[dam-]    sau3AI    nlaIV
              dpnI[dam+]          mboI/ndeII[dam-]  aluI
              dpnII[dam-]         dpnI[dam+]        hpaII
     nlaIII  alwI[dam-]           dpnII[dam-] bsaWI
5301 GCACAACATG GGGGATCATG TAACTCGCCT TGATCGTTGG GAACCGGAGC TGAATGAAGC CATACCAAAC GACGAGCGTG ACACCACGAT GCCAGCAGCA
     CGTGTTGTAC CCCCTAGTAC ATTGAGCGGA ACTAGCAACC CTTGGCCTCG ACTTACTTCG GTATGGTTTG CTGCTCGCAC TGTGGTGCTA CGGTCGTCGT mspI
                                          hpaII
              hinPI                       scrFI
              mstI                                                                                           sau96I
              aviII/fspI    bsrI     aluI  ncII            tru9I   fokI                                      avaII
              maeII hhaI/cfoI tru9I  rmaI  dsaV            mseI    bsrI   aciI                               asuI
              psp1406I            mseI  maeI  cauII        aseI/asnI/vspI  mnlI
5401 ATGGCAACAA CGTTGCGCAA ACTATTAACT GGCGAACTAC TTACTCCTAGC TTCCCGGCAA CAATTAATAG ACTGGATGGA GGCGGATAAA GTTGCAGGAC
     TACCGTTGTT GCAACGCGTT TGATAATTGA CCGCTTGATG AATGAGATCG AAGGGCCGTT GTTAATTATC TGACCTACCT CCGCCTATTT CAACGTCCTG bglI                                                                     thaI
              sau96I                                             mspI                  fnuDII/mvnI                 haeIII/palI
              haeIII/palI                                        hpaII                 bstUI                       sau96I
              hinPI  asuI     mspI                               cfr10I         bsmAI  aciI           fnu4HI       nlaIV
              hhaI/cfoI       hpaII       gsuI/bpmI              nlaIV  hphI    bsaI   bsh1236I    bbvI bsrI asuI
5501 CACTTCTGCG CTCGGCCCTT CCGGCTGGCT GGTTTATTGC TGATAAATCT GGAGCCGGTG AGCGGTGGTC TCGCGGTATC ATTGCAGCAC TGGGGCCAGA
     GTGAAGACGC GAGCCGGGAA GGCCGACCGA CCAAATAACG ACTATTTAGA CCTCGGCCAC TCGCCACCAG AGCGCCATAG TAACGTCGTG ACCCCGGTCT ddeI
                                                                                              sau3AI      nlaIV
              pleI                                                                            mboI/ndeII[dam-]   mnlI         tru9I
              hinfI                                                                           dpnI[dam+]    hgiCI             mseI
     mnlI     eaml105I                                  fokI                                  dpnII[dam-]   banI
5601 TGGTAAGCCC TCCCGTATCG TAGTTAATCTA CACGACGGGG AGTCAGGCAA CTATGGATGA ACGAAATAGA CAGATCGCTG AGATAGGTGC CTCACTGATT
     ACCATTCGGG AGGGCATAGC ATCAATAGAT GTGCTGCCCC TCAGTCCGTT GATACCTACT TGCTTTATCT GTCTAGCGAC TCTATCCACG GAGTGACTAA
```

```
                                                                scrFI
                                                                nciI
                                                                mspI
                                                                hpaII
                           fnu4HI                               dsaV                                                            aciI
                           bbvI                                 pleI                                                            nspBII
           alwNI           fnu4HI                               hinfI                                       mspI                fnu4HI
           bsrI            bbvI    bsrI                         cauII                                       hpaII               bbvI
      maeIII               bbvI    bsrI                                                                     bsaWI               hinPI  mcrI
                                                                                                            maeII               hhaI/cfoI 6101 TAATCCTGTT ACCAGTGGCT GCTGCCAGTG GCGATAAGTC GTGTCTTACC GGGTTGGACT CAAGACGATA GTTACCGGAT AAGGGCCAGC GGTCGGGCTG
     ATTAGGACAA TGGTCACCGA CGACGGTCAC CGCTATTCAG CACAGAATGG CCCAACCTGA GTTCTGCTAT CAATGGCCTA TTCCGGTCG CCAGCCCGAC hgiAI/aspHI
                 bsp1286
                 bsiHKAI
                 bmyI                                                                                               hinPI
                 apaLI/snoI                                                                                         hhaI/cfoI
                 alw44I/snoI   aluI                          ddeI          scfI                                     haeII 6201 AACGGGGGT TCGTGCACAC AGCCCAGCTT GGAGCGAACG ACCTACACCG AACTGAGATA CCTACAGCGT GAGCATTGAG AAAGCGCCAC GCTTCCCGAA
     TTGCCCCCCA AGCACGTGTG TCGGGTCGAA CCTCGCTTGC TTGACTCTAT GGATGTCGCA CTCGTAACTC TTTCGCGGTG CGAAGGGCTT scrFI
                                                                              mvaI           scrFI
                                                                              ecoRII  mvaI
                                                                              dsaV    ecoRII
                                                       mspI                   bstNI   dsaV
                                                       hpaII                  bsaJI   bstNI
                                                       bsII    fnu4HI         hinPI/cfoI  aluI  apyI[dcm+]  apyI[dcm+]
                       aciI       bsaWI    aciI        hhaI/cfoI 6301 GGGAGAAAGG CGGACAGTA TCCGGTAAGC GGCAGGGTCG GAACAGGAGA GCGCACGAGG GAGCTTCCAG GGGGAAACGC CTGGTATCTT TATAGTCCTG
     CCCTCTTTCC GCCTGTCCAT AGGCCATTCG CCGTCCCAGC CTTGTCCTCT CGCGTGCTCC CTCGAAGGTC CCCCTTTGCG GACCATAGAA ATATCAGGAC haeIII/palI
                                                                                                              fnu4HI
                                                                                                              aciI
                                               nlaIV                                                          thaI   bslI
                       taqI                    aciI                                                           fnuDII/mvnI
            mnlI  drdI  hgaI   sfaNI                                                                          bstUI
                                                                                                              bsh1236I      nlaIV 6401 TCGGGTTCG CCACCTCTGA CTTGAGCGTC GATTTTTGTG ATGCTCGTCA GGGGGCGGA GCCTATGAA AAACGCCAGC AACGCGGCCT TTTTACGGTT
     AGCCCAAAGC GGTGGAGACT GAACTCGCAG CTAAAAACAC TACGAGCAGT CCCCCCGCCT CGGATACCTT TTTGCGGTCG TTGCGCCGGA AAAATGCCAA
```

FIG. 6R

```
         haeIII/palI
         haeI
       scrFI
      mvaI bslI
      ecoRII
      dsaV                                                                          tfiI
      bstNI              haeIII/palI  nspHI                                         hinfI                                        aciI              aluI       bsrBI
      apyI[dcm+]  haeI   hhaI/cfoI    afIII                                                                                                                   aciI
6501 CCTGGCCTT TGCTCACAT GTTCTTTCCT GGGTTATCCC CTGATTCTGT GGATAACCGT ATTACCGCCT TTGAGTGAGC TGATACCGCT
     GGACCGGAAA ACGAGTGTA CAAGAAAGGA CCCAATAGGG GACTAAGACA CCTATTGGCA TAATGGCGGA AACTCACTCG ACTATGGCGA thaI
                                                                                                                    fnuDII/mvnI
                                                                                                                    bstUI
                                                                                                                    bsh1236I
                                                                                                                    hinPI
                                                                                                                    hhaI/cfoI
                                                                                                                    thaI
                                                                                                                    fnuDII/mvnI
                                     fnu4HI             sapI hinPI                                                  bstUI   haeIII/palI          tru9I
                                     bbvI pleI          mboII hhaI/cfoI                                             bsh1236I                     tfiI aseI/asnI/vspI
          aciI                       hinPI hinfI        earI/ksp632I                       mnlI    bslI    eaeI     cfrI hinfI msel
        fnu4HI     mcrI              hhaI/cfoI    mnlI    aciI   haeII            aciI             aciI             cfrI
6601 CGCCGCAGCC GAACGACAGG GCGCAGCGAG TCAGTGAGCG AGGAAGCGGA ATACGCGCCA AGAGCGCCCA ATACGCAAAC CGCCTCTCCC CGCGCGTTGG CCGATTCATT
     GCGGCGTCGG CTTGCTGTCC CGCGTCGCTC AGTCACTCGC TCCTTCGCCT TATGCGCGGT TCTCGCGGGT TATGCGTTTG GCGGAGAGGG GCGCGCAACC GGCTAAGTAA scrFI
                                                                                                                     mvaI
                                                                                                                     ecoRII
                                                                                                                     dsaV
           aluI                                                             tru9I                                    nlaIV bstNI
           pvuII                                                             mseI                                    hgiCI apyI[dcm+]
         nspBII                bsrI         aciI          hinPI           aseI/asnI/vspI            maeIII           banI bsaJI
6701 AATCCAGCTG GCACGACAGG TTTCCCGACT GGAAAGCGGG CAGTGAGCGC AACGCAATTA ATGTGAGTTA CCTCACTCAT TAGGCACCCC AGGCTTTACA
     TTAGGTCGAC CGTGCTGTCC AAAGGGCTGA CCTTTCGCCC GTCACTCGCG TTGCGTTAAT TACACTCAAT GGAGTGAGTA ATCCGTGGGG TCCGAAATGT tru9I
                                                                                                                     mseI
                                                                                                                     aseI/asnI/vspI
                       aciI                                                                                          xmnI
                     bsrBI                                                                          alul    nlaIII   asp700
6801 CTTTATGCTT CCGGCTCGTA TGTTGTGTGG AATTGTGAGC GGATAACAAT TTCACACAGG AAACAGCTAT GACCATGATT ACGAATTAA
     GAAATACGAA GGCCGAGCAT ACAACACACC TTAACACTCG CCTATTGTTA AAGTGTGTCC TTTGTCGATA CTGGTACTAA TGCTTAATT >length: 6889
```

```
     scrFI
     ncil                  tfiI
     mspI                  hinfI
     hpaII         aciI
     dsaV          thaI                                               fnu4HI
     cauII         fnuDII/mvnI                                        bbvI
                   bstUI                maeII        aciI             nspBII
                   bsh1236I       maeIII  rsaI       mnlI             aciI    nlaIII
                                          csp6I scfI
401  CCGGAACGG TGCATTGGAA CGCGGATTCC CCGTGCCAAG AGTGACGTAA GTACCGCCTA TAGAGCGATA AGAGGATTTT ATCCCCGCTG CCATCATGGT
     GGCCCTTGCC ACGTAACCTT GCGCCTAAGG GGCACGGTTC TCACTGCATT CATGGCGGAT ATCTCGCTAT TCTCCTAAAA TAGGGGCGAC GGTAGTACCA haeIII/palI
                                                               haeI
                                                               scrFI
                                                               mvaI     bsrBI                       rsaI
                                                               ecoRII                               csp6I
                                                               dsaV
                                                               bstNI    aciI                       xmnI
                                    pflMI               bsmAI  apyI[dcm+]  mnlI  ddeI              asp700  scaI
     taqI     sfaNI                 bslI                bsaI   bsaJI
501  TCGACCATTG AACTGCATCG TCGCCGTGTC CCAAAATATG GGGATTGGCA AGAACGGAGA CCTACCCTGG CCTCCGCTCA GGAACGAGTT CAAGTACTTC
     AGCTGGTAAC TTGACGTAGC AGCGGCACAG GGTTTTATAC CCCTAACCGT TCTTGCCTCT GGATGGGACC GGAGGCGAGT CCTTGCTCAA GTTCATGAAG scrFI
                                                                            mvaI
                                                                            ecoRII
                                                                            dsaV
                        eco57I                    tfiI                      bstNI
                        mboII                     hinfI                     apyI[dcm+]           tfiI        tru9I
                        earI/ksp632I         alwNI       hphI               sexAI                hinfI      mseI
          mnlI                                                                        ddeI mboII taqI       ahaIII/draI
601  CAAAGAATGA CCACAACCTC TTCAGTGGAA AGTCACCTT TATGGGTGAGA ATCTGGTGAT TAGACCACTA ATACCCATCC TTTTGGACCA AAAAACCTGGT TCTCCATTCC TGAGAAGAAT CGACCTTTAA
     GTTTCTTACT GGTGTTGGAG AAGTCACCTT CCATTTGTCT TAGACCACTA ATACCCATCC TTTTGGACCA AAGAACGGTT TTCAAACCTA CTACGGAAATT GCTGAAATT sstI
                                                   sacI
                                                   hgiJII
                                                   hgiAI/aspHI
                                                   ecl136II
                                                   bsp1286
                                                   bsiHKAI
                                                   bmyI
                                            bslI  mnlI  alul banII                     bstXI       foki sfaNI mseI
       tru9I                                                                                                tru9I
       mseI         ddeI                                                                                    aflII/bfrI
       aseI/asnI/vspI
701  AGGACAGAAT TAATATAGTT CTCAGTAGAG AACTCAAAGA ACCACCACGA GGAGCTCATT TTCTTGCCAA AAGTTTGGAT GATGCCTTAA GACTTATTGA
     TCCTGTCTTA ATTATATCAA GAGTCATCTC TTGAGTTTCT TGGTGGTGCT CCTCGAGTAA AAGAACGGTT TTCAAACCTA CTACGGAATT CTGAATAACT
```

```
                                                            sau96I
                                                            avaII
                                                            asuI
                                                            scrFI
                                                            mvaI
                                                            ecoRII
                                                            dsaV
                                                            bstNI
                                                            apyI[dcm+]                mnlI      taqI  apoI
           maeIII                                 bslI bsaJI                           bsaJI     claI/bsp106   ecoRI
        hphI   scfI     fokI
1201 ATACGATTTA GGTGACACTA TAGATAACAT CCACTTTGCC TTTCTCTCCA CAGGTGTCCA CTCCCAGTC CAACTGCACC TCGGTTCTAT CGATTGAATT
     TATGCTAAAT CCACTGTGAT ATCTATTGTA GGTGAAACGG AAAGAGAGGT GTCCACAGGT GAGGGTCCAG GTTGACGTGG AGCCAAGATA GCTAACTTAA scrFI
                                                                                                   mvaI
                                                                                                   ecoRII
                                                                                                   dsaV
       nlaIII                                                                                      bstNI  fnu4HI
       styI                                                                                        apyI[dcm+]
       pflMI                                        rsaI                  aluI                     haeI       bbvI
       ncoI                                         gsuI/bpmI             pvuII       pleI              hinfI  acil haeIII/palI
       dsaI              rmaI                       bsrI   csp6I          nspBII
       bslI fokI         maeI
       bsaJI    nlaIII fokI
1301 CCACCATGGG ATGGTCATGT ATCATCCTTT TTCTAGTAGC AACTGCAACT CAGAAGTTCA GGATACATT GAGTACATT TCTGCGCGTG GCCTGGTGCA
     GGTGGTACCC TACCAGTACA TAGTAGGAAA AAGATCATCG TTGACGTTGA GTCTTCAAGT CCTCATGTAA AAGATCATCG AGACCGCCAC CGGACCACGT
```

```
                                                                                                          scrFI
                                                                                                          mvaI
                                                                                                          ecoRII
                                                                                                          dsaV
                                                                                                          bstNI
                                                                                                          apyI[dcm+]
                                                                                                          hinPI
                                                                                                          hhaI/cfoI
                                                                                      mnlI                nlaIV
                                                                                      xhoI                narI
                                                                                      paeR7I              kasI
                                                                                      avaI                hinlI/acyI
                                                                                      hgiAI/aspHI         hgiCI
                                                                                      bsp1286             haeII
                                                                                      bsiHKAI    fnu4HI   banI
                                                              mnlI                    bmyI taqI bbvI      ahaII/bsaHI
    scfI                                                                                                                                                           scrFI
    pstI                                                                                                                                                           mvaI
    bsgI           ddeI drdI                                                                                                                                       ecoRII
    bspMI                                                                                                                                                          dsaV
1601 ACCTGCAGAT GAACAGCCTG CGTGCTGAGG ACACTGCCGT CTATTATTGT GCTGAGGCA GCCACTATTT CGGGCCCTGG CACTTCGCCG TGTGGGGTCA
     TGGACGTCTA CTTGTCGGAC GCACGACTCC TGTGACGGCA GATAATAACA CGACTCCGT CGGTGATAAA GCCCGGGACC GTGAAGCGGC ACACCCCAGT sau96I
                                               haeIII/palI
                                               sau96I                                                                                       bstNI
                                               nlaIV                                nlaIV                                                   bsaJI
                                               hgiJII                               hgiCI                                                   sau96I
                                               bsp1286                                                                                      haeIII/palI
                                                                                                                                            asuI
             scrFI                  bsp120I              banI            mboII  dsaV              hgiAI/aspHI                               fnu4HI
             mvaI                              bmyI      scrFI                  bstNI             bsp1286              bsiHKAI    bsp1286 aciI apyI[dcm+]
             ecoRII                            banII     mvaI                   bsaJI             bsiHKAI              bmyI mnlI  bmyI nspBII bsaJI
             dsaV                              asuI      ecoRII          bpuAI apyI[dcm+] mnlI    bmyI nspPI           mnlI
             bstNI hphI                    apaI ecoO109I/draII           bbsI  bsaJI
             apyI[dcm+] bsmAI              styI asuI
     bsaJI maeIII   mnlI       haeIII/palI   bsaJI
     nlaIV bstEII esp3I bsaJI mnlI
1701 AGGAACCCTG GTCACCGTCT CCTCGGCCTC CACCAAGGGC CCATCGGTCT TCCCCCTGGC ACCCTCCTCC AAGAGCACCT CTGGGGGCAC AGCGGCCCTG
     TCCTTGGGAC CAGTGGCAGA GGAGCCGGAG GTGGTTCCCG GGTAGCCAGA AGGGGGACCG TGGGAGGAGG TTCTCGTGGA GACCCCCGTG TCGCCGGGAC
```

FIG. 9G

```
      scrFI
      mvaI
      ecoRII
      ecoNI                                                         hinPI
      dsaV                                                          nlaIV
      bstNI                                                 narI
      bslI                                                                           hgiAI/aspHI
      apyI[dcm+]                               hphI                         kasI
      fnu4HI                                            mspI        hinlI/acyI    bsp1286    bsiHKAI    hpaII
      bbvI              bslI    tthIIII/aspI           hpaII              hgiCI              bmyI      scrFI
                        bsaWI   ageI   maeIII          cfr10I             haeII                         nciI
                                                                          banI          fnu4HI         dsaV
                                                      ddeI hhaI/cfoI nspBII  ahaII/bsaHI acil apaLI/snoI alw44I/snoI cauII   scfI
1801  GGCTGCCTGG TCAAGGACTA CTTCCCGAA CCGGTGACGG TGTCGTGGAA CTCAGGCGCC CTGACCAGCG GGTGCACAC CTTCCCGGCT GTCCTACAGT
      CCGACGGACC AGTTCCTGAT GAAGGGCTT GGCCACTGCC ACAGCACCTT GAGTCCGCGG GACTGGTCGC CCACGTGTG GAAGGCCGA CAGGATGTCA nlaIV
      ddeI pleI                               fnu4HI  hgiCI
      mnlI hinfI                              bbvI    banI                     tfiI
      eco81I        mnlI fnu4HI maeIII bsp1286 rmaI           bsp1286          hinfI                              styI
      bsu36I/mstII/sauI ddeI bbvI    hphI      bmyI   maeI aluI   bmyI         maeII                              bsaJI
1901  CCTCAGGACT CTACTCCCTC AGCAGCGTG TGACTGTGCC CCTAGCAGC TGGGCACCC AGACCTACAT CTGCAACGTG AATCACAAGC CCAGCAACAC
      GGAGTCCTGA GATGAGGGAG TCGTCGCACC ACTGACACGG GGATCGTCG AACCCGTGGG TCTGATGTA GACGTTGCAC TTAGTGTTCG GGTCGTTGTG eam1105I
                                                                                       sau96I
                                                                              scrFI
                                                                              mvaI  avaII
                                                                              ecoRII
                                                                              dsaV
                                            nlaIII                            bstNI   asuI                    mboII mboII
                                            nspI     bsp1286                  bsaJI   nlaIV           bpuAI earI/ksp632I
             hgiJIII                        nspHI    bmyI    alwNI            apyI[dcm+]                  bbsI   mnlI
             bsp1286
             bmyI
             banII      maeIII
2001  CAAGGTGGAC AAGAAAGTTG AGCCCAAATC TTGTGACAAA ACTCACACAT GCCCACCGTG CCCAGCACCT GAACTCCTGG GGGACCGTC AGTCTTCCTC
      GTTCCACCTG TTCTTTCAAC TCGGGTTTAG AACACTGTTT TGAGTGTGTA CGGGTGGCAC GGGTCGTGGA CTTGAGGACC CCCTGGCAG TCAGAAGGAG
```

FIG. 9H

```
                                                                                                          drdI   mnlI
                                                                                                   mboII  ddeI
                                                                        nlaIII                     bpuAI  eco81I
                                 sau96I                                 nspI                       bbsI   bsu36I/mstII/sauI
                                 nlaIV                           mnlI   ddeI maeIII
                                 avaII                    cauII  eco81I nspHI
                                 mspI                     asuI   bsu36I/mstII/sauI                          maeII
                                 scrFI              bspHI[dam-]  CCCTGAGT CACATGCGTG TGAGCCACGA AGACCCTGAG GTCAAGTTCA
                                 nciI        rcaI   mnlI dpnII[dam-] GGGACTCCA GTGTACGCAC ACTCGGTGCT TCTGGGACTC CAGTTCAAGT
                                 sau3AI hpaII
                                 mboI/ndeII[dam-]
                                 dpnI[dam+]             nlaIII  dsaV
                           styI  nlaIII
2101 TTCCCCCCAA AACCCAAGGA CACCCTCATG ATCTCCCGGA
     AAGGGGGGTT TTGGGTTCCT GTGGGAGTAC TAGAGGGCCT
                                                                        aciI
                                                                        thaI
                                                                        fnuDII/mvnI
                                                                        bstUI
                                                                        bsh1236I
                                                                        sacII/sstII
                                                                        nspBII
                                                                        kspI
                                                             maeII      dsaI
                                                             rsaI       bsaJI            rsaI
                                                             csp6I      aciI             csp6I
                    bsrI bsaAI            mnlI       fnu4HI  mnlI  csp6I maeII   bsaI                 hgaI  hphI  bslI
2201 ACTGGTACGT GGACGGCGTG GAGGTGCATA ATGCCAAGAC AAAGCCGCGG GAGGAGCAGT GTACCGTGTG GTCAGCGTCC TCACCGTCCT
     TGACCATGCA CCTGCGCCAC CTCGCGCGAC TACGGTTCTG TTTCGGCGCC CTCCTCGTCA TGTTGTCGTG CAGTGCACAC AGTGCGCAGGA
     scrFI
     mvaI bsrI
     ecoRII
     dsaV                                                                                                       fnu4HI
     bstNI                                         rsaI                 bsmAI                                   bbvI
     apyI[dcm+]                                    csp6I       bsaI                        mnlI      taqI
2301 GCACCAGGAC TGGCTGAATG GCAAGGAGTA CAAGTGCAAG GTCTCCAACA AAGCCCTCCC AGCCCCCATC GAGAAAACCA TCTCCAAAGC
     CGTGGTCCTG ACCGACTTAC CGTTCCTCAT GTTCACGTTC CAGAGGTTGT TTCGGGAGGG TCGGGGGTAG CTCTTTTGGT AGAGGTTTCG
```

FIG. 9I

```
                                           scrFI
                                           nciI
                                           mspI
                                           hpaII
                                           dsaV
                                           cauII
                                           xmaI/pspAI
                                           smaI
                                           scrFI              scrFI
                                           nciI               mvaI
                                           dsaV               ecoRII
                                           cauII              dsaV                      scrFI
                          rsaI       fokI  mboII              bstNI                     mvaI
                          csp6I      bslI  bsaJI              apyI[dcm+]                ecoRII
         aval             bsp1407I   bslI  avaI earI/ksp632I  sexAI  bspMI apyI[dcm+]   dsaV          bstNI
2401  CCCGAGAAC CACAGGTGTA CACCCTGCCC CCATCCGGG AAGAGATGAC CAAGAACCAG GTCAGCCTGA CCTGCCTGGT CAAAGGCTTC TATCCCAGCC
      GGGCTCTTG GTGTCCACAT GTGGGACGGG GGTAGGCCCC TTCTCTACTG GTTCTTGGTC CAGTCGGACT GGACGGACCA GTTTCCGAAG ATAGGGTCGC
        dsaI
        bslI                                                                                                mnlI
        bsaJI       fnu4HI                                                             pleI       nlaIV  mboII scfI    aluI
                    bbvI hpaII                                                   mnlI  hinfI              mboII        TCTACAGCAA
2501  ACATCGCCGT GGAGTGGGAG AGCAATGGGC AGCCGGAGAA CAACTACAAG ACCACGCCTC CCGTGCTGGA CTCCGACGGC TCCTTCTTCC TCTACAGCAA
      TGTAGCGGCA CCTCACCCTC TCGTTACCCG TCGGCCTCTT GTTGATGTTC TGGTGCGGAG GGCACGACCT GAGGCTGCCG AGGAAGAAGG AGATGTCGTT
                                        bpuAI
                                        bbsI                                      nlaIII                               sapI
        dsaI                             maeII                                    ppu10I                         mboII mnlI
        bsaJI          fnu4HI       xmnI mboII                                    nsiI/avaIII                    earI/ksp632I bslI
        hphI     bspMI bbvI         aspI700       nlaIII                sfaNI     mnlI
2601  GCTCACCGTG GACAAGAGCA GGTGGCAGCA GGGAACGTC TTCTCATGCT CCGTGATGCA TGAGGCTCTG CACAACCACT ACACGCAGAA GAGCCTCTCC
      CGAGTGGCAC CTGTTCTCGT CCACCGTCGT CCCCTTGCAG AAGAGTACGA GGCACTACGT ACTCCGAGAC GTGTTGGTGA TGTGCGTCTT CTCGGAGAGG
         scrFI                          styI
         nciI                           aciI
         mspI                 taqI      fnu4HI   sau96I
         hpaII                salI      sfiI ncoI haeIII/palI
         dsaV            rmaI hincII/hindII     haeIII/palI                    aluI
         cauII           maeI accI  scfI pstI   eaeI dsaI asuI                 fnu4HI
      bsmAI       sau96I  pleI      bsgI        aluI cfrI bsaJI                bbvI
                  haeIII/palI hinfI bspMI       hindIII bglI nlaIII            maeIII
2701  CTGTCTCCGG GTAAATGAGT GCGACGGCC CTGCAGAAGC TTGGCCCGCCA TGGCCCAACT TGTTTATTGC AGCTTATATAT GGTTACAAAT
      GACAGAGGCC CATTACTCA CGCTGCCGGG ATCTCAGCTG GACGTCTTCG AACCGGGCGGT ACCGGGTTGA ACAAATAACG TCGAATATTA CCAATGTTTA
```

FIG. 9J

```
                                                                                                    taqI[dam-]
                                                                                                    claI/bspI06[dam-]
                                                                                                    sau3AI
                                                                                                    mboI/ndeII[dam-]
                                                                                                    dpnI[dam+]
                                                                                                    dpnII[dam-]
                                                            rmaI                         nlaIII    alwI[dam-]
                                              bsmI         maeI
        sfaNI     apoI
2801 AAAGCAATAG CATCACAAAT TTCACAAATA AAGCATTTTT TTCACTGCAT TCTAGTTGTG GTTTGTCCAA ACTCATCAAT GTATCTTATC ATGTCTGGAT
     TTTCGTTATC GTAGTGTTTA AAGTGTTTAT TTCGTAAAAA AAGTGACGTA AGATCAACAC CAAACAGGTT TGAGTAGTTA CATAGAATAG TACAGACCTA
           tru9I                                                     rsaI
           xmnI                                                      csp6I
     sau3AI aseI/asnI/vspI       styI                                nlaIV
     mboI/ndeII[dam-]            ncoI                                kpnI
     dpnI[dam+]      fnu4HI  haeI                                    hgiCI
     dpnII[dam-]        bbvI  dsaI haeIII/palI                       banI                              aluI
     pvuI/bspCI mseI    hinPI    bsaJI                                asp718     mnlI                  pvuII
     mcrI  asp700   hhaI/cfoI  nlaIII          mnlI      mnlI         acc65I   ddeI aciI               nspBII
2901 CGATCGGGAA TTAATTCGGC GCAGCACCAT GGCCTGAAAT AACCCTGAAA AGAGAACTT GGTTAGGTAC CTTCTGAGGC GGAAAGAACC AGCTGTGGAA
     GCTAGCCCTT AATTAAGCCG CGTCGTGGTA CCGGACTTTA TTGGAGACTT TCTCCTTGAA CCAATCCATG GAAGACTCCG CCTTTCTTGG TCGACACCTT
                             nlaIV
                             scrFI                                                    scrFI
                             mvaI                                                     mvaI
                             ecoRII                           ppu10I                  ecoRII
                             dsaV                             nsiI/avaIII             dsaV
                             bstNI                            nlaIII
                             apyI[dcm+]                          sphI                           bstNI
                               bsaJI                            nspI sfaNI                      apyI[dcm+]
                                                                 nspHI                           sexAI              bsaJI
3001 TGTGTGTCAG TTAGGGTGTG GAAAGTCCCC AGCCTCCCCA GCAGGCAGAA GTATGCAAAG CATGCATCTC AATTAGTCAG CAACCAGGTG TGGAAAGTCC
     ACACACAGTC AATCCCACAC CTTTCAGGGG TCGGAGGGGT CGTCCGTCTT CATACGTTTC GTACGTAGAG TTAATCAGTC GTTGGTCCAC ACCTTTCAGG
       nlaIV                  sfaNI
       scrFI               ppu10I
       mvaI                nsiI/avaIII
       ecoRII                 nlaIII
       dsaV                    sphI
       bstNI              nspI
       apyI[dcm+]         nspHI                   aciI              aciI   fokI              aciI
3101 CCAGGCTCCC CAGCAGGCAG AAGTATGCAA AGCATGCATC TCAATTAGTC AGCAACCATA GTCCCGCCCC TAACTCCGCC CATCCCGCCC CTAACTCCGC
     GGTCCGAGGG GTCGTCCGTC TTCATACGTT TCGTACGTAG AGTTAATCAG TCGTTGGTAT CAGGGCGGGG ATTGAGGCGG GTAGGGCGGG GATTGAGGCG
```

FIG. 9K

```
                                                   nlaIII
                                                    styI
                                                    ncoI                                              fnu4HI
                            bslI dsaI                                                                 sfiI mnlI
         bsrI aciI          aciI bsaJI                                                                haeIII/palI
                                                                              haeIII/palI bsaJI bglI      ddeI              mnlI
                                                                              mnlI mnlI aciI   haeIII/palI                  mnlI
3201 CCAGTTCCGC CCATTCTCCG CCCATGGCT GACTAATTTT TTTTATTTAT GCAGAGGCCG AGGCCGCTC GGCCTCTGAG CTATTCCAGA AGTAGTGAGG
     GGTCAAGGCG GGTAAGAGGC GGGTACCGA CTGATTAAAA AAAATAAATA CGTCTCCGGC TCCGGCGAG CCGGAGACTC GATAAGGTCT TCATCACTCC fnu4HI                hinPI
                                 rmaI                        mcrI                 hhaI/cfoI
                                 styI                        eagI/xmaIII/eclXI    thaI
                                 bsaJI                       eaeI                 fnuDII/mvnI
                                 blnI                 bsrBI                bstUI                 bspMI
                                 avrII                xhoI notI   tru9I     bsh1236I       scfI
                                 haeIII/palI          paeR71 haeIII/palI   hinPI      tru9I  pstI
                                 stuI                   avaI fnu4HI   pacI     hhaI/cfoI mseI bsgI
                                 haeI                              mseI         bssHII  ahaIII/draI    maeIII
                                 mnlI maeI    aluI    mnlI aciI aciI  mseI ascI    swaI  sse8387I   aluI    bsrI
3301 AGGCTTTTTT GGAGGCCTAG GCTTTTGCAA AAAGCTGTTA CCTCGAGCGG CCGCTTAATT AAGGCGCGCC ATTTAAATCC TGCAGGTAAC AGCTTGGCAC
     TCCGAAAAAA CCTCCGGATC CGAAAACGTT TTTCGACAAT GGAGCTCGCC GGCGAATTAA TTCCGCGCGG TAAATTTAGG ACGTCCATTG TCGAACCGTG scrFI
                                    mvaI
                                    ecoRII
                                    dsaV
                                    bstNI
          haeIII/palI                apyI[dcm+]
          eaeI                       bsaJI                                                              aluI
          cfrI      maeII maeIII     maeIII         tru9I             fnu4HI                            pvuII         mboII
                          bsrI                      mseI              bbvI fokI                         nspBII        earI/ksp6321
3401 TGGCCGTGCT TTTACAACGT CGTGACTGGG AAAACCCTGG CGTTACCCAA CTTAATCGCC TTGCAGCACA TCCCCCCTTC GCCAGCTGGC GTAATAGCGA
     ACCGGCAGCA AAATGTTGCA GCACTGACCC TTTTGGGACC GCAATGGGTT GAATTAGCGG AACGTCGTGT AGGGGGGAAG CGGTCGACCG CATTATCGCT hinPI
                                                      hhaI/cfoI
                                                      nlaIV
                                                      narI
                   sau3AI                             kasI
                   mboI/ndeII[dam-]                   hinlI/acyI
                    dpnI[dam+]                        hgiCI
           sau96I   dpnII[dam-]                       haeII    aciI
           haeIII/palI                                banI    sfaNI
           asuI     pvuI/bspCI                        ahaII/bsaHI               sfaNI   aciI
     mnlI aciI    mcrI                       bglI                                                                    
3501 AGAGGCCCGC ACCGATCGCC CTTCCCAACA GTTGCGTAGC CTGAATGGCG AATGGCGCCT GATGCGGTAT TTTCTCCTTA CGCATCTGTG CGGTATTTCA
     TCTCCGGGCG TGGCTAGCGG GAAGGGTTGT CAACGCATCG GACTTACCGC TTACCGCGGA CTACGCCATA AAAGAGGAAT GCGTAGACAC GCCATAAAGT
```

FIG. 9L

```
                                       aciI
                                       fnu4HI                              fnu4HI
                        hinPI          aciI                                hinPI
                        hhaI/cfoI      thaI                                hhaI/cfoI
                        thaI           fnuDII/mvnI                         thaI
                        fnuDII/mvnI    bstUI              hinPI            fnuDII/mvnI
                        bstUI          bsh1236I           hhaI/cfoI hinPI  bstUI
              rsaI      scfI fnu4HI    tru9I bsh1236I                      bsh1236I       aciI
    aciI maeII   csp6I  bslI  aciI     mseI hhaI/cfoI     maeIII bbvI      maeIII         maeII
3601 CACCGCATAC GTCAAAGCAA CCATAGTACG CGCCTGTAG CGGCGCATTA AGCGCGGCGG GTGTGGTGGT TACGGCCAGC GTGACCGCTA CACTTGCCAG
     GTGGCGTATG CAGTTTCGTT GGTATCATGC GCGGACATC GCCGCGTAAT TCGCGCCGCC CACACCACCA ATGCGGCGTCG CACTGGCGAT GTGAACGGTC hinPI                                                                                        nlaIV
         hhaI/cfoI                                                 mspI                               hgiJII
         haeII                                                     hpaII                              bsp1286
    rmaI bsrBI                                                     naeI                               bmyI
    maeI aciI            mboII          maeII cfr10I       aluI                                       banII
3701 CGCCCTAGCG CCCGCTCCTT TGCTTTCTT CTCGCCGGCTT TCGCCGGTCA GCTCTAAATC GGGGGCTCCC TTTAGGGTTC
     GCGGGATCGC GGGCGAGGAA AGCGAAAGAA GAGCGGCCGAA AGCGGCCGAGT CGAGATTTAG CCCCCGAGGG AAATCCCAAG nlaIV
                 hgiCI taqI                       maeII    haeIII/palI                                    maeII
                 banI  mnlI                       draIII   sau96I                                         drdI
                                             hphI bsaAI    asuI
3801 CGATTAGTG CTTTACGGCA CCTCGACCCC AAAAAACTTG ATTTGGGTGA TGGTTCACGT AGTGGGCCAT CGCCCTGATA GACGGTTTTT CGCCCTTTGA
     GCTAATCAC GAAATGCCGT GGAGCTGGGG TTTTTTGAAC TAAACCCACT ACCAAGTGCA TCACCCGGTA CGCGGACTAT CTGCCAAAAA GCGGGAAACT bslI
        pleI     tru9I      pleI                     bslI  avaI
        hinfI    maeII mseI hinfI
3901 CGTTGGAGTC CACGTTCTTT AATAGTGGAC TCTTGTTCCA AACTGGAACA ACACTCAACC CTATCTCGGG CTATTCTTTT GATTATAAG GGATTTTGCC
     GCAACCTCAG GTGCAAGAAA TTATCACCTG AGAACAAGGT TGACCTTGT TGTGAGTTGG GATAGAGCCC GATAAGAAAA CTAAATATTC CCTAAAACGG thaI                                              hgiAI/aspHI
                                              fnuDII/mvnI                                       bsp1286
                                              bstUI                                             bsiHKAI
                   tru9I              tru9I                              maeII                  bmyI    ddeI
                   mseI         aluI  mseI    apoI tru9I                 tru9I                  apaLI/snoI rsaI
        haeIII/palI                           apoI bsh1236I mseI         mseI    sspI psp1406I  alw44I/snoI csp6I
4001 GATTTCGGCC TATTGGTTAA AAAATGAGCT GATTAACAA AAATTAACG CGAATTTAA CAAATATTA ACGTTTACAA TTTTATGGTG CACTCTCAGT
     CTAAAGCCGG ATAACCAATT TTTTACTCGA CTAAATTGT TTTAATTGC GCTTAAATT GTTTATAAT TGCAAATGTT AAAATACCAC GTGAGAGTCA
```

FIG. 9M

```
                                                                                    hinPI
                                                                                    hhaI/cfoI
                                                                                    thaI
                                                                                    fnuDII/mvnI
                                                              hinPI                 bstUI
                                            maeIII           fnu4HI                 nspBII bsh1236I
                                            maeII bsrI    nlaIII hhaI/cfoI          aciI   hgaI
                 aciI                       bsaAI tthlllI/aspI bbvI      aciI
                 fnu4HI    tru9I      aciI
                 sfaNI     mseI
4101 ACAATCTGCT CTGATGCCGC ATAGTTAAGC CAACTCCGCT ATCGCTACGT GACTGGGTCA TGGCTGCGCC CGACACCCG CCAACACCCG CTGACGCGCC
     TGTTAGACGA GACTACGGCG TATCAATTCG GTTGAGGCGA TAGCGATGCA CTGACCCAGT ACCGACGCGG GCTGTGGGC GGTTGTGGGC GACTGCGCGG thaI
                                                                                                        fnuDII/mvnI
                                                                                                        bstUI
                                                          scrFI                                         bsh1236I
                                                          nciI                                          hinPI
                     mspI                                 mspI                                          hhaI/cfoI
                     hpaII                       bsmAI            nspI                                  thaI
                     scrFI                       esp3I hpaII fnu4HI                                     fnuDII/mvnI
                     nciI    aciI                bslI   dsaV aluI nspHI                                 bstUI
                     dsaV sfaNI                       cauII bbvI nlaIII    mnlI hphI  hphI              bsh1236I
     drdI            cauII fokI      aluI maeIII
4201 CTGACGGGCT TGTCTGCTCC CGGCATCCGC TTACAGACAA GCTGTGACCG TCTCCGGAG CTGCATGTGT CAGAGGTTTT CACCGTCATC ACCGAAACGC
     GACTGCCCGA ACAGACGAGG GCCGTAGGCG AATGTCTGTT CGACACTGGC AGAGGCCCTC GACGTACACA GTCTCCAAAA GTGGCAGTAG TGGCTTTGCG maeII
                         mnlI                                                               hinlI/acyI
                         haeIII/palI                                                        ahaII/bsaHI
            mboII        sau96I                            nlaIII                           ddeI aatII
            bpuAI        asuI                 tru9I        rcaI
     mnlI   bbsI         ecoO109I/draII       mseI         bspHI
4301 GCGAGGCAGT ATTCTTGAAG ACGAAAGGGC CTCGTGATAC GCCTATTTT ATAGGTTAAT GTCATGATAA TAATGGTTTC TTAGACGTCA GGTGGCACTT
     CGCTCCGTCA TAAGAACTTC TGCTTTCCCG GAGCACTATG CGGATAAAA TATCCAATTA CAGTACTATT ATTACCAAAG AATCTGCAGT CCACCGTGAA nlaIV
             aciI
             thaI                                                      rcaI
             fnuDII/mvnI                                               bspHI
             bstUI                                                     bsrBI  bsmAI
             bsh1236I                                                  aciI   nlaIII                    sspI
             hinPI
             hhaI/cfoI
4401 TTCGGGAAA TGTGCGCGGA ACCCCTATTT GTTTATTTTT CTAAATACAT TCAAATATGT ATCCGCTCAT GAGACAATAA CCCTGATAAA TGCTTCAATA
     AAGCCCCTTT ACACGCGCCT TGGGGATAAA CAAATAAAAA GATTTATGTA AGTTTATACA TAGGCGAGTA CTCTGTTATT GGGACTATTT ACGAAGTTAT mboII
            earI/ksp632I                                           fnu4HI
                                                                   aciI                hphI
4501 ATATTGAAAA AGGAAGAGTA TGAGTATTCA ACATTTCCGT GTCGCCCTTA TTCCCTTTTT TGCGGCATTT TGCCTTCCTG TTTTTGCTCA CCCAGAAACG
     TATAACTTTT TCCTTCTCAT ACTCATAAGT TGTAAAGGCA CAGCGGGAAT AAGGGAAAAA ACGCCGTAAA ACGGAAGGAC AAAAACGAGT GGGTCTTTGC
```

FIG. 9N

```
                                                  hgiAI/aspHI
                                                  bsp1286
                                                  bsiHKAI
                              sau3AI                                     sau3AI nspBII        sau3AI
                              mboI/ndeII[dam-]                           mboI/ndeII[dam-]     mboI/ndeII[dam-]
                              dpnI[dam+] bmyI                            dpnI[dam+]           dpnI[dam+]
                              dpnII[dam-]                                dpnII[dam-]          dpnII[dam-]
                                                                         bstYI/xhoI           alwI[dam-]
                 eco57I         apaLI/snoI                               bsrI dpnII[dam-]                                                       mboII
        hphI     sfaNI mboII[dam-]  alw44I/snoI maeIII taqI alwI[dam-]   aciI bstYI/xhoI                                            sau3AI       mboI/ndeII[dam-]
4601 CTGGTGAAAG TAAAAGATGC TGAAGATCAG TTGGGTGCAC GAGTGGGTTA CATCGAACTG GATCTCAACA GCGGTAAGAT CCTTGAGAGT TTTCGCCCCG
     GACCACTTTC ATTTTCTACG ACTTCTAGTC AACCCACGTG CTCACCCAAT GTAGCTTGAC CTAGAGTTGT CGCCATTCTA GGAACTCTCA AAAGCGGGGC
                                                          scrFI
                                                          ncil
                                            aciI          mspI
                                            thaI          hpaII
                                            fnuDII/mvnI   dsaV
                                            bstUI         cauII
                                            bsh1236I      hinlI/acyI
                                            hinPI         hgaI                                                              aciI
                                            hhaI/cfoI     ahaII/bsaHI   bcgI      mcrI                                      fnu4HI
                                                                                                                  fnu4HI
                     hgiAI/aspHI                                                                                  bbvI      nlaIII
      maeII          bsp1286                                                                             maeIII
      psp1406I  tru9I       bsiHKAI                                                             nlaIII
      xmnI      bmyI        mseI                                            sfaNI  fokI nlaIII  sau3AI
      asp700    bmyI        ahaIII/draI                                                         mboI/ndeII[dam-]             sau3AI
4701 AAGAACGTTT TCCAATGATG AGCACTTTTA AAGTTCTGCT ATGTGGCGCG GTATTATCCC GTGATGACGC CGGGCAAGAG CAACTCGGTC GCCGCATACA
     TTCTTGCAAA AGGTTACTAC TCGTGAAAAT TTCAAGACGA TACACCGCGC CATAATAGGG CACTACTGCG GCCCGTTCTC GTTGAGCCAG CGGCGTATGT
                                                                                                          dpnI[dam+]        mboI/ndeII[dam-]
                                                                                                          dpnII[dam-]       dpnI[dam+]
              rsaI                                                                                        alwI[dam-]        dpnII[dam-]
              csp6I bsrI
         ddeI scaI hphI  maeIII                                                                                             fnu4HI
4801 CTATTCTCAG AATGACTTGG TTGAGTACTC ACCAGTCACA GAAAAGCATC TTACGGATGG CATGACAGTA AGAGAATTAT GCAGTGCTGC CATAACCATG
     GATAAGAGTC TTACTGAACC AACTCATGAG TGGTCAGTGT CTTTTCGTAG AATGCCTACC GTACTGTCAT TCTCTTAATA CGTCACGACG GTATTGGTAC
                                                         sau96I                                                  maeIII
                                                         avaII                                                   nlaIII
                          haeIII/palI                    asuI                                                    sau3AI
                          eaeI                           sau3AI                                                  mboI/ndeII[dam-]     sau3AI
                          cfrI                           mboI/ndeII[dam-]                                        dpnI[dam+]           mboI/ndeII[dam-]
                          fnu4HI                         dpnI[dam+]                                              dpnII[dam-]          dpnI[dam+]
                          aciI                           dpnII[dam-]                                 aluI aciI   alwI[dam-]           dpnII[dam-]
                                                         pvuI/bspCI
                                                         mcrI  mnlI                       nlaIII                                      dpnII[dam-]
4901 AGTGATAACA CTGGCGCCAA CTTACTTCTG ACAACGATCG GAGGACCGAA GCTTTTTTGC ACAACATGGG GGATCATGTA ACTCGCCTTG
     TCACTATTGT GACGCCGGTT GAATGAAGAC TGTTGCTAGC CTCCTGGCTT CGAAAAAACG TGTTGTACCC CCTAGTACAT TGAGCGGAAC
```

```
                                                       sau3AI
                                                       mboI/ndeII[dam-]
                                                       dpnI[dam+]    sau3AI
                                                       dpnII[dam-]   mboI/ndeII[dam-]   thaI
                                                       bstYI/xhoII   dpnI[dam+]         fnuDII/mvnI
                                                                     dpnII[dam-]        bstUI
                                       sau3AI          alwI[dam-]                       bsh1236I
                                       mboI/ndeII[dam-]                                 hinPI        fnu4HI
                                       dpnI[dam+]  mboI[dam-]                           hhaI/cfoI    bbvI
             hgaI                      dpnII[dam-]               bstYI/xhoII
             ddeI
5501 TTTTCGTTCCT ACTGAGCGTC AGACCCCGTA GAAAAGATCA AAGGATCTTC TTGAGATCCT TTTTTTCTGC GGTAATCTG CTGCTTGCAA ACAAAAAAAC
     AAAAGCAAGG TGACTCGCAG TCTGGGGCAT CTTTTCTAGT TTCCTAGAAG AACTCTAGGA AAAAAAGACG CCATTAGAC GACGAACGTT TGTTTTTTTG
                                       sau3AI
                                       mboI/ndeII[dam-]
                                       dpnI[dam+]
                                       dpnII[dam-]
                                       alwI[dam-]
                           aciI        mspI
                aciI       nspBII      hpaII         aluI                         bsrI         hinPI
      rmaI     maeI        bslI   haeI haeIII/palI                                maeIII  eco57I   hhaI/cfoI
5601 CACCGCTACC AGCGGTGGTT TGTTTGCCGG ATCAAGAGCT ACCAACTCTT TTTCCGAAGG TAACTGGCTT CAGCAGAGCG CAGATACCAA ATACTGTCCT
     GTGGCGATGG TCGCCACCAA ACAAACGGCC TAGTTCTCGA TGGTTGAGAA AAAGGCTTCC ATTGACCGAA GTCGTCTCGC GTCTATGGTT TATGACAGGA
                                                                                                    fnu4HI
                                                                scfI           mnlI           alwNI bbvI
                                                                     aciI                     bsrI  fnu4HI
                                                                     nspBII                   maeIII bbvI    bsrI
5701 TCTAGTGTAG CCGTAGTTAG GCCACCACTT CAAGAACTCT GTAGCACCGC CTACATACCT CGCTCTGCTA ATCCTGTTAC CAGTGGCTGC TGCCAGTGGC
     AGATCACATC GGCATCAATC CGGTGGTGAA GTTCTTGAGA CATCGTGGCG GATGTATGGA GCGAGACGAT TAGGACAATG GTCACCGACG ACGGTCACCG
                scrFI
                nciI                                                    aciI
                mspI                                                    nspBII
                hpaII                            mspI                   fnu4HI              hgiAI/aspHI
                dsaV          pleI               hpaII                  bbvI                bsp1286
                cauII         hinfI              bsaWI                  hinPI  mcrI         bsiHKAI
                              haeIII/palI        maeIII                 hhaI/cfoI           bmyI
                                                                                            apaLI/snoI
                                                                                            alw44I/snoI  aluI
5801 GATAAGTCGT GTCTTACCGG GTTGGACTCA AGACGATAGT TACCGGATAA GGCGCAGCGG TCGGGCTGAA CGGGGGGTTC GTGCACACAG CCCAGCTTGG
     CTATTCAGCA CAGAATGGCC CAACCTGAGT TCTGCTATCA ATGGCCTATT CCGCGTCGCC AGCCCGACTT GCCCCCCAAG CACGTGTGTC GGGTCGAACC
```

FIG. 9Q

```
                                   hinPI
                                   hhaI/cfoI                                              mspI
                                   haeII                                                  hpaII
           ddeI   scfI                                       aciI                         bslI      fnu4HI
5901 AGCGAAGCGAC CTACACCGAA CTGAGATACC TACAGGCGTGA GCATTGAGAA AGCGCCACGC TTCCCGAAGG GAGAAAGGCG GACAGGTATC CGGTAAGCGG  bsaWI  aciI
     TCGCTTGCTG GATGTGGCTT GACTCTATGG ATGTCGCACT CGTAACTCTT TCGCGGTGCG AAGGGCTTCC CTCTTTCCGC CTGTCCATAG GCCATTCGCC scrFI
                                        mvaI              scrFI
                                        ecoRII  mvaI
                                        dsaV    ecoRII
                                        bstNI   dsaV
              hinPI  mnlI               bsaJI   bstNI                                                             mnlI drdI   taqI
              hhaI/cfoI alul  aluI apyI[dcm+]   apyI[dcm+]                                                                   hgaI
6001 CAGGGTCGGA ACAGGAGAGC GCACGAGGGA GCTTCCAGGG GGAAACGCCT GGTATCTTTA TAGTCCTGTC GGGTTTCGCC ACCTCTGACT TGAGCGTCGA ACTCGCAGCT
     GTCCCAGCCT TGTCCTCTCG CGTGCTCCCT CGAAGGTCCC CCTTTGCGGA CCATAGAAAT ATCAGGACAG CCCAAAGCGG TGGAGACTGA ACTCGCAGCT haeIII/palI
                                                   haeIII/palI
                                                   fnu4HI  scrFI
                                                   aciI    mvaI
                                                           ecoRII
                                                   thaI bslI    dsaV                                             nlaIII
                                                   fnuDII/mvnI  bstNI bslI                                         nspI
                                                   bstUI        apyI[dcm+]                            haeIII/palI nspHI
                                                   bsh1236I     nlaIV  haeI                           haeI        aflIII
6101 TTTTTGTGAT GCTCCGTCAGG GGGGCGGAGC CTATGGAAAA ACGGCCAGCAA CGCGGCCTTT TTACGGTTCC TGGCCTTTTG CTGGCCTTTT GCTCACATGT
     AAAAACACTA CGAGCAGTCC CCCCGCCTCG GATACCTTTT TGCCGGTCGTT GCGCCGGAAA AATGCCAAGG ACCGGAAAAC GACCGGAAAA CGAGTGTACA fnu4HI
                                                                                                  bbvI pleI
                       nlaIV                                                    fnu4HI            hinPI hinfI
           sfaNI       aciI                                           bsrBI     bbvI              hhaI/cfoI
           tfiI                                                       aciI      aciI
           hinfI                                 aluI                 fnu4HI    mcrI
6201 TCTTTCCTGC GTTATCCCCT GATTCTGTGG ATAACCGTAT TACCGCCTTT GAGTGAGCTG ATACCGCTCG CCGCAGCCGA ACGACCGAGC GCAGCGAGTC
     AGAAAGGACG CAATAGGGGA CTAAGACACC TATTGGCATA ATGGCGGAAA CTCACTCGAC TATGGCGAGC GGCGTCGGCT TGCTGGCTCG CGTCGCTCAG
```

FIG. 9R

```
                                                                                          thaI
                                                                                          fnuDII/mvnI
                                                                                          bstUI
                                                                                          bsh1236I
                                                                                          hinPI
                                                                                          hhaI/cfoI
                                                                                          thaI
                                                                                          fnuDII/mvnI
                                                                                          bstUI                         tru9I     aluI
                                                                                          bsh1236I haeIII/palI          pvuII
                                                                         mnlI             bslI   eaeI  tfiI aseI/asnI/vspI            bsrI
                       sapI hinPI                              aciI      aciI   cfrI      hinfI   mseI   nspBII
                       mboII hhaI/cfoI
                       earI/ksp632I
       mnlI  aciI        haeII
6301 AGTGAGCGAG GAAGCGGAAG AGCGCCCAAT ACGCAAACCG CCTCTCCCCG CGCGGTTGGCC GATTCATTAA TCCAGCTGGC ACGACAGGTT TCCCGACTGG
     TCACTCGCTC CTTCGCCTTC TCGCGGGTTA TGCGTTTGGC GGAGAGGGGC GCGCCAACCGG CTAAGTAATT AGGTCGACCG TGCTGTCCAA AGGGCTGACC scrFI
                                                                                mvaI
                                                                                ecoRII
                                                                                dsaV
                                                                      nlaIV bstNI
                                                tru9I                 hgiCI apyI[dcm+]                        mspI
           hinPI       mseI       maeIII        mseI                  banI bsaJI                              hpaII
     aciI  hhaI/cfoI   aseI/asnI/vspI mnlI      aseI/asnI/vspI
6401 AAAGGGGGCA GTGAGCGCAA CGCAATTAAT GTGAGTTACC TCACTCATTA GGCACCCCAG GCTTTACACT TTATGCTTCC GGCTCGTATG TTGTGTGGAA
     TTTCGCCCGT CACTCGCGTT GCGTTAATTA CACTCAATGG AGTGAGTAAT CCGTGGGGTC CGAAATGTGA AATACGAAGG CCGAGCATAC AACACACCTT tru9I
                                                                   mseI
                                                                   aseI/asnI/vspI
                                                                   xmnI
           aciI                                            nlaIII  asp700
           bsrBI                                aluI                GAATTAA
6501 TTGTGAGCGG ATAACAATTT CACACAGGAA ACAGCTATGA CCATGATTAC GAATTAA
     AACACTCGCC TATTGTTAAA GTGTGTCCTT TGTCGATACT GGTACTAATG CTTAATT
```

>length: 6557

FIG. 10A

```
       aluI
       sstI
       sacI
       hgiJII
       hgiAI/aspHI
       ecl136II
       bsp1286
       bsiHKAI
       bmyI                    rmaI      tru9I
       banII                   maeI      mseI
    taqI                   speI     aseI/asnI/vspI                                                              thaI
                                                                                                                fnuDII/mvnJ
                                                                                                                bstUI
                                                                                              bslI              bsh1236I
                                                                                                                aciI maeIII
  1 TTCGAGCTCG CCCGACATTG ATTATTGACT AGTAATCAAT TACGGGTCA TTAGTTCATA GCCCATATAT GGAGTTCCGC GTTACATAAC
    AAGCTCGAGC GGGCTGTAAC TAATAACTGA TCAATAATTA ATGCCCCAGT AATCAAGTAT CGGGTATATA CCTCAAGGCG CAATGTATTG scrFI
              mvaI
              ecoRII
              dsaV
              aciI                          maeII
              bglI bstNI                    hinlI/acyI
              sau96I                        ahaII/bsaHI
              haeIII/palI                   aatII                     maeII              maeIII
              asuI apyI[dcm+]          aciI                                                    maeIII
101 TTACGGTAAA TGGCCCGCCT GGCTGACCGC CCAACGACCC CGGCCCATTG ACGTCAATAA TGACGTATGT TCCCATAGTA ACGCCAATAG GGACTTTCCA
    AATGCCATTT ACCGGGCGGA CCGACTGGCG GGTTGCTGGG GCCGGGTAAC TGCAGTTATT ACTGCATACA AGGGTATCAT TGCGGTTATC CCTGAAAGGT maeII                                                                                            .maeII
    hinlI/acyI                                                                                        hinlI/acyI
    ahaII/bsaHI                                                                                       ahaII/bsaHI
    aatII                         bglI                  rsaI                                          aatII
                                                        csp6I              ndeI
201 TTGACGTCAA TGGGTGGAGT ATTTACGGTA AACTGCCCAC TTGGCAGTAC ATCAAGTGTA TCATATGCCA CTATTGACGT CAATGACGGT
    AACTGCAGTT ACCCACCTCA TAAATGCCAT TTGACGGGTG AACCGTCATG TAGTTCACAT AGTATACGGT GATAACTGCA GTTACTGCCA scrFI
              mvaI
              ecoRII
         aciI
       bglI dsaV                          rsaI                          maeII                      nlaIII
       sau96I bstNI                       csp6I                         snaBI                styI
       haeIII/palI                                                          bsaAI                  ncoI
       asuI apyI[dcm+]  bsrI nlaIII                                                                dsaI hphI aciI
                                                                                              bsaJI      sfaNI
301 AAATGGCCCG CCTGGCATTA TGCCCAGTGA ACGGGCATGG GGACTTTCC TACTTGGCAG TACATCTACG TATTAGTCAT CGCTATTACC ATGTGATGC
    TTTACCGGGC GGACCGTAAT ACGGGTCATG TGCCCGTACC CCTGAAAGG ATGAACCGTC ATGTAGATGC ATAATCAGTA GCGATAATGG TACCACTACG
```

FIG. 10B

```
                                                        maeII
                                                        hinlI/acyI           nlaIV
                                 pleI                   ahaII/bsaHI          hgiCI
         rsaI        aciI        hinfI        bsmAI     aatII                banI
         csp6I
401 GGTTTTGGCA GTACATCAAT GGGCGTGGAT AGCGGTTTGA CTCACGGGGA TTTCCAAGTC TCCACCCCAT TGACGTCAAT GGGAGTTTGT TTTGGCACCA
    CCAAAACCGT CATGTAGTTA CCCGCACCTA TCGCCAAACT GAGTGCCCCT AAAGGTTCAG AGGTGGGGTA ACTGCAGTTA CCCTCAAACA AAACCGTGGT
                                                                                                      aluI
                                                                                                      sstI
                                                                                                      sacI
                                                                                                      hgiJII
                                                                                                      hgiAI/aspHI
                                                                                                      ecl136II
                                                                                                      bsp1286
                                                                                                      bsiHKAI
                                                                        rsaI                          bmyI
                                                                        csp6I       mnlI              banII
                        maeIII      aciI         hgaI       aciI
501 AAATCAACGG GACTTTCCAA AATGTCGTAA CAACTCCGCC CCATTGACGC TAGGCGTGTA CGGTGGGAGG TCTATATAAG CAGAGCTCGT
    TTTAGTTGCC CTGAAAGGTT TTACAGCATT GTTGAGGCGG GGTAACTGCG ATCCGCACAT GCCACCCTCC AGATATATTC GTCTCGAGCA
                                                                                          haeIII/palI
                                                                                          mcrI
                                                                                          eagI/xmaIII/eclXI
                                                                                          eaeI
                                                                                          cfrI
                                                                                          fnu4HI
                                                                                          aciI
                                                                                          thaI
                                                                                          fnuDII/mvnI
                      esp3I                              sau96I       sacII/sstII
              scrFI                                           avaII   nspBII
              mvaI bsmAI                                      asuI    kspI   scrFI
              ecoRII                                          nlaIV   dsaI   nciI
              dsaV                                    scrFI           bglI bslI   mspI
              bstNI  hinlI/acyI                       nciI     sau3AI mnlI bstUI
              apyI[dcm+]                              mspI     mboI/ndeII[dam-] hpaII
              sau3AI gsuI/bpmI                 mboII  hpaII    dpnI[dam+]    bsaJI dsaV
              mboI/ndeII[dam-]                 bpuAI  dsaV     dpnII[dam-]   bsh1236I
              dpnI[dam+] hgaI  ahaII/bsaHI     bbsI   cauII    alwI[dam-]    aciI  cauII
              dpnII[dam-]               mnlI
601 TTAGTGAACC GTCAGATCGC CTGAGACGAC CATCCACGCT GTTTTGACCT CCATAGAAGA CACCGGACCT GATCCAGCCT CGGCGGCCGG GAACGGTGCA
    AATCACTTGG CAGTCTAGCG GACTCTGCGG GTAGGTGCGA CAAAACTGGA GGTATCTTCT GTGGCCTGGA CTAGGTCGGA GCCGCCGGCC CTTGCCACGT
```

FIG. 10C

```
            tfiI                                                                                       fnu4HI
    aciI                                                              bstXI                           aciI
    thaI hinfI                              aciI            sau96I    styI                            thaI
    fnuDII/mvnI         maeII rsaI          pleI scfI haeIII/palI                                     fnuDII/mvnI tru9I
    bstUI               maeIII csp6I        scfI hinfI asuI  bsaJI                                    bstUI         mseI
    bsh1236I                                                                                          bsh1236I      aseI/asnI/vspI
701 TTGGAACGCG GATTCCCCGT GCCAAGAGTG ACGTAAGTAC CGCCTATAGA GTCTATAGGC CCACCCCCTT GGCTTCGTTA GAACGCGGCT ACAATAATA
    AACCTTGCGC CTAAGGGGCA CGGTTCTCAC TGCATTCATG GCGGATATCT CAGATATCCG GGTGGGGGAA CCGAAGCAAT CTTGCGCCGA TGTTAATTAT sau96I
                                                                                                avaII
                                                                                                asuI
                                                                                                scrFI
                                                                                                mvaI
                                                                                                ecoRII
                                                                                                dsaV
                                                                                                bstNI
                                                                                                apyI[dcm+]
                       maeIII              scfI        fokI                                     bslI bsaJI
                       hphI    scfI
801 CATAACCTTA TGTATCATAC ACATACGATT TAGGTGACAC TATAGAATAA CATCCACTTT GCCTTTCTCT CCACAGGTGT CCACTCCCAG GTCCAACTGC
    GTATTGGAAT ACATAGTATG TGTATGCTAA ATCCACTGTG ATATCTTATT GTAGGTGAAA CGGAAAGAGA GGTGTCCACA CAGGTTGACG hinII/acyI
                                              ahaII/bsaHI
                                              aatII
                                     thaI                        taqI[dam-]
                                     fnuDII/mvnI                 sau3AI                         bsmAI
                                     bstUI                       mboI/ndeII[dam-]               esp3I
                    aluI taqI        aciI maeII                  dpnI[dam+]         tth111I/aspI
    mnlI            hindIII          hphI bsh1236I       taqI    dpnII[dam-] taqI   hgaI        sfaNI
    bsaJI  ddeI     claI/bsp106
901 ACCTCGGTTC TAAGCTTATC GATATGAAAA AGCCTGAACT CACCGCGACG TCTGTCGAGA AGTTTCTGAT CGAAAAGTTC GACAGGTCT CCGACCTGAT
    TGGAGCCAAG ATTCGAATAG CTATACTTTT TCGGACTTGA GTGGCGCTGC AGACAGCTCT TCAAAGACTA GCTTTTCAAG CTGTCGCAGA GGCTGGACTA hinPI
              aluI                   tfiI                                                       fnu4HI
              fnu4HI                 hinfI            taqI                                      bbvI
    mnlI      bbvI    mnlI mboII     aluI             mnlI              aciI                    aluI hhaI/cfoI
1001 GCAGCTCTCG GAGGGCGAAG AATCTCGTGC TTTCAGCTTC GATGTAGGAG TGTCCTGCGG GTAAATAGCT GCGCCGATGG TTTCTACAAA
     CGTCGAGAGC CTCCCGCTTC TTAGAGCACG AAAGTCGAAG CTACATCCTC ACAGGACGCC CATTTATCGA CGCGGCTACC AAAGATGTTT
```

FIG. 10D

```
                        hinPI
                        hhaI/cfoI      mspI
                            thaI       hpaII
                            aciI       mroI
                       haeIII/palI     bspMII
             mcrI fnuDII/mvnI          bspEI
             eagI/xmaIII/eclXI bsaWI
             eaeI bstUI       tfiI
    sau3AI   cfrI bsh1236I hinfI                              ecoRI
    mboI/ndeII[dam-]
    dpnI[dam+]   sfaNI fnu4HI bslI   accIII                    apoI                                              sfaNI  aciI
    dpnII[dam-]
1101 GATCGTTATG TTTATCGGCA CTTTGCATCG GCCGCGCTCC CGATTCCGGA AGTGCTTGAC ATTGGGGAAT TCAGCGAGAG CCTGACCTAT TGCATCTCCC
     CTAGCAATAC AAATAGCCGT GAAACGTAGC CGGCGCGAGG GCTAAGGCCT TCACGAACTG TAACCCCTTA AGTCGCTCTC GGACTGGATA ACGTAGAGGG mcrI
                                                                                                             eagI/xmaIII/eclXI
                                                                                                             eaeI
                                                                                                             fnu4HI
                                                                 styI                    sau3AI  aciI
                                                                 ncoI                    mboI/ndeII[dam-]
                                                       thaI      dsaI                    dpnI[dam+]          sau3AI
                                                       fnuDII/mvnI                       dpnII[dam-]         mboI/ndeII[dam-]
                                                fnu4HI  bstUI  haeIII/palI                                   dpnI[dam+]
                                                bbvI  mcrI     bsh1236I bsaJI sfaNI      fnu4HI              dpnII[dam-]
                                                scfI  mspI     hpaII  mnlI nlaIII        pvuI/bspCI haeIII/palI
                                          nspBII pstI  cfr10I aciI haeI foki mcrI bbvI cfrI dpnII[dam-]
                                          aciI  bsgI   AGCCGGTCGC GGAGGCCATG GATGGCATCG CTGCGGCCGA
1201 GCCGTGCACA GGGTGTCACG TTGCAACACC TGCCTGAAAC CGAACTGCCC GCTGTTCTGC AGCCGGTCGC GGAGGCCATG GATGGCATCG CTGCGGCCGA
     CGGCACGTGT CCCACAGTGT AACGTTGTGG ACGGACTTTG GCTTGACGGG CGACAAGACG TCGGCCAGCG CCTCCGGTAC CTACGCTAGC GACGCCGGCT thaI    sau3AI
                                  sau96I                                            fnuDII/mvnI        nlaIII
                                  avaII                                             bstUI   mboI/ndeII[dam-]
                                  asuI                                              bsh1236I  dpnI[dam+]
                            sau96I rsrII/cspI                                       hinPI    dpnI[dam-]
                      aciI  haeIII/palI aciI  tfiI                                  ndeI hhaI/cfoI  alwI[dam-]
              ddeI    bsrBI asuI  cpoI   hinfI                         nlaIII
1301 TCTTAGCCAG ACGAGCGGGT TCGCCCATT CGGACCGCAA GCCTGGCGTT GGAATCGGTC AATACACTAC ATGGCGTGAT TTCATATGCG CGATTGCTGA TCCCCATGTG
     AGAATCGGTC TGCTCGCCCA AGCCGGGTAA GCCTGGCGTT CCTTAGCCAG GCCTGGCGTT CCTTAGCCAG TTATGTGATG TACCGCACTA AAGTATACGC GCTAACGACT AGGGGTACAC draIII
                                hinPI                                                                                  nlaIV
                                hhaI/cfoI                                                                              hgiCI
                                thaI                                                     bsaJI                         banI
                                fnuDII/mvnI                                               haeIII/palI                  mspI
                            tth111I/aspI  bstUI                                sfaNI      sau96I         bslI          hpaII
               bsrI   drdI  hgaI     bsh1236I  taqI    aluI                    asuI mnlI                 hpaII
1401 TATCACTGGC AAACTGTGAT GGACGACACC GTCAGTGCGT CCGTCGCGCA GGCTCTCGAT GAGCTGATGC TTTGGGCCGA GGACTGCCCC GAAGTCCGGC
     ATAGTGACCG TTTGACACTA CCTGCTGTGG CAGTCACGCA GGCAGCGCGT CCGAGAGCTA CTCGACTACG AAACCCGGCT CCTGACGGGG CTTCAGGCCG
```

FIG. 10E

```
                                                                                                       fnu4HI
                                                                                                       thaI
                                                                                                       fnuDII/mvnI
                                                                                                       bstUI
                                                                                                       bsh1236I
                                                                                                       sacII/sstII
                                                                                                       nspBII
                                                                                                       kspI
                                                                                                       dsaI
                                                                                                       bsaJI
                                                                                                       aciI
                                                                                                       fnu4HI
                                                                                                       sau3AI aciI
                                                                                                       mboI/ndeII[dam-]
                                                                                                       dpnI[dam+]
                                                                                             tfiI bsII  dpnII[dam-]
                                                            gsuI/bpmI                        hinfI     alwI[dam-]
              aciI                         aciI       bsrI    mnlI
              fnu4HI                       nspBII
              haeIII/palI
              eaeI  aciI
      aciI    cfrI  nspBII
      thaI
      fnuDII/mvnI
      hgiAI/aspHI
      bsp1286
      bsiHKAI
      bmyI bstUI
      apaLI/snoI
      alw44I/snoI
      mnlI  bsh1236I   nlaIV
1501  ACCTCGTGCA CGCGGATTTC GGCTCCAACA ATGTCCTGAC GGACAATGGC CGCATAACAG CGGTCATTGA CTGGAGCGAG GCGATGTTCG GGGATTCCCA
      TGGAGCACGT GCGCCTAAAG CCGAGGTTGT TACAGGACTG CCTGTTACCG GCGTATTGTC GCCAGTAACT GACCTCGCTC CGCTACAAGC CCCTAAGGGT mspI
                                                                          hpaII
                                                                          mroI
                                                                          bspMII
                                                                          bspEI
                                                   dsaI                   bsaWI
                                                   haeIII/palI            fokI
                                   mboII mnlI bsaJI              rsaI  aciI  sfaNI      aluI
              mnlI  gsuI/bpmI                             fnu4HI  csp6I bsrBI mnlI accIII
      mnlI    mboII                                       bbvI   maeII  taqI  mnlI accIII
1601  ATACGAGGTC GCCAACATCT TCTTCTGGAG GCCGTGGTTG GCTTGTATGG AGCAGCAGAC GTACTTCGAG CGGAGGCATC CGGAGCTTGC AGGATCGCCG
      TATGCTCCAG CGGTTGTAGA AGAAGACCTC CGGCACCAAC CGAACATACC TCGTCGTCTG CATGAAGCTC GCCTCCGTAG GCCTCGAACG TCCTAGCGGC scrFI
      nciI
      mspI
      hpaII                                                            aluI
      dsaV                                                             fnu4HI                     hinPI    hgaI
      cauII             aciI                  aluI  hincII/hindII taqI  sfaNI           bbvI     hhaI/cfoI taqI  drdI
      nlaIV                                                                                                      sfaNI
1701  CGGCTCCGGG CGTATATGCT CCGCATTGGT CTTGACCAAC TCTATCAGAG CTTGGTTGAC GGCAATTTCG ATGATGCAGC TTGGGCGCAG GGTCGATGCG
      GCCGAGGCCC GCATATACGA GGCGTAACCA GAACTGGTTG AGATAGTCTC GAACCAACTG CCGTTAAAGC TACTACGTCG AACCCGCGTC CCAGCTACGC
```

FIG. 10F

```
           nlaIV                                                              haeIII/palI
         mspI                                                               mcrI
       hpaII    scrFI                                                     eagI/xmaIII/eclXI
       bsll     ncil                                                      eael
     mroI      mspI                                                       cfrI
     bspMII   hpaII                                                       fnu4HI
     bspEI[dam-]                                                          aciI
     bsaWI   dsaV                                                         thaI
     accIII[dam-]                                                         fnuDII/mvnI
     sau3AI     cauII                                                     bstUI
     mboI/ndeII[dam-]                                            bsh1236I   sau96I              rsaI
     dpnI[dam+]                                           rsaI   hinPI     avaII               csp6I
     dpnII[dam-]                                          csp6I  hhaI/cfoI asuI                scaI
     alwI[dam-]                                  aciI
1801 ACGCAATCGT CCGATCCCGA GCCGGACTG TCGGGCGTAC ACAAATCGCC CGCAGAAGCG CGGCCGTCTG GACCGGATGGC TGTGTAGAAG TACTCGCCGA
     TGCGTTAGCA GGCTAGGGCT CGGCCCTGAC AGCCCGCATG TGTTTAGCGG GCGTCTTCGC GCCGGCAGAC CTGGCTACCG ACACATCTTC ATGAGCGGCT
                                                                                      scrFI
                                                                                      nciI
                                                                                      mspI
                                                                                      hpaII
                                                                                      dsaV
                                                                              xmaI/pspAI
                                                                                      smaI
                                                                                      scrFI
                                                                                      nciI
                                                                                      dsaV
                                                                                      cauII
                                                                                      bsaJI
                                                                                      avaI
                                                                                      bsaJI
                                                                              sau3AI
                                                                              mboI/ndeII[dam-]
                                                                              dpnI[dam+]
                                                                              dpnII[dam-]
                                                                              alwI[dam-]
                                                                              nlaIV  cauII                      sau96I
                                                                              bstYI/xhoII                 aciI  haeIII/palI
                                                                mcrI          bamHI bsaJI ecoRI           fnu4HI   asuI
                                                                bslI          alwI[dam-]    apoI          bglI   nlaIII
                                                        sfaNI                                             sfiI   styI
                                                                                                          eaeI   ncoI
                                                                                                          cfrI   dsaI
        hinII/acyI                                                                                   taqI haeIII/palI
        hgaI        mnlI                                                                             claI/bsp106 bsaJI
        ahaII/bsaHI  bsaJI
1901 TAGTGGAAAC CGACGCCCCA GCACTCGTCC GAGGGCAAAG GAATAGAGTA GATGCCGACC GAAGGATCCC CGGGGAATTC AATCGATGGC CGCCATGGCC
     ATCACCCTTTG GCTGCGGGGT CGTGAGCAGG CTCCCGTTTC CTTATCTCAT CTACGGCTGG CTTCCTAGGG GCCCCTTAAG TTAGCTACCG GCGGTACCGG
```

FIG. 10G

```
             aluI                                                                        rmaI
             fnu4HI                                                                      bsmI maeI
             bbvI            maeIII           sfaNI     apoI
2001 CAACTTGTTT ATTGCAGCTT ATAATGGTTA CAAATAAAGC AATAGCATCA CAAATTTCAC AAATAAAGCA TTTTTTTCAC TGCATTCTAG TTGTGGTTTG
     GTTGAACAAA TAACGTCGAA TATTACCAAT GTTTATTTCG TTATCGTAGT GTTTAAAGTG TTTATTTCGT AAAAAAAGTG ACGTAAGATC AACACCAAAC sau3AI
                                       mboI/ndeII[dam-]
                                       dpnI[dam+]
                                       dpnII[dam-]
                                       pvuI/bspCI
                                       mcrI
                                       taqI[dam-] tru9I                haeIII/palI
                                       claI/bsp106[dam-]                haeI
                                       sau3AI     mseI         fnu4HI styI
                                       mboI/ndeII[dam-]        bbvI    ncoI
                                       dpnI[dam-]  xmnI        hinPI   dsaI
                                       dpnII[dam-] aseI/asnI/vspI      bsaJI
                   nlaIII     alwI[dam-] asp700     hhaI/cfoI nlaIII      mnlI      mnlI
2101 TCCAAACTCA TCAATGTATC TTATCATGTC TGGATCGATC GGGAATTAAT TCGGCGCAGC ACCATGGCCT GAAATAACCT CTGAAAGAGG AACTTGGTTA
     AGGTTTGAGT AGTTACATAG AATAGTACAG ACCTAGCTAG CCCTTAATTA AGCCGCGTCG TGGTACCGGA CTTTATTGGA GACTTTCTCC TTGAACCAAT nlaIV                                   sfaNI
     rsaI                                                    scrFI                                     ppu10I
     csp6I                                                   mvaI                                   nsiI/avaIII
     nlaIV                                                   ecoRII                                    nlaIII
     kpnI                                                    dsaV                                      sphI
     hgiCI                                                   bstNI                                     nspI
     banI             aluI                                   apyI[dcm+]                                nspHI
     asp718   mnlI    pvuII                                  bsaJI
     acc65I   ddeI    aciI    nspBII
2201 GGTACCTTCT GAGGCGGAAA GAACCAGCTG TGGAATGTGT GTCAGTTAGG GTGTGGAAAG TCCCCAGGCT CCCCAGCAGG CAGAAGTATG CAAAGCATGC
     CCATGGAAGA CTCCGCCTTT CTTGGTCGAC ACCTTACACA CAGTCAATCC CACACCTTTC AGGGGTCCGA GGGGTCGTCC GTCTTCATAC GTTTCGTACG nlaIV
                    scrFI                             ppu10I
                    mvaI                              nsiI/avaIII
                    ecoRII                               nlaIII
                    dsaV
                    bstNI                                     sphI
                    apyI[dcm+]                                nspI sfaNI
           sexAI    bsaJI                                         nspHI                                     aciI
2301 ATCTCAATTA GTCAGCAACC AGGTGTGGAA AGTCCCCAGG CTCCCCAGCA GGCAGAAGTA TGCAAAGCAT GCATCTCAAT TAGTCAGCAA CCATAGTCCC
     TAGAGTTAAT CAGTCGTTGG TCCACACCTT TCAGGGGTCC GAGGGGTCGT CCGTCTTCAT ACGTTTCGTA CGTAGAGTTA ATCAGTCGTT GGTATCAGGG
```

FIG. 10H

```
                                                                                                    fnu4HI
                                                                                                    bglI
                                                                                                   sfiI
                                                                                                   haeIII/palI
                                                                   nlaIII                        mnlI
                                                                   styI                       haeIII/palI
                                                                   ncoI                     mnlI bsaJI aciI
                 aciI                  bsrI                    bslI dsaI
           aciI fokI              aciI        aciI             aciI bsaJI
2401 GCCCCTAACT CCGCCCATCC CGCCCCTAAC TCCGCCCAGT TCCGCCCATT CTCCGCCCCA TGGCTGACTA ATTTTTTTTA TTTATGCAGA GGCCGAGGCC
     CGGGGATTGA GGCGGGTAGG GCGGGGATTG AGGCGGGTCA AGGCGGGTAA GAGGCGGGGT ACCGACTGAT TAAAAAAAAT AAATACGTCT CCGGCTCCGG scrFI
                                                                                          nciI
                                                                                          mspI
                                                                                          hpaII
                                                                                          dsaV
                                                                                        haeIII/palI
                                                          styI                         mcrI
                                                          bsaJI                        eagI/xmaIII/eclXI
                                                          blnI                         eaeI
                                                        haeIII/palI           rmaI      cfrI
      haeIII/palI                                      stuI rmaI             maeI     mspI cauII
    mnlI      ddeI                    mnlI              haeI maeI           nheI      hpaII
    bsaJI mnlI   aluI              mnlI               mnlI avrII           aluI aluI
2501 GCCTCGGCCT CTGAGCTATT CCAGAAGTAG TGAGGAGGCT TTTTTGGAGG CCTAGGCTTT TGCAAAAAGC TAGCTTATCC GGCCGGGAAC GGTGCATTGG
     CGGAGCCGGA GACTCGATAA GGTCTTCATC ACTCCTCCGA AAAAACCTCC GGATCCGAAA ACGTTTTTCG ATCGAATAGG CCGGCCCTTG CCACGTAACC tfiI
       hinfI
     aciI                                                                                 fnu4HI
    thaI                                                                                  aciI
    fnuDII/mvnI                                                    bstXI                 thaI
    bstUI                               aciI           scfI  sau96I    styI             fnuDII/mvnI  tru9I
    bsh1236I            pleI        rsaI           pleI     haeIII/palI                 bstUI        mseI
                        hinfI       csp6I  scfI    hinfI    asuI       bsaJI            bsh1236I   aseI/asnI/vspI
2601 AACGCGGATT CCCCGTGCCA AGAGTCAGGT AAGTACCGCC TATAGAGTCT ATAGGCCCAC CCCCTTGGCT TCGTTAGAAC GCGGCTACAA TTAATACATA
     TTGCGCCTAA GGGGCACGGT TCTCAGTCCA TTCATGGCGG ATATCTCAGA TATCCGGGTG GGGGAACCGA AGCAATCTTG CGCCGATGTT AATTATGTAT
```

FIG. 10I

```
                                                                                                    sau96I
                                                                                                    avaII
                                                                                                    asuI
                                                                                                    scrFI
                                                                                                    mvaI
                                                                                                    ecoRII                    rmaI
                                                                                                    dsaV              thaI    maeI
                                                                                                    bstNI             fnuDII/mvnI
                                                                                                    apyI[dcm+]             bstUI  nheI
                                                                         bslI bsaJI                 mnlI   bsh1236I alu1
                                                                                                    bsaJI nruI   aluI
       sau3AI
       mboI/ndeII[dam-]
       dpnI[dam+]
       dpnII[dam-]
       alwI[dam-]
       taqI[dam-]
       claI/bsp106[dam-]
       sau3AI
       mboI/ndeII[dam-]
       dpnI[dam+]
       dpnII[dam-]
       alwI[dam-]                    fokI
2701 ACCTTTTGGA TCGATCCTAC TGACACTGAC ATCCACTTTT TCTTTTTCTC CACAGGTGTC CACTCCCAGG TCCAACTGCA CCTCGGTTCG CGAAGCTAGC
     TGGAAAACCT AGCTAGGATG ACTGTGACTG TAGGTGAAAA AGAAAAAGAG GTGTCCACAG GTGAGGGTCC AGGTTGACGT GGAGCCAAGC GCTTCGATCG nlaIII
                             styI
                             pflMI
                             ncoI
              sfaNI   ecoRI  dsaI                                                     rsaI                aluI
              fnu4HI taqI apoI  bslI fokI              rmaI              gsuI/bpmI                  pvuII tth111I/aspI
              bbvI claI/bsp106  bsaJI    nlaIII fokI   maeI              bsrI  csp6I    ecoRV nspBII  bsrI
2801 TTGGGCTGCA TCGATTGAAT TCCACCATGG GATGGTCATG TATCATCCTT TTTCTAGTAG CAACTGCAAC TGGAGTACAT TCAGATATCC AGCTGACCCA
     AACCCGACGT AGCTAACTTA AGGTGGTACC CTACCAGTAC ATAGTAGGAA AAAGATCATC GTTGACGTTG ACCTCATGTA AGTCTATAGG TCGACTGGGT aluI
       sstI
       sacI
       hgiJII
       hgiAI/aspHI
       ecl136II
       bsp1286
       bsiHKAI
       bmyI                         hphI
       banII                        maeIII  bspMI
       avaI       aciI    mnlI      bstEII  hphI    bsrI         taqI       hphI  aluI  nlaIII   bsrIII
2901 GTCCCGAGC TCCCTGTCCG CCTCTGTGGG CGATAGGGTC ACCATCACCT GCCGTGCCAG TCAGAGCGTC GATTACGATG GTGATAGCTA CATGAACTGG
     CAGGGCTCG AGGGACAGGC GGAGACACCC GCTATCCCAG TGGTAGTGGA CGGCACGGTC AGTCTCGCAG CTAATGCTAC CACTATCGAT GTACTTGACC
```

FIG. 10J

```
                                                                                         mspI
                                                                                         hpaII
                                                                                         bslI
                                                                              sau3AI      bsaWI
                                                                              mboI/ndeII[dam-]
                                                    gsuI/bpmI                 dpnI[dam+]
                                                    scrFI
                                                    mvaI          dpnII[dam-]                       styI
                                            haeIII/palI                  alwI[dam-]                 bsaJI
                                                    ecoRII                    nlaIV                 rsaI
                                      fnu4HI        dsaV                      bstYI/xhoI            csp6I
                                              aciI  bstNI                           bamHI           nlaIV
                                      thaI mnlI     apyI[dcm+]                            alwI[dam-] kpnI
                             scrFI    fnuDII/mvnI         pleI                                      hgiCI
                             mvaI         bstUI  rsaI pleI gsuI/bpmI                                banI
                             ecoRII       bsh1236I csp6I hinfI hinfI                                asp718
                             dsaV                                                                   acc65I
                             bstNI  aluI                                sau3AI
                             apyI[dcm+]                                 mboI/ndeII[dam-]
                                                                        dpnI[dam+]
                                                                             dpnII[dam-]
                                                                                  alwI[dam-]
                                                                                       nlaIV
                                                                                       bstYI/xhoI
                                                                                       bamHI rsaI
                                                                                       mnlI  csp6I
                                                                                       maeIII alwI[dam-]
3001 TATCAACAGA AACCAGGAAA AGCTCCGAAA CTACTGATTT ACGCGGCCTC GTACCTGGAG TCTGGAGTCC CTTCTCGCTT CTCTGGATCC GGTTCTGGAA
     ATAGTTGTCT TTGGTCCTTT TCGAGGCTTT GATGACTAAA TGCGCCGGAG CATGGACCTC AGACCTCAGG GAAGAGCGAA GAGACCTAGG CCAAGACCCT fnu4HI mboII
                                    bbvI   bpuAI
                                    scfI   bbsI
                                    pstI  mspI
                                    bsgI  hpaII
                                              mboII
                                              bpuAI   aciI
                            fnu4HI            bbsI    mboII
3101 CGGATTTCAC TCTGACCATC AGCAGTCTGC AGCCGGAAGA CTTCGCAACT TATTACTGTC AGCAAAGTCA CGAGGATCCG TACACATTTG GACAGGGTAC
     GCCTAAAGTG AGACTGGTAG TCGTCAGACG TCGGCCTTCT GAAGCGTTGA ATAATGACAG TCGTTTCAGT GCTCCTAGGC ATGTGTAAAC CTGTCCCATG sau3AI
     mboI/ndeII[dam-]
     dpnI[dam+]         fnu4HI                                                                      mnlI
     dpnII[dam-]        bbvI
3201 CAAGGTGGAG ATCAAACGAA CTGTGGCTGC ACCATCTGTC TTCATCTTCC CGCCATCTGA TGAGCAGTTG AAATCTGGAA CTGCCCTCTGT TGTGTGCCTG
     GTTCCACCTC TAGTTTGCTT GACACCGACG TGGTAGACAG AAGTAGAAGG GCGGTAGACT ACTCGTCAAC TTTAGACCTT GACGGAGACA ACACACGGAC scrFI
                                                                                  mvaI
                                                                                  ecoRII
                                                                                  dsaV
                       haeIII/palI                                                bstNI
               xmnI    haeI  rsaI                                                 apyI[dcm+]
               asp700  mnlI  csp6I                             mnlI     maeIII bsaJI         maeIII
3301 CTGAATAACT TCTATCCCAG AGAGGCCAAA GTACAGTGGA AGGTGGATAA CGCCCTCCAA TCGGGTAACT CCCAGGAGAG TGTCACAGAG CAGGACAGCA
     GACTTATTGA AGATAGGGTC TCTCCGGTTT CATGTCACCT TCCACCTATT GCGGGAGGTT AGCCCATTGA GGGTCCTCTC ACAGTGTCTC GTCCTGTCGT
```

FIG. 10K

```
                                                                                                    sstI
                                                                                                    sacI
                                                                                                    hgiJII
                                                                                                    hgiAI/aspHI
                                                                                                    ecl136II
                                                                                                    bsp1286
                                                                                                    bsiHKAI
                                                                                                    bmyI
                                                                                                    haeIII/palI
                                                                                                    sau96I alUI
                                                                                                    asuI banII
                            ddeI                                                                    eco0109I/draII
                            celII/espI                                                        hphI
                            bpu1102I                                              accI         maeIII  alwNI  ddeI
         scfI mnlI  ddeI fnu4HI  hgaI              TGACGCTGAG CAAAGCAGAC TACGAGAAAC ACAAAGTCTA CGCCTGCGAA GTCACCCATC AGGGCCTGAG
              scfI  ddeI  bbvI  fnu4HI             ACTGCGACTC GTTTCGTCTG ATGCTCTTTG TGTTTCAGAT GCGGACGCTT CAGTGGGTAG TCCCGGACTC
3401 AGGACAGCAC CTACAGCCTC AGCAGCACCC
     TCCTGTCGTG GATGTCGGAG TCGTCGTGGG sau96I
                                                              nlaIII
                                                              aciI   haeIII/palI
                                                              fnu4HI asuI
                                                              bglI styI                            aluI
                                                              sfiI ncoI                            fnu4HI
                                        aluI                  eaeI dsaI                            bbvI
                                        hindIII               cfrI bsaJI                 maeIII
              maeIII    aluI            tru9I        taqI haeIII/palI
3501 CTCGCCCGTC ACAAAGAGCT TCAACAGGGG AGAGTGTTAA GCTTCGATGG CCGCCATGGC CCAACTTGTT TATTGCAGCT TATAATGGTT ACAAATAAAG
     GAGCGGGCAG TGTTTCTCGA AGTTGTCCCC TCTCACAATT CGAAGCTACC GGCGGTACCG GGTTGAACAA ATAACGTCGA ATATTACCAA TGTTTATTTC sau3AI
                                                                                                    mboI/ndeII[dam-]
                                                                                                    dpnI[dam+]
                                                                                                    dpnII[dam-]
                                                                                                    pvuI/bspCI
                                                                                                    mcrI
                                                                                                    taqI[dam-]
                                                                                                    claI/bsp106[dam-]
                                                                                                    sau3AI
                                                                                                    mboI/ndeII[dam-]
                                          rmaI                                                      dpnI[dam+]
             sfaNI   apoI                 bsmI maeI                                        nlaIII   dpnII[dam-]  alwI[dam-]
3601 CAATGCGATT ACAAATTTCA CAAATAAAGC ATTTTTTTCA CTGCATTCTA GTTGTGGTTT GTCCAAACTC ATCAATGTAT CTTATCATGT CTGGATCGAT
     GTTATCGTAG TGTTTAAAGT GTTTATTTCG TAAAAAAAGT GACGTAAGAT CAACACCAAA CAGGTTTGAG TAGTTACATA GAATAGTACA GACCTAGCTA
```

```
                                                                                                              scrFI
                                                                                                              mvaI
                                                                                                              ecoRII
                      styI                                                                                    dsaV
                      bsaJI                                                                                   bstNI
                      blnI                                                                                    apyI[dcm+]        tru9I
           haeIII/palI              haeIII/palI                                                               bsaJI maeIII       mseI
           stuI rmaI        tru9I   eaeI
           haeI maeI        mseI    cfrI                 maeIII
       mnlI avrII    hpaI aluI           bsrI       maeII  bsrI
                aluI hincII/hindII
4101 TTTTTGGAG GCCTAGGCTT TTGCAAAAAG CTGTTAACAG CTTGGCACTG GCCGTCGTTT TACAACGTCG TGACTGGGAA AACCCTGGCG TTACCAACT
     AAAAAACCTC CGGATCCGAA AACGTTTTTC GACAATTGTC GAACCGTGAC CGGCAGCAAA ATGTTGCAGC ACTGACCCTT TTGGGACCGC AATGGGTTGA
                                                                  sau3AI
                                                                  mboI/ndeII[dam-]
                                                          sau96I  dpnI[dam+]
                                                       haeIII/palI
                              aluI          mnlI aciI    dpnII[dam-]                                bglI
                              pvuII       mboII asuI     pvuI/bspCI
                     fnu4HI   nspBII     earI/ksp632I    mcrI
            bbvI fokI
4201 TAATCGCCTT GCAGCACATC CCCCCTTCGC AATAGGAAG AGGCCCGCAC CGATCGCCCT TCCCAACAGT TGCGTAGCCT GAATGGCGAA
     ATTAGCGGAA CGTCGTGTAG GGGGGAAGCG TTATCGCTTC TCCGGGCGTG GCTAGCGGGA AGGGTTGTCA ACGCATCGGA CTTACCGCTT hinPI
     hhaI/cfoI                                                                 hinPI
     nlaIV                                                                     hhaI/cfoI
     narI                                                                      thaI
     kasI                                                                      fnuDII/mvnI            hinPI
     hinlI/acyI                                                                bstUI            hinPI hhaI/cfoI
     hgiCI                                                                     bsh1236I          hhaI/cfoI tru9I
     haeII aciI                                          sfaNI aciI  aciI maeII   rsaI    scfI fnu4HI   mseI
     banI sfaNI                                                                   csp6I bslI aciI   maeIII
     ahaII/bsaHI
4301 TGGCGCCTGA TGCGGTATTT TCTCCCTTACG CATCTGTGCG GTATTTCACA CCGCATACGT CAAAGCAACC ATAGTACGCG CCCTGTAGCG GCGCATTAAG
     ACCGCGGACT ACGCCATAAA AGAGGAATGC GTAGACACGC CATAAAGTGT GGCGTATGCA GTTTCGTTGG TATCATGCGC GGGACATCGC CGCGTAATTC fnu4HI
           aciI       hinPI
           fnu4HI     hhaI/cfoI            hinPI
           aciI       thaI                 hhaI/cfoI
           thaI       fnuDII/mvnI          haeII
           fnuDII/mvnI bstUI      hinPI rmaI
           bstUI      bsh1236I aciI      hhaI/cfoI bsrBI
           bsh1236I       maeIII bbvI maeIII     haeII maeI aciI      mboII          maeII
4401 CGCGGCGGGT GTGGTGGTTA CGGCAGCGT GACCGCTACA CTTGCCAGCG CCCTAGCGCC CCTTCCTTCT GCTTTCTTCC CGCCACGTTC
     GCGCCGCCCA CACCACCAAT GCCGTCGCA CTGGCGATGT GAACGGTCGC GGGATCGCGG GGAAGGAAGA CGAAAGAAGG GCGGTGCAAG
```

FIG. 10N

```
                            nlaIV                                                                    mnlI
                            hgiJII                                                                   nlaIV
                            bsp1286                                                                  hgiCI
         mspI               bmyI                                                                     banI
         hpaII              banII                            nlaIV                                   taqI                                              hphI
         naeI                                                                                                                                         
         cfr10I     aluI                                                                                                                              
   4501  GCCGGGCTTTC CCCGTCAAGC TCTAAATCGG GGGCTCCCTT TAGGGTTCCG ATTTAGTGCT TTACGGCACC TCGACCCCAA AAAACTTGAT TTGGGTGATG
         CGGCCGAAAG GGGCAGTTCG AGATTTAGCC CCCGAGGGAA ATCCCAAGGC TAAATCACGA AATGCCGTGG AGCTGGGGTT TTTTGAACTA AACCCACTAC maeII   haeIII/palI                               maeII   pleI         tru9I                                   pleI
         draIII  sau96I                                    drdI    hinfI maeII  msel                                    hinfI         bsrI
         bsaAI   asuI                                                                                                                  
   4601  GTTCACGTAG TGGGCCATCG CCCTGATAGA CGGTTTTTCG TTGGAGTCCA CGTTCTTTAA TAGTGGACTC TTGTTCCAAA CTGAACAAC
         CAAGTGCATC ACCCGGTAGC GGGACTATCT GCCAAAAAGC AACCTCAGGT GCAAGAAATT ATCACCTGAG AACAAGGTTT GACTTGTTG thaI
                                                                                                                        fnuDII/mvnI
                                                                         tru9I                                          bstUI
                                                                         msel                     tru9I                 bsh1236I
         bslI                                                  haeIII/palI               aluI     msel   apoI msel      apoI
         bslI   avaI                                                                                                    
   4701  ACTCAACCCT ATCTCGGGCT ATTCTTTTGA TTTATAAGGG ATTTTGCCGA TTTCGGCCTA TTGGTTAAAA AATGAGCTGA TTTAACAAAA ATTTAACGCG
         TGAGTTGGGA TAGAGCCCGA TAAGAAAACT AAATATTCCC TAAACGGCT AAAGCCGGAT AACCAATTTT TTACTCGACT AAATTGTTTT TAAATTGCGC hgiAI/aspHI
                                    bsp1286
                                    bsiHKAI                                                                                    tthlllI/aspI
                        maeII       bmyI   ddeI               aciI                                                             maeII
                 tru9I              apaLI/snoI  rsaI          fnu4HI            tru9I                                          maeII
         tru9I   msel   sspI psp1406I         alw44I/snoI csp6I       sfaNI     msel          aciI   bsaAI bsrI
         msel                                                                                                                  
   4801  AATTTTAACA AAATATTAAC GTTACAATT TTATGGTGCA CTCTCAGTAC AATCTGCTCT GATGCCGCAT AGTTAAGCCA ACTCCGCTAT CGCTACGTGA
         TTAAAATTGT TTTATAATTG CAATGTTAA AATACCACGT GAGAGTCATG TTAGACGAGA CTACGGCGTA TCAATTCGGT TGAGGCGATA GCGATGCACT hinPI
                                 hhaI/cfoI                    mspI
                                 thaI                         hpaII
                        hinPI    fnuDII/mvnI                  scrFI                                            bsmAI
                        fnu4HI   bstUI                        ncil    aciI                                     esp3I
                        bbvI              nspBI  bsh1236I     dsaV  sfaNI                                      bslI
         nlaIII  hhaI/cfoI  aciI   aciI hgaI  drdI            cauII foKI        aluI maeIII
   4901  CTGGGTCATG GCTGCGCCCC GACACCCGCC AACACCCGCT GACGGGCTTG TCTGCTCCCG GCATCCGCCT ACAGACAAGC TGTGACCGTC
         GACCCAGTAC CGACGCGGGG CTGTGGGCGG TTGTGGGCGA CTGCCCGAAC AGACGAGGGC CGTAGGCGGA TGTCTGTTCG ACACTGGCAG
```

FIG. 100

```
                                                           thaI
                                                           fnuDII/mvnI
                                                           bstUI
                                                           bsh1236I
                                                           hinPI
                                                           hhaI/cfoI                         mnlI
                                         thaI                                                haeIII/palI
                                         fnuDII/mvnI                              mboII      sau96I
       scrFI                             bstUI mnlI                               bpuAI      asuI
       nciI                              bsh1236I                                 bbsI       ecoO109I/draII
       mspI          nspI
       hpaII fnu4HI
       dsaV aluI nspHI
       cauII bbvI nlaIII    mnlI hphI     hphI
5001 TCCGGGAGCT GCATGTGTCA GAGGTTTTCA CCGTCATCAC CGAAACGCGC GAGGCAGTAT TCTTGAAGAC GAAAGGGCCT CGTGATACGC CTATTTTTAT
     AGGCCCTCGA CGTACACAGT CTCCAAAAGT GGCAGTAGTG GCTTTGCGCG CTCCGTCATA AGAACTTCTG CTTTCCCGGA GCACTATGCG GATAAAAATA nlaIV
                                                                          aciI
                                                                          thaI
                                                                          fnuDII/mvnI
                                                                          bstUI
                                maeII                                     bsh1236I
                                hinII/acyI                                hinPI
                  nlaIII        ahaII/bsaHI                               hhaI/cfoI
       tru9I rcaI               ddeI aatII
       mseI bspHI                                                                          mboII
       bsrBI bsmAI                                                                         earI/ksp632I
       aciI nlaIII                                              sspI
5101 AGTTAATGT CATGATAATA ATGGTTTCTT AGACGTCAGG TGGCACTTTT CGGGGAAATG TGCGCGGAAC CCCTATTTGT TTATTTTCT AAATACATTC
     TCCAATTACA GTACTATTAT TACCAAAGAA TCTGCAGTCC ACCGTGAAAA GCCCCTTTAC ACGCGCCTTG GGGATAAACA AATAAAAAGA TTTATGTAAG rcaI
         bspHI
5201 AAATATGTAT CCGCTCATGA GACAATAACC CTGATAAATG CTTCAATAAT ATTGAAAAAG GAAGAGTATG AGTATTCAAC ATTTCCGTGT CGCCCTTATT
     TTTATACATA GGCGAGTACT CTGTTATTGG GACTATTTAC GAAGTTATTA TAACTTTTTC CTTCTCATAC TCATAAGTTG TAAAGGCACA GCGGGAATAA hgiAI/aspHI
                                                                                                        bspl286
                                                                                                        bsiHKAI
                                                                                           sau3AI
                                                                                           mboI/ndeII[dam-]
                                                                                           dpnI[dam+] bmyI
                                                                                           dpnII[dam-]
                                                                                                        apaLI/snoI
       fnu4HI                                                                                           alw44I/snoI maeIII
       aciI                       hphI                      eco57I
5301 CCCTTTTTTG CGGCATTTTG CCTTCCTGTT TTTGCTCACC CAGAAACGCT GGTGAAAGTA AAAGATGCTG AAGATCAGTT GGGTGCACGA GTGGGTTACA
     GGGAAAAAAC GCCGTAAAAC GGAAGGACAA AAACGAGTGG GTCTTTGCGA CCACTTTCAT TTTCTACGAC TTCTAGTCAA CCCACGTGCT CACCCAATGT
```

FIG. 10P

```
          sau3AI
          mboI/ndeII[dam-]              sau3AI                                                                                    aciI
          dpnI[dam+]                    mboI/ndeII[dam-]                                                                          thaI
          dpnII[dam-]                   dpnI[dam+]                                                   hgiAI/aspHI                  fnuDII/mvnI
          bstYI/xhoII                   dpnII[dam-]                                   psp1406I       bsp1286 tru9I                bstUI
          bsrI          nspBII          alwI[dam-]                                    xmnI           bsiHKAI mseI                 bsh1236I
   taqI   alwI[dam-]    aciI            bstYI/xhoII                                   asp700                     ahaIII/draI      hinPI
                                                                  mboII maeII         bmyI          aha III/draI                 hhaI/cfoI
5401 TCGAACTGGA TCTCAACAGC GGTAAGATCC TTGAGAGTTT TCGCCCCGAA GAACGTTTTC CAATGATGAG CACTTTTAAA GTTCTGCTAT GTGGCGCGGT
     AGCTTGACCT AGAGTTGTCG CCATTCTAGG AACTCTCAAA AGCGGGGGCTT CTTGCAAAAG GTTACTACTC GTGAAAATTT CAAGACGATA CACCGCGCCA scrFI
                     nciI
                     mspI
                     hpaII
                     dsaV
                     cauII
             hinfI/acyI                                                                                       rsaI
             hgaI                                                        aciI                                 csp6I bsrI
             ahaII/bsaHI     bcgI  mcrI fnu4HI              ddeI                                              scaI hphI maeIII      sfaNI
5501 ATTATCCCGT GATGACGCCG GGCAAGAGCA ACTCGGTCGC CGCATACACT ATTCTCAGAA TGACTTGGTT GCGGCCAACT TACTTCTGAC CAGTCACAGA AAAGCATCTT
     TAATAGGGCA CTACTGCGGC CCGTTCTCGT TGAGCCAGCG GCGTATGTGA TAAGAGTCTT ACTGAACCAA CGCCGGTTGA ATGAAGACTG GTCAGTGTCT TTTCGTAGAA sau96I
                                                                                                                          avaII
                                                                                  haeIII/palI                             asuI
                                                                                  eaeI                                    sau3AI
                                                                                  cfrI                                    mboI/ndeII[dam-]
                                                                                  fnu4HI                                  dpnI[dam+]
                                                                                  aciI                                    dpnII[dam-]
                                                            mspI                                                          pvuI/bspCI
                  fnu4HI                       sau3AI       nlaIV                                                         mcrI mnlI
          foki   bbvI          nlaIII          mboI/ndeII[dam-]
5601 ACGGATGGCA TGACAGTAAG AGAATTATGC AGTGCTGCCA TAACCATGAG TGATAACACT ATTGGTACTC ACTATTGTGA CGCCGGTTGA ATGAAGACTG TTGCTAGCCT CCTGGCTTCC
     TGCCTACCGT ACTGTCATTC TCTTAATACG TCACGACGGT ATTGGTACTC TGATAACACT ATTGGTACTC ACTATTGTGA CGCCGGTTGA ATGAAGACTG TTGCTAGCCT CCTGGCTTCC nlaIII
                sau3AI maeIII
                mboI/ndeII[dam-]        sau3AI
                dpnI[dam+]               mboI/ndeII[dam-]
             alwI[dam-]                  dpnI[dam+]           hpaII
     aluI aciI       nlaIII dpnII[dam-]  dpnII[dam-] bsaWI aluI                                                                         maeIII
5701 AGCTAACCGC TTTTTTGCAC AACATGGGGG ATCATGTAAC TCGCCTTGAT CGTTGGGAAC CGGAGCTGAA CGGAGCCATA CCAAACGACG AGCGTGACAC
     TCGATTGGCG AAAAAACGTG TTGTACCCCC TAGTACATTG AGCGGAACTA GCAACCCTTG GCCTCGACTT ACTTCGGTAT GGTTTGCTGC TCGCACTGTG
```

FIG. 10Q

```
                                              hinPI
                                              mstI                          mspI
                                              aviII/fspI          bsrI      hpaII
                               fnu4HI         maeII hhaI/cfoI     tru9I     scrFI                            tru9I    fokI
                  sfaNI        bbvI           pspl406I            mseI      alul nciI                        mseI     bsrI       aciI
                                                                            rmaI dsaV                        aseI/asnI/vspI      mnlI
                                                                            maeI cauII
5801 CACGATGCCA GCAGCAATGG CAACAACGTT GCGCAAACTA TTAACTGGCG AACTACTTAC TCTAGCTTCC CGGCAACAAT TAATAGACTG GATGGAGGCG
     GTGCTACGGT CGTCGTTACC GTTGTTGCAA CGCGTTTGAT AATTGACCGC TTGATGAATG AGATCGAAGG GCCGTTGTTA ATTATCTGAC CTACCTCCGC bglI                                                                 aciI
                                              sau96I                                           mspI                thaI
                                              haeIII/palI                                      hpaII               fnuDII/mvnI
                         sau96I               hinPI   mspI                                     cfr10I              bstUI
                         avaII                hhaI/cfoI hpaII                                  nlaIV hphI                        fnu4HI
                         asuI                                                                  gsuI/bpmI bsmAI                   bbvI
                                                                                                          bsaI bsh1236I
5901 GATAAAGTTG CAGGACCACT TCTGCGCTCG GCCCTTCCGG CTGGCTGGTT TATTGCTGAT AAATCTGGAG CCGGTGAGCG TGGGTCTCGC GGTATCATTG
     CTATTTCAAC GTCCTGGTGA AGACGCGAGC CGGGAAGGCC GACCGACCAA ATAACGACTA TTTAGACCTC GGCCACTCGC ACCCAGAGCG CCATAGTAAC ddeI
                sau96I                                                                                                 sau3AI
                asuI                                                                                                   mboI/ndeII[dam-]
                nlaIV                                       pleI                                                       dpnI[dam+]
          bsrI haeIII/palI           mnlI                   hinfI                    fokI                              dpnII[dam-]
6001 CAGGACTGGG GCCAGATGGT AAGCCCTCCC GTATCGTAGT TATCTCACACG ACGGGGAGTC AGGCAACTAT GGATGAACGA AATAGACAGA TCGCTGAGAT
     GTCCTGACCC CGGTCTACCA TTCGGGAGGG CATAGCATCA ATAGATGTGC TGCCCCCTCAG TCCGTTGATA CCTACTTGCT TTATCTGTCT AGCGACTCTA hphI
                                                                                                                                rmaI
                                                                                                                                sau3AI
                                                                                                                                mboI/ndeII[dam-]
                                                                                                                                dpnI[dam+]
                                                                                                          tru9I                 dpnII[dam-]
          mnlI                                                                                            mseI                  bstYI/xhoII
          nlaIV                                                                                tru9I      ahaIII/draI maeI      alwI[dam-]
          hgiCI        tru9I                                                                   mseI       tru9I
          banI         mseI            maeIII                                                  ahaIII/draI  mseI mseI
6101 AGGTGCCTCA CTGATTAAGC ATTGGTAACT GTCAGACCAA GTTTACTCAT ATATACTTTA GATTGATTTA AAACTTCATT TTTAATTTAA AAGGATCTAG
     TCCACGGAGT GACTAATTCG TAACCATTGA CAGTCTGGTT CAAATGAGTA TATATGAAAT CTAACTAAAT TTTGAAGTAA AAATTAAATT TTCCTAGATC
```

```
                                                                          scrFI
                                                                          mvaI            scrFI
                                                                          ecoRII  mvaI
                                                                          dsaV    ecoRII
                                                         scrFI            bstNI   dsaV
                                                         mvaI             bsaJI   bstNI
                                                         ecoRII           apyI[dcm+]
                                          hinPI  mnlI    dsaV
                    mspI                  hhaI/cfoI alu I bstNI
                    hpaII                                 bsaJI                       fnu4HI
                    bslI   fnu4HI                         apyI[dcm+]                  aciI
                    bsaWI  aciI                                                       thaI
           aciI                                                                       fnuDII/mvnI
                                                                                      bstUI
                                                                         nlaIV        bsh1236I
                                                                         aciI
6701 CGCCACGCTT CCCGAAGGGA GAAAGGCGGA GTAAGCGGCA GGGTCGGAAC AGGAGAGCGC ACGAGGGAGC TTCCAGGGGG AAACGCCTGG
     GCGGTGCGAA GGGCTTCCCT CTTTCCGCCT CATTCGCCGT CCCAGCCTTG TCCTCTCGCG TGCTCCCTCG AAGGTCCCCC TTTGCGGACC taqI    sfaNI
                            mnlI drdI      hgaI
6801 TATCTTTATA GTCCTGTCGG GTTTCGCCAC CTCTGACTTG AGCGTCGATT TTTGTGATGC TCGTCAGGGG GGCGGAGCCT ATGGAAAAAC GCCAGCAACG
     ATAGAAATAT CAGGACAGCC CAAAGCGGTG GAGACTGAAC TCGCAGCTAA AAACACTACG AGCAGTCCCC CCGCCTCGGA TACCTTTTTG CGGTCGTTGC haeIII/palI
                scrFI                                        nlaIII              tfiI
                mvaI                                                             hinfI
                ecoRII                             nspI
                dsaV                               nspHI
                bstNI bslI       haeIII/palI       aflIII
          bslI  apyI[dcm+] haeI
          haeIII/palI nlaIV haeI                                                              aciI
6901 CGGCCTTTTT ACGGTTCCTG GCCCTTTTGC TCACATGTTC TTTCCTGGCT TATCCCCTGA TTCTGTGGAT AACCGTATTA CCGCCTTTGA
     GCCGGAAAAA TGCCAAGGAC CGGGAAAACG AGTGTACAAG AAAGGACCGA ATAGGGGACT AAGACACCTA TTGGCATAAT GGCGGAAACT
```

FIG. 10T

```
                                                                                                              thaI
                                                                                                              fnuDII/mvnI
                                                                                                              bstUI
                                                                                                              bsh1236I
                                                                                                              hinPI
                                                                                                              hhaI/cfoI
                                                                                                              thaI
                                                                                                              fnuDII/mvnI
                                                                                                              bstUI
                                                                                           hinPI              bsh1236I
                                                                                           sapI hhaI/cfoI                   nlaIV
                                                                                           mboII                            hgiCI
                                                                                           earI/ksp632I             mnlI   banI
                                                         fnu4HI                            aciI  haeII              aciI
                                                         bbvI  pleI                                                        bslI
                                            fnu4HI       hinPI hinfI                                                       aciI
                                            bbvI  hhaI/cfoI         mnlI                              tru9I
                         bsrBI aciI                                              bsrI aciI            hinPI   msel  maeIII  aseI/asnI/vspI mnlI
              alul       aciI fnu4HI mcrI                                                              hhaI/cfoI   aseI/asnI/vspI
7001 GTGAGCTGAT ACCGCTCGCC GCAGCCGAAC GACCGAGCGC AGCGAGTCAG AGCGGAAGAG TGAGCGAGGA CGCCCAATAC AGCGGAAGAG CGCAAACCGCC TCTCCCCGCG
     CACTCGACTA TGGCGAGCGG CGTCGGCTTG CTGGCTCGCG TCGCTCAGTC TCGCCTTCTC ACTCGCTCCT GCGGGTTATG TCGCCTTCTC GCGTTGGCGG AGAGGGGCGC
                      tru9I         aluI
              haeIII/palI   pvuII
              eaeI  tfiI  mseI nspBII
              cfrI  hinfI aseI/asnI/vspI         bsrI     aciI
7101 CGTTGGCCGA TTCATTAATC CAGCTGGCAC GACAGGTTTC CCGACTGGAA AGCGGGCAGT CCGCCCGTCA GAGCGCAACG CAATTAATGT GAGTTACCTC ACTCATTAGG
     GCAACCGGCT AAGTAATTAG GTCGACCGTG CTGTCCAAAG GGCTGACCTT TCGCCCGTCA GGCGGGCAGT CTCGCGTTGC GTTAATTACA CTCAATGGAG TGAGTAATCC scrFI
           mvaI
           ecoRII
           dsaV
           bstNI                                          aciI
           apyI[dcm+]              mspI                   bsrBI
           bsaJI                   hpaII                                                                  aluI   nlaIII            xmnI
7201 CACCCCAGGC TTTACACTTT ATGCTTCCGG CTCGTATGTT GTGTGGAATT GTGAGCGGAT AACAATTTCA CACAGAAAAC AGCTATGACC ATGATTACGA
     GTGGGGTCCG AAATGTGAAA TACGAAGGCC GAGCATACAA CACACCTTAA CACTCGCCTA TTGTTAAAGT GTGTCTTTTG TCGATACTGG TACTAATGCT tru9I
      msel
      aseI/asnI/vspI
7301 ATTAA
     TAATT >length: 7305
```

METHOD FOR SELECTING HIGH-EXPRESSING HOST CELLS

BACKGROUND OF THE INVENTION

1. Field of the Invention

This invention relates to a method of selecting for high-expressing host cells, a method of producing a protein of interest in high yields and a method of producing eukaryotic cells having multiple copies of a sequence encoding a protein of interest.

2. Description of the Related Art

The discovery of methods for introducing DNA into living host cells in a functional form has provided the key to understanding many fundamental biological processes, and has made possible the production of important proteins and other molecules in commercially useful quantities.

Despite the general success of such gene transfer methods, several common problems exist that may limit the efficiency with which a gene encoding a desired protein can be introduced into and expressed in a host cell. One problem is knowing when the gene has been successfully transferred into recipient cells. A second problem is distinguishing between those cells that contain the gene and those that have survived the transfer procedures but do not contain the gene. A third problem is identifying and isolating those cells that contain the gene and that are expressing high levels of the protein encoded by the gene.

In general, the known methods for introducing genes into eukaryotic cells tend to be highly inefficient. Of the cells in a given culture, only a small proportion take up and express exogenously added DNA, and an even smaller proportion stably maintain that DNA.

Identification of those cells that have incorporated a product gene encoding a desired protein typically is achieved by introducing into the same cells another gene, commonly referred to as a selectable gene, that encodes a selectable marker. A selectable marker is a protein that is necessary for the growth or survival of a host cell under the particular culture conditions chosen, such as an enzyme that confers resistance to an antibiotic or other drug, or an enzyme that compensates for a metabolic or catabolic defect in the host cell. For example, selectable genes commonly used with eukaryotic cells include the genes for aminoglycoside phosphotransferase (APH), hygromycin phosphotransferase (hyg), dihydrofolate reductase (DHFR), thymidine kinase (tk), neomycin, puromycin, glutamine synthetase, and asparagine synthetase.

The method of identifying a host cell that has incorporated one gene on the basis of expression by the host cell of a second incorporated gene encoding a selectable marker is referred to as cotransfectation (or cotransfection). In that method, a gene encoding a desired polypeptide and a selection gene typically are introduced into the host cell simultaneously, although they may be introduced sequentially. In the case of simultaneous cotransfectation, the gene encoding the desired polypeptide and the selectable gene may be present on a single DNA molecule or on separate DNA molecules prior to being introduced into the host cells. Wigler et al., *Cell*, 16:777 (1979). Cells that have incorporated the gene encoding the desired polypeptide then are identified or isolated by culturing the cells under conditions that preferentially allow for the growth or survival of those cells that synthesize the selectable marker encoded by the selectable gene.

The level of expression of a gene introduced into a eukaryotic host cell depends on multiple factors, including gene copy number, efficiency of transcription, messenger RNA (mRNA) processing, stability, and translation efficiency. Accordingly, high level expression of a desired polypeptide typically will involve optimizing one or more of those factors.

For example, the level of protein production may be increased by covalently joining the coding sequence of the gene to a "strong" promoter or enhancer that will give high levels of transcription. Promoters and enhancers are nucleotide sequences that interact specifically with proteins in a host cell that are involved in transcription. Kriegler, *Meth. Enzymol.*, 185:512 (1990); Maniatis et al., *Science*, 236:1237 (1987). Promoters are located upstream of the coding sequence of a gene and facilitate transcription of the gene by RNA polymerase. Among the eukaryotic promoters that have been identified as strong promoters for high-level expression are the SV40 early promoter, adenovirus major late promoter, mouse metallothionein-1 promoter, Rous sarcoma virus long terminal repeat, and human cytomegalovirus immediate early promoter (CMV).

Enhancers stimulate transcription from a linked promoter. Unlike promoters, enhancers are active when placed downstream from the transcription initiation site or at considerable distances from the promoter, although in practice enhancers may overlap physically and functionally with promoters. For example, all of the strong promoters listed above also contain strong enhancers. Bendig, *Genetic Engineering*, 7:91 (Academic Press, 1988).

The level of protein production also may be increased by increasing the gene copy number in the host cell. One method for obtaining high gene copy number is to directly introduce into the host cell multiple copies of the gene, for example, by using a large molar excess of the product gene relative to the selectable gene during cotransfectation. Kaufman, *Meth. Enzymol.*, 185:537 (1990). With this method, however, only a small proportion of the cotransfected cells will contain the product gene at high copy number. Furthermore, because no generally applicable, convenient method exists for distinguishing such cells from the majority of cells that contain fewer copies of the product gene, laborious and time-consuming screening methods typically are required to identify the desired high-copy number transfectants.

Another method for obtaining high gene copy number involves cloning the gene in a vector that is capable of replicating autonomously in the host cell. Examples of such vectors include mammalian expression vectors derived from Epstein-Barr virus or bovine papilloma virus, and yeast 2-micron plasmid vectors. Stephens & Hentschel, *Biochem. J.*, 248:1 (1987); Yates et al, *Nature*, 313:812 (1985); Beggs, *Genetic Engineering*, 2:175 (Academic Press, 1981).

Yet another method for obtaining high gene copy number involves gene amplification in the host cell. Gene amplification occurs naturally in eukaryotic cells at a relatively low frequency. Schimke, *J. Biol. Chem.*, 263:5989 (1988). However, gene amplification also may be induced, or at least selected for, by exposing host cells to appropriate selective pressure. For example, in many cases it is possible to introduce a product gene together with an amplifiable gene into a host cell and subsequently select for amplification of the marker gene by exposing the cotransfected cells to sequentially increasing concentrations of a selective agent. Typically the product gene will be coamplified with the marker gene under such conditions.

The most widely used amplifiable gene for that purpose is a DHFR gene, which encodes a dihydrofolate reductase enzyme. The selection agent used in conjunction with a DHFR gene is methotrexate (Mtx). A host cell is cotransfected with a product gene encoding a desired protein and a DHFR gene, and transfectants are identified by first culturing the cells in culture medium that contains Mtx. A suitable host cell when a wild-type DHFR gene is used is the Chinese Hamster Ovary (CHO) cell line deficient in DHFR activity, prepared and propagated as described by Urlaub & Chasin, *Proc. Nat. Acad. Sci. U.S.A.*, 77:4216 (1980). The transfected cells then are exposed to successively higher amounts of Mtx. This leads to the synthesis of multiple copies of the DHFR gene, and concomitantly, multiple copies of the product gene. Schimke, *J. Biol. Chem.*, 263:5989 (1988); Axel at al, U.S. Pat. No. 4,399,216; Axel et al., U.S. Pat. No. 4,634,665. Other references directed to cotransfection of a gene together with a genetic marker that allows for selection and subsequent amplification include Kaufman in *Genetic Engineering*, ed. J. Setlow (Plenum Press, New York), Vol. 9 (1987); Kaufman and Sharp, *J. Mol. Biol.*, 159:601 (1982); Ringold et al., *J. Mol. Appl. Genet.*, 1:165–175 (1981); Kaufman et al., *Mol. Cell Biol.*, 5:1750–1759(1985); Kaetzel and Nilson, *J. Biol. Chem.*, 263:6244–6251 (1988); Hung et al., *Proc. Natl. Acad. Sci. U.S.A.*, 83:261–264 (1986); Kaufman et al, *EMBO J.*, 6:87–93 (1987); Johnston and Kucey, *Science*, 242:1551–1554 (1988); Urlaub et al, *Cell*, 33:405–412 (1983).

To extend the DHFR amplification method to other cell types, a mutant DHFR gene that encodes a protein with reduced sensitivity to methotrexate may be used in conjunction with host cells that contain normal numbers of an endogenous wild-type DHFR gene. Simonsen and Levinson, *Proc. Natl. Acad. Sci. U.S.A.*, 80:2495 (1983); Wigler et al., *Proc. Natl. Acad. Sci. U.S.A.*, 77:3567–3570 (1980); Haber and Schimke, *Somatic Cell Genetics*, 8:499–508 (1982).

Alternatively, host cells may be co-transfected with the product gene, a DHFR gene, and a dominant selectable gene, such as a neo$^r$ gene. Kim and Wold, *Cell*, 42:129 (1985); Capon et al, U.S. Pat. No. 4,965, 199. Transfectants are identified by first culturing the cells in culture medium containing neomycin (or the related drug G418), and the transfectants so identified then are selected for amplification of the DHFR gene and the product gene by exposure to successively increasing amounts of Mtx.

As will be appreciated from this discussion, the selection of recombinant host cells that express high levels of a desired protein generally is a multi-step process. In the first step, initial transfectants are selected that have incorporated the product gene and the selectable gene. In subsequent steps, the initial transfectants are subject to further selection for high-level expression of the selectable gene and then random screening for high-level expression of the product gene. To identify cells expressing high levels of the desired protein, typically one must screen large numbers of transfectants. The majority of transfectants produce less than maximal levels of the desired protein. Further, Mtx resistance in DHFR transformants is at least partially conferred by varying degrees of gene amplification. Schimke, *Cell*, 37:705–713 (1984). The inadequacies of co-expression of the non-selected gene have been reported by Wold et al., *Proc. Natl. Acad. Sci. U.S.A.*, 76:5684–5688 (1979). Instability of the amplified DNA is reported by Kaufman and Schimke, *Mol. Cell Biol.*, 1:1069–1076 (1981); Haber and Schimke, *Cell*, 26:355–362 (1981); and Fedespiel et al, *J. Biol. Chem.*, 259:9127–9140 (1984).

Several methods have been described for directly selecting such recombinant host cells in a single step. One strategy involves co-transfecting host cells with a product gene and a DHFR gene, and selecting those cells that express high levels of DHFR by directly culturing in medium containing a high concentration of Mtx. Many of the cells selected in that manner also express the co-transfected product gene at high levels. Page and Sydenham, *Bio/Technolgy*, 9:64 (1991). This method for single-step selection suffers from certain drawbacks that limit its usefulness. High-expressing cells obtained by direct culturing in medium containing a high level of a selection agent may have poor growth and stability characteristics, thus limiting their usefulness for long-term production processes. Page and Snyderman, *Bio/Technology*, 9:64 (1991). Single-step selection for high-level resistance to Mtx may produce cells with an altered, Mtx-resistant DHFR enzyme, or cells that have altered Mtx transport properties, rather than cells containing amplified genes. Haber et al, *J. Biol. Chem.*, 256:9501 (1981);Assaraf and Schimke, *Proc. Natl. Acad. Sci. U.S.A.*, 84:7154 (1987).

Another method involves the use of polycistronic mRNA expression vectors containing a product gene at the 5' end of the transcribed region and a selectable gene at the 3' end. Because translation of the selectable gene at the 3' end of the polycistronic mRNA is inefficient, such vectors exhibit preferential translation of the product gene and require high levels of polycistronic mRNA to survive selection. Kaufman, *Meth. Enzymol.*, 185:487 (1990); Kaufman, *Meth. Enzymol.*, 185:537 (1990); Kaufman et al., *EMBO J.*, 6:187 (1987). Accordingly, cells expressing high levels of the desired protein product may be obtained in a single step by culturing the initial transfectants in medium containing a selection agent appropriate for use with the particular selectable gene. However, the utility of these vectors is variable because of the unpredictable influence of the upstream product reading frame on selectable marker translation and because the upstream reading frame sometimes becomes deleted during methotrexate amplification (Kaufman et al, *J. Mol. Biol.*, 159:601–621 [1982]; Levinson, *Methods in Enzymology*, San Diego: Academic Press, Inc. [1990]). Later vectors incorporated an internal translation initiation site derived from members of the picornavirus family which is positioned between the product gene and the selectable gene (Pelletier et al, *Nature*, 334:320 [1988]; Jang et al, *J. Virol.*, 63:1651 [1989]).

A third method for single-step selection involves use of a DNA construct with a selectable gene containing an intron within which is located a gene encoding the protein of interest. See U.S. Pat. No. 5,043,270 and Abrams et al., *J. Biol. Chem.*, 264(24): 14016–14021 (1989). In yet another single-step selection method, host cells are co-transfected with an intron-modified selectable gene and a gene encoding the protein of interest. See WO 92/17566, published Oct. 15, 1992. The intron-modified gene is prepared by inserting into the transcribed region of a selectable gene an intron of such length that the intron is correctly spliced from the corresponding mRNA precursor at low efficiency, so that the amount of selectable marker produced from the intron-modified selectable gene is substantially less than that produced from the starting selectable gene. These vectors help to insure the integrity of the integrated DNA construct, but transcriptional linkage is not achieved as selectable gene and the protein gene are driven by separate promoters.

Other mammalian expression vectors that have single transcription units have been described. Retroviral vectors have been constructed (Cepko at al, *Cell*, 37:1053–1062 [1984]) in which a cDNA is inserted between the endogenous Moloney murine leukemia virus (M-MuLV) splice donor and splice acceptor sites which are followed by a neomycin resistance gene. This vector has been used to express a variety of gene products following retroviral infection of several cell types.

With the above drawbacks in mind, it is one object of the present invention to increase the level of homogeneity with regard to expression levels of stable clones transfected with a product gene of interest, by expressing a selectable marker (DHFR) and the protein of interest from a single promoter.

It is another object to provide a method for selecting stable, recombinant host cells that express high levels of a desired protein product, which method is rapid and convenient to perform, and reduces the numbers of transfected cells which need to be screened. Furthermore, it is an object to allow high levels of single and two unit polypeptides to be rapidly generated from clones or pools of stable host cell transfectants.

It is an additional object to provide expression vectors which bias for active integration events (i.e. have an increased tendency to generate transformants wherein the DNA construct is inserted into a region of the genome of the host cell which results in high level expression of the product gene) and can accommodate a variety of product genes without the need for modification.

SUMMARY OF THE INVENTION

Accordingly, the present invention is directed to a DNA construct (DNA molecule) alternative terminology comprising a 5' transcriptional initiation site and a 3' transcriptional termination site, a selectable gene (preferably an amplifiable gene) and a product gene provided 3' to the selectable gene, a transcriptional regulatory region regulating transcription of both the selectable gene and the product gene, the selectable gene positioned within an intron defined by a splice donor site and a splice acceptor site. The splice donor site preferably comprises an effective splice donor sequence as herein defined and thereby regulates expression of the product gene using the transcriptional regulatory region.

In another embodiment, the invention provides a method for producing a product of interest comprising culturing a eukaryotic cell which has been transfected with the DNA construct described above, so as to express the product gene and recovering the product.

In a further embodiment, the invention provides a method for producing eukaryotic cells having multiple copies of the product gene comprising transfecting eukaryotic cells with the DNA construct described above (where the selectable gene is an amplifiable gene), growing the cells in a selective medium comprising an amplifying agent for a sufficient time for amplification to occur, and selecting cells having multiple copies of the product gene. Preferably transfection of the cells is achieved using electroporation.

After transfection of the host cells, most of the transfectants fail to exhibit the selectable phenotype characteristic of the protein encoded by the selectable gene, but surprisingly a small proportion of the transfectants do exhibit the selectable phenotype, and among those transfectants, the majority are found to express high levels of the desired product encoded by the product gene. Thus, the invention provides an improved method for the selection of recombinant host cells expressing high levels of a desired product, which method is useful with a wide variety of eukaryotic host cells and avoids the problems inherent in existing cell selection technology.

BRIEF DESCRIPTION OF THE DRAWINGS

FIG. 1B depicts the DNA constructs of Example 1. The various splice donor sequences are depicted, i.e., wild type ras splice donor sequence (WT ras), mutant ras splice donor sequence (MUTANT ras) and non-functional splice donor sequence (▲GT). The probes used for Northern blot analysis in Example 1 are shown in FIG. 1B. FIG. 1C depicts the DNA constructs of Example 2 and FIG. 1D depicts the DNA construct of Example 3 used for expression of anti-IgE $V_H$.

FIGS. 3A–3S depict the nucleotide sequence (SEQ ID NO: 1) of the DHFR/intron-(WT ras SD)-tPA expression vector of Example 1.

In FIG. 5A greater than 100 clones from each vector transfection were mixed, plated in 24 well plates, and assayed by tPA ELISA at "saturation". In FIG. 5B, twenty clones chosen at random derived from each of the vectors were assayed by tPA ELISA at "saturation". In FIG. 5C, the pools mentioned in FIG. 5A (except the ΔGT pool) were exposed to 200 nM Mtx to select for DHFR amplification and then pooled and assayed for tPA expression.

Figure 6A:
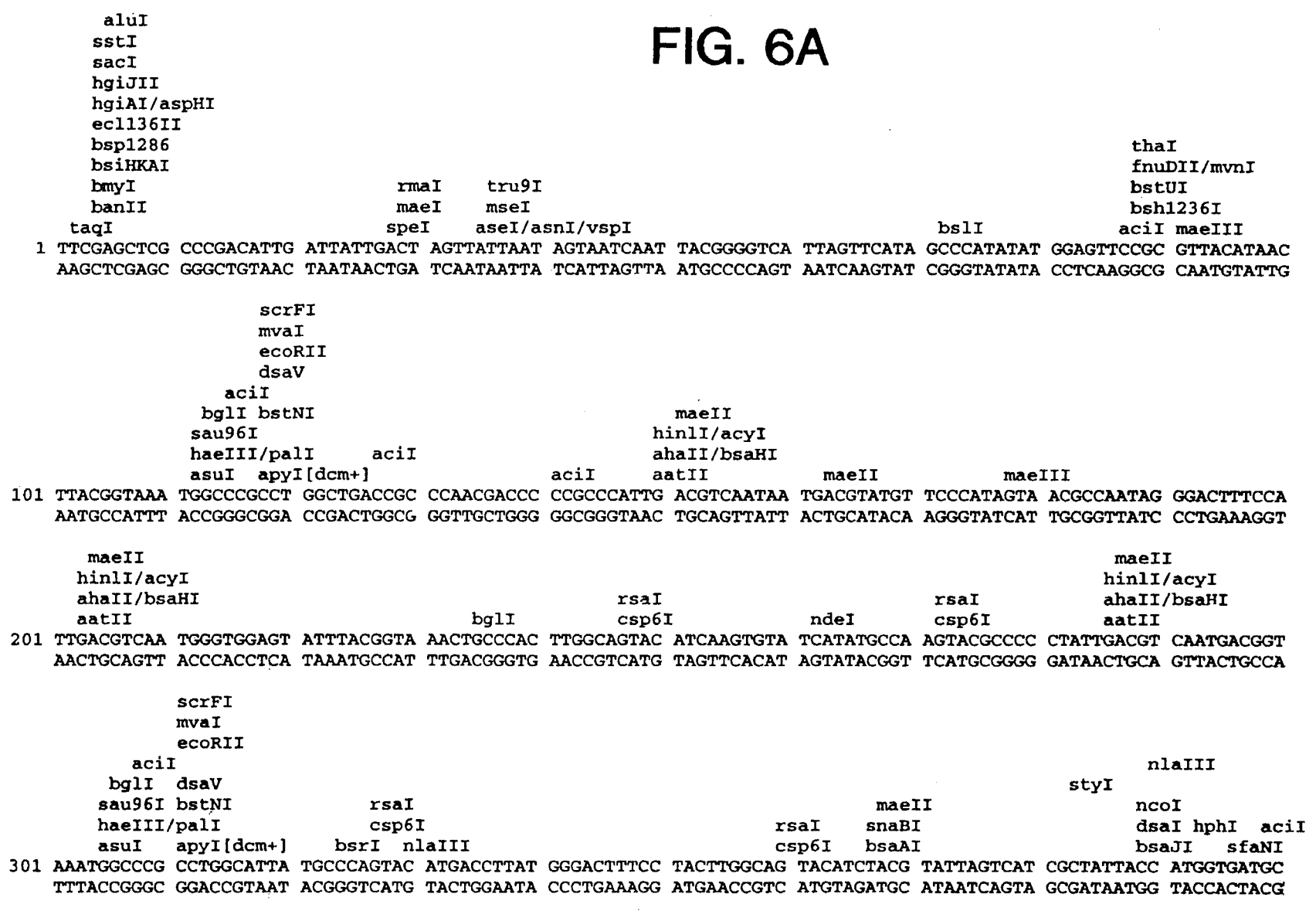
Figure 6F:
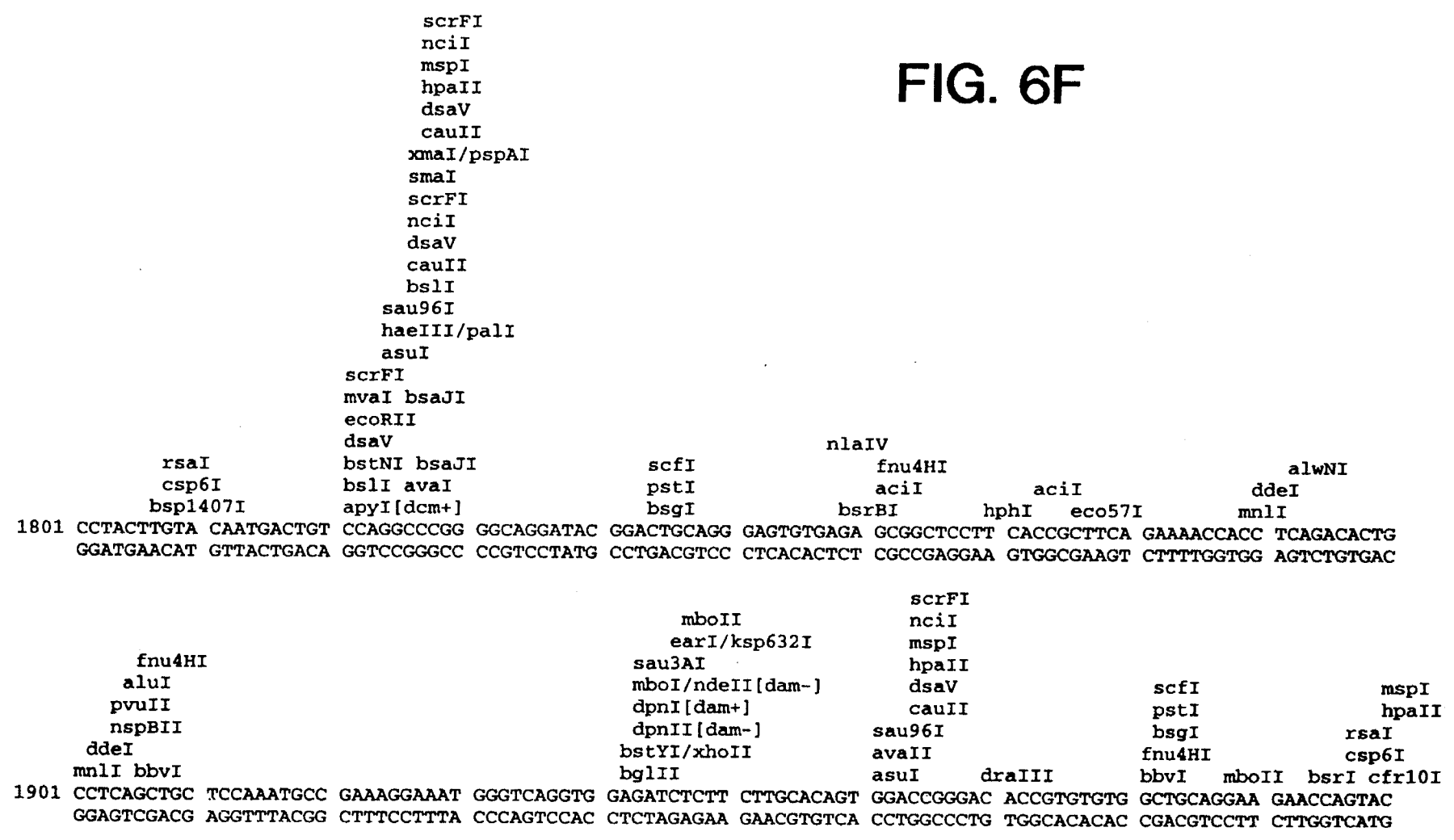
Figure 6J:
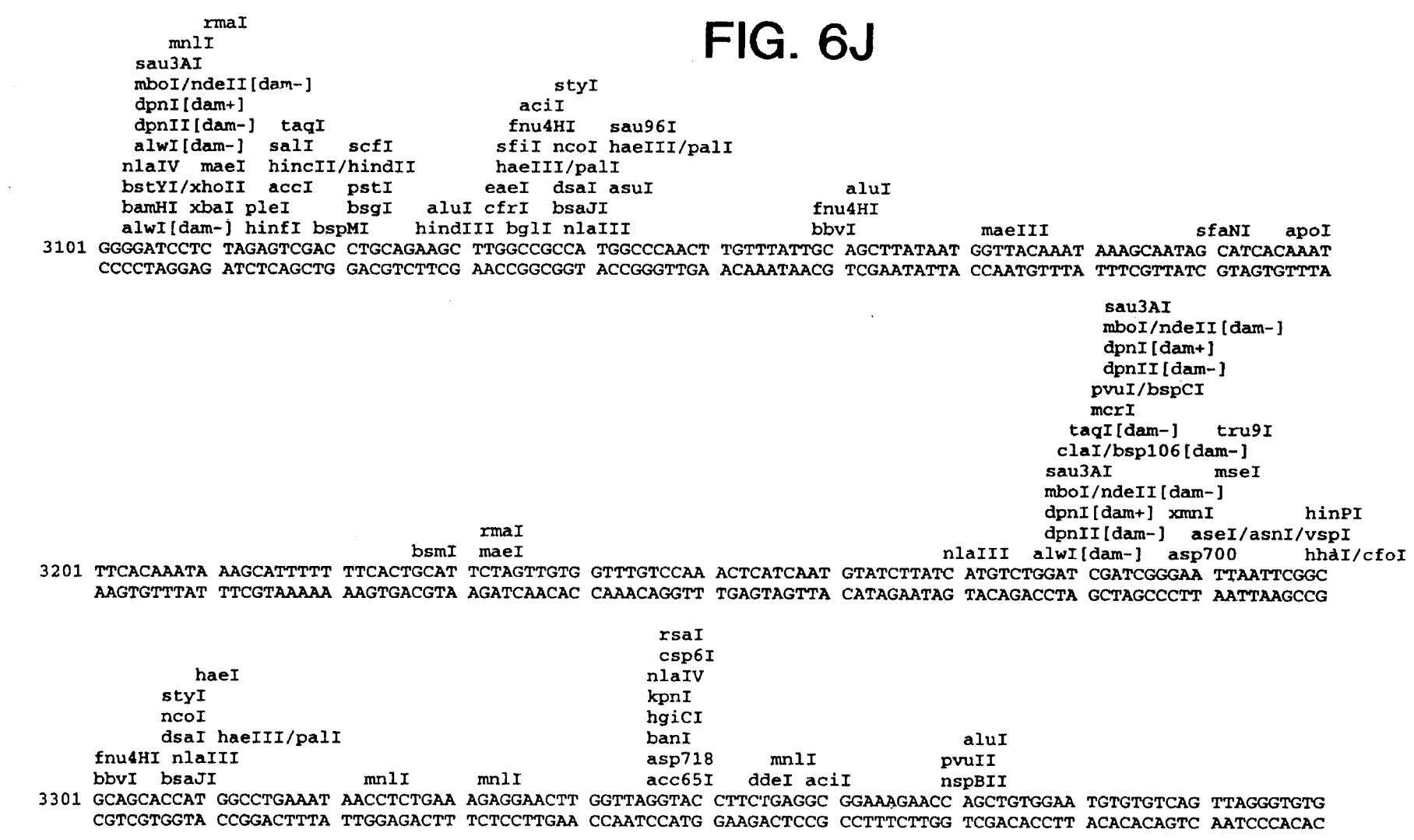
Figure 6P:
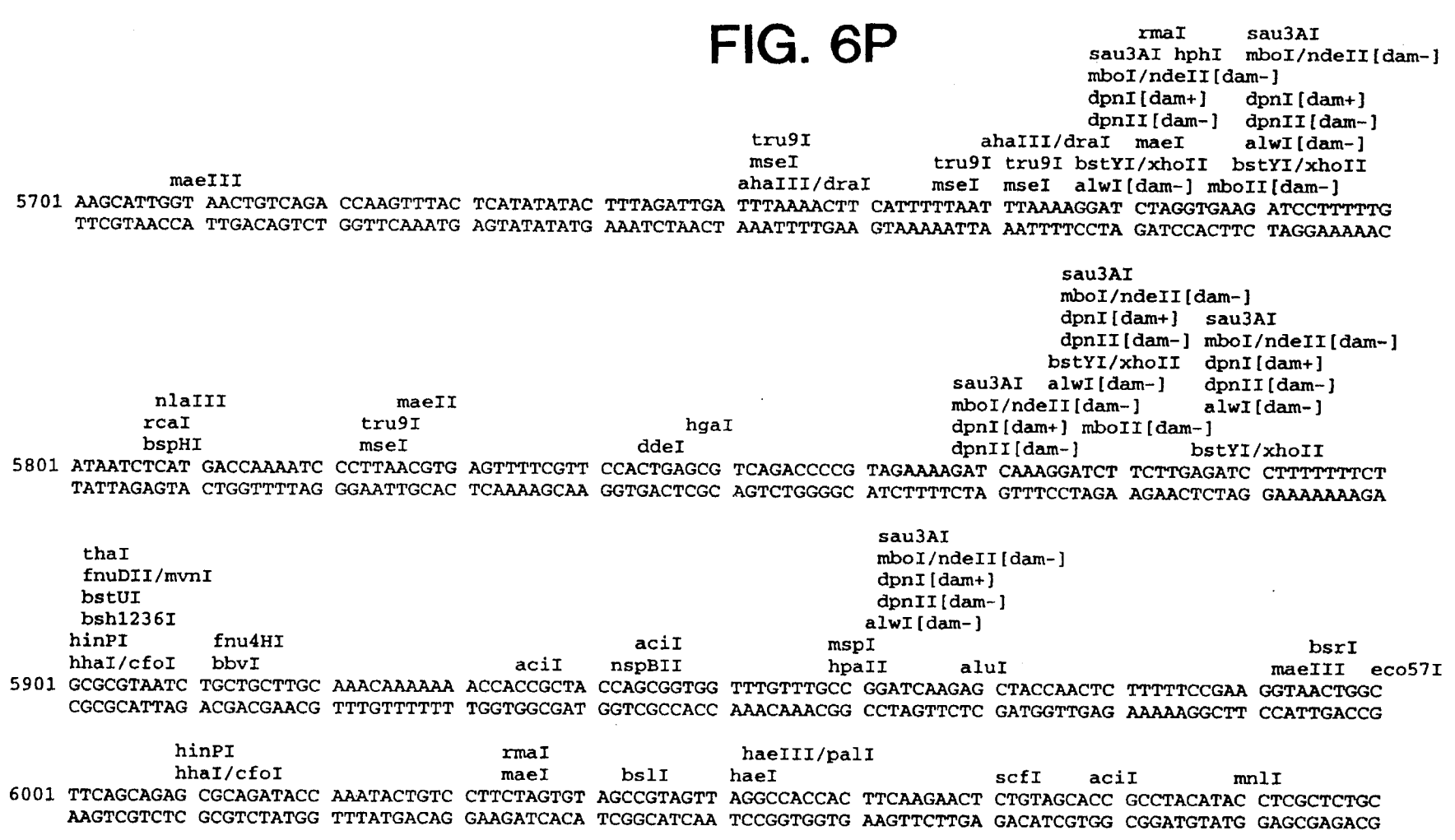

FIGS. 6A–6R depict the nucleotide sequence (SEQ ID NO: 2) of the DHFR/intron-(WT ras SD)-TNFr-IgG expression vector of Example 2.

FIGS. 9A–9R depict the nucleotide sequence (SEQ ID NO: 3) of the anti-IgE $V_H$ expression vector of Example 3.

Figure 10L:
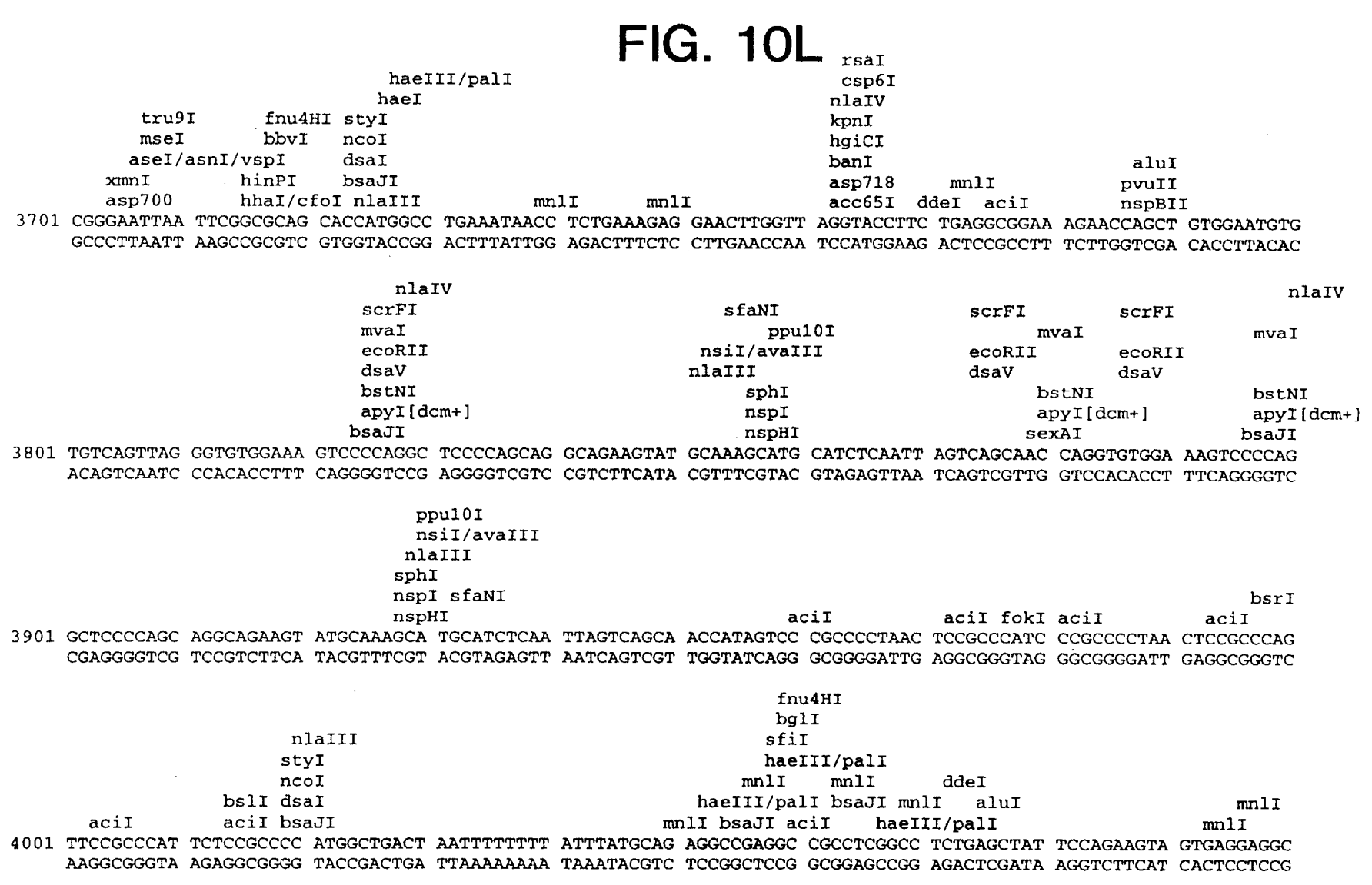
Figure 10R:
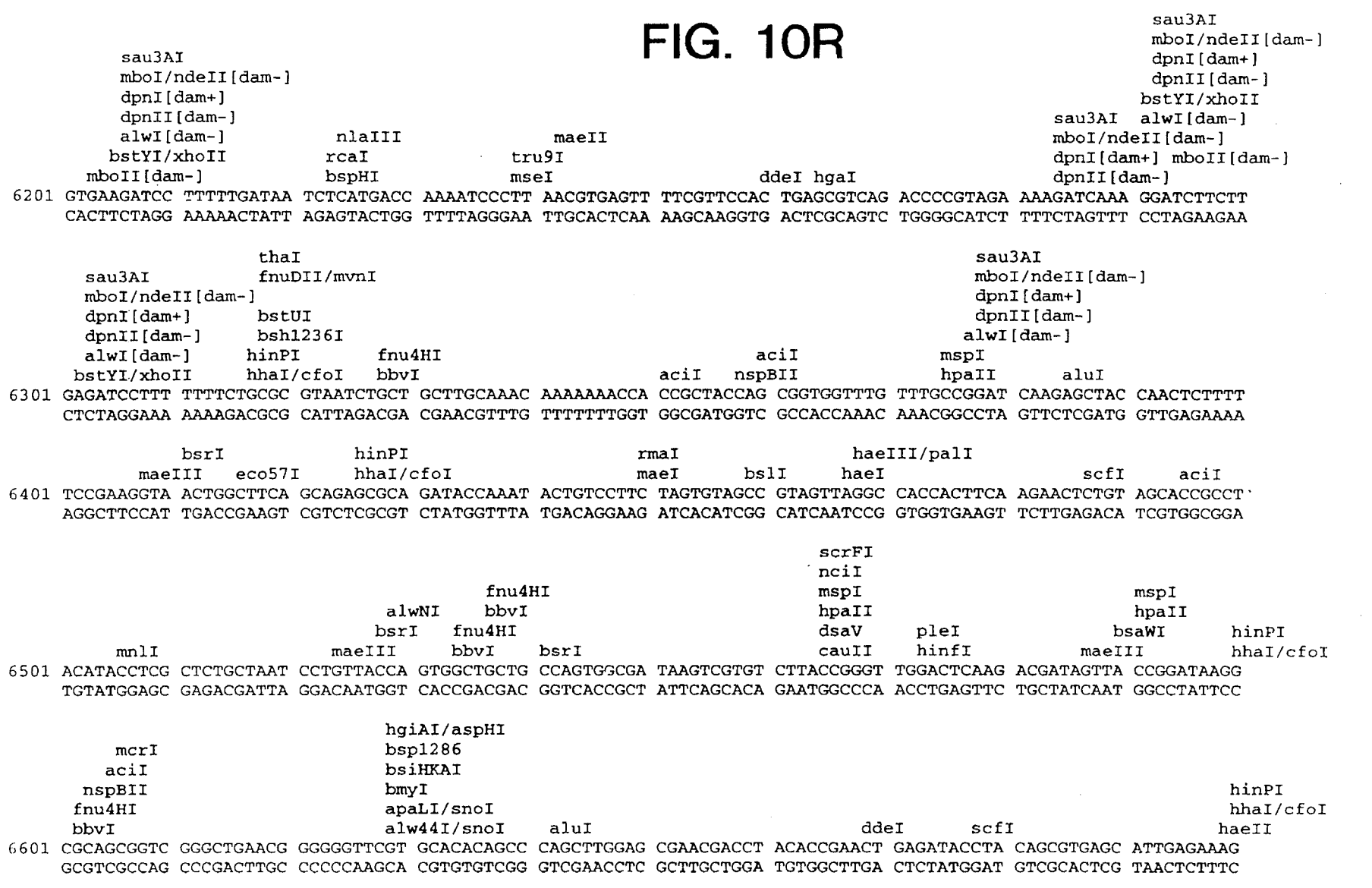

FIGS. 10A–10T depict the nucleotide sequence (SEQ ID NO: 4) of the anti-IgE $V_L$ expression vector of Example 3.

DESCRIPTION OF THE PREFERRED EMBODIMENTS

Figure 1A:
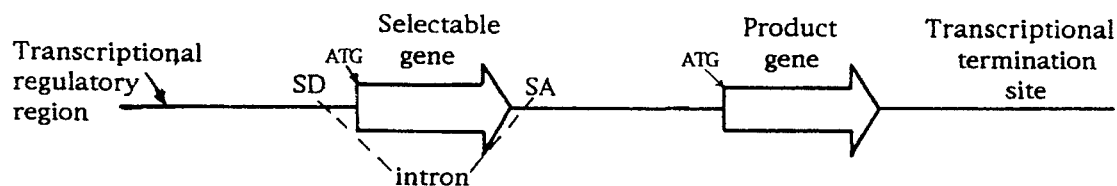
FIGS. 1A–1D illustrate schematically various DNA constructs encompassed by the instant invention. The large arrows represent the selectable gene and the product gene, the V formed by the dashed lines shows the region of the precursor RNA internal to the 5' splice donor site (SD) and 3' splice acceptor site (SA) that is excised from vectors that contain a functional SD. The transcriptional regulatory region, selectable gene, product gene and transcriptional termination site are depicted in FIG. 1A.

Definitions:

The "DNA construct" disclosed herein comprises a non-naturally occurring DNA molecule which can either be provided as an isolate or integrated in another DNA molecule e.g. in an expression vector or the chromosome of an eukaryotic host cell.

The term "selectable gene" as used herein refers to a DNA that encodes a selectable marker necessary for the growth or survival of a host cell under the particular cell culture conditions chosen. Accordingly, a host cell that is transformed with a selectable gene will be capable of growth or survival under certain cell culture conditions wherein a non-transfected host cell is not capable of growth or survival. Typically, a selectable gene will confer resistance to a drug or compensate for a metabolic or catabolic defect in the host cell. Examples of selectable genes are provided in the following table. See also Kaufman, *Methods in Enzymology*, 185:537–566 (1990), for a review of these.

TABLE 1

Selectable Genes and their Selection Agents

| Selection Agent | Selectable Gene |
| --- | --- |
| Methotrexate | Dihydrofolate reductase |
| Cadmium | Metallothionein |
| PALA | CAD |
| Xyl-A-or adenosine and 2'-deoxycoformycin | Adenosine deaminase |
| Adenine, azaserine, and coformycin | Adenylate deaminase |
| 6-Azauridine, pyrazofuran | UMP Synthetase |
| Mycophenolic acid | IMP 5'-dehydrogenase |
| Mycophenolic acid with limiting xanthine | Xanthine-guanine phosphoribosyltransferase |
| Hypoxanthine, aminoopterin, and thymidine (HAT) | Mutant HGPRTase or mutant thymidine kinase |
| 5-Fluorodeoxyuridine | Thymidylate synthetase |
| Multiple drugs e.g. adriamycin, vincristine or colchicine | P-glycoprotein 170 |
| Aphidicolin | Ribonucleotide reductase |
| Methionine sulfoximine | Glutamine synthetase |
| β-Aspartyl hydroxamate or Albizziin | Asparagine synthetase |
| Canavanine | Arginosuccinate synthetase |
| α-Difluoromethylornithine | Ornithine decarboxylase |
| Compactin | HMG-CoA reductase |
| Tunicamycin | N-Acetylglucosaminyl transferase |
| Borrelidin | Threonyl-tRNA synthetase |
| Ouabain | $Na^+K^+$-ATPase |

The preferred selectable gene is an amplifiable gene. As used herein, the term "amplifiable gene" refers to a gene which is amplified (i.e. additional copies of the gene are generated which survive in intrachromosomal or extrachromosomal form) under certain conditions. The amplifiable gene usually encodes an enzyme (i.e. an amplifiable marker) which is required for growth of eukaryotic cells under those conditions. For example, the gene may encode DHFR which is amplified when a host cell transformed therewith is grown in Mtx. According to Kaufman, the selectable genes in Table 1 above can also be considered amplifiable genes. An example of a selectable gene which is generally not considered to be an amplifiable gene is the neomycin resistance gene (Cepko et al, supra).

As used herein, "selective medium" refers to nutrient solution used for growing eukaryotic cells which have the selectable gene and therefore includes a "selection agent". Commercially available media such as Ham's F10 (Sigma), Minimal Essential Medium ([MEM], Sigma), RPMl-1640 (Sigma), and Dulbecco's Modified Eagle's Medium ([DMEM], Sigma) are exemplary nutrient solutions. In addition, any of the media described in Ham and Wallace, *Meth. Enz.*, 58:44 (1979), Barnes and Sato, *Anal. Biochem.*, 102:255 (1980), U.S. Pat. Nos. 4,767,704; 4,657,866; 4,927,762; or 4,560,655; WO 90/03430; WO 87/00195; U.S. Pat. Re. 30,985; or U.S. Pat. No. 5,122,469, the disclosures of all of which are incorporated herein by reference, may be used as culture media. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The preferred nutrient solution comprises fetal bovine serum.

The term "selection agent" refers to a substance that interferes with the growth or survival of a host cell that is deficient in a particular selectable gene. Examples of selection agents are presented in Table 1 above. The selection agent preferably comprises an "amplifying agent" which is defined for purposes herein as an agent for amplifying copies of the amplifiable gene, such as Mtx if the amplifiable gene is DHFR. See Table 1 for examples of amplifying agents.

As used herein, the term "transcriptional initiation site" refers to the nucleic acid in the DNA construct corresponding to the first nucleic acid incorporated into the primary transcript, i.e., the mRNA precursor, which site is generally provided at, or adjacent to, the 5' end of the DNA construct.

The term "transcriptional termination site" refers to a sequence of DNA, normally represented at the 3' end of the DNA construct, that causes RNA polymerase to terminate transcription.

As used herein, "transcriptional regulatory region" refers to a region of the DNA construct that regulates transcription of the selectable gene and the product gene. The transcriptional regulatory region normally refers to a promoter sequence (i.e. a region of DNA involved in binding of RNA polymerase to initiate transcription) which can be constitutive or inducible and, optionally, an enhancer (i.e. a cis-acting DNA element, usually from about 10–300 bp, that acts on a promoter to increase its transcription).

As used herein, "product gene" refers to DNA that encodes a desired protein or polypeptide product. Any product gene that is capable of expression in a host cell may be used, although the methods of the invention are particularly suited for obtaining high-level expression of a product gene that is not also a selectable or amplifiable gene. Accordingly, the protein or polypeptide encoded by a product gene typically will be one that is not necessary for the growth or survival of a host cell under the particular cell culture conditions chosen. For example, product genes suitably encode a peptide, or may encode a polypeptide sequence of amino acids for which the chain length is sufficient to produce higher levels of tertiary and/or quaternary structure.

Examples of bacterial polypeptides or proteins include, e.g., alkaline phosphatase and β-lactamase. Examples of mammalian polypeptides or proteins include molecules such as renin; a growth hormone, including human growth hormone, and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin- 3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; chimeric proteins such as immunoadhesins and fragments of any of the above-listed polypeptides.

The product gene preferably does not consist of an anti-sense sequence for inhibiting the expression of a gene present in the host. Preferred proteins herein are therapeutic proteins such as TGF-β, TGF-α, PDGF, EGF, FGF, IGF-I, DNase, plasminogen activators such as t-PA, clotting factors such as tissue factor and factor VIII, hormones such as relaxin and insulin, cytokines such as IFN-y, chimeric proteins such as TNF receptor IgG immunoadhesin (TNFr-IgG) or antibodies such as anti-IgE.

The term "intron" as used herein refers to a nucleotide sequence present within the transcribed region of a gene or within a messenger RNA precursor, which nucleotide sequence is capable of being excised, or spliced, from the messenger RNA precursor by a host cell prior to translation. Introns suitable for use in the present invention are suitably prepared by any of several methods that are well known in the art, such as purification from a naturally occurring nucleic acid or de novo synthesis. The introns present in many naturally occurring eukaryotic genes have been identified and characterized. Mount, *Nuc. Acids Res.*, 10:459 (1982). Artificial introns comprising functional splice sites also have been described. Winey et al., *Mol. Cell Biol.*, 9:329 (1989); Gatermann et al, *Mol. Cell Biol.*, 9:1526 (1989). Introns may be obtained from naturally occurring nucleic acids, for example, by digestion of a naturally occurring nucleic acid with a suitable restriction endonuclease, or by PCR cloning using primers complementary to sequences at the 5' and 3' ends of the intron. Alternatively, introns of defined sequence and length may be prepared synthetically using various methods in organic chemistry. Narang et al., *Meth. Enzymol.*, 68:90 (1979); Caruthers et al, *Meth. Enzymol.*, 154:287 (1985); Froehler et al, *Nuc. Acids Res.*, 14:5399 (1986).

As used herein "splice donor site" or "SD" refers to the DNA sequence immediately surrounding the exon-intron boundary at the 5' end of the intron, where the "exon" comprises the nucleic acid 5' to the intron. Many splice donor sites have been characterized and Ohshima et al, *J. Mol. Biol.*, 195:247–259(1987) provides a review of these. An "efficient splice donor sequence" refers to a nucleic acid sequence encoding a splice donor site wherein the efficiency of splicing of messenger RNA precursors having the splice donor sequence is between about 80 to 99% and preferably 90 to 95% as determined by quantitative PCR. Examples of efficient splice donor sequences include the wild type (WT) ras splice donor sequence and the GAC:GTAAGT sequence of Example 3. Other efficient splice donor sequences can be readily selected using the techniques for measuring the efficiency of splicing disclosed herein.

The terms "PCR" and "polymerase chain reaction" as used herein refer to the in vitro amplification method described in U.S. Pat. No. 4,683,195 (issued Jul. 28, 1987). In general, the PCR method involves repeated cycles of primer extension synthesis, using two DNA primers capable of hybridizing preferentially to a template nucleic acid comprising the nucleotide sequence to be amplified. The PCR method can be used to clone specific DNA sequences from total genomic DNA, cDNA transcribed from cellular RNA, viral or plasmid DNAs. Wang & Mark, in *PCR Protocols*, pp.70–75 (Academic Press, 1990); Scharf, in *PCR Protocols*, pp. 84–98; Kawasaki & Wang, in *PCR Technology*, pp. 89–97 (Stockton Press, 1989). Reverse transcription-polymerase chain reaction (RT-PCR) can be used to analyze RNA samples containing mixtures of spliced and unspliced mRNA transcripts. Fluorescently tagged primers designed to span the intron are used to amplify both spliced and unspliced targets. The resultant amplification products are then separated by gel electrophoresis and quantitated by measuring the fluorescent emission of the appropriate band(s). A comparison is made to determine the amount of spliced and unspliced transcripts present in the RNA sample.

One preferred splice donor sequence is a "consensus splice donor sequence". The nucleotide sequences surrounding intron splice sites, which sequences are evolutionarily highly conserved, are referred to as "consensus splice donor sequences". In the mRNAs of higher eukaryotes, the 5' splice site occurs within the consensus sequence AG:GUAAGU (wherein the colon denotes the site of cleavage and ligation). In the mRNAs of yeast, the 5'0 splice site is bounded by the consensus sequence :GUAUGU. Padgett, et al, *Ann. Rev. Biochem.*, 55:1119 (1986).

The expression "splice acceptor site" or "SA" refers to the sequence immediately surrounding the intron-exon boundary at the 3' end of the intron, where the "exon" comprises the nucleic acid 3' to the intron. Many splice acceptor sites have been characterized and Ohshima et al., *J. Mol. Biol.*, 195:247–259 (1987) provides a review of these. The preferred splice acceptor site is an efficient splice acceptor site which refers to a nucleic acid sequence encoding a splice acceptor site wherein the efficiency of splicing of messenger RNA precursors having the splice acceptor site is between about 80 to 99% and preferably 90 to 95% as determined by quantitative PCR. The splice acceptor site may comprise a consensus sequence. In the mRNAs of higher eukaryotes, the 3' splice acceptor site occurs within the consensus sequence $(U/C)_{11}NCAG:G$. In the mRNAs of yeast, the 3' acceptor splice site is bounded by the consensus sequence (C/U)AG:. Padgett, et al, supra.

As used herein "culturing for sufficient time to allow amplification to occur" refers to the act of physically culturing the eukaryotic host cells which have been transformed with the DNA construct in cell culture media containing the amplifying agent, until the copy number of the amplifiable gene (and preferably also the copy number of the product gene) in the host cells has increased relative to the transformed cells prior to this culturing.

The term "expression" as used herein refers to transcription or translation occurring within a host cell. The level of expression of a product gene in a host cell may be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook, et al., *Molecular Cloning: A Laboratory Manual*, pp. 7.3–7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook, et al., *Molecular Cloning: A Laboratory Manual*, pp. 18.1–18.88 (Cold Spring Harbor Laboratory Press, 1989).

Modes for Carrying Out the Invention

Methods and compositions are provided for enhancing the stability and/or copy number of a transcribed sequence in order to allow for elevated levels of a RNA sequence of interest. In general, the methods of the present invention involve transfecting a eukaryotic host cell with an expression vector comprising both a product gene encoding a desired polypeptide and a selectable gene (preferably an amplifiable gene).

Selectable genes and product genes may be obtained from genomic DNA, cDNA transcribed from cellular RNA, or by in vitro synthesis. For example, libraries are screened with probes (such as antibodies or oligonucleotides of about 20–80 bases) designed to identify the selectable gene or the product gene (or the protein(s) encoded thereby). Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989). An alternative means to isolate the selectable gene or product gene is to use PCR methodology as described in section 14 of Sambrook et al, supra.

A preferred method of practicing this invention is to use carefully selected oligonucleotide sequences to screen cDNA libraries from various tissues known to contain the selectable gene or product gene. The oligonucleotide sequences selected as probes should be of sufficient length and sufficiently unambiguous that false positives are minimized.

The oligonucleotide generally is labeled such that it can be detected upon hybridization to DNA in the library being screened. The preferred method of labeling is to use $^{32}P$-labeled ATP with polynucleotide kinase, as is well known in the art, to radiolabel the oligonucleotide. However, other methods may be used to label the oligonucleotide, including, but not limited to, biotinylation or enzyme labeling.

Sometimes, the DNA encoding the selectable gene and product gene is preceded by DNA encoding a signal sequence having a specific cleavage site at the N-terminus of the mature protein or polypeptide. In general, the signal sequence may be a component of the expression vector, or it may be a part of the selectable gene or product gene that is inserted into the expression vector. If a heterologous signal sequence is used, it preferably is one that is recognized and processed (i.e., cleaved by a signal peptidase) by the host cell. For yeast secretion the native signal sequence may be substituted by, e.g., the yeast invertase leader, alpha factor leader (including Saccharomyces and Kluyveromyces α-factor leaders, the latter described in U.S. Pat. No. 5,010,182 issued 23 Apr. 1991), or acid phosphatase leader, the C. albicans glucoamylase leader (EP 362,179 published 4 Apr. 1990), or the signal described in WO 90/13646 published 15 November 1990. In mammalian cell expression the native signal sequence of the protein of interest is satisfactory, although other mammalian signal sequences may be suitable, such as signal sequences from secreted polypeptides of the same or related species, as well as viral secretory leaders, for example, the herpes simplex gD signal. The DNA for such precursor region is ligated in reading frame to the selectable gene or product gene.

As shown in FIG. 1A, the selectable gene is generally provided at the 5' end of the DNA construct and this selectable gene is followed by the product gene. Therefore, the full length (non-spiced) message will contain DHFR as the first open reading frame and will therefore generate DHFR protein to allow selection of stable transfectants. The full length message is not expected to generate appreciable amounts of the protein of interest as the second AUG in a dicistronic message is an inefficient initiator of translation in mammalian cells (Kozak, *J. Cell Biol.*, 115: 887–903[1991]).

The selectable gene is positioned within an intron. Introns are noncoding nucleotide sequences, normally present within many eukaryotic genes, which are removed from newly transcribed mRNA precursors in a multiple-step process collectively referred to as splicing.

A single mechanism is thought to be responsible for the splicing of mRNA precursors in mammalian, plant, and yeast cells. In general, the process of splicing requires that the 5' and 3' ends of the intron be correctly cleaved and the resulting ends of the mRNA be accurately joined, such that a mature mRNA having the proper reading frame for protein synthesis is produced. Analysis of a variety of naturally occurring and synthetically constructed mutant genes has shown that nucleotide changes at many of the positions within the consensus sequences at the 5' and 3' splice sites have the effect of reducing or abolishing the synthesis of mature mRNA. Sharp, *Science*, 235:766 (1987); Padgett, et al., *Ann. Rev. Biochem.*, 55:1119 (1986); Green, *Ann. Rev. Genet.*, 20:671 (1986). Mutational studies also have shown that RNA secondary structures involving splicing sites can affect the efficiency of splicing. Solnick, *Cell*, 43:667 (1985); Konarska, et al, *Cell*, 42:165 (1985).

The length of the intron may also affect the efficiency of splicing. By making deletion mutations of different sizes within the large intron of the rabbit beta-globin gene, Wieringa, et al. determined that the minimum intron length necessary for correct splicing is about 69 nucleotides. *Cell*, 37:915 (1984). Similar studies of the intron of the adenovirus E1A region have shown that an intron length of about 78 nucleotides allows correct splicing to occur, but at reduced efficiency. Increasing the length of the intron to 91 nucleotides restores normal splicing efficiency, whereas truncating the intron to 63 nucleotides abolishes correct splicing. Ulfendahl, et al., *Nuc. Acids Res.*, 13:6299 (1985).

To be useful in the invention, the intron must have a length such that splicing of the intron from the mRNA is efficient. The preparation of introns of differing lengths is a routine matter, involving methods well known in the art, such as de novo synthesis or in vitro deletion mutagenesis of an existing intron. Typically, the intron will have a length of at least about 150 nucleotides, since introns which are shorter than this tend to be spliced less efficiently. The upper limit for the length of the intron can be up to 30 kB or more. However, as a general proposition, the intron is generally less than about 10 kB in length.

The intron is modified to contain the selectable gene not normally present within the intron using any of the various known methods for modifying a nucleic acid in vitro. Typically, a selectable gene will be introduced into an intron by first cleaving the intron with a restriction endonuclease, and then covalently joining the resulting restriction fragments to the selectable gene in the correct orientation for host cell expression, for example by ligation with a DNA ligase enzyme.

The DNA construct is dicistronic, i.e. the selectable gene and product gene are both under the transcriptional control of a single transcriptional regulatory region. As mentioned above, the transcriptional regulatory region comprises a promoter. Suitable promoting sequences for use with yeast hosts include the promoters for 3-phosphoglycerate kinase (Hitzeman at al, *J. Biol. Chem.*, 255:2073 [1980]) or other glycolytic enzymes (Hess et al, *J. Adv. Enzyme Reg.*, 7:149 [1968]; and Holland, *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al, EP 73,657A. Yeast enhancers also are advantageously used with yeast promoters.

Expression control sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide.

Product gene transcription from vectors in mammalian host cells is controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the product gene, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209:1422–1427 (1980); Pavlakis et al, *Proc. Natl. Acad. Sci. U.S.A.*, 78:7398–7402 (1981). The immediate early promoter of the human cytomegalovirus (CMV) is conveniently obtained as a HindIII E restriction fragment. Greenaway et al., *Gene*, 18:355–360 (1982). A system for expressing DNA in mammalian hosts using. the bovine papilloma virus as a vector is disclosed in U.S. Pat. No 4,419,446. A modification of this system is described in U.S. Pat. No. 4,601,978. See also Gray et al, *Nature*, 295:503–508 (1982) on expressing cDNA encoding immune interferon in monkey cells;, Reyes et al., *Nature*, 297:598–601 (1982) on expression of human β-interferon cDNA in mouse cells under the control of a thymidine kinase promoter from herpes simplex virus, Canaani and Berg, *Proc. Natl. Acad. Sci. U.S.A.*, 79:5166–5170 (1982) on expression of the human interferon β1 gene in cultured mouse and rabbit cells, and Gorman et al, *Proc. Natl. Acad. Sci. U.S.A.*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Preferably the transcriptional regulatory region in higher eukaryotes comprises an enhancer sequence. Enhancers are relatively orientation and position independent having been found 5' (Lainins et al, *Proc. Natl. Acad. Sci. U.S.A.*, 78:993 [1981 ])and 3' (Lusky et al, *Mol. Cell Bio.*, 3:1108 [1983]) to the transcription unit, within an intron (Banerji et al., *Cell*, 33:729 [1983]) as well as within the coding sequence itself (Osborne et al., *Mol. Cell Bio.*, 4:1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer (CMV), the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the product gene, but is preferably located at a site 5' from the promoter.

The DNA construct has a transcriptional initiation site following the transcriptional regulatory region and a transcriptional termination region following the product gene (see FIG. 1A). These sequences are provided in the DNA construct using techniques which are well known in the art.

The DNA construct normally forms part of an expression vector which may have other components such as an origin of replication (i.e., a nucleic acid sequence that enables the vector to replicate in one or more selected host cells) and, if desired, one or more additional selectable gene(s). Construction of suitable vectors containing the desired coding and control sequences employs standard ligation techniques. Isolated plasmids or DNA fragments are cleaved, tailored, and religated in the form desired to generate the plasmids required.

Generally, in cloning vectors the origin of replication is one that enables the vector to replicate independently of the host chromosomal DNA, and includes origins of replication or autonomously replicating sequences. Such sequences are well known. The 2μ plasmid origin of replication is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coil* and then the same vector is transfected into yeast or mammalian cells for expression even though it is not capable of replicating independently of the host cell chromosome.

For analysis to confirm correct sequences in plasmids constructed, plasmids from the transformants are prepared, analyzed by restriction, and/or sequenced by the method of Messing et al., *Nucleic Acids Res.*, 9:309 (1981)or by the method of Maxam at al, *Methods in Enzymology*, 65:499 (1980).

The expression vector having the DNA construct prepared as discussed above is transformed into a eukaryotic host cell. Suitable host cells for cloning or expressing the vectors herein are yeast or higher eukaryote cells.

Eukaryotic microbes such as filamentous fungi or yeast are suitable hosts for vectors containing the product gene. *Saccharomyces cerevisiae*, or common baker's yeast, is the most commonly used among lower eukaryotic host microorganisms. However, a number of other genera, species, and strains are commonly available and useful herein, such as *S. pombe* [Beach and Nurse, *Nature*, 290:140 (1981 )], *Kluyveromyces lactis* [Louvencourt at al, *J. Bacteriol.*, 737 (1983)], yarrowia [EP 402,226], *Pichia pastoris* [EP 183, 070], *Trichoderma reesia* [EP 244,234], *Neurospora crassa* [Case et al, *Proc. Natl. Acad. Sci. U.S.A.*, 76:5259–5263 (1979)], and Aspergillus hosts such as *A. nidulans* [Ballance at al., *Biochem. Biophys. Res. Commune*, 112:284–289 (1983); Tilburn et al., *Gene*, 26:205–221 (1983); Yelton et al., *Proc. Natl. Acad. Sci. U.S.A.*, 81:1470–1474(1984)] and *A. niger* [Kelly and Hynes, *EMBO J.*, 4:475–479 (1985)].

Suitable host cells for the expression of the product gene are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosphila melanogaster* (fruitfly), and *Bombyx mori* host cells have been identified. See, e.g., Luckow et al, *Bio/Technology*, 6:47–55 (1988); Miller at al, in *Genetic Engineering*, Setlow, J. K. et al., eds., Vol. 8 (Plenum Publishing, 1986), pp. 277–279; and Maeda et al., *Nature*, 315:592–594(1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the product gene. During incubation of the plant cell culture with *A. tumefaciens*, the product gene is transferred to the plant cell host such that it is transfected, and will, under appropriate conditions, express the product gene. In addition, regulatory and signal sequences compatible with plant cells are available, such as the nopaline synthase promoter and polyadenylation signal sequences. Depicker at al, *J. Mol. Appl. Gen.*, 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al, *J. Gen Virol.*, 36:59 [1977]); baby hamster kidney cells (BHK, ATCC CCL 10); Chinese hamster ovary cells/ -DHFR (CHO, Urlaub and Chasin, *Proc. Natl. Acad. Sci. U.S.A.*, 77:4216 [1980]); dp12.CHO cells (EP 307,247 published 15 March 1989); mouse sertoli cells (TM4, Mather, *Biol. Reprod.*, 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51 ); TRI cells (Mather et al, *Annals N.Y. Acad. Sci.*, 383:44–68 [1982]); MRC 5 cells; FS4 cells; and a human hepatoma line (Hep G2).

Host cells are transformed with the above-described expression or cloning vectors of this invention and cultured in conventional nutrient media modified as appropriate for inducing promoters, selecting transformants, or amplifying the genes encoding the desired sequences.

Infection with Agrobacterium turnefaciens is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456–457 (1978) may be used. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130:946 (1977) and Hsiao at al, *Proc. Natl. Acad. Sci.* (*U.S.A.*), 76:3829 (1979). However, other methods for introducing DNA into cells such as by nuclear injection or by protoplast fusion may also be used.

In the preferred embodiment the DNA is introduced into the host cells using electroporation. See Andreason, *J. Tiss. Cult. Meth.*, 15:56–62 (1993), for a review of electroporation techniques useful for practicing the instantly claimed invention. It was discovered that electroporation techniques for introducing the DNA construct into the host cells were preferable over calcium phosphate precipitation techniques insofar as the latter could cause the DNA to break up and forming concantemers.

The mammalian host cells used to express the product gene herein may be cultured in a variety of media as discussed in the definitions section above. The media contains the selection agent used for selecting transformed host cells which have taken up the DNA construct (either as an intra- or extra-chromosomal element). To achieve selection of the transformed eukaryotic cells, the host cells may be grown in cell culture plates and individual colonies expressing the selectable gene (and thus the product gene) can be isolated and grown in growth medium until the nutrients are depleted. The host cells are then analyzed for transcription and/or transformation as discussed below. The culture conditions, such as temperature, pH, and the like, are those previously used with the host cell selected for expression, and will be apparent to the ordinarily skilled artisan.

Gene amplification and/or expression may be measured in a sample directly, for example, by conventional Southern blotting, Northern blotting to quantitate the transcription of mRNA (Thomas, *Proc. Natl. Acad. Sci. U.S.A.*, 77:5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescens, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734–738 (1980).

In the preferred embodiment, the mRNA is analyzed by quantitative PCR (to determine the efficiency of splicing) and protein expression is measured using ELISA as described in Example 1 herein.

The product of interest preferably is recovered from the culture medium as a secreted polypeptide, although it also may be recovered from host cell lysates when directly expressed without a secretory signal. When the product gene is expressed in a recombinant cell other than one of human origin, the product of interest is completely free of proteins or polypeptides of human origin. However, it is necessary to purify the product of interest from recombinant cell proteins or polypeptides to obtain preparations that are substantially homogeneous as to the product of interest. As a first step, the culture medium or lysate is centrifuged to remove particulate cell debris. The product of interest thereafter is purified from contaminant soluble proteins and polypeptides, for example, by fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel electrophoresis using, for example, Sephadex G-75; chromatography on plasminogen columns to bind the product of interest and protein A Sepharose columns to remove contaminants such as IgG.

The following examples are offered by way of illustration only and are not intended to limit the invention in any manner. All patent and literature references cited herein are expressly incorporated by reference.

EXAMPLE 1 tPA production using the dicistronic expression vectors

It was sought to increase the level of homogeneity with regard to expression levels of stable clones by expressing a selectable marker (such as DHFR) and the protein of interest from a single promoter. These vectors divert most of the transcript to product expression while linking it at a fixed ratio to DHFR expression via differential splicing.

Vectors were constructed which were derived from the vector pRK (Suva et al., *Science*, 237:893–896 [1987]) which contains an intron between the cytomegalovirus immediate early promoter (CMV) and the cDNA that encodes the polypeptide of interest. The intron of pRK is 139 nucleotides in length, has a splice donor site derived from cytomegalovirus immediate early gene (CMVIE), and a splice acceptor site from an IgG heavy chain variable region ($V_H$) gene (Eaton et al., *Biochem.*, 25:8343 [1986]).

DHFR/intron vectors were constructed by inserting an EcoRV linker into the BSTX1 site present in the intron of pRK7. An 830 base-pair fragment containing a mouse DHFR coding fragment was inserted to obtain DHFR intron expression vectors which differ only in the sequence that comprises the splice donor site. Those sequences were altered by overlapping PCR mutagenesis to obtain sequences that match splice donor sites found between exons 3 and 4 of normal and mutant Ras genes. PCR was also used to destroy the splice donor site.

A mouse DHFR cDNA fragment (Simonsen et al., *Proc. Natl. Acad. Sci. U.S.A.*, 80:2495–2499 [1983]) was inserted into the intron of this vector 59 nucleotides downstream of the splice donor site. The splice donor site of this vector was altered by mutagenesis to change the ratio of spliced to non-spliced message in transfected cells. It has previously been shown that a single nucleotide change (G to A) converted a relatively efficient splice donor site found in the normal ras gene into an inefficient splice site (Cohen et al., *Nature*, 334:119–124 [1988]). This effect has been demonstrated in the context of the ras gene and confirmed when these sequences were transferred to human growth hormone constructs (Cohen et al., *Cell*, 58:461–472 [1989]). Additionally, a non functional 5' splice site (GT to CA) was constructed as a control (ΔGT). A polylinker was inserted 35 nucleotides downstream of the 3' splice site to accept the cDNA of interest. A vector containing tPA (Pennica at al, *Nature*, 301:214–221 [1983]) was linearized downstream of the polyadenylation site before it was introduced into CHO cells (Potter et al., *Proc. Natl. Acad. Sci. U.S.A.*, 81:7161 [1984]).

Figure 3D:
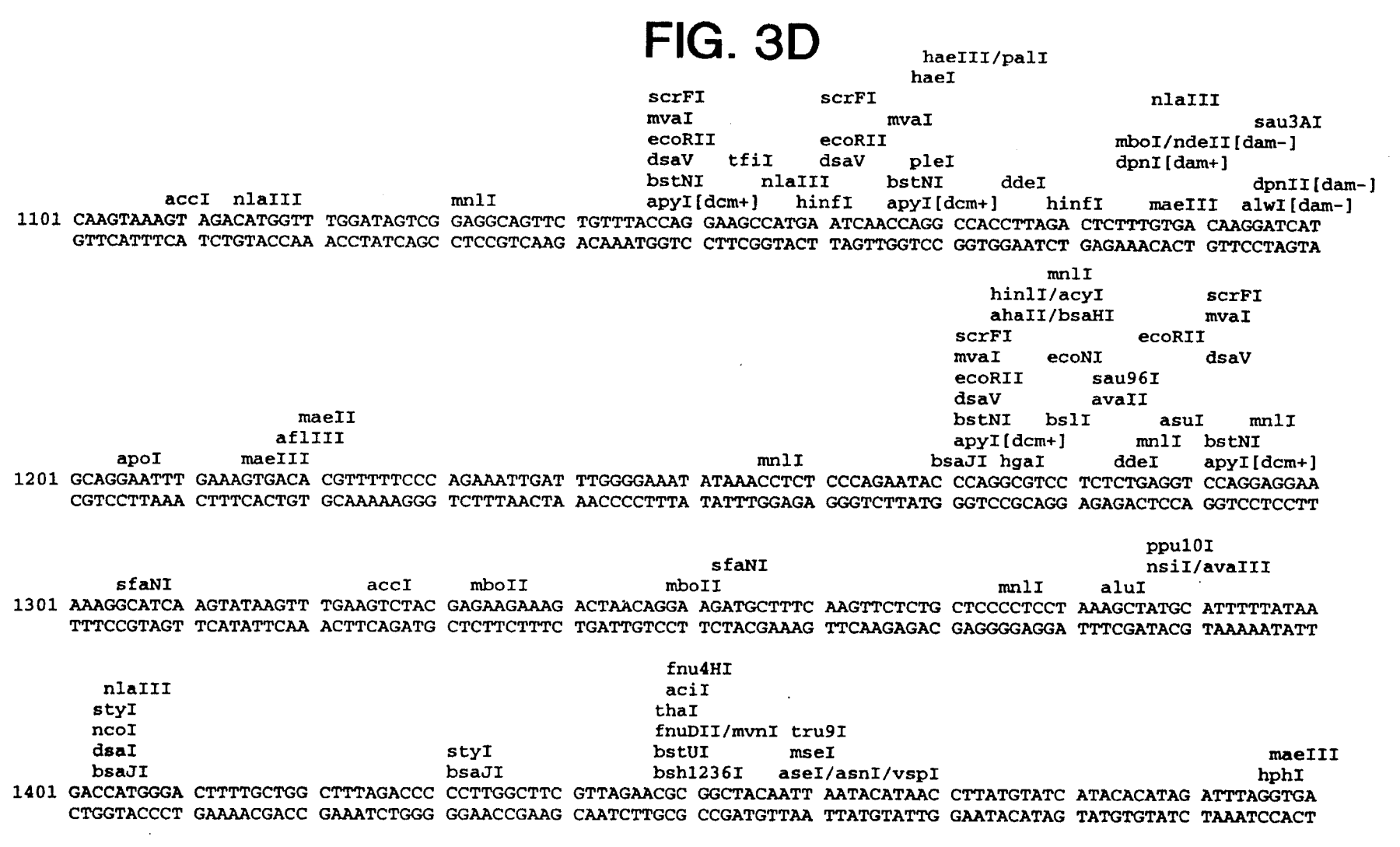
Figure 3F:
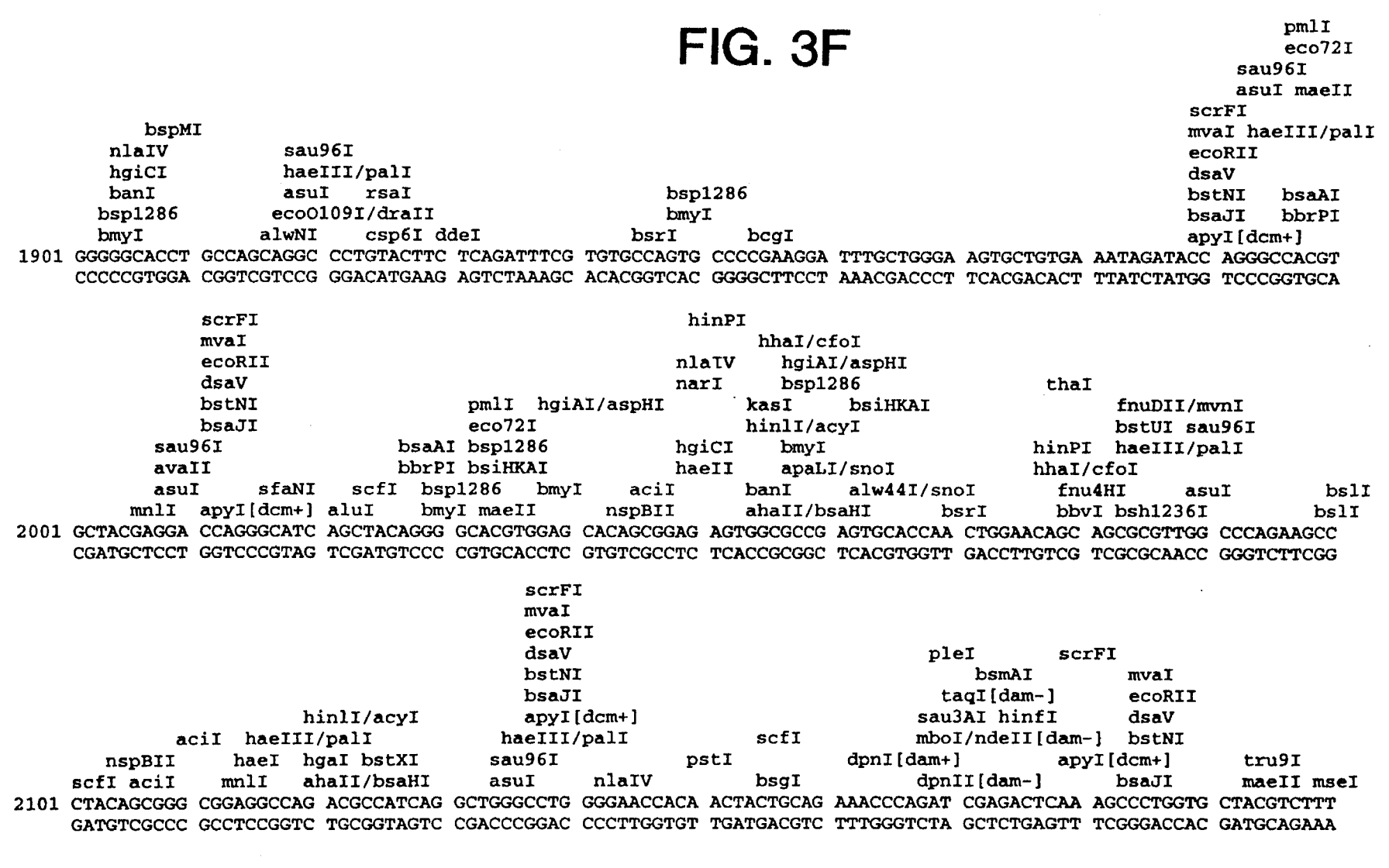
Figure 3H:
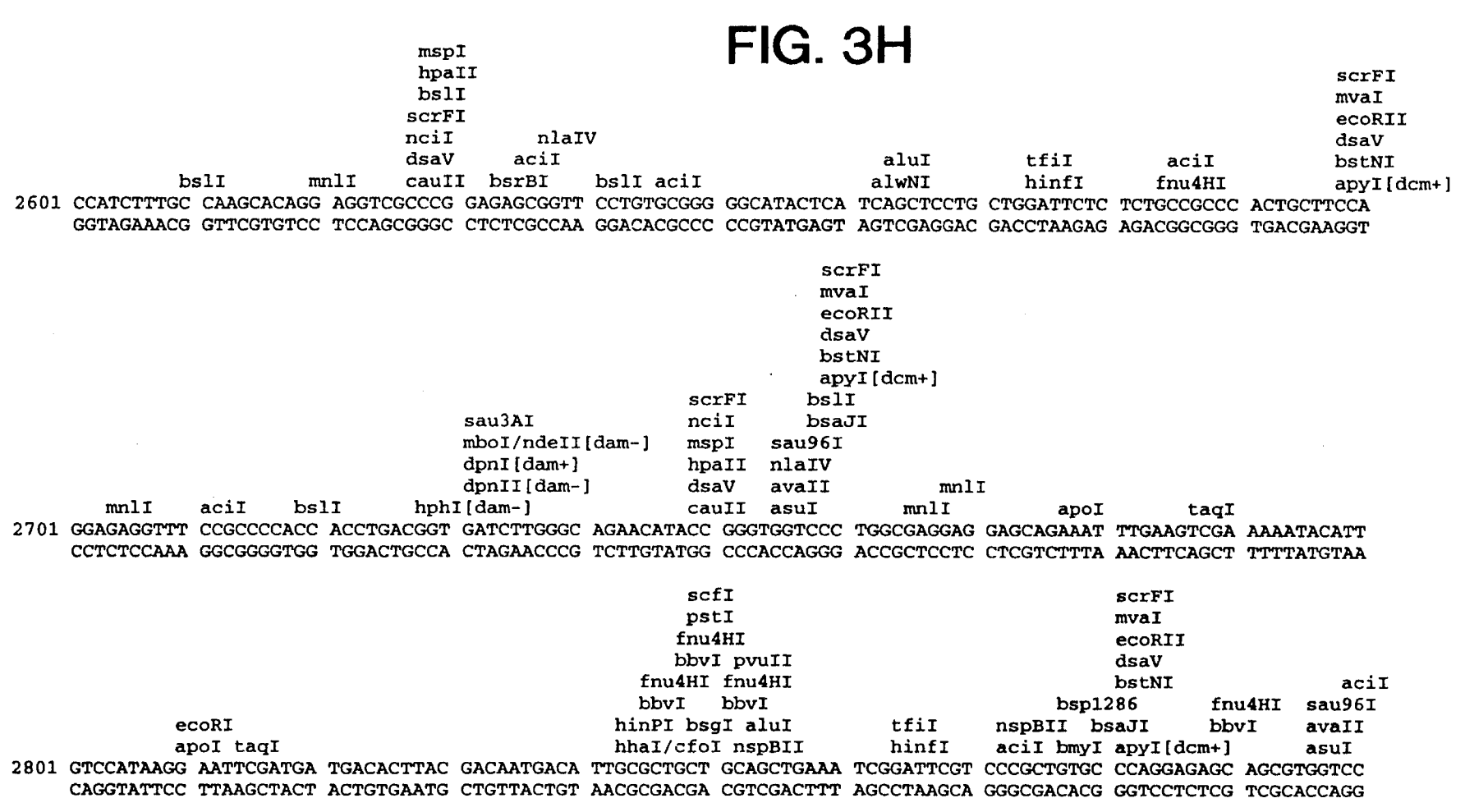

Plasmid DNA's that contained DHFR/intron, tPA and (a) wild type ras (WT ras), i.e. FIG. 3 (SEQ ID NO: 1), (b) mutant ras, or (c) non-functional splice donor site (ΔGT) were introduced into CHO DHFR minus cells by electroporation. The intron vectors were each linearized downstream of the polyadenylation site by restriction endonuclease treatment. The control vector was linearized downstream of the second polyadenylation site. The DNA's were ethanol precipitated after phenol/chloroform extraction and were resuspended in 20 μl 1/10 Tris EDTA. Then, 10 μg of DNA was incubated with $10^7$ CHO.dp12 cells (EP 307,247 published 15 Mar. 1989) in 1 ml of PBS on ice for 10 min. before electroporation at 400 volts and 330 μf using a BRL Cell Porator.

Cells were returned to ice for 10 min. before being plated into non-selective medium. After 24 hours cells were fed nucleoside-free medium to select for stable DHFR+ clones which were pooled. The pooled DHFR+ clones were lysed and mRNA's were prepared.

Figure 1B:
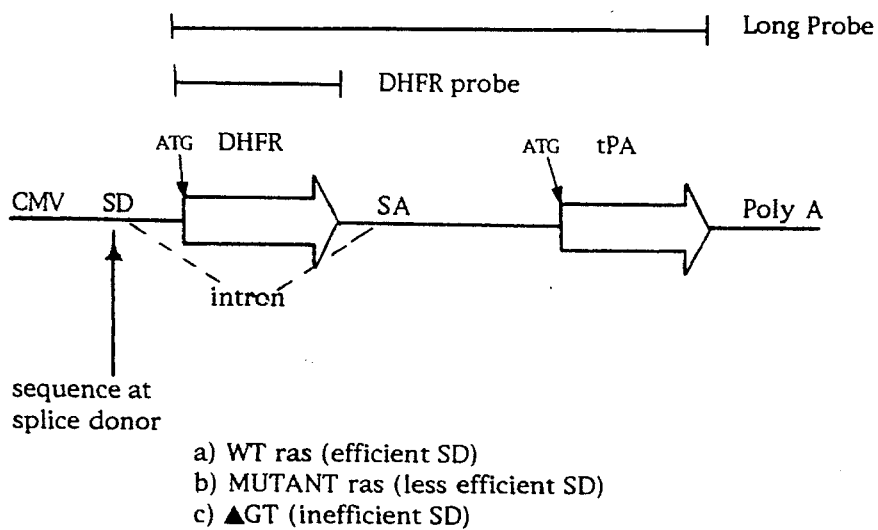

To prepare the mRNA, RNA was extracted from 5×10⁷ cells which were grown from pools of more than 200 clones derived from the stable transfection of the three vectors, the essential construction of which is shown in FIG. 1B and from non-transfected CHO cells. RNA was purified over oligo-DT cellulase (Collaborative Biomedical Products). 10 µg of mRNA was then subjected to Northern blotting which involved running the mRNA on a 1.2% agarose, 6.6% formaldehyde gel, and transferring it to a nylon filter (Stratagene Duralon-UV membrane), prehybridized, probed and washed according to the manufacturer's instructions.

The filter was probed sequentially using probes (shown in FIG. 1B) that would detect (a) the full length message, (b) both full length and spliced message, or (c) beta actin. Probing with the long probe showed that the vector that contains the efficient splice donor site (i.e. WT ras) generates predominately a mRNA of the size predicted for the spliced product while the other two vectors gave rise primarily to a mRNA that corresponds in size to non-spliced message. The DHFR probe detected only full length message and demonstrated that the WT ras splice donor derived vector generates very little full length message with which to confer a DHFR positive phenotype.

Figure 2:
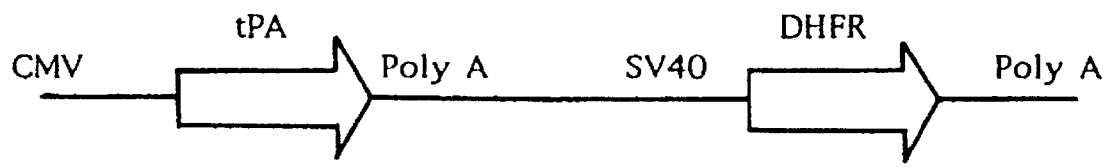
FIG. 2 depicts schematically the control DNA construct used in Example 1.
Figure 4:
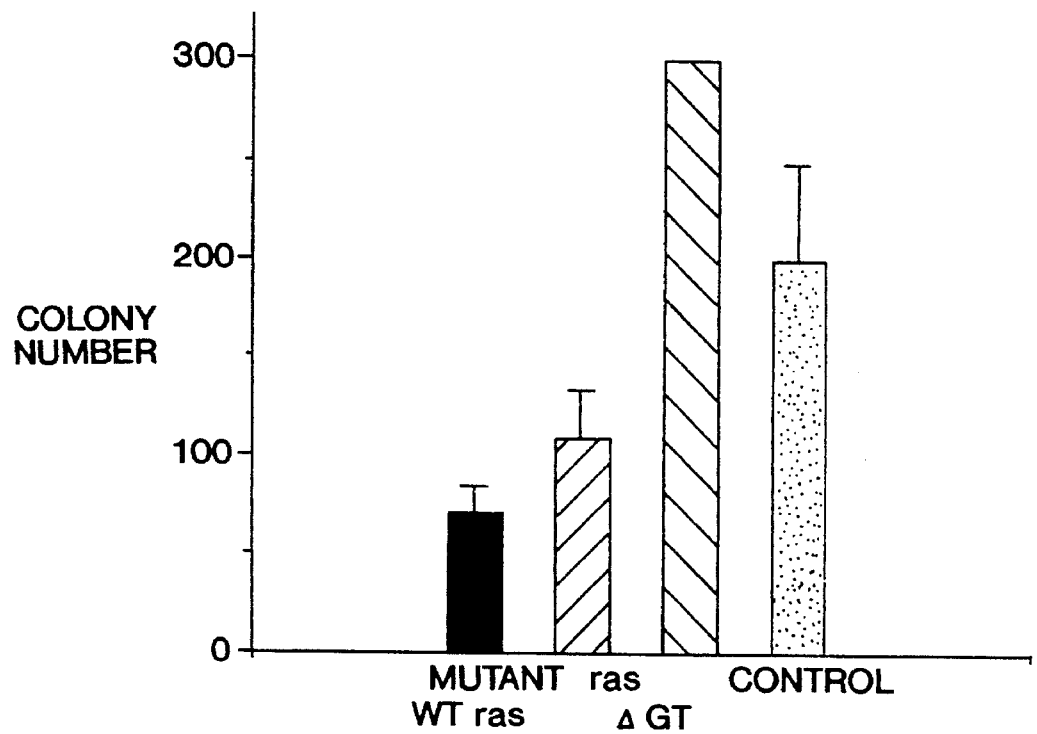
FIG. 4 is a bar graph which shows the number of colonies that form in selective medium after electroporation of linearized duplicate miniprep DNA's prepared in parallel from the three vectors shown in FIG. 1B (i.e. with wild type ras splice donor sequence [WT ras], mutant ras splice donor sequence [MUTANT ras] and non-functional splice donor sequence [ΔGT]) and from the control vector that has DHFR under control of SV40 promoter and tPA under control of CMV promoter (see FIG. 2). Cells were selected in nucleoside free medium and counted with an automated colony counter.

FIG. 4 shows the number of DHFR positive colonies obtained after duplicate electroporations with the three intron vectors described above and from a conventional vector that has a CMV promoter driving tPA and a SV40 promoter driving DHFR (see FIG. 2). The increase in colony number parallels the increase in full length message that accumulates with the modification of the splice donor sites. The conventional vector efficiently generates colonies and does not vary significantly from the ΔGT construct.

The level of tPA expression was determined by seeding cells in 1 ml of F12:DMEM (50:50, with 5% FBS) in 24 well dishes to near confluency. Growth of the cells continued until the media was exhausted. Media was then assayed by ELISA for tPA production. Briefly, anti-tPA antibody was coated onto the wells of an ELISA microtiter plate, media samples were added to the wells followed by washing. Binding of the antigen (tPA) was then quantified using horse radish peroxidase (HRPO) labelled anti-tPA antibody.

Figure 5A:
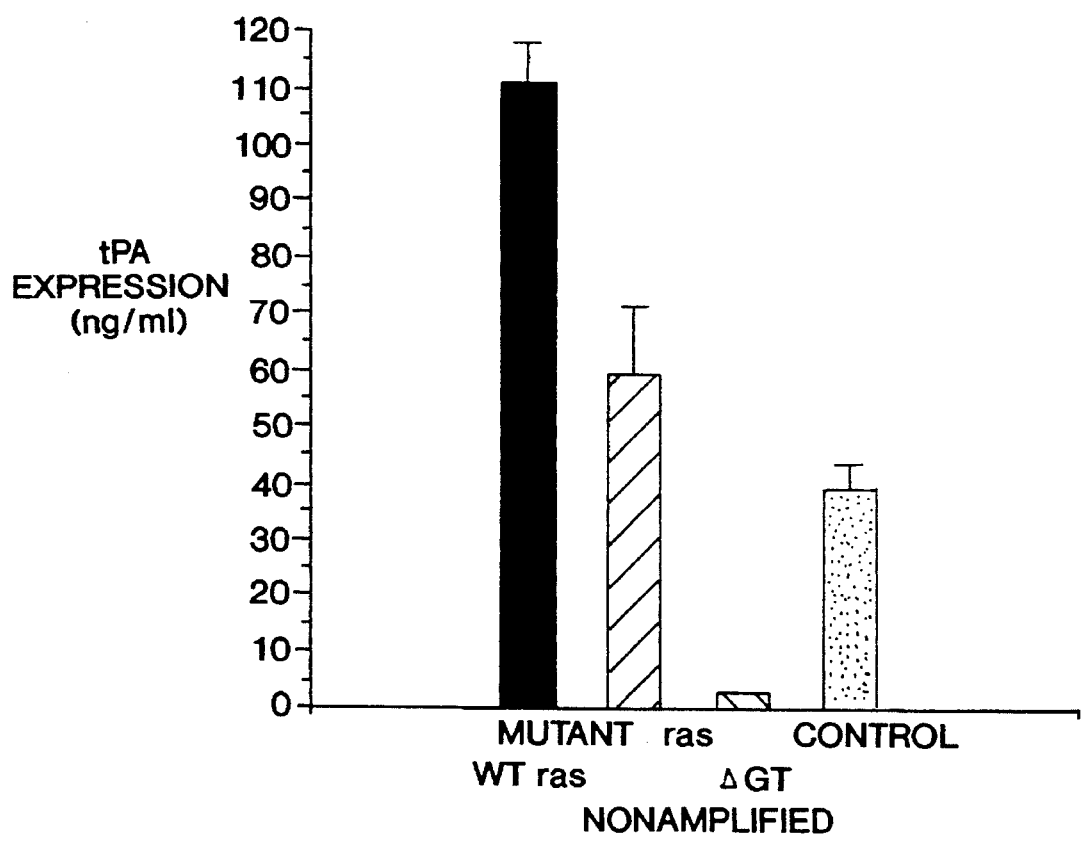
FIGS. 5A–C are bar graphs depicting expression of tPA from stable pools and clones generated from the vectors shown in FIG. 1B.

FIG. 5A depicts the titers of secreted tPA protein after pooling the clones of each group shown in FIG. 4. While the number of colonies increased with a weakening of splice donor function, the inverse was seen with respect to tPA expression. The expression levels are consistent with the RNA products that are observed; as more of the dicistronic message is spliced an increased amount of message will contain tPA as the first open reading frame resulting in increased tPA expression. A mutation of GT to CA in the splice donor site results in an abundance of DHFR positive colonies which express undetectable levels of tPA, possibly resulting from inefficient utilization of the second AUG. Importantly, FIG. 5A also shows that expression levels obtained from one of the dicistronic vectors (with WT ras SD) was about threefold higher than that obtained with the control vector containing a CMV promoter/enhancer driving tPA, SV40 promoter/enhancer controlling DHFR and SV40 polyadenylation signals controlling the expression of tPA and DHFR.

Figure 5B:
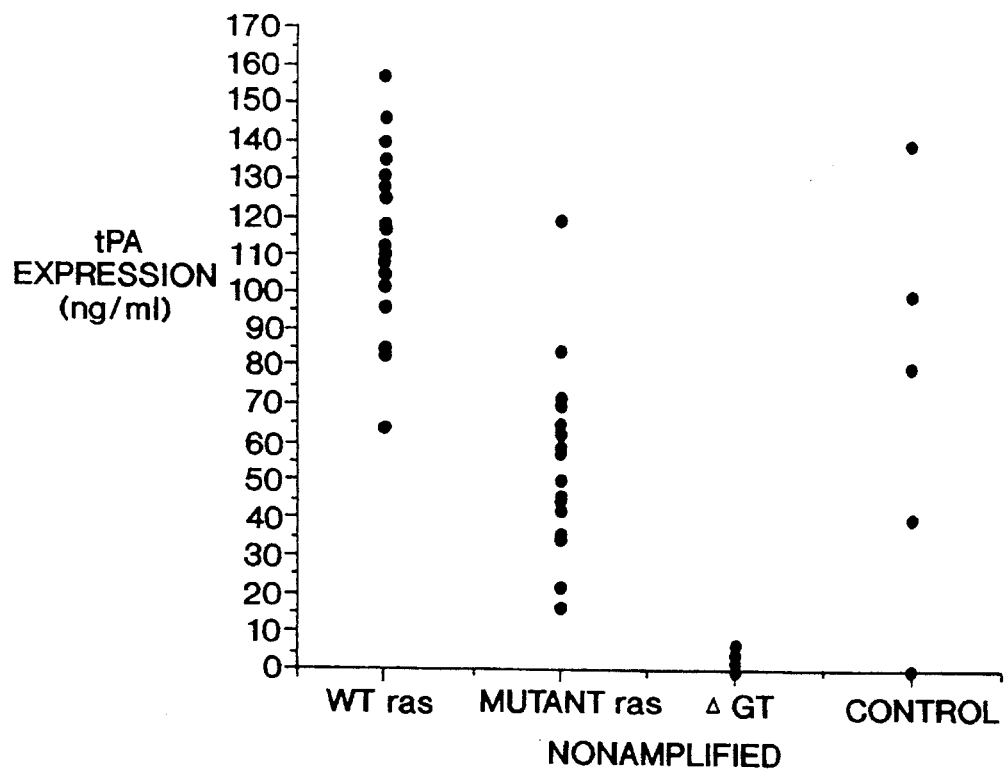

Additionally, the homogeneity of expression in the pools was investigated. FIG. 5B shows that all 20 clones generated by the WT ras splice donor site derived dicistronic vectors express detectable levels of tPA while only 4 of 20 clones generated by the control vector express tPA. None of the clones transfected with the non-splicing (ΔGT) vector expressed tPA levels detectable by ELISA. This finding is consistent with previous observations that relatively few clones generated by conventional vectors make useful levels of protein.

Figure 5C:
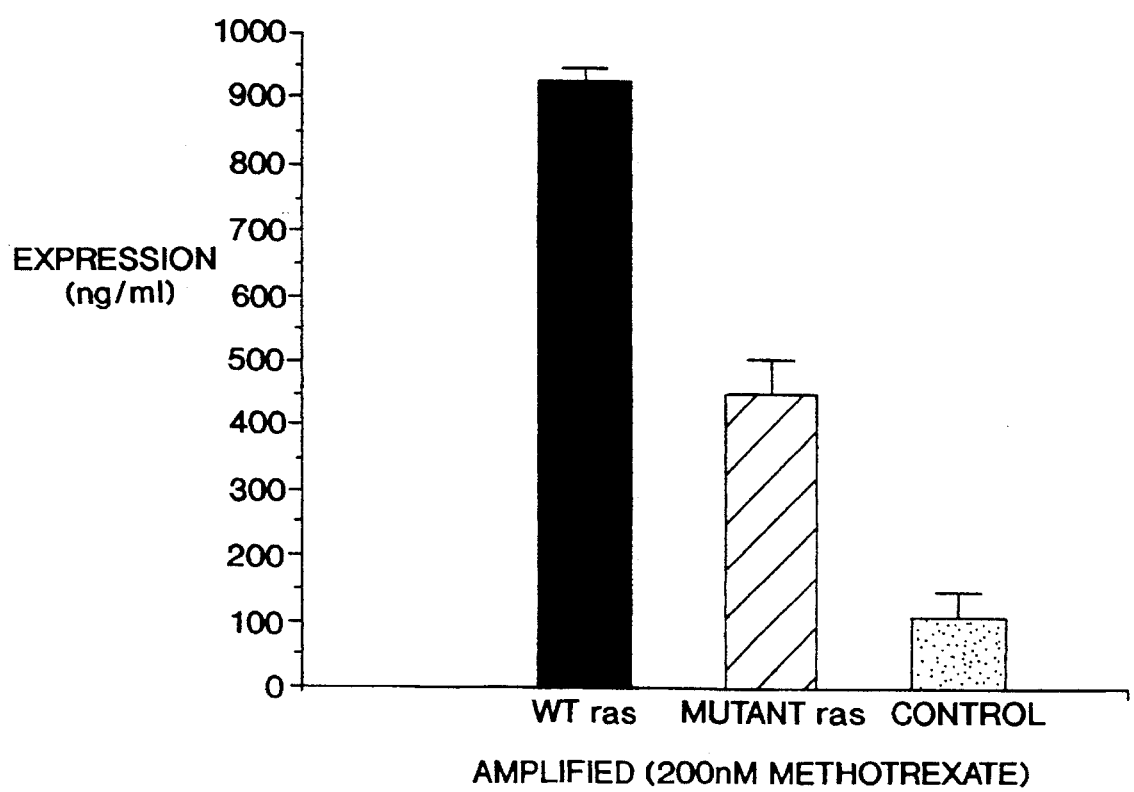

Expression of tPA was increased following methotrexate amplification of pools. FIG. 5C shows that 2 of the dicistronic vector derived pools (i.e. with WT ras and MUTANT ras SD sites) increased in expression markedly (8.4 and 7.7 fold), while the pool generated by the conventional vector increased only slightly (2.8 fold) when each was subjected to 200 nM Mtx. An overall increase of 9 fold was obtained using the best dicistronic (WT ras SD) versus the conventional vector following amplification. Growth of the highest expressing amplified pool in nutrient rich production medium yielded titers of 4.2 µg/ml tPA.

It was shown that manipulation of the splice donor sequence alters the ratio of spliced to full length message and the number of colonies that form in selective medium. It was also shown that dicistronic expression vectors generate clones that express high levels of recombinant proteins. Surprisingly, it was possible to isolate high expressors which had the efficient WT ras splice donor site by selection for DHFR⁺ cells despite the efficiency with which the DHFR gene was spliced from the RNA precursors formed in these cells.

EXAMPLE 2

TNFr-IgG production using the dicistronic expression vectors

Figure 1C:
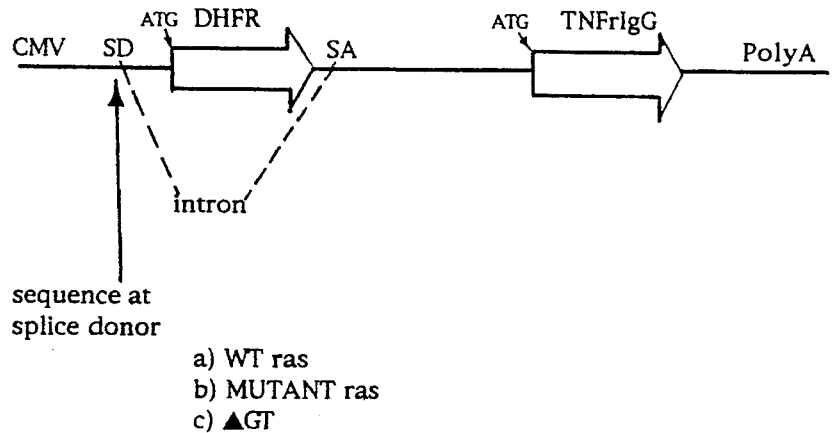

To prove the general applicability of this approach, a second product was evaluated in the dicistronic vector system containing, as the DNA of interest, an immunoadhesin (TNFr-IgG) capable of binding tumor necrosis factor (TNF) (Ashkenazi et al, *Proc. Natl. Acad. Sci. U.S.A.*, 88:10535–10539 [1991]). The experiments described in Example 1 above were essentially repeated except that the product gene encoded the immunoadhesin TNFr-IgG. Plasmid DNA's that contained a TNFr-IgG cDNA and (a) WT ras, i.e. FIG. 6 (SEQ ID NO: 2), (b) mutant ras or (c) nonfunctional splice donor site (ΔGT) were introduced into the dp12.CHO cells as discussed for Example 1. See FIG. 1C for an illustration of the DNA constructs.

Figure 7A:
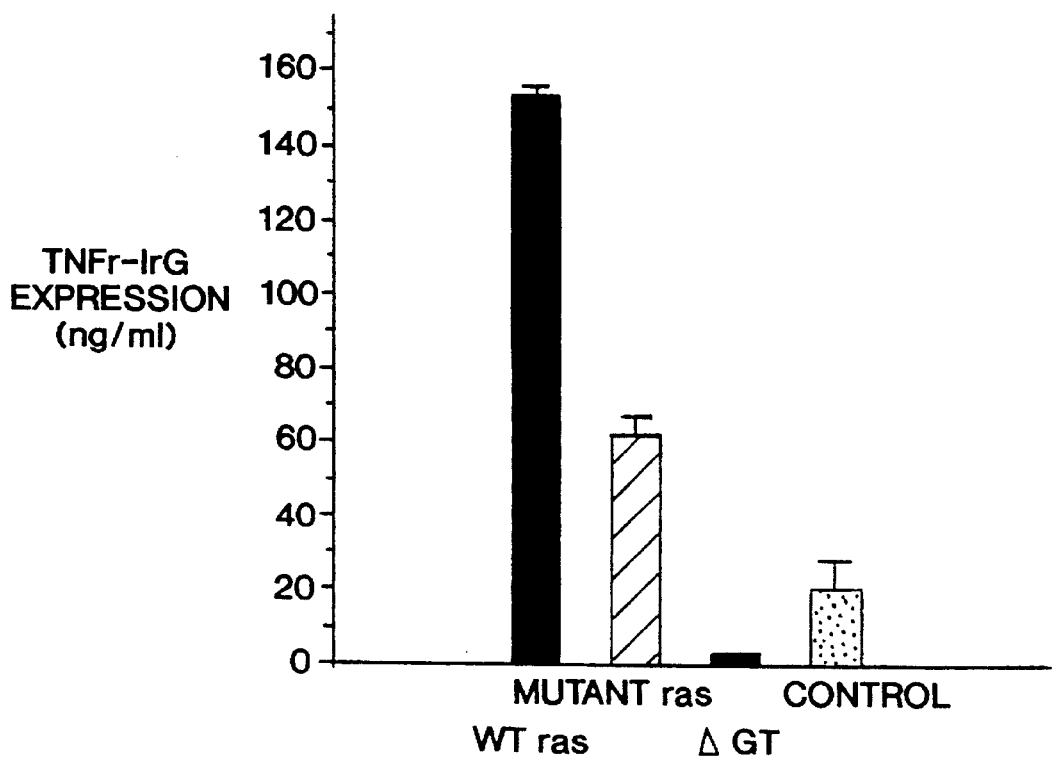
FIGS. 7A–B are bar graphs depicting expression of TNFr-IgG using dicistronic or control vectors (see Example 2). Vectors containing TNFr-IgG (but otherwise identical to those described for tPA expression in Example 1) were constructed (see FIG. 1C), introduced into dp 12.CHO cells by electroporation, pooled, and assayed for product expression before (FIG. 7A) and after (FIG. 7B) being subjected to amplification in 200 nM Mtx.
Figure 7B:
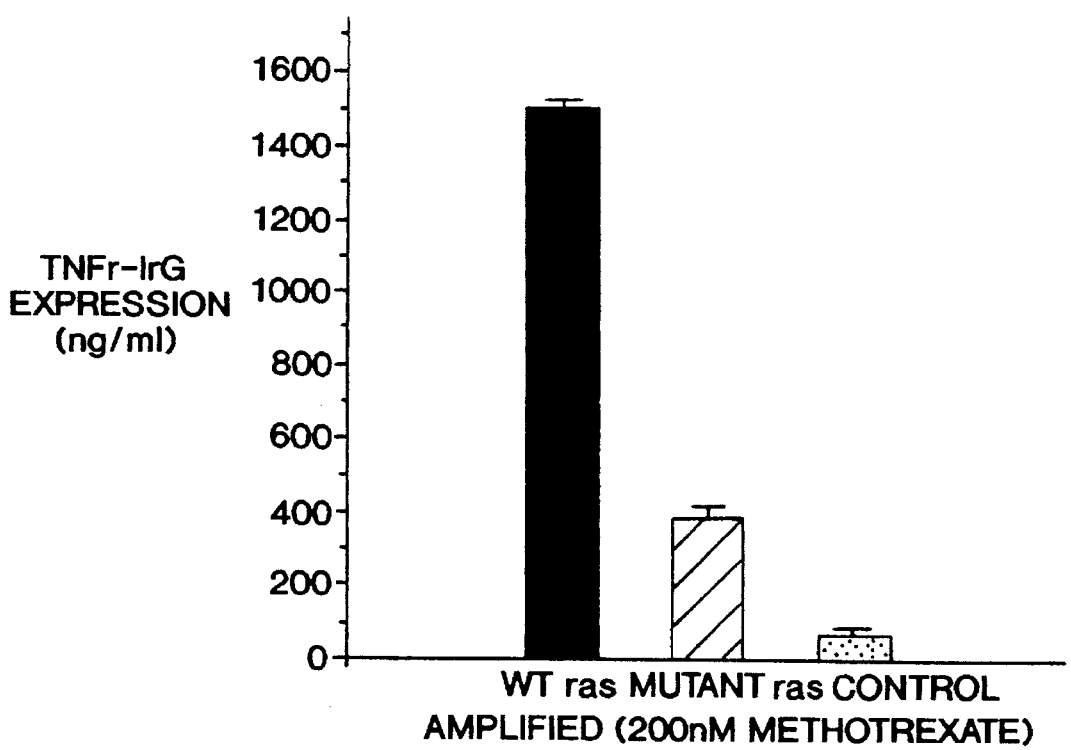
Figure 8:
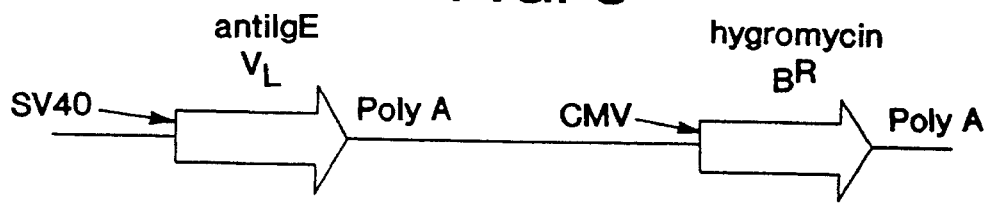
FIG. 8 depicts schematically the DNA construct used for expression of the $V_L$ of anti-IgE in Example 3.

It was discovered that the number of DHFR positive colonies generated by three of these vectors was similar to that seen with the tPA constructs. Expression of TNFr-IgG also paralleled that seen with the tPA constructs (FIG. 7A). Amplification of pools from two of the constructs showed a marked increase in expression of immunoadhesin (9.6 and 6.8 fold) (FIG. 7B). The best of these amplified pools expressed 9.5 µg/ml when grown in nutrient rich production medium.

Thus, it was again shown that dicistronic expression vectors generate clones that express high levels of recombinant proteins. Furthermore, contrary to expectations, it was discovered that isolation of high product expressing host DHFR⁺ cells was possible using an efficient splice donor site (i.e. the WT ras splice donor site).

EXAMPLE 3

Antibody production using a dicistronic expression vector

Figure 1D:
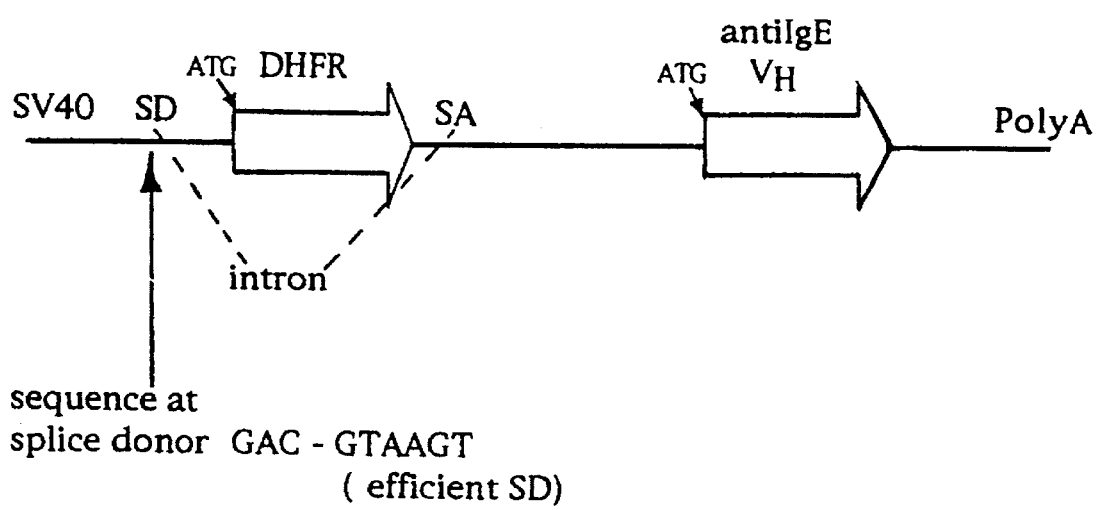
Figure 9A:
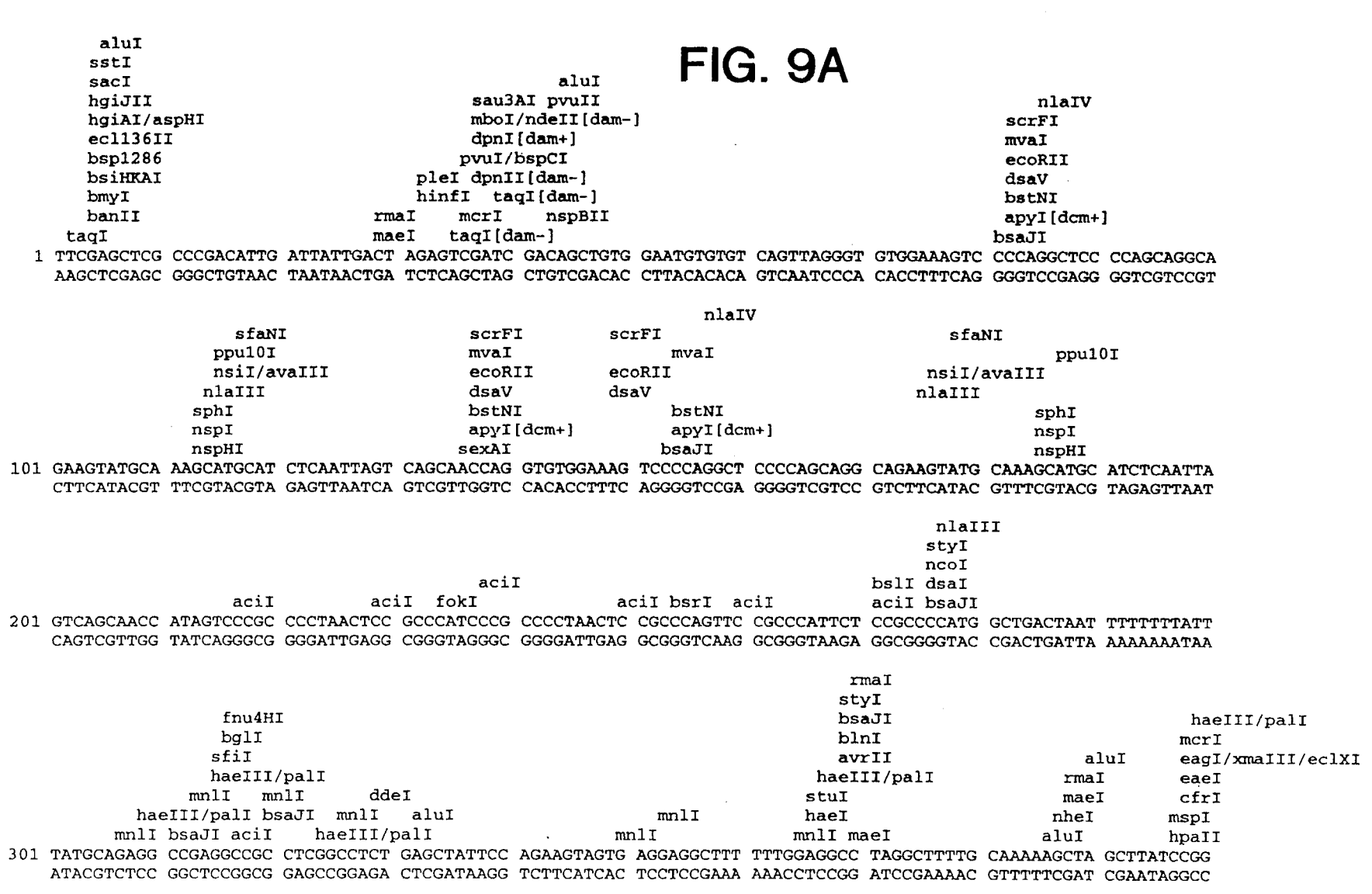
Figure 9C:
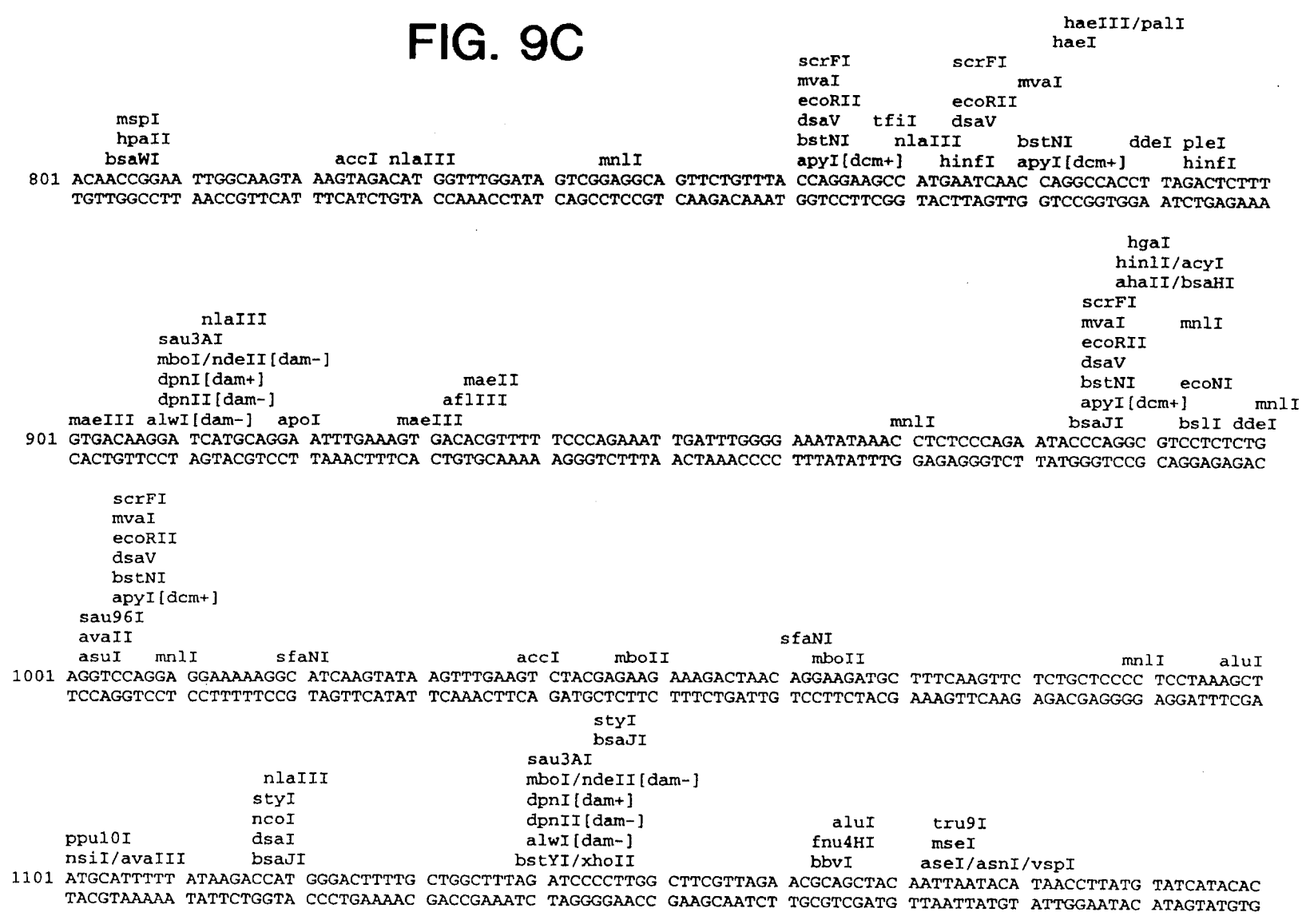

The usefulness of this system for antibody expression was evaluated by testing production of an antibody directed against IgE (Presta et al., *Journal of Immunology*, 151:2623–2632 [1993]). Further, the flexibility of the system with regard to transcription initiation was tested by replacing the CMV promoter/enhancer present in the previous vectors with the promoter/enhancer derived from the early region of SV40 virus (Griffin, B., Structure and Genomic Organization of SV40 and Polyoma Virus, In J. Tooze [Ed] DNA Tumor Viruses, Cold Spring Harbor Laboratory, Cold Spring Harbor, N.Y.). The heavy chain of the antibody was inserted downstream of DHFR as described in the earlier tPA and TNFr-IgG constructs. Additionally, a new splice donor site sequence (GAC:GTAAGT) was engineered into the vector which matches the consensus splice donor site more closely than did the splice donor sites present in the vectors tested in Examples 1 and 2. The resultant expression vector is shown in FIGS. 1D and 9.

It was discovered that this vector produced fewer colonies than the vectors previously tested, and produced predominantly a spliced RNA product. A second vector was constructed to have the light chain of the antibody under control of the SV40 promoter/enhancer and poly-A and the hygromycin B resistance gene under control of the CMV promoter/enhancer and SV40 poly-A. These vectors were linearized at unique HpaI sites downstream of the poly-A signal, mixed at a ratio of light chain vector to heavy chain vector of 10:3 and electroporated into CHO cells using an optimized protocol (as discussed in Examples 1 and 2).

Figure 11:
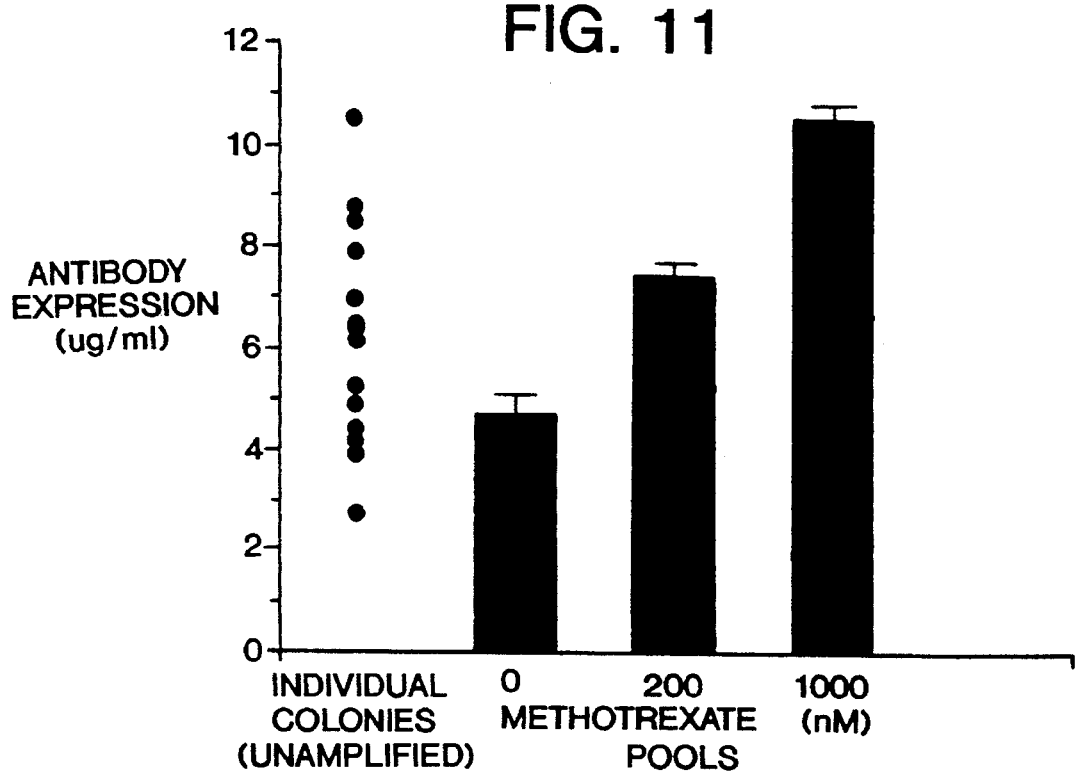
FIG. 11 is a bar graph depicting anti-IgE expression in Example 3. Heavy ($V_H$) and light ($V_L$) chain expression vectors were constructed, co-electroporated into CHO cells, clones were selected and assayed for antibody expression. Additionally, pools were established and assessed with regard to expression before and after Mtx selection at 200 nM and 1 μM.

FIG. 11 shows the levels of antibody expressed by clones and pools after selection in hygromycin B followed by selection for DHFR expression. All 20 of the clones analyzed expressed high levels of antibody when grown in rich medium and varied from one another by only a factor of four. A pool of antibody producing clones was generated and assayed shortly after it was established. That pool was grown continuously for 6 weeks without a significant decrease in productivity demonstrating that its stability was sufficient to generate gram quantities of protein from its large scale culture.

The pool was subjected to methotrexate amplification at 200 nM and 1 μM and achieved a greater than 2 fold increase in antibody titer. The 1 μM Mtx resistant pool achieved a titer of 41 mg/L when grown under optimal conditions in suspension culture.

The structure of the expressed antibody was examined. Proteins expressed by the 200 nM methotrexate resistant pool and by a well characterized expression clone generated by conventional vectors (Presta et al. [1993], supra) were metabolically labeled with $S^{35}$ cysteine and methionine. In particular, confluent 35 mm plates of cells were metabolically labeled with 50 μCi each S-35 methionine and S-35 cysteine (Amersham) in serum free cysteine and methionine free F12:DMEM. After one hour, nutrient rich production media was added and labeled proteins were allowed to "chase" into the medium for six more hours. Proteins were run on a 12% SDS/PAGE gel (NOVEX) non-reduced or following reduction with B-mercaptoethanol. Dried gels were exposed to film for 16 hours. CHO control cells were also labeled.

The majority of the antibody protein is secreted with a molecular weight of about 155 kilodaltons, consistent with a properly disulfide-linked antibody molecule with 2 light and 2 heavy chains. Upon reduction the molecular weight shifts to 2 approximately equally abundant proteins of 22.5 and 55 kilodaltons. The protein generated from the pool is indistinguishable from the antibody produced by the well characterized expression clone, with no apparent increase of free heavy or light chain expressed by the pool.

CONCLUSION

The efficient expression system described herein utilizes vectors consisting of promoter/enhancer elements followed by an intron containing the selectable marker coding sequence, followed by the cDNA of interest and a polyadenylation signal.

Several splice donor site sequences were tested for their effect on colony number and expression of the cDNA of interest, A non-functional splice donor site, splice donor sites found in an intron between exons 3 and 4 of mutant ras) and normal (WT ras) forms of the Harvey Ras gene and another efficient SD site (see Example 3) were used. The vectors were designed to direct expression of dicistronic primary transcripts. Within a transfected cell some of the transcripts remain full length while the remainder are spliced to excise the DHFR coding sequence. When the splice donor site is weakened or destroyed an increase in colony number is observed.

Expression levels show the inverse pattern, with the most efficient splice donor sites generating the highest levels of tPA, TNFr immunoadhesin or anti-IgE $V_H$.

The homogeneity of expression of clones generated by the ras splice donor site intron DHFR vectors was compared to clones generated from a conventional vector with a separate promoter/enhancer and polyadenylation signal for each DHFR and tPA. The DHFR intron vector gives rise to colonies that are much more homogeneous with regard to expression than those generated by the conventional vector. Non-expressing clones derived from the conventional vector may be the result of breaks in the tPA or TNFr-IgG domain of the plasmid during integration into the genome or the result of methylation of promoter elements (Busslinger et al., Cell, 34:197–206 [1983]; Watt et al, Genes and Development, 2:1136–1143 [1988]) driving tPA or TNFr-IgG expression. Promoter silencing by methylation or breaks in the DHFR-intron vectors would very likely render them incapable of conferring a DHFR positive phenotype.

It was found that pools generated by the DHFR-intron vectors could be amplified in methotrexate and would increase in expression by a factor of 8.4 (tPA), or 9.8 (TNFr-IgG). Pools from conventional vectors increased by only 2.8 and 3.0 fold for tPA and TNFr-IgG when amplified similarly. Amplified pools resulted in 9 fold higher tPA levels and 15 fold higher TNFr-IgG levels when compared to the conventional vector amplified pools.

Without being limited to any theory, the increase in expression of methotrexate resistant pools derived from the dicistronic vectors is likely due to the transcriptional linkage of DHFR and the product; when cells are selected for increased DHFR expression they consistently over-express product. Conventional approaches lack selectable marker and cDNA expression linkage and therefore methotrexate amplification often generates DHFR overexpression without the concomitant increase in product expression.

A further increase of 4 and 6.3 fold in expression were obtained when amplified tPA and TNFr-IgG pools were transferred from the media used for the selections and amplifications to a nutrient rich production medium.

In Example 3, the expression vector had a splice donor site that more closely matches the consensus splice donor sequence and had the heavy chain of a humanized anti-IgE antibody inserted downstream. This vector was linearized and co-electroporated with a second linearized vector that expresses the hygromycin resistance gene and the light chain of the antibody each under the control of its own promoter/enhancer and poly-A signals. An excess of light chain expression vector over the heavy chain dicistronic expression vector was used to bias in favor of light chain expression. Clones and a pool were generated after hygromycin B and DHFR selections. The clones were found to express relatively consistent, high levels of antibody, as did the pool. The 1 μM pool achieved a titer of 41 mg/L when grown under optimal conditions in suspension culture.

The anti-IgE antibody was assessed by metabolic labeling followed by SDS/PAGE under reducing and non reducing conditions and found to be indistinguishable from the protein expressed by a highly characterized clonal cell line. Of particular importance is the finding that no free light chain is observed in the pool relative to the clone.

A stable expression system for CHO cells has been developed that produces high levels of recombinant proteins rapidly and with less effort than that required by other expression systems. The vector system generates stable clones that express consistently high levels thereby reducing the number of clones that must be screened to obtain a highly productive clonal line. Alternatively, pools have been used to conveniently generate moderate to high levels of protein. This approach may be particularly useful when a number of related proteins are to be expressed and compared.

Without being limited to this theory, it is possible the vectors that have very efficient splice donor sites generate very productive clones because so little transcript remains non spliced that only integration events that lead to the generation of high levels of RNA produce enough DHFR protein to give rise to colonies in selective medium. The high level of spliced message from such clones is then translated into abundant amounts of the protein of interest. Pools of clones made concurrently by introducing conventional vectors expressed lower levels of protein, and were unstable with regard to long term expression, and expression could not be appreciably increased when the cells were subjected to methotrexate amplification.

The system developed herein is versatile in that it allows high levels of single and multiple subunit polypeptides to be rapidly generated from clones or pools of stable transfectants. This expression system combines the advantages of transient expression systems (rapid and labor non intensive generation of research amounts of protein) with the concurrent development of highly productive stable production cell lines.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 7360 bases
( B ) TYPE: nucleic acid
( C ) STRANDEDNESS: double
( D ) TOPOLOGY: linear ( x i ) SEQUENCE DESCRIPTION: SEQ ID NO:1:

```
TTCGAGCTCG  CCCGACATTG  ATTATTGACT  AGTTATTAAT  AGTAATCAAT  50
TACGGGGTCA  TTAGTTCATA  GCCCATATAT  GGAGTTCCGC  GTTACATAAC  100
TTACGGTAAA  TGGCCCGCCT  GGCTGACCGC  CCAACGACCC  CCGCCCATTG  150
ACGTCAATAA  TGACGTATGT  TCCCATAGTA  ACGCCAATAG  GGACTTTCCA  200
TTGACGTCAA  TGGGTGGAGT  ATTTACGGTA  AACTGCCCAC  TTGGCAGTAC  250
ATCAAGTGTA  TCATATGCCA  AGTACGCCCC  CTATTGACGT  CAATGACGGT  300
AAATGGCCCG  CCTGGCATTA  TGCCCAGTAC  ATGACCTTAT  GGGACTTTCC  350
TACTTGGCAG  TACATCTACG  TATTAGTCAT  CGCTATTACC  ATGGTGATGC  400
GGTTTTGGCA  GTACATCAAT  GGGCGTGGAT  AGCGGTTTGA  CTCACGGGGA  450
TTTCCAAGTC  TCCACCCCAT  TGACGTCAAT  GGGAGTTTGT  TTTGGCACCA  500
AAATCAACGG  GACTTTCCAA  AATGTCGTAA  CAACTCCGCC  CCATTGACGC  550
AAATGGGCGG  TAGGCGTGTA  CGGTGGGAGG  TCTATATAAG  CAGAGCTCGT  600
TTAGTGAACC  GTCAGATCGC  CTGGAGACGC  CATCCACGCT  GTTTTGACCT  650
CCATAGAAGA  CACCGGGACC  GATCCAGCCT  CCGCGGCCGG  GAACGGTGCA  700
TTGGAACGCG  GATTCCCCGT  GCCAAGAGTG  CTGTAAGTAC  CGCCTATAGA  750
GCGATAAGAG  GATTTTATCC  CCGCTGCCAT  CATGGTTCGA  CCATTGAACT  800
GCATCGTCGC  CGTGTCCCAA  AATATGGGGA  TTGGCAAGAA  CGGAGACCTA  850
CCCTGCCCTC  CGCTCAGGAA  CGCGTTCAAG  TACTTCCAAA  GAATGACCAC  900
```

```
AACCTCTTCA GTGGAAGGTA AACAGAATCT GGTGATTATG GGTAGGAAAA  950
CCTGGTTCTC CATTCCTGAG AAGAATCGAC CTTTAAAGGA CAGAATTAAT 1000
ATAGTTCTCA GTAGAGAACT CAAAGAACCA CCACGAGGAG CTCATTTTCT 1050
TGCCAAAAGT TTGGATGATG CCTTAAGACT TATTGAACAA CCGGAATTGG 1100
CAAGTAAAGT AGACATGGTT TGGATAGTCG GAGGCAGTTC TGTTTACCAG 1150
GAAGCCATGA ATCAACCAGG CCACCTTAGA CTCTTTGTGA CAAGGATCAT 1200
GCAGGAATTT GAAAGTGACA CGTTTTTCCC AGAAATTGAT TTGGGGAAAT 1250
ATAAACCTCT CCCAGAATAC CCAGGCGTCC TCTCTGAGGT CCAGGAGGAA 1300
AAAGGCATCA AGTATAAGTT TGAAGTCTAC GAGAAGAAAG ACTAACAGGA 1350
AGATGCTTTC AAGTTCTCTG CTCCCCTCCT AAAGCTATGC ATTTTTATAA 1400
GACCATGGGA CTTTTGCTGG CTTTAGACCC CCTTGGCTTC GTTAGAACGC 1450
GGCTACAATT AATACATAAC CTTATGTATC ATACACATAG ATTTAGGTGA 1500
CACTATAGAA TAACATCCAC TTTGCCTTTC TCTCCACAGG TGTCACTCCA 1550
GGTCAACTGC ACCTCGGTTC TAAGCTTGGG CTGCAGGTCG CCGTGAATTT 1600
AAGGGACGCT GTGAAGCAAT CATGGATGCA ATGAAGAGAG GGCTCTGCTG 1650
TGTGCTGCTG CTGTGTGGAG CAGTCTTCGT TTCGCCCAGC CAGGAAATCC 1700
ATGCCCGATT CAGAAGAGGA GCCAGATCTT ACCAAGTGAT CTGCAGAGAT 1750
GAAAAACGC AGATGATATA CCAGCAACAT CAGTCATGGC TGCGCCCTGT 1800
GCTCAGAAGC AACCGGGTGG AATATTGCTG GTGCAACAGT GGCAGGGCAC 1850
AGTGCCACTC AGTGCCTGTC AAAAGTTGCA GCGAGCCAAG GTGTTTCAAC 1900
GGGGGCACCT GCCAGCAGGC CCTGTACTTC TCAGATTTCG TGTGCCAGTG 1950
CCCCGAAGGA TTTGCTGGGA AGTGCTGTGA AATAGATACC AGGGCCACGT 2000
GCTACGAGGA CCAGGGCATC AGCTACAGGG GCACGTGGAG CACAGCGGAG 2050
AGTGGCGCCG AGTGCACCAA CTGGAACAGC AGCGCGTTGG CCCAGAAGCC 2100
CTACAGCGGG CGGAGGCCAG ACGCCATCAG GCTGGGCCTG GGAACCACA 2150
ACTACTGCAG AAACCCAGAT CGAGACTCAA AGCCCTGGTG CTACGTCTTT 2200
AAGGCGGGGA AGTACAGCTC AGAGTTCTGC AGCACCCCTG CCTGCTCTGA 2250
GGGAAACAGT GACTGCTACT TTGGGAATGG GTCAGCCTAC CGTGGCACGC 2300
ACAGCCTCAC CGAGTCGGGT GCCTCCTGCC TCCCGTGGAA TTCCATGATC 2350
CTGATAGGCA AGGTTTACAC AGCACAGAAC CCCAGTGCCC AGGCACTGGG 2400
CCTGGGCAAA CATAATTACT GCCGGAATCC TGATGGGGAT GCCAAGCCCT 2450
GGTGCCACGT GCTGAAGAAC CGCAGGCTGA CGTGGGAGTA CTGTGATGTG 2500
CCCTCCTGCT CCACCTGCGG CCTGAGACAG TACAGCCAGC CTCAGTTTCG 2550
CATCAAAGGA GGGCTCTTCG CCGACATCGC CTCCCACCCC TGGCAGGCTG 2600
CCATCTTTGC CAAGCACAGG AGGTCGCCCG GAGAGCGGTT CCTGTGCGGG 2650
GGCATACTCA TCAGCTCCTG CTGGATTCTC TCTGCCGCCC ACTGCTTCCA 2700
GGAGAGGTTT CCGCCCCACC ACCTGACGGT GATCTTGGGC AGAACATACC 2750
GGGTGGTCCC TGGCGAGGAG GAGCAGAAAT TTGAAGTCGA AAAATACATT 2800
GTCCATAAGG AATTCGATGA TGACACTTAC GACAATGACA TTGCGCTGCT 2850
GCAGCTGAAA TCGGATTCGT CCCGCTGTGC CCAGGAGAGC AGCGTGGTCC 2900
```

-continued

```
GCACTGTGTG CCTTCCCCCG GCGGACCTGC AGCTGCCGGA CTGGACGGAG 2950
TGTGAGCTCT CCGGCTACGG CAAGCATGAG GCCTTGTCTC CTTTCTATTC 3000
GGAGCGGCTG AAGGAGGCTC ATGTCAGACT GTACCCATCC AGCCGCTGCA 3050
CATCACAACA TTTACTTAAC AGAACAGTCA CCGACAACAT GCTGTGTGCT 3100
GGAGACACTC GGAGCGGCGG GCCCCAGGCA AACTTGCACG ACGCCTGCCA 3150
GGGCGATTCG GGAGGCCCCC TGGTGTGTCT GAACGATGGC CGCATGACTT 3200
TGGTGGGCAT CATCAGCTGG GGCCTGGGCT GTGGACAGAA GGATGTCCCG 3250
GGTGTGTACA CCAAGGTTAC CAACTACCTA GACTGGATTC GTGACAACAT 3300
GCGACCGTGA CCAGGAACAC CCGACTCCTC AAAAGCAAAT GAGATCCCGC 3350
CTCTTCTTCT TCAGAAGACA CTGCAAAGGC GCAGTGCTTC TCTACAGACT 3400
TCTCCAGACC CACCACACCG CAGAAGCGGG ACGAGACCCT ACAGGAGAGG 3450
GAAGAGTGCA TTTTCCCAGA TACTTCCCAT TTTGGAAGTT TCAGGACTT 3500
GGTCTGATTT CAGGATACTC TGTCAGATGG GAAGACATGA ATGCACACTA 3550
GCCTCTCCAG GAATGCCTCC TCCCTGGGCA GAAGTGGGGG GAATTCAATC 3600
GATGGCCGCC ATGGCCCAAC TTGTTTATTG CAGCTTATAA TGGTTACAAA 3650
TAAAGCAATA GCATCACAAA TTTCACAAAT AAAGCATTTT TTTCACTGCA 3700
TTCTAGTTGT GGTTTGTCCA AACTCATCAA TGTATCTTAT CATGTCTGGA 3750
TCGATCGGGA ATTAATTCGG CGCAGCACCA TGGCCTGAAA TAACCTCTGA 3800
AAGAGGAACT TGGTTAGGTA CCTTCTGAGG CGGAAAGAAC CAGCTGTGGA 3850
ATGTGTGTCA GTTAGGGTGT GGAAAGTCCC CAGGCTCCCC AGCAGGCAGA 3900
AGTATGCAAA GCATGCATCT CAATTAGTCA GCAACCAGGT GTGGAAAGTC 3950
CCCAGGCTCC CCAGCAGGCA GAAGTATGCA AAGCATGCAT CTCAATTAGT 4000
CAGCAACCAT AGTCCCGCCC CTAACTCCGC CCATCCCGCC CCTAACTCCG 4050
CCCAGTTCCG CCCATTCTCC GCCCCATGGC TGACTAATTT TTTTTATTTA 4100
TGCAGAGGCC GAGGCCGCCT CGGCCTCTGA GCTATTCCAG AAGTAGTGAG 4150
GAGGCTTTTT TGGAGGCCTA GGCTTTTGCA AAAAGCTGTT AACAGCTTGG 4200
CACTGGCCGT CGTTTTACAA CGTCGTGACT GGGAAAACCC TGGCGTTACC 4250
CAACTTAATC GCCTTGCAGC ACATCCCCCC TTCGCCAGCT GGCGTAATAG 4300
CGAAGAGGCC CGCACCGATC GCCCTTCCCA ACAGTTGCGT AGCCTGAATG 4350
GCGAATGGCG CCTGATGCGG TATTTTCTCC TTACGCATCT GTGCGGTATT 4400
TCACACCGCA TACGTCAAAG CAACCATAGT ACGCCCCTG TAGCGGCGCA 4450
TTAAGCGCGG CGGGTGTGGT GGTTACGCGC AGCGTGACCG CTACACTTGC 4500
CAGCGCCCTA GCGCCCGCTC CTTTCGCTTT CTTCCCTTCC TTTCTCGCCA 4550
CGTTCGCCGG CTTTCCCCGT CAAGCTCTAA ATCGGGGGCT CCCTTTAGGG 4600
TTCCGATTTA GTGCTTTACG GCACCTCGAC CCCAAAAAAC TTGATTTGGG 4650
TGATGGTTCA CGTAGTGGGC CATCGCCCTG ATAGACGGTT TTTCGCCCTT 4700
TGACGTTGGA GTCCACGTTC TTTAATAGTG GACTCTTGTT CCAAACTGGA 4750
ACAACACTCA ACCCTATCTC GGGCTATTCT TTTGATTTAT AAGGGATTTT 4800
GCCGATTTCG GCCTATTGGT TAAAAAATGA GCTGATTTAA CAAAAATTTA 4850
ACGCGAATTT TAACAAAATA TTAACGTTTA CAATTTTATG GTGCACTCTC 4900
```

```
AGTACAATCT GCTCTGATGC CGCATAGTTA AGCCAACTCC GCTATCGCTA 4950
CGTGACTGGG TCATGGCTGC GCCCCGACAC CCGCCAACAC CCGCTGACGC 5000
GCCCTGACGG GCTTGTCTGC TCCCGGCATC CGCTTACAGA CAAGCTGTGA 5050
CCGTCTCCGG GAGCTGCATG TGTCAGAGGT TTTCACCGTC ATCACCGAAA 5100
CGCGCGAGGC AGTATTCTTG AAGACGAAAG GGCCTCGTGA TACGCCTATT 5150
TTTATAGGTT AATGTCATGA TAATAATGGT TTCTTAGACG TCAGGTGGCA 5200
CTTTTCGGGG AAATGTGCGC GGAACCCCTA TTTGTTTATT TTTCTAAATA 5250
CATTCAAATA TGTATCCGCT CATGAGACAA TAACCCTGAT AAATGCTTCA 5300
ATAATATTGA AAAAGGAAGA GTATGAGTAT TCAACATTTC CGTGTCGCCC 5350
TTATTCCCTT TTTTGCGGCA TTTTGCCTTC CTGTTTTTGC TCACCCAGAA 5400
ACGCTGGTGA AAGTAAAAGA TGCTGAAGAT CAGTTGGGTG CACGAGTGGG 5450
TTACATCGAA CTGGATCTCA ACAGCGGTAA GATCCTTGAG AGTTTTCGCC 5500
CCGAAGAACG TTTTCCAATG ATGAGCACTT TTAAAGTTCT GCTATGTGGC 5550
GCGGTATTAT CCCGTGATGA CGCCGGGCAA GAGCAACTCG GTCGCCGCAT 5600
ACACTATTCT CAGAATGACT TGGTTGAGTA CTCACCAGTC ACAGAAAAGC 5650
ATCTTACGGA TGGCATGACA GTAAGAGAAT TATGCAGTGC TGCCATAACC 5700
ATGAGTGATA ACACTGCGGC CAACTTACTT CTGACAACGA TCGGAGGACC 5750
GAAGGAGCTA ACCGCTTTTT TGCACAACAT GGGGGATCAT GTAACTCGCC 5800
TTGATCGTTG GGAACCGGAG CTGAATGAAG CCATACCAAA CGACGAGCGT 5850
GACACCACGA TGCCAGCAGC AATGGCAACA ACGTTGCGCA AACTATTAAC 5900
TGGCGAACTA CTTACTCTAG CTTCCCGGCA ACAATTAATA GACTGGATGG 5950
AGGCGGATAA AGTTGCAGGA CCACTTCTGC GCTCGGCCCT TCCGGCTGGC 6000
TGGTTTATTG CTGATAAATC TGGAGCCGGT GAGCGTGGGT CTCGCGGTAT 6050
CATTGCAGCA CTGGGGCCAG ATGGTAAGCC CTCCCGTATC GTAGTTATCT 6100
ACACGACGGG GAGTCAGGCA ACTATGGATG AACGAAATAG ACAGATCGCT 6150
GAGATAGGTG CCTCACTGAT TAAGCATTGG TAACTGTCAG ACCAAGTTTA 6200
CTCATATATA CTTTAGATTG ATTTAAAACT TCATTTTTAA TTTAAAAGGA 6250
TCTAGGTGAA GATCCTTTTT GATAATCTCA TGACCAAAAT CCCTTAACGT 6300
GAGTTTTCGT TCCACTGAGC GTCAGACCCC GTAGAAAAGA TCAAAGGATC 6350
TTCTTGAGAT CCTTTTTTTC TGCGCGTAAT CTGCTGCTTG CAAACAAAAA 6400
AACCACCGCT ACCAGCGGTG GTTTGTTTGC CGGATCAAGA GCTACCAACT 6450
CTTTTTCCGA AGGTAACTGG CTTCAGCAGA GCGCAGATAC CAAATACTGT 6500
CCTTCTAGTG TAGCCGTAGT TAGGCCACCA CTTCAAGAAC TCTGTAGCAC 6550
CGCCTACATA CCTCGCTCTG CTAATCCTGT TACCAGTGGC TGCTGCCAGT 6600
GGCGATAAGT CGTGTCTTAC CGGGTTGGAC TCAAGACGAT AGTTACCGGA 6650
TAAGGCGCAG CGGTCGGGCT GAACGGGGGG TTCGTGCACA CAGCCCAGCT 6700
TGGAGCGAAC GACCTACACC GAACTGAGAT ACCTACAGCG TGAGCATTGA 6750
GAAAGCGCCA CGCTTCCCGA AGGGAGAAAG GCGGACAGGT ATCCGGTAAG 6800
CGGCAGGGTC GGAACAGGAG AGCGCACGAG GGAGCTTCCA GGGGGAAACG 6850
CCTGGTATCT TTATAGTCCT GTCGGGTTTC GCCACCTCTG ACTTGAGCGT 6900
```

| | | | | |
|---|---|---|---|---|
| CGATTTTTGT | GATGCTCGTC | AGGGGGGCGG | AGCCTATGGA | AAAACGCCAG 6950 |
| CAACGCGGCC | TTTTTACGGT | TCCTGGCCTT | TTGCTGGCCT | TTTGCTCACA 7000 |
| TGTTCTTTCC | TGCGTTATCC | CCTGATTCTG | TGGATAACCG | TATTACCGCC 7050 |
| TTTGAGTGAG | CTGATACCGC | TCGCCGCAGC | CGAACGACCG | AGCGCAGCGA 7100 |
| GTCAGTGAGC | GAGGAAGCGG | AAGAGCGCCC | AATACGCAAA | CCGCCTCTCC 7150 |
| CCGCGCGTTG | GCCGATTCAT | TAATCCAGCT | GGCACGACAG | GTTTCCCGAC 7200 |
| TGGAAAGCGG | GCAGTGAGCG | CAACGCAATT | AATGTGAGTT | ACCTCACTCA 7250 |
| TTAGGCACCC | CAGGCTTTAC | ACTTTATGCT | TCCGGCTCGT | ATGTTGTGTG 7300 |
| GAATTGTGAG | CGGATAACAA | TTTCACACAG | GAAACAGCTA | TGACCATGAT 7350 |
| TACGAATTAA | | | | 7360 |

(2) INFORMATION FOR SEQ ID NO:2:

(i) SEQUENCE CHARACTERISTICS:
        (A) LENGTH: 6889 bases
        (B) TYPE: nucleic acid
        (C) STRANDEDNESS: double
        (D) TOPOLOGY: linear (xi) SEQUENCE DESCRIPTION: SEQ ID NO:2:

| | | | | |
|---|---|---|---|---|
| TTCGAGCTCG | CCCGACATTG | ATTATTGACT | AGTTATTAAT | AGTAATCAAT 50 |
| TACGGGGTCA | TTAGTTCATA | GCCCATATAT | GGAGTTCCGC | GTTACATAAC 100 |
| TTACGGTAAA | TGGCCCGCCT | GGCTGACCGC | CCAACGACCC | CCGCCCATTG 150 |
| ACGTCAATAA | TGACGTATGT | TCCCATAGTA | ACGCCAATAG | GGACTTTCCA 200 |
| TTGACGTCAA | TGGGTGGAGT | ATTTACGGTA | AACTGCCCAC | TTGGCAGTAC 250 |
| ATCAAGTGTA | TCATATGCCA | AGTACGCCCC | CTATTGACGT | CAATGACGGT 300 |
| AAATGGCCCG | CCTGGCATTA | TGCCCAGTAC | ATGACCTTAT | GGGACTTTCC 350 |
| TACTTGGCAG | TACATCTACG | TATTAGTCAT | CGCTATTACC | ATGGTGATGC 400 |
| GGTTTTGGCA | GTACATCAAT | GGGCGTGGAT | AGCGGTTTGA | CTCACGGGGA 450 |
| TTTCCAAGTC | TCCACCCCAT | TGACGTCAAT | GGGAGTTTGT | TTTGGCACCA 500 |
| AAATCAACGG | GACTTTCCAA | AATGTCGTAA | CAACTCCGCC | CCATTGACGC 550 |
| AAATGGGCGG | TAGGCGTGTA | CGGTGGGAGG | TCTATATAAG | CAGAGCTCGT 600 |
| TTAGTGAACC | GTCAGATCGC | CTGGAGACGC | CATCCACGCT | GTTTTGACCT 650 |
| CCATAGAAGA | CACCGGGACC | GATCCAGCCT | CCGCGGCCGG | GAACGGTGCA 700 |
| TTGGAACGCG | GATTCCCCGT | GCCAAGAGTG | CTGTAAGTAC | CGCCTATAGA 750 |
| GCGATAAGAG | GATTTATCC | CCGCTGCCAT | CATGGTTCGA | CCATTGAACT 800 |
| GCATCGTCGC | CGTGTCCCAA | AATATGGGGA | TTGGCAAGAA | CGGAGACCTA 850 |
| CCCTGCCCTC | CGCTCAGGAA | CGCGTTCAAG | TACTTCCAAA | GAATGACCAC 900 |
| AACCTCTTCA | GTGGAAGGTA | ACAGAATCT | GGTGATTATG | GGTAGGAAAA 950 |
| CCTGGTTCTC | CATTCCTGAG | AAGAATCGAC | CTTTAAGGA | CAGAATTAAT 1000 |
| ATAGTTCTCA | GTAGAGAACT | CAAAGAACCA | CCACGAGGAG | CTCATTTTCT 1050 |
| TGCCAAAAGT | TTGGATGATG | CCTTAAGACT | TATTGAACAA | CCGGAATTGG 1100 |
| CAAGTAAAGT | AGACATGGTT | TGGATAGTCG | GAGGCAGTTC | TGTTTACCAG 1150 |
| GAAGCCATGA | ATCAACCAGG | CCACCTTAGA | CTCTTTGTGA | CAAGGATCAT 1200 |

```
GCAGGAATTT  GAAAGTGACA  CGTTTTTCCC  AGAAATTGAT  TTGGGGAAAT  1250
ATAAACCTCT  CCCAGAATAC  CCAGGCGTCC  TCTCTGAGGT  CCAGGAGGAA  1300
AAAGGCATCA  AGTATAAGTT  TGAAGTCTAC  GAGAAGAAAG  ACTAACAGGA  1350
AGATGCTTTC  AAGTTCTCTG  CTCCCCTCCT  AAAGCTATGC  ATTTTTATAA  1400
GACCATGGGA  CTTTTGCTGG  CTTTAGACCC  CCTTGGCTTC  GTTAGAACGC  1450
GGCTACAATT  AATACATAAC  CTTATGTATC  ATACACATAG  ATTTAGGTGA  1500
CACTATAGAA  TAACATCCAC  TTTGCCTTTC  TCTCCACAGG  TGTCACTCCA  1550
GGTCAACTGC  ACCTCGGTTC  TATCGATTGA  ATTCCCCGGC  CATAGCTGTC  1600
TGGCATGGGC  CTCTCCACCG  TGCCTGACCT  GCTGCTGCCG  CTGGTGCTCC  1650
TGGAGCTGTT  GGTGGGAATA  TACCCCTCAG  GGGTTATTGG  ACTGGTCCCT  1700
CACCTAGGGG  ACAGGGAGAA  GAGAGATAGT  GTGTGTCCCC  AAGGAAAATA  1750
TATCCACCCT  CAAAATAATT  CGATTGCTG   TACCAAGTGC  CACAAAGGAA  1800
CCTACTTGTA  CAATGACTGT  CCAGGCCCGG  GGCAGGATAC  GGACTGCAGG  1850
GAGTGTGAGA  GCGGCTCCTT  CACCGCTTCA  GAAAACCACC  TCAGACACTG  1900
CCTCAGCTGC  TCCAAATGCC  GAAAGGAAAT  GGGTCAGGTG  GAGATCTCTT  1950
CTTGCACAGT  GGACCGGGAC  ACCGTGTGTG  GCTGCAGGAA  GAACCAGTAC  2000
CGGCATTATT  GGAGTGAAAA  CCTTTTCCAG  TGCTTCAATT  GCAGCCTCTG  2050
CCTCAATGGG  ACCGTGCACC  TCTCCTGCCA  GGAGAAACAG  AACACCGTGT  2100
GCACCTGCCA  TGCAGGTTTC  TTTCTAAGAG  AAAACGAGTG  TGTCTCCTGT  2150
AGTAACTGTA  AGAAAAGCCT  GGAGTGCACG  AAGTTGTGCC  TACCCCAGAT  2200
TGAGAATGTT  AAGGGCACTG  AGGACTCAGG  CACCACAGAC  AAGAGAGTTG  2250
AGCTCAAAAC  CCCACTTGGT  GACACAACTC  ACACATGCCC  ACGGTGCCCA  2300
GAGCCCAAAT  CTTGTGACAC  ACCTCCCCCG  TGCCCACGGT  GCCCAGAGCC  2350
CAAATCTTGT  GACACACCTC  CCCCATGCCC  ACGGTGCCCA  GAGCCCAAAT  2400
CTTGTGACAC  ACCTCCCCCA  TGCCCACGGT  GCCCAGCACC  TGAACTCCTG  2450
GGAGGACCGT  CAGTCTTCCT  CTTCCCCCCA  AAACCCAAGG  ATACCCTTAT  2500
GATTTCCCGG  ACCCCTGAGG  TCACGTGCGT  GGTGGTGGAC  GTGAGCCACG  2550
AAGACCCCGA  GGTCCAGTTC  AAGTGGTACG  TGGACGGCGT  GGAGGTGCAT  2600
AATGCCAAGA  CAAAGCCGCG  GGAGGAGCAG  TTCAACAGCA  CGTTCCGTGT  2650
GGTCAGCGTC  CTCACCGTCC  TGCACCAGGA  CTGGCTGAAC  GGCAAGGAGT  2700
ACAAGTGCAA  GGTCTCCAAC  AAAGCCCTCC  CAGCCCCCAT  CGAGAAAACC  2750
ATCTCCAAAA  CCAAAGGACA  GCCCCGAGAA  CCACAGGTGT  ACACCCTGCC  2800
CCCATCCCGG  GAGGAGATGA  CCAAGAACCA  GGTCAGCCTG  ACCTGCCTGG  2850
TCAAAGGCTT  CTACCCCAGC  GACATCGCCG  TGGAGTGGGA  GAGCAGCGGG  2900
CAGCCGGAGA  ACAACTACAA  CACCACGCCT  CCCATGCTGG  ACTCCGACGG  2950
CTCCTTCTTC  CTCTACAGCA  AGCTCACCGT  GGACAAGAGC  AGGTGGCAGC  3000
AGGGGAACAT  CTTCTCATGC  TCCGTGATGC  ATGAGGCTCT  GCACAACCGC  3050
TTCACGCAGA  AGAGCCTCTC  CCTGTCTCCG  GGTAAATGAG  TGCGACGGCC  3100
GGGGATCCTC  TAGAGTCGAC  CTGCAGAAGC  TTGGCCGCCA  TGGCCCAACT  3150
TGTTTATTGC  AGCTTATAAT  GGTTACAAAT  AAAGCAATAG  CATCACAAAT  3200
```

| | | | | |
|---|---|---|---|---|
| TTCACAAATA | AAGCATTTTT | TTCACTGCAT | TCTAGTTGTG | GTTTGTCCAA 3250 |
| ACTCATCAAT | GTATCTTATC | ATGTCTGGAT | CGATCGGGAA | TTAATTCGGC 3300 |
| GCAGCACCAT | GGCCTGAAAT | AACCTCTGAA | AGAGGAACTT | GGTTAGGTAC 3350 |
| CTTCTGAGGC | GGAAAGAACC | AGCTGTGGAA | TGTGTGTCAG | TTAGGGTGTG 3400 |
| GAAAGTCCCC | AGGCTCCCCA | GCAGGCAGAA | GTATGCAAAG | CATGCATCTC 3450 |
| AATTAGTCAG | CAACCAGGTG | TGGAAAGTCC | CCAGGCTCCC | CAGCAGGCAG 3500 |
| AAGTATGCAA | AGCATGCATC | TCAATTAGTC | AGCAACCATA | GTCCGCCCC 3550 |
| TAACTCCGCC | CATCCCGCCC | CTAACTCCGC | CCAGTTCCGC | CCATTCTCCG 3600 |
| CCCCATGGCT | GACTAATTTT | TTTTATTTAT | GCAGAGGCCG | AGGCCGCCTC 3650 |
| GGCCTCTGAG | CTATTCCAGA | AGTAGTGAGG | AGGCTTTTTT | GGAGGCCTAG 3700 |
| GCTTTTGCAA | AAAGCTGTTA | ACAGCTTGGC | ACTGGCCGTC | GTTTACAAC 3750 |
| GTCGTGACTG | GGAAAACCCT | GGCGTTACCC | AACTTAATCG | CCTTGCAGCA 3800 |
| CATCCCCCCT | TCGCCAGCTG | GCGTAATAGC | GAAGAGGCCC | GCACCGATCG 3850 |
| CCCTTCCCAA | CAGTTGCGTA | GCCTGAATGG | CGAATGGCGC | CTGATGCGGT 3900 |
| ATTTTCTCCT | TACGCATCTG | TGCGGTATTT | CACACCGCAT | ACGTCAAAGC 3950 |
| AACCATAGTA | CGCGCCCTGT | AGCGGCGCAT | TAAGCGCGGC | GGGTGTGGTG 4000 |
| GTTACGCGCA | GCGTGACCGC | TACACTTGCC | AGCGCCCTAG | CGCCCGCTCC 4050 |
| TTTCGCTTTC | TTCCCTTCCT | TTCTCGCCAC | GTTCGCCGGC | TTTCCCCGTC 4100 |
| AAGCTCTAAA | TCGGGGGCTC | CCTTTAGGGT | TCCGATTTAG | TGCTTTACGG 4150 |
| CACCTCGACC | CCAAAAAACT | TGATTTGGGT | GATGGTTCAC | GTAGTGGGCC 4200 |
| ATCGCCCTGA | TAGACGGTTT | TTCGCCCTTT | GACGTTGGAG | TCCACGTTCT 4250 |
| TTAATAGTGG | ACTCTTGTTC | CAAACTGGAA | CAACACTCAA | CCCTATCTCG 4300 |
| GGCTATTCTT | TTGATTTATA | AGGGATTTTG | CCGATTTCGG | CCTATTGGTT 4350 |
| AAAAAATGAG | CTGATTTAAC | AAAAATTTAA | CGCGAATTTT | AACAAAATAT 4400 |
| TAACGTTTAC | AATTTTATGG | TGCACTCTCA | GTACAATCTG | CTCTGATGCC 4450 |
| GCATAGTTAA | GCCAACTCCG | CTATCGCTAC | GTGACTGGGT | CATGGCTGCG 4500 |
| CCCCGACACC | CGCCAACACC | CGCTGACGCG | CCCTGACGGG | CTTGTCTGCT 4550 |
| CCCGGCATCC | GCTTACAGAC | AAGCTGTGAC | CGTCTCCGGG | AGCTGCATGT 4600 |
| GTCAGAGGTT | TTCACCGTCA | TCACCGAAAC | GCGCGAGGCA | GTATTCTTGA 4650 |
| AGACGAAAGG | GCCTCGTGAT | ACGCCTATTT | TTATAGGTTA | ATGTCATGAT 4700 |
| AATAATGGTT | TCTTAGACGT | CAGGTGGCAC | TTTTCGGGGA | AATGTGCGCG 4750 |
| GAACCCCTAT | TTGTTTATTT | TTCTAAATAC | ATTCAAATAT | GTATCCGCTC 4800 |
| ATGAGACAAT | AACCCTGATA | AATGCTTCAA | TAATATTGAA | AAAGGAAGAG 4850 |
| TATGAGTATT | CAACATTTCC | GTGTCGCCCT | TATTCCCTTT | TTTGCGGCAT 4900 |
| TTTGCCTTCC | TGTTTTTGCT | CACCCAGAAA | CGCTGGTGAA | AGTAAAAGAT 4950 |
| GCTGAAGATC | AGTTGGGTGC | ACGAGTGGGT | TACATCGAAC | TGGATCTCAA 5000 |
| CAGCGGTAAG | ATCCTTGAGA | GTTTTCGCCC | CGAAGAACGT | TTTCCAATGA 5050 |
| TGAGCACTTT | TAAAGTTCTG | CTATGTGGCG | CGGTATTATC | CCGTGATGAC 5100 |
| GCCGGGCAAG | AGCAACTCGG | TCGCCGCATA | CACTATTCTC | AGAATGACTT 5150 |
| GGTTGAGTAC | TCACCAGTCA | CAGAAAAGCA | TCTTACGGAT | GGCATGACAG 5200 |

```
TAAGAGAATT  ATGCAGTGCT  GCCATAACCA  TGAGTGATAA  CACTGCGGCC    5250
AACTTACTTC  TGACAACGAT  CGGAGGACCG  AAGGAGCTAA  CCGCTTTTTT    5300
GCACAACATG  GGGGATCATG  TAACTCGCCT  TGATCGTTGG  GAACCGGAGC    5350
TGAATGAAGC  CATACCAAAC  GACGAGCGTG  ACACCACGAT  GCCAGCAGCA    5400
ATGGCAACAA  CGTTGCGCAA  ACTATTAACT  GGCGAACTAC  TTACTCTAGC    5450
TTCCCGGCAA  CAATTAATAG  ACTGGATGGA  GGCGGATAAA  GTTGCAGGAC    5500
CACTTCTGCG  CTCGGCCCTT  CCGGCTGGCT  GGTTTATTGC  TGATAAATCT    5550
GGAGCCGGTG  AGCGTGGGTC  TCGCGGTATC  ATTGCAGCAC  TGGGGCCAGA    5600
TGGTAAGCCC  TCCCGTATCG  TAGTTATCTA  CACGACGGGG  AGTCAGGCAA    5650
CTATGGATGA  ACGAAATAGA  CAGATCGCTG  AGATAGGTGC  CTCACTGATT    5700
AAGCATTGGT  AACTGTCAGA  CCAAGTTTAC  TCATATATAC  TTTAGATTGA    5750
TTTAAAACTT  CATTTTTAAT  TTAAAAGGAT  CTAGGTGAAG  ATCCTTTTTG    5800
ATAATCTCAT  GACCAAAATC  CCTTAACGTG  AGTTTTCGTT  CCACTGAGCG    5850
TCAGACCCCG  TAGAAAAGAT  CAAAGGATCT  TCTTGAGATC  CTTTTTTTCT    5900
GCGCGTAATC  TGCTGCTTGC  AAACAAAAAA  ACCACCGCTA  CCAGCGGTGG    5950
TTTGTTTGCC  GGATCAAGAG  CTACCAACTC  TTTTTCCGAA  GGTAACTGGC    6000
TTCAGCAGAG  CGCAGATACC  AAATACTGTC  CTTCTAGTGT  AGCCGTAGTT    6050
AGGCCACCAC  TTCAAGAACT  CTGTAGCACC  GCCTACATAC  CTCGCTCTGC    6100
TAATCCTGTT  ACCAGTGGCT  GCTGCCAGTG  GCGATAAGTC  GTGTCTTACC    6150
GGGTTGGACT  CAAGACGATA  GTTACCGGAT  AAGGCGCAGC  GGTCGGGCTG    6200
AACGGGGGGT  TCGTGCACAC  AGCCCAGCTT  GGAGCGAACG  ACCTACACCG    6250
AACTGAGATA  CCTACAGCGT  GAGCATTGAG  AAAGCGCCAC  GCTTCCCGAA    6300
GGGAGAAAGG  CGGACAGGTA  TCCGGTAAGC  GGCAGGGTCG  GAACAGGAGA    6350
GCGCACGAGG  GAGCTTCCAG  GGGGAAACGC  CTGGTATCTT  TATAGTCCTG    6400
TCGGGTTTCG  CCACCTCTGA  CTTGAGCGTC  GATTTTGTG   ATGCTCGTCA    6450
GGGGGGCGGA  GCCTATGGAA  AAACGCCAGC  AACGCGGCCT  TTTTACGGTT    6500
CCTGGCCTTT  TGCTGGCCTT  TTGCTCACAT  GTTCTTTCCT  GCGTTATCCC    6550
CTGATTCTGT  GGATAACCGT  ATTACCGCCT  TTGAGTGAGC  TGATACCGCT    6600
CGCCGCAGCC  GAACGACCGA  GCGCAGCGAG  TCAGTGAGCG  AGGAAGCGGA    6650
AGAGCGCCCA  ATACGCAAAC  CGCCTCTCCC  CGCGCGTTGG  CCGATTCATT    6700
AATCCAGCTG  GCACGACAGG  TTTCCCGACT  GGAAAGCGGG  CAGTGAGCGC    6750
AACGCAATTA  ATGTGAGTTA  CCTCACTCAT  TAGGCACCCC  AGGCTTTACA    6800
CTTTATGCTT  CCGGCTCGTA  TGTTGTGTGG  AATTGTGAGC  GGATAACAAT    6850
TTCACACAGG  AAACAGCTAT  GACCATGATT  ACGAATTAA                 6889
```

( 2 ) INFORMATION FOR SEQ ID NO:3:

( i ) SEQUENCE CHARACTERISTICS:
        ( A ) LENGTH: 6557 bases
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
TTCGAGCTCG  CCCGACATTG  ATTATTGACT  AGAGTCGATC  GACAGCTGTG    50
```

```
GAATGTGTGT CAGTTAGGGT GTGGAAAGTC CCCAGGCTCC CCAGCAGGCA  100
GAAGTATGCA AAGCATGCAT CTCAATTAGT CAGCAACCAG GTGTGGAAAG  150
TCCCCAGGCT CCCCAGCAGG CAGAAGTATG CAAAGCATGC ATCTCAATTA  200
GTCAGCAACC ATAGTCCCGC CCCTAACTCC GCCCATCCCG CCCCTAACTC  250
CGCCCAGTTC CGCCCATTCT CCGCCCCATG GCTGACTAAT TTTTTTATT   300
TATGCAGAGG CCGAGGCCGC CTCGGCCTCT GAGCTATTCC AGAAGTAGTG  350
AGGAGGCTTT TTTGGAGGCC TAGGCTTTTG CAAAAAGCTA GCTTATCCGG  400
CCGGGAACGG TGCATTGGAA CGCGGATTCC CCGTGCCAAG AGTGACGTAA  450
GTACCGCCTA TAGAGCGATA AGAGGATTTT ATCCCCGCTG CCATCATGGT  500
TCGACCATTG AACTGCATCG TCGCCGTGTC CCAAAATATG GGGATTGGCA  550
AGAACGGAGA CCTACCCTGG CCTCCGCTCA GGAACGAGTT CAAGTACTTC  600
CAAAGAATGA CCACAACCTC TTCAGTGGAA GGTAAACAGA ATCTGGTGAT  650
TATGGGTAGG AAAACCTGGT TCTCCATTCC TGAGAAGAAT CGACCTTTAA  700
AGGACAGAAT TAATATAGTT CTCAGTAGAG AACTCAAAGA ACCACCACGA  750
GGAGCTCATT TTCTTGCCAA AAGTTTGGAT GATGCCTTAA GACTTATTGA  800
ACAACCGGAA TTGGCAAGTA AAGTAGACAT GGTTTGGATA GTCGGAGGCA  850
GTTCTGTTTA CCAGGAAGCC ATGAATCAAC CAGGCCACCT TAGACTCTTT  900
GTGACAAGGA TCATGCAGGA ATTTGAAAGT GACACGTTTT TCCCAGAAAT  950
TGATTTGGGG AAATATAAAC CTCTCCCAGA ATACCCAGGC GTCCTCTCTG 1000
AGGTCCAGGA GGAAAAAGGC ATCAAGTATA AGTTTGAAGT CTACGAGAAG 1050
AAAGACTAAC AGGAAGATGC TTTCAAGTTC TCTGCTCCCC TCCTAAAGCT 1100
ATGCATTTTT ATAAGACCAT GGGACTTTTG CTGGCTTTAG ATCCCCTTGG 1150
CTTCGTTAGA ACGCAGCTAC AATTAATACA TAACCTTATG TATCATACAC 1200
ATACGATTTA GGTGACACTA TAGATAACAT CCACTTTGCC TTTCTCTCCA 1250
CAGGTGTCCA CTCCCAGGTC CAACTGCACC TCGGTTCTAT CGATTGAATT 1300
CCACCATGGG ATGGTCATGT ATCATCCTTT TTCTAGTAGC AACTGCAACT 1350
GGAGTACATT CAGAAGTTCA GCTGGTGGAG TCTGGCGGTG GCCTGGTGCA 1400
GCCAGGGGGC TCACTCCGTT TGTCCTGTGC AGTTTCTGGC TACTCCATCA 1450
CCTCCGGATA TAGCTGGAAC TGGATCCGTC AGGCCCGGG  TAAGGGCCTG 1500
GAATGGGTTG CATCGATTAC GTATGCCGGA TCGACTAACT ATAACCCTAG 1550
CGTCAAGGGC CGTATCACTA TAAGTCGCGA CGATTCCAAA AACACATTCT 1600
ACCTGCAGAT GAACAGCCTG CGTGCTGAGG ACACTGCCGT CTATTATTGT 1650
GCTCGAGGCA GCCACTATTT CGGCGCCTGG CACTTCGCCG TGTGGGGTCA 1700
AGGAACCCTG GTCACCGTCT CCTCGGCCTC CACCAAGGGC CCATCGGTCT 1750
TCCCCCTGGC ACCCTCCTCC AAGAGCACCT CTGGGGGCAC AGCGGCCCTG 1800
GGCTGCCTGG TCAAGGACTA CTTCCCCGAA CCGGTGACGG TGTCGTGGAA 1850
CTCAGGCGCC CTGACCAGCG GCGTGCACAC CTTCCCGGCT GTCCTACAGT 1900
CCTCAGGACT CTACTCCCTC AGCAGCGTGG TGACTGTGCC CTCTAGCAGC 1950
TTGGGCACCC AGACCTACAT CTGCAACGTG AATCACAAGC CCAGCAACAC 2000
CAAGGTGGAC AAGAAAGTTG AGCCCAAATC TTGTGACAAA ACTCACACAT 2050
```

5,561,053

41

-continued

42

```
GCCCACCGTG CCCAGCACCT GAACTCCTGG GGGGACCGTC AGTCTTCCTC 2100
TTCCCCCCAA AACCCAAGGA CACCCTCATG ATCTCCCGGA CCCCTGAGGT 2150
CACATGCGTG GTGGTGGACG TGAGCCACGA AGACCCTGAG GTCAAGTTCA 2200
ACTGGTACGT GGACGGCGTG GAGGTGCATA ATGCCAAGAC AAAGCCGCGG 2250
GAGGAGCAGT ACAACAGCAC GTACCGTGTG GTCAGCGTCC TCACCGTCCT 2300
GCACCAGGAC TGGCTGAATG GCAAGGAGTA CAAGTGCAAG GTCTCCAACA 2350
AAGCCCTCCC AGCCCCCATC GAGAAAACCA TCTCCAAAGC CAAAGGGCAG 2400
CCCCGAGAAC CACAGGTGTA CACCCTGCCC CCATCCCGGG AAGAGATGAC 2450
CAAGAACCAG GTCAGCCTGA CCTGCCTGGT CAAAGGCTTC TATCCCAGCG 2500
ACATCGCCGT GGAGTGGGAG AGCAATGGGC AGCCGGAGAA CAACTACAAG 2550
ACCACGCCTC CCGTGCTGGA CTCCGACGGC TCCTTCTTCC TCTACAGCAA 2600
GCTCACCGTG GACAAGAGCA GGTGGCAGCA GGGGAACGTC TTCTCATGCT 2650
CCGTGATGCA TGAGGCTCTG CACAACCACT ACACGCAGAA GAGCCTCTCC 2700
CTGTCTCCGG GTAAATGAGT GCGACGGCCC TAGAGTCGAC CTGCAGAAGC 2750
TTGGCCGCCA TGGCCCAACT TGTTTATTGC AGCTTATAAT GGTTACAAAT 2800
AAAGCAATAG CATCACAAAT TTCACAAATA AAGCATTTTT TCACTGCAT 2850
TCTAGTTGTG GTTTGTCCAA ACTCATCAAT GTATCTTATC ATGTCTGGAT 2900
CGATCGGGAA TTAATTCGGC GCAGCACCAT GGCCTGAAAT AACCTCTGAA 2950
AGAGGAACTT GGTTAGGTAC CTTCTGAGGC GGAAAGAACC AGCTGTGGAA 3000
TGTGTGTCAG TTAGGGTGTG GAAAGTCCCC AGGCTCCCCA GCAGGCAGAA 3050
GTATGCAAAG CATGCATCTC AATTAGTCAG CAACCAGGTG TGGAAAGTCC 3100
CCAGGCTCCC CAGCAGGCAG AAGTATGCAA AGCATGCATC TCAATTAGTC 3150
AGCAACCATA GTCCCGCCCC TAACTCCGCC CATCCCGCCC CTAACTCCGC 3200
CCAGTTCCGC CCATTCTCCG CCCCATGGCT GACTAATTTT TTTTATTTAT 3250
GCAGAGGCCG AGGCCGCCTC GGCCTCTGAG CTATTCCAGA AGTAGTGAGG 3300
AGGCTTTTTT GGAGGCCTAG GCTTTTGCAA AAAGCTGTTA CCTCGAGCGG 3350
CCGCTTAATT AAGGCGCGCC ATTTAAATCC TGCAGGTAAC AGCTTGGCAC 3400
TGGCCGTCGT TTTACAACGT CGTGACTGGG AAAACCCTGG CGTTACCCAA 3450
CTTAATCGCC TTGCAGCACA TCCCCCCTTC GCCAGCTGGC GTAATAGCGA 3500
AGAGGCCCGC ACCGATCGCC CTTCCCAACA GTTGCGTAGC CTGAATGGCG 3550
AATGGCGCCT GATGCGGTAT TTTCTCCTTA CGCATCTGTG CGGTATTTCA 3600
CACCGCATAC GTCAAAGCAA CCATAGTACG CGCCCTGTAG CGGCGCATTA 3650
AGCGCGGCGG GTGTGGTGGT TACGCGCAGC GTGACCGCTA CACTTGCCAG 3700
CGCCCTAGCG CCCGCTCCTT TCGCTTTCTT CCCTTCCTTT CTCGCCACGT 3750
TCGCCGGCTT TCCCCGTCAA GCTCTAAATC GGGGCTCCC TTTAGGGTTC 3800
CGATTTAGTG CTTTACGGCA CCTCGACCCC AAAAAACTTG ATTTGGGTGA 3850
TGGTTCACGT AGTGGGCCAT CGCCCTGATA GACGGTTTTT CGCCCTTTGA 3900
CGTTGGAGTC CACGTTCTTT AATAGTGGAC TCTTGTTCCA AACTGGAACA 3950
ACACTCAACC CTATCTCGGG CTATTCTTTT GATTTATAAG GGATTTTGCC 4000
GATTTCGGCC TATTGGTTAA AAAATGAGCT GATTTAACAA AAATTTAACG 4050
```

```
CGAATTTTAA CAAAATATTA ACGTTTACAA TTTTATGGTG CACTCTCAGT 4100
ACAATCTGCT CTGATGCCGC ATAGTTAAGC CAACTCCGCT ATCGCTACGT 4150
GACTGGGTCA TGGCTGCGCC CCGACACCCG CCAACACCCG CTGACGCGCC 4200
CTGACGGGCT TGTCTGCTCC CGGCATCCGC TTACAGACAA GCTGTGACCG 4250
TCTCCGGGAG CTGCATGTGT CAGAGGTTTT CACCGTCATC ACCGAAACGC 4300
GCGAGGCAGT ATTCTTGAAG ACGAAAGGGC CTCGTGATAC GCCTATTTTT 4350
ATAGGTTAAT GTCATGATAA TAATGGTTTC TTAGACGTCA GGTGGCACTT 4400
TTCGGGGAAA TGTGCGCGGA ACCCCTATTT GTTTATTTTT CTAAATACAT 4450
TCAAATATGT ATCCGCTCAT GAGACAATAA CCCTGATAAA TGCTTCAATA 4500
ATATTGAAAA AGGAAGAGTA TGAGTATTCA ACATTTCCGT GTCGCCCTTA 4550
TTCCCTTTTT TGCGGCATTT TGCCTTCCTG TTTTTGCTCA CCCAGAAACG 4600
CTGGTGAAAG TAAAAGATGC TGAAGATCAG TTGGGTGCAC GAGTGGGTTA 4650
CATCGAACTG GATCTCAACA GCGGTAAGAT CCTTGAGAGT TTTCGCCCCG 4700
AAGAACGTTT TCCAATGATG AGCACTTTTA AAGTTCTGCT ATGTGGCGCG 4750
GTATTATCCC GTGATGACGC CGGGCAAGAG CAACTCGGTC GCCGCATACA 4800
CTATTCTCAG AATGACTTGG TTGAGTACTC ACCAGTCACA GAAAAGCATC 4850
TTACGGATGG CATGACAGTA AGAGAATTAT GCAGTGCTGC CATAACCATG 4900
AGTGATAACA CTGCGGCCAA CTTACTTCTG ACAACGATCG GAGGACCGAA 4950
GGAGCTAACC GCTTTTTTGC ACAACATGGG GGATCATGTA ACTCGCCTTG 5000
ATCGTTGGGA ACCGGAGCTG AATGAAGCCA TACCAAACGA CGAGCGTGAC 5050
ACCACGATGC CAGCAGCAAT GGCAACAACG TTGCGCAAAC TATTAACTGG 5100
CGAACTACTT ACTCTAGCTT CCCGGCAACA ATTAATAGAC TGGATGGAGG 5150
CGGATAAAGT TGCAGGACCA CTTCTGCGCT CGGCCCTTCC GGCTGGCTGG 5200
TTTATTGCTG ATAAATCTGG AGCCGGTGAG CGTGGGTCTC GCGGTATCAT 5250
TGCAGCACTG GGGCCAGATG GTAAGCCCTC CCGTATCGTA GTTATCTACA 5300
CGACGGGGAG TCAGGCAACT ATGGATGAAC GAAATAGACA GATCGCTGAG 5350
ATAGGTGCCT CACTGATTAA GCATTGGTAA CTGTCAGACC AAGTTTACTC 5400
ATATATACTT TAGATTGATT TAAAACTTCA TTTTTAATTT AAAAGGATCT 5450
AGGTGAAGAT CCTTTTTGAT AATCTCATGA CCAAAATCCC TTAACGTGAG 5500
TTTTCGTTCC ACTGAGCGTC AGACCCCGTA GAAAAGATCA AAGGATCTTC 5550
TTGAGATCCT TTTTTCTGC GCGTAATCTG CTGCTTGCAA ACAAAAAAAC 5600
CACCGCTACC AGCGGTGGTT TGTTTGCCGG ATCAAGAGCT ACCAACTCTT 5650
TTTCCGAAGG TAACTGGCTT CAGCAGAGCG CAGATACCAA ATACTGTCCT 5700
TCTAGTGTAG CCGTAGTTAG GCCACCACTT CAAGAACTCT GTAGCACCGC 5750
CTACATACCT CGCTCTGCTA ATCCTGTTAC CAGTGGCTGC TGCCAGTGGC 5800
GATAAGTCGT GTCTTACCGG GTTGGACTCA AGACGATAGT TACCGGATAA 5850
GGCGCAGCGG TCGGGCTGAA CGGGGGGTTC GTGCACACAG CCCAGCTTGG 5900
AGCGAACGAC CTACACCGAA CTGAGATACC TACAGCGTGA GCATTGAGAA 5950
AGCGCCACGC TTCCCGAAGG GAGAAAGGCG GACAGGTATC CGGTAAGCGG 6000
CAGGGTCGGA ACAGGAGAGC GCACGAGGGA GCTTCCAGGG GGAAACGCCT 6050
```

-continued

```
GGTATCTTTA TAGTCCTGTC GGGTTTCGCC ACCTCTGACT TGAGCGTCGA 6100
TTTTTGTGAT GCTCGTCAGG GGGGCGGAGC CTATGGAAAA ACGCCAGCAA 6150
CGCGGCCTTT TTACGGTTCC TGGCCTTTTG CTGGCCTTTT GCTCACATGT 6200
TCTTTCCTGC GTTATCCCCT GATTCTGTGG ATAACCGTAT TACCGCCTTT 6250
GAGTGAGCTG ATACCGCTCG CCGCAGCCGA ACGACCGAGC GCAGCGAGTC 6300
AGTGAGCGAG GAAGCGGAAG AGCGCCCAAT ACGCAAACCG CCTCTCCCCG 6350
CGCGTTGGCC GATTCATTAA TCCAGCTGGC ACGACAGGTT TCCCGACTGG 6400
AAAGCGGGCA GTGAGCGCAA CGCAATTAAT GTGAGTTACC TCACTCATTA 6450
GGCACCCCAG GCTTTACACT TTATGCTTCC GGCTCGTATG TTGTGTGGAA 6500
TTGTGAGCGG ATAACAATTT CACACAGGAA ACAGCTATGA CCATGATTAC 6550
GAATTAA                                                 6557
```

( 2 ) INFORMATION FOR SEQ ID NO:4:

( i ) SEQUENCE CHARACTERISTICS:
        ( A ) LENGTH: 7305 bases
        ( B ) TYPE: nucleic acid
        ( C ) STRANDEDNESS: double
        ( D ) TOPOLOGY: linear ( x i ) SEQUENCE DESCRIPTION: SEQ ID NO:4:

```
TTCGAGCTCG CCCGACATTG ATTATTGACT AGTTATTAAT AGTAATCAAT 50
TACGGGGTCA TTAGTTCATA GCCCATATAT GGAGTTCCGC GTTACATAAC 100
TTACGGTAAA TGGCCCGCCT GGCTGACCGC CCAACGACCC CCGCCCATTG 150
ACGTCAATAA TGACGTATGT TCCCATAGTA ACGCCAATAG GGACTTTCCA 200
TTGACGTCAA TGGGTGGAGT ATTTACGGTA AACTGCCCAC TTGCAGTAC 250
ATCAAGTGTA TCATATGCCA AGTACGCCCC CTATTGACGT CAATGACGGT 300
AAATGGCCCG CCTGGCATTA TGCCCAGTAC ATGACCTTAT GGGACTTTCC 350
TACTTGGCAG TACATCTACG TATTAGTCAT CGCTATTACC ATGGTGATGC 400
GGTTTTGGCA GTACATCAAT GGGCGTGGAT AGCGGTTTGA CTCACGGGGA 450
TTTCCAAGTC TCCACCCCAT TGACGTCAAT GGGAGTTTGT TTTGGCACCA 500
AAATCAACGG GACTTTCCAA AATGTCGTAA CAACTCCGCC CCATTGACGC 550
AAATGGGCGG TAGGCGTGTA CGGTGGGAGG TCTATATAAG CAGAGCTCGT 600
TTAGTGAACC GTCAGATCGC CTGGAGACGC CATCCACGCT GTTTTGACCT 650
CCATAGAAGA CACCGGGACC GATCCAGCCT CCGCGGCCGG GAACGGTGCA 700
TTGGAACGCG GATTCCCCGT GCCAAGAGTG ACGTAAGTAC CGCCTATAGA 750
GTCTATAGGC CCACCCCCTT GGCTTCGTTA GAACGCGGCT ACAATTAATA 800
CATAACCTTA TGTATCATAC ACATACGATT TAGGTGACAC TATAGAATAA 850
CATCCACTTT GCCTTTCTCT CCACAGGTGT CCACTCCCAG GTCCAACTGC 900
ACCTCGGTTC TAAGCTTATC GATATGAAAA AGCCTGAACT CACCGCGACG 950
TCTGTCGAGA AGTTTCTGAT CGAAAAGTTC GACAGCGTCT CCGACCTGAT 1000
GCAGCTCTCG GAGGGCGAAG AATCTCGTGC TTTCAGCTTC GATGTAGGAG 1050
GGCGTGGATA TGTCCTGCGG GTAAATAGCT GCGCCGATGG TTTCTACAAA 1100
GATCGTTATG TTTATCGGCA CTTTGCATCG GCCGCGCTCC CGATTCCGGA 1150
```

| | | | | |
|---|---|---|---|---|
| AGTGCTTGAC | ATTGGGGAAT | TCAGCGAGAG | CCTGACCTAT | TGCATCTCCC 1200 |
| GCCGTGCACA | GGGTGTCACG | TTGCAACACC | TGCCTGAAAC | CGAACTGCCC 1250 |
| GCTGTTCTGC | AGCCGGTCGC | GGAGGCCATG | GATGCGATCG | CTGCGGCCGA 1300 |
| TCTTAGCCAG | ACGAGCGGGT | TCGGCCCATT | CGGACCGCAA | GGAATCGGTC 1350 |
| AATACACTAC | ATGGCGTGAT | TTCATATGCG | CGATTGCTGA | TCCCCATGTG 1400 |
| TATCACTGGC | AAACTGTGAT | GGACGACACC | GTCAGTGCGT | CCGTCGCGCA 1450 |
| GGCTCTCGAT | GAGCTGATGC | TTTGGGCCGA | GGACTGCCCC | GAAGTCCGGC 1500 |
| ACCTCGTGCA | CGCGGATTTC | GGCTCCAACA | ATGTCCTGAC | GGACAATGGC 1550 |
| CGCATAACAG | CGGTCATTGA | CTGGAGCGAG | GCGATGTTCG | GGATTCCCA 1600 |
| ATACGAGGTC | GCCAACATCT | TCTTCTGGAG | GCCGTGGTTG | GCTTGTATGG 1650 |
| AGCAGCAGAC | GTACTTCGAG | CGGAGGCATC | CGGAGCTTGC | AGGATCGCCG 1700 |
| CGGCTCCGGG | CGTATATGCT | CCGCATTGGT | CTTGACCAAC | TCTATCAGAG 1750 |
| CTTGGTTGAC | GGCAATTTCG | ATGATGCAGC | TTGGGCGCAG | GGTCGATGCG 1800 |
| ACGCAATCGT | CCGATCCGGA | GCCGGGACTG | TCGGGCGTAC | ACAAATCGCC 1850 |
| CGCAGAAGCG | CGGCCGTCTG | GACCGATGGC | TGTGTAGAAG | TACTCGCCGA 1900 |
| TAGTGGAAAC | CGACGCCCCA | GCACTCGTCC | GAGGGCAAAG | GAATAGAGTA 1950 |
| GATGCCGACC | GAAGGATCCC | CGGGGAATTC | AATCGATGGC | CGCCATGGCC 2000 |
| CAACTTGTTT | ATTGCAGCTT | ATAATGGTTA | CAAATAAAGC | AATAGCATCA 2050 |
| CAAATTTCAC | AAATAAAGCA | TTTTTTTCAC | TGCATTCTAG | TTGTGGTTTG 2100 |
| TCCAAACTCA | TCAATGTATC | TTATCATGTC | TGGATCGATC | GGGAATTAAT 2150 |
| TCGGCGCAGC | ACCATGGCCT | GAAATAACCT | CTGAAAGAGG | AACTTGGTTA 2200 |
| GGTACCTTCT | GAGGCGGAAA | GAACCAGCTG | TGGAATGTGT | GTCAGTTAGG 2250 |
| GTGTGGAAAG | TCCCCAGGCT | CCCCAGCAGG | CAGAAGTATG | CAAAGCATGC 2300 |
| ATCTCAATTA | GTCAGCAACC | AGGTGTGGAA | AGTCCCCAGG | CTCCCCAGCA 2350 |
| GGCAGAAGTA | TGCAAAGCAT | GCATCTCAAT | TAGTCAGCAA | CCATAGTCCC 2400 |
| GCCCCTAACT | CCGCCCATCC | CGCCCCTAAC | TCCGCCCAGT | TCCGCCCATT 2450 |
| CTCCGCCCCA | TGGCTGACTA | ATTTTTTTTA | TTTATGCAGA | GGCCGAGGCC 2500 |
| GCCTCGGCCT | CTGAGCTATT | CCAGAAGTAG | TGAGGAGGCT | TTTTGGAGG 2550 |
| CCTAGGCTTT | TGCAAAAGC | TAGCTTATCC | GGCCGGGAAC | GGTGCATTGG 2600 |
| AACGCGGATT | CCCCGTGCCA | AGAGTCAGGT | AAGTACCGCC | TATAGAGTCT 2650 |
| ATAGGCCCAC | CCCCTTGGCT | TCGTTAGAAC | GCGGCTACAA | TTAATACATA 2700 |
| ACCTTTTGGA | TCGATCCTAC | TGACACTGAC | ATCCACTTTT | TCTTTTCTC 2750 |
| CACAGGTGTC | CACTCCCAGG | TCCAACTGCA | CCTCGGTTCG | CGAAGCTAGC 2800 |
| TTGGGCTGCA | TCGATTGAAT | TCCACCATGG | GATGGTCATG | TATCATCCTT 2850 |
| TTTCTAGTAG | CAACTGCAAC | TGGAGTACAT | TCAGATATCC | AGCTGACCCA 2900 |
| GTCCCCGAGC | TCCCTGTCCG | CCTCTGTGGG | CGATAGGGTC | ACCATCACCT 2950 |
| GCCGTGCCAG | TCAGAGCGTC | GATTACGATG | GTGATAGCTA | CATGAACTGG 3000 |
| TATCAACAGA | AACCAGGAAA | AGCTCCGAAA | CTACTGATTT | ACGCGGCCTC 3050 |
| GTACCTGGAG | TCTGGAGTCC | CTTCTCGCTT | CTCTGGATCC | GGTTCTGGGA 3100 |
| CGGATTTCAC | TCTGACCATC | AGCAGTCTGC | AGCCGGAAGA | CTTCGCAACT 3150 |

```
TATTACTGTC AGCAAAGTCA CGAGGATCCG TACACATTTG GACAGGGTAC 3200
CAAGGTGGAG ATCAAACGAA CTGTGGCTGC ACCATCTGTC TTCATCTTCC 3250
CGCCATCTGA TGAGCAGTTG AAATCTGGAA CTGCCTCTGT TGTGTGCCTG 3300
CTGAATAACT TCTATCCCAG AGAGGCCAAA GTACAGTGGA AGGTGGATAA 3350
CGCCCTCCAA TCGGGTAACT CCCAGGAGAG TGTCACAGAG CAGGACAGCA 3400
AGGACAGCAC CTACAGCCTC AGCAGCACCC TGACGCTGAG CAAAGCAGAC 3450
TACGAGAAAC ACAAAGTCTA CGCCTGCGAA GTCACCCATC AGGGCCTGAG 3500
CTCGCCCGTC ACAAGAGCT TCAACAGGGG AGAGTGTTAA GCTTCGATGG 3550
CCGCCATGGC CCAACTTGTT TATTGCAGCT TATAATGGTT ACAAATAAAG 3600
CAATAGCATC ACAAATTTCA CAAATAAAGC ATTTTTTTCA CTGCATTCTA 3650
GTTGTGGTTT GTCCAAACTC ATCAATGTAT CTTATCATGT CTGGATCGAT 3700
CGGGAATTAA TTCGGCGCAG CACCATGGCC TGAAATAACC TCTGAAAGAG 3750
GAACTTGGTT AGGTACCTTC TGAGGCGGAA AGAACCAGCT GTGGAATGTG 3800
TGTCAGTTAG GGTGTGGAAA GTCCCCAGGC TCCCCAGCAG GCAGAAGTAT 3850
GCAAAGCATG CATCTCAATT AGTCAGCAAC CAGGTGTGGA AAGTCCCCAG 3900
GCTCCCCAGC AGGCAGAAGT ATGCAAAGCA TGCATCTCAA TTAGTCAGCA 3950
ACCATAGTCC CGCCCCTAAC TCCGCCCATC CCGCCCCTAA CTCCGCCCAG 4000
TTCCGCCCAT TCTCCGCCCC ATGGCTGACT AATTTTTTTT ATTTATGCAG 4050
AGGCCGAGGC CGCCTCGGCC TCTGAGCTAT TCCAGAAGTA GTGAGGAGGC 4100
TTTTTTGGAG GCCTAGGCTT TTGCAAAAAG CTGTTAACAG CTTGGCACTG 4150
GCCGTCGTTT TACAACGTCG TGACTGGGAA AACCCTGGCG TTACCCAACT 4200
TAATCGCCTT GCAGCACATC CCCCCTTCGC CAGCTGGCGT AATAGCGAAG 4250
AGGCCCGCAC CGATCGCCCT TCCCAACAGT TGCGTAGCCT GAATGGCGAA 4300
TGGCGCCTGA TGCGGTATTT TCTCCTTACG CATCTGTGCG GTATTTCACA 4350
CCGCATACGT CAAAGCAACC ATAGTACGCG CCCTGTAGCG GCGCATTAAG 4400
CGCGGCGGGT GTGGTGGTTA CGCGCAGCGT GACCGCTACA CTTGCCAGCG 4450
CCCTAGCGCC CGCTCCTTTC GCTTTCTTCC CTTCCTTTCT CGCCACGTTC 4500
GCCGGCTTTC CCCGTCAAGC TCTAAATCGG GGCTCCCTT TAGGGTTCCG 4550
ATTTAGTGCT TTACGGCACC TCGACCCCAA AAAACTTGAT TTGGGTGATG 4600
GTTCACGTAG TGGGCCATCG CCCTGATAGA CGGTTTTTCG CCCTTTGACG 4650
TTGGAGTCCA CGTTCTTTAA TAGTGGACTC TTGTTCCAAA CTGGAACAAC 4700
ACTCAACCCT ATCTCGGGCT ATTCTTTTGA TTTATAAGGG ATTTTGCCGA 4750
TTTCGGCCTA TTGGTTAAAA AATGAGCTGA TTTAACAAAA ATTTAACGCG 4800
AATTTTAACA AAATATTAAC GTTTACAATT TTATGGTGCA CTCTCAGTAC 4850
AATCTGCTCT GATGCCGCAT AGTTAAGCCA ACTCCGCTAT CGCTACGTGA 4900
CTGGGTCATG GCTGCGCCCC GACACCCGCC AACACCCGCT GACGCGCCCT 4950
GACGGGCTTG TCTGCTCCCG GCATCCGCTT ACAGACAAGC TGTGACCGTC 5000
TCCGGGAGCT GCATGTGTCA GAGGTTTTCA CCGTCATCAC CGAAACGCGC 5050
GAGGCAGTAT TCTTGAAGAC GAAAGGGCCT CGTGATACGC CTATTTTTAT 5100
AGGTTAATGT CATGATAATA ATGGTTTCTT AGACGTCAGG TGGCACTTTT 5150
```

| | | | | |
|---|---|---|---|---|
| CGGGGAAATG | TGCGCGGAAC | CCCTATTTGT | TTATTTTTCT | AAATACATTC 5200 |
| AAATATGTAT | CCGCTCATGA | GACAATAACC | CTGATAAATG | CTTCAATAAT 5250 |
| ATTGAAAAAG | GAAGAGTATG | AGTATTCAAC | ATTTCCGTGT | CGCCCTTATT 5300 |
| CCCTTTTTTG | CGGCATTTTG | CCTTCCTGTT | TTTGCTCACC | CAGAAACGCT 5350 |
| GGTGAAAGTA | AAAGATGCTG | AAGATCAGTT | GGGTGCACGA | GTGGGTTACA 5400 |
| TCGAACTGGA | TCTCAACAGC | GGTAAGATCC | TTGAGAGTTT | TCGCCCCGAA 5450 |
| GAACGTTTTC | CAATGATGAG | CACTTTTAAA | GTTCTGCTAT | GTGGCGCGGT 5500 |
| ATTATCCCGT | GATGACGCCG | GGCAAGAGCA | ACTCGGTCGC | CGCATACACT 5550 |
| ATTCTCAGAA | TGACTTGGTT | GAGTACTCAC | CAGTCACAGA | AAAGCATCTT 5600 |
| ACGGATGGCA | TGACAGTAAG | AGAATTATGC | AGTGCTGCCA | TAACCATGAG 5650 |
| TGATAACACT | GCGGCCAACT | TACTTCTGAC | AACGATCGGA | GGACCGAAGG 5700 |
| AGCTAACCGC | TTTTTTGCAC | AACATGGGGG | ATCATGTAAC | TCGCCTTGAT 5750 |
| CGTTGGGAAC | CGGAGCTGAA | TGAAGCCATA | CCAAACGACG | AGCGTGACAC 5800 |
| CACGATGCCA | GCAGCAATGG | CAACAACGTT | GCGCAAACTA | TTAACTGGCG 5850 |
| AACTACTTAC | TCTAGCTTCC | CGGCAACAAT | TAATAGACTG | GATGGAGGCG 5900 |
| GATAAAGTTG | CAGGACCACT | TCTGCGCTCG | GCCCTTCCGG | CTGGCTGGTT 5950 |
| TATTGCTGAT | AAATCTGGAG | CCGGTGAGCG | TGGGTCTCGC | GGTATCATTG 6000 |
| CAGCACTGGG | GCCAGATGGT | AAGCCCTCCC | GTATCGTAGT | TATCTACACG 6050 |
| ACGGGGAGTC | AGGCAACTAT | GGATGAACGA | AATAGACAGA | TCGCTGAGAT 6100 |
| AGGTGCCTCA | CTGATTAAGC | ATTGGTAACT | GTCAGACCAA | GTTTACTCAT 6150 |
| ATATACTTTA | GATTGATTTA | AAACTTCATT | TTTAATTTAA | AAGGATCTAG 6200 |
| GTGAAGATCC | TTTTTGATAA | TCTCATGACC | AAAATCCCTT | AACGTGAGTT 6250 |
| TTCGTTCCAC | TGAGCGTCAG | ACCCCGTAGA | AAAGATCAAA | GGATCTTCTT 6300 |
| GAGATCCTTT | TTTTCTGCGC | GTAATCTGCT | GCTTGCAAAC | AAAAAAACCA 6350 |
| CCGCTACCAG | CGGTGGTTTG | TTTGCCGGAT | CAAGAGCTAC | CAACTCTTTT 6400 |
| TCCGAAGGTA | ACTGGCTTCA | GCAGAGCGCA | GATACCAAAT | ACTGTCCTTC 6450 |
| TAGTGTAGCC | GTAGTTAGGC | CACCACTTCA | AGAACTCTGT | AGCACCGCCT 6500 |
| ACATACCTCG | CTCTGCTAAT | CCTGTTACCA | GTGGCTGCTG | CCAGTGGCGA 6550 |
| TAAGTCGTGT | CTTACCGGGT | TGGACTCAAG | ACGATAGTTA | CCGGATAAGG 6600 |
| CGCAGCGGTC | GGGCTGAACG | GGGGGTTCGT | GCACACAGCC | CAGCTTGGAG 6650 |
| CGAACGACCT | ACACCGAACT | GAGATACCTA | CAGCGTGAGC | ATTGAGAAAG 6700 |
| CGCCACGCTT | CCCGAAGGGA | GAAAGGCGGA | CAGGTATCCG | GTAAGCGGCA 6750 |
| GGGTCGGAAC | AGGAGAGCGC | ACGAGGGAGC | TTCCAGGGGG | AAACGCCTGG 6800 |
| TATCTTTATA | GTCCTGTCGG | GTTTCGCCAC | CTCTGACTTG | AGCGTCGATT 6850 |
| TTTGTGATGC | TCGTCAGGGG | GGCGGAGCCT | ATGGAAAAAC | GCCAGCAACG 6900 |
| CGGCCTTTTT | ACGGTTCCTG | GCCTTTTGCT | GGCCTTTTGC | TCACATGTTC 6950 |
| TTTCCTGCGT | TATCCCCTGA | TTCTGTGGAT | AACCGTATTA | CCGCCTTTGA 7000 |
| GTGAGCTGAT | ACCGCTCGCC | GCAGCCGAAC | GACCGAGCGC | AGCGAGTCAG 7050 |
| TGAGCGAGGA | AGCGGAAGAG | CGCCCAATAC | GCAAACCGCC | TCTCCCCGCG 7100 |
| CGTTGGCCGA | TTCATTAATC | CAGCTGGCAC | GACAGGTTTC | CCGACTGGAA 7150 |

| | | | | | |
|---|---|---|---|---|---|
| AGCGGGCAGT | GAGCGCAACG | CAATTAATGT | GAGTTACCTC | ACTCATTAGG | 7200 |
| CACCCCAGGC | TTTACACTTT | ATGCTTCCGG | CTCGTATGTT | GTGTGGAATT | 7250 |
| GTGAGCGGAT | AACAATTTCA | CACAGGAAAC | AGCTATGACC | ATGATTACGA | 7300 |
| ATTAA | | | | | 7305 |

I claim:

1. A DNA construct comprising in order from 5' to 3':
   a) a transcriptional regulatory region;
   b) a transcriptional initiation site;
   c) a selectable gene positioned within an intron defined by a 5' splice donor site comprising an efficient splice donor sequence such that the efficiency of splicing a messenger RNA having said splice donor sequence is between about 80% and 99% as determined by quantitative PCR, and a 3' splice acceptor site;
   d) a product gene encoding a product of interest; and
   e) a transcriptional termination site;
wherein the transcriptional regulatory region regulates transcription of both the selectable gene and the product gene.

2. The DNA construct of claim 1 wherein the splice donor site comprises a consensus splice donor sequence.

3. The DNA construct of claim 1 wherein the splice donor site comprises the sequence GACGTAAGT.

4. The DNA construct of claim 1 wherein the selectable gene is an amplifiable gene.

5. The DNA construct of claim 4 wherein the amplifiable gene is DHFR.

6. The DNA construct of claim 1 wherein the transcriptional regulatory region comprises a promoter and an enhancer.

7. A vector comprising the DNA construct of claim 1.

8. The vector of claim 7 wherein the selectable gene of the DNA construct is an amplifiable gene.

9. The vector of claim 7 that is capable of replication in a eukaryotic host.

10. A eukaryotic host cell comprising the vector of claim 9.

11. A eukaryotic host cell comprising the DNA construct of claim 4.

12. A eukaryotic host cell comprising the DNA construct of claim 1 integrated into a chromosome of the host cell.

13. The host cell of claim 12 that is a mammalian cell.

14. A method for producing a product of interest comprising culturing the host cell of claim 10 so as to express the product gene and recovering the product from the host cell culture.

15. The method of claim 14 further comprising recovering the product from the culture medium.

16. The method of claim 14 wherein the selectable gene is an amplifiable gene and the splice donor site comprises an efficient splice donor sequence.

17. A method for producing a product of interest comprising culturing the host cell of claim 11 so as to express the product gene in a selective medium comprising an amplifying agent for sufficient time to allow amplification to occur, and recovering the product.

18. A method for producing eukaryotic cells having multiple copies of a product gene comprising transforming eukaryotic cells with the DNA construct of claim 4 growing the cells in a selective medium comprising an amplifying agent for a sufficient time for amplification to occur, and selecting cells having multiple copies of the product gene.

19. The method of claim 18 further comprising culturing the selected cell 80 as to express the product gene and recovering from the selected cells the product of interest.

20. The method of claim 18 wherein the DNA construct is introduced into the eukaryotic cells by electroporation.

* * * * *

UNITED STATES PATENT AND TRADEMARK OFFICE
CERTIFICATE OF CORRECTION

PATENT NO.    : 5,561,053
DATED         : October 1, 1996
INVENTOR(S)   : Craig W. Crowley It is certified that error appears in the above-identified patent and that said Letters Patent is hereby corrected as shown below:

Column 54,
Line 37, please delete "cell 80" and insert therefor -- cells so --.

Signed and Sealed this

Twenty-first Day of January, 2003

JAMES E. ROGAN
*Director of the United States Patent and Trademark Office*